(12) United States Patent
Sabin

(10) Patent No.: US 10,328,030 B2
(45) Date of Patent: *Jun. 25, 2019

(54) COMPOSITIONS AND METHODS OF USE FOR TREATMENT OF MAMMALIAN DISEASES

(76) Inventor: Robert Sabin, Mill Neck, NY (US)

(*) Notice: Subject to any disclaimer, the term of this patent is extended or adjusted under 35 U.S.C. 154(b) by 1286 days.

This patent is subject to a terminal disclaimer.

(21) Appl. No.: 11/192,752

(22) Filed: Jul. 29, 2005

(65) Prior Publication Data

US 2006/0147512 A1 Jul. 6, 2006

Related U.S. Application Data

(63) Continuation-in-part of application No. 10/888,576, filed on Jul. 9, 2004, now Pat. No. 7,449,196.

(60) Provisional application No. 60/598,179, filed on Aug. 2, 2004, provisional application No. 60/666,135, filed on Mar. 29, 2005.

(51) Int. Cl.
| | | |
|---|---|---|
| *A61K 33/34* | (2006.01) | |
| *A61K 9/127* | (2006.01) | |
| *A61K 9/50* | (2006.01) | |
| *A61K 9/51* | (2006.01) | |
| *A61K 41/00* | (2006.01) | |
| *A61K 45/06* | (2006.01) | |

(52) U.S. Cl.
CPC .......... *A61K 9/5161* (2013.01); *A61K 9/5036* (2013.01); *A61K 9/5192* (2013.01); *A61K 33/34* (2013.01); *A61K 41/0038* (2013.01); *A61K 45/06* (2013.01)

(58) Field of Classification Search
CPC .... A61K 9/5036; A61K 9/5161; A61K 45/06; A61K 33/34; A61K 41/0038; A61K 9/5192
See application file for complete search history.

(56) References Cited

U.S. PATENT DOCUMENTS

| 3,197,458 | A | * | 7/1965 | Floramo ............. C08B 37/0021 106/31.36 |
| --- | --- | --- | --- | --- |
| 4,256,652 | A | | 3/1981 | Kidani et al. |
| 4,871,538 | A | | 10/1989 | Yim et al. |
| 4,952,607 | A | | 8/1990 | Sorenson et al. |
| 5,616,327 | A | | 4/1997 | Judd et al. |
| 5,632,982 | A | | 5/1997 | Sussman et al. |
| 6,218,378 | B1 | | 4/2001 | Berners-Price et al. |
| 6,306,403 | B1 | | 10/2001 | Donovan |
| 6,375,634 | B1 | * | 4/2002 | Carroll ............. A61K 47/48938 604/13 |
| 6,471,976 | B1 | * | 10/2002 | Taylor ................... A01N 37/04 424/409 |
| 6,581,606 | B2 | | 6/2003 | Kutzko et al. |
| 6,706,759 | B1 | * | 3/2004 | Kennedy ....................... 514/499 |
| 6,927,206 | B2 | | 8/2005 | Patt ................................... 514/6 |
| 7,001,924 | B2 | | 2/2006 | Giordano et al. |
| 7,365,060 | B2 | | 4/2008 | Rokita et al. |
| 8,617,572 | B2 | | 12/2013 | Blumenfeld |
| 8,927,520 | B2 | | 1/2015 | Pochet et al. |
| 9,125,907 | B2 | | 9/2015 | Shaari |
| 2003/0091621 | A1 | | 5/2003 | Tardi et al. ................... 424/450 |
| 2003/0104043 | A1 | | 6/2003 | Brown et al. |
| 2004/0204385 | A1 | | 10/2004 | Leech |
| 2004/0224005 | A1 | * | 11/2004 | Gabbay .................. A01N 57/20 424/443 |

FOREIGN PATENT DOCUMENTS

| CA | 2190011 | | 9/2000 | |
|---|---|---|---|---|
| CA | 2225822 | | 2/2010 | |
| CA | 2496005 | | 7/2013 | |
| JP | O H1-503548 | | 11/1989 | |
| JP | 07-138155 | | 5/1995 | |
| PL | 134562 | | 2/1982 | |
| SI | 20721 | | 6/2006 | |
| WO | 88/09347 | | 12/1988 | |
| WO | 00/04908 | | 2/2000 | |
| WO | WO 02/087598 | * | 11/2002 | ............. A61K 33/34 |
| WO | WO 2002087598 A1 | * | 11/2002 | |
| WO | 2014181329 A1 | | 11/2014 | |

OTHER PUBLICATIONS

MedlinePlus malaria Hepatitis C: [online] retrieved from: http://www.nlm.nih.gov/medlineplus/ency/article/000284.htm; retrieved on Aug. 12, 2008.*

MedlinePlus malaria Ebola hemorrhagic fever: [online] retrieved from: http://www.nlm.nih.gov/medlineplus/ency/article/001339.htm; retrieved on Aug. 12, 2008.*

MedlinePlus malaria: [online] retrieved from: http://www.nlm.nih.gov/medlineplus/ency/article/000621.htm; retrieved on Aug. 12, 2008.*

Wieczorek et al. (Archivum Immunologiae et Therapiae Experimentalis 1983, 31(5), 707-713).*

MSDS Copper (II) chloride dihydrate [online] retrieved from http://avogadro.chem.iastate.edu/MSDS/CuCl2-2H2O.htm; retrieved on Aug. 12, 2008.*

MSDS marshite [online] retrieved from http://www.espi-metals.com/msds's/copperiodide.pdf; retrieved on Aug. 12, 2008.*

Tabata et al. (Journal of Controlled Release 1999, 59, 187-196).*

(Continued)

*Primary Examiner* — Doan T Phan

(74) *Attorney, Agent, or Firm* — Alfred M. Walker; Jennifer P. Yancy

(57) ABSTRACT

This disclosure relates to a Composition having medicinal properties for use with mammalian diseases such as anti-cancer properties and methods of use, anti-viral properties and methods of use, anti-protozoan properties and methods of use, and anti-bacterial properties and methods of use in mammals. A chemical Composition for use as a pharmaceutical of a biologically acceptable copper compound and may include other components such as iron, which is transported to afflicted cells in a pharmaceutical acceptable carrier.

16 Claims, 161 Drawing Sheets

(56) References Cited

OTHER PUBLICATIONS

MedlinePlus Medical Encyclopedia: Cancer [online] Jul. 14, 2006 retrieved Oct. 18, 2006 retrieved from the internet http://www.nlm.nih.gov/medlineplus/ency/article/000583.htm pp. 1-4.*
Haddow et al. J. Nat. Cancer Inst. 1960, 24, 109-147 Note that this is in two pdf files.*
Norkus et al. (Carbohydrate Polymers 2002, 50, 159-164).*
Mitic et al. (Russian Journal of Physical Chemisry 2007, 81(9), 1433-1437).*
Lugovaya et al. (Translation from Khimiko-Farmatsevticheskii Zhurnal 1976, 10(11), 111-113).*
Chaoyong Ma (2004). "Animal Models of Disease." Modern Drug Discovery, 30-36.*
Shanks et al. (2009). "Review: Are Animal Models Predictive for Human?" Philosophy, Ethics, and Humanities for Medicine, 4(2), 1-20.*
DailyMed—"infed (Iron Dextran)." Retrieved on May 26, 2015. Retrieved from the internet <URL: http://dailymed.nlm.nih.gov/dailymed/archives/fdaDrugInfo.cfm?archiveid=6294>.*
Strohs et al. Free Radical Biology&Medicine. 1995;18(2):321-336.*
Grass et al. Applied and Environmental Microbiology 2011;77(5):1541-1547.*
Merck Manuals—"Viral Infections." Retrieved on Apr. 21, 2015. Retrieved from the internet <URL:http://www.merckmanuals.com/home/infections/viral-infections/overview-of-viral-infections>.*
Breastcancer.org. "What to do if your genetic test results are positive." Retrieved on Jan. 27, 2016. Retrieved from the Internet <URL: http://www.breastcancer.org/symptoms/testing/genetic/pos_results>.*
National Cancer Institute—"Breast cancer treatment." Retrieved on Jan. 27, 2016. Retrieved form the internet <URL: http://www.cancer.gov/types/breast/patient/breast-treatment-pdq#section/_185>.*
Mayo Clinic—"Leukemia—Treatment and Drugs." Retrieved on Jan. 27, 2016. Retrieved from the internet <URL: http://www.mayoclinic.org/diseases-conditions/leukemia/basics/treatment/con-20024914>.*
Cakic et al., Spectroscopy, 22 (2008): 177-185.*
Lu et al., Cancer Gene Ther. Jan.-Feb. 1999; 6(1): 64-72.*
Ma, ChaoYong. Modern Drug Discovery. Jun. 2004; pp. 30-36.*
Carbone et al. Seminars in Cancer Biology, 2004, 14: 399-405.*
Kunz-Schughart et al. Journal of Biomolecular Screening, 2004, 9:273-285.*
Kamb, Alexander. Nature Review. Feb. 2005, 4: 161-165.*
Chereson, Rasma. Basic Pharmaceutics: Chapter 8. 1996, pp. 8-1 to 8-17.*
Burkh, Jens. "Animal Models for the study of Hepatitis C Virus infection and Related Liver Disease." Gastroenterology, 2012, 142: 1279-1287. (Year: 2012).*
Kehati et al. "Advances and Challenges in Studying Hepatitis B Virus in Vitro." Viruses, Jan. 2016, 8(1): pp. 1-17. (Year: 2016).*
Hessell et al. "Animal Models in HIV-1 Protection and Therapy." Curr Opin HIV AIDS. Author manuscript., May 2016, pp. 1-12. Year: 2016).*
Dowall et al. "Chloroquine inhibited Ebola virus replication in vitro but failed to protect against infection and disease in the in vivo guinea pig model." Journal of General Virology, 2015, 96: 3484-3492. (Year: 2015).*
Govorkova et al. "Susceptible of Highly Pathogenic H5N1 Influenza Viruses to the Neuraminidase Inhibitor Oseltamivir Differs in Vitro and in a Mouse Model." Jul. 2009, p. 3088-3096. (Year: 2009).*
Kumar et al. "Current challenges in drug discovery for tuberculosis." Expert Opinion in Drug Discovery, 2017, 12(1): 1-4. (Year: 2017).*
Rolain et al. "Recommendations for Treatment of Human Infections Caused by Bartonella Species." Antimicrobial Agents and Chemotherapy, Jun. 2004, p. 1921-1933. (Year: 2004).*
Manfredi et al. "Bartonellosis: Suggestive Case Reports in Adult and Pediatric Patients and Therapeutic Issue." The Brazilian Journal of Infectious Diseases, 2006, 10(6): 411-415. (Year: 2006).*
Coelho et al. "In Vitro and In Vivo Miltefosine Susceptibility of Leishmania amazonensis Isolate from a Patient with Diffuse Cutaneous Leishmaniasis." PLOS Neglected Tropical Disease, Jul. 2014, 8(7): pp. 1-11. (Year: 2014).*
Duffy et al. "Routine in Vitro Culture of Plasmodium falciparum: Experimental Consequences?" Trends in Parasitology, Jul. 2018, 34(7): 564-575. (Year: 2018).*
Chatelain et al. "Translational challenges of animal models in Chagas disease drug development: a review." Drug Design, Development and Therapy, 2015, 9: 4807-4823. (Year: 2015).*
Tabata et al. Journal of Controlled Release, 1999, 59, 187-196. (Year: 1999).*
Alza Corporation, *Alza's Stealth® Liposomal Technology: Current Therapies and Future Opportunities*, Delivery Times Issues and Opinions, vol. II, Issue 1, 1-11, 2002.
The American Cancer Society, *Consumers Guide to Cancer Drugs*, Jones and Bartlett Publishers, (2000), pp. 1-448.
The American Cancer Society report, *Cancer Facts and Figures 2003*, p. 4, (2003).
Armstrong, Lance *It's Not About the Bike*, Berkley Publishing, (2000).
Aruoma, *Copper ion-dependent damage to the base pairs in DNA in the presence of hydrogen peroxide*, Biochem. Jour., 273: 601-4(1991) 1 page abstract.
Auerbach, *Intravenous Iron Optimizes the Response to Recombinant Human Erythropoietin in Cancer Patients with Chemotherapy-Related Anemia: A Multicenter, Open-Label, Randomized Trial*, J. of Clin. Oncology, 22:7-1301-1307 (2004).
Awasthi, *Circulation and Biodistribution Profiles of Long-Circulating PEG Liposomes of Various Sizes in Rabbits*, Int. Journal of Pharmaceutics 253 (2003) 121-122.
Baquiran, *Cancer Chemotherapy Handbook*, Lippincott, p. 85 (2001) p. 85.
Besarab, *An Indistinct Balance: The Safety and Efficacy of Parenteral Iron Therapy*, Journal of American Society of Nephrology, vol. 10, No. 9, 23 pp. (Sep. 1999).
Brem, *Angiogenesis and Cancer Control: From Concept to Therapeutic Trial*, Cancer Control Jour., 6 (5):436-458 (1999).
Brem, et al., *Phase II Trial of Copper Depletion as Angiosuppresive Treatment in Newly Diagnosed Glioblastoma Multiforme: Final Report*, Journal of Clinical Oncology vol. 22, No. 14S , (2004) 1 page abstract.
Brewer, Control of Copper in Wilson's Disease and Diseases of Neovascularization, such as Cancer, *Handbook of Copper Pharmacology and Toxicology*, Humana Press, Chap. 27, (2002).
Brewer. *Copper Control as an Antiangiogenic Anticancer Therapy: Lessons from.Treating Wilson's Disease*, Exp. Bio. and Med., 226(7):665-673 (2001).
Brewer, et al., *Treatment of Metastatic Cancer with Tetrathiomolybdate, an Anticopper, Antiangiogenesis Agent: Phase I Study*, Clin. Cancer Res., 6:1-10 (2000).
Clarke et al., Applied and Envir. Microbio., May 1987 pp. 917-922.
Collery, et al., *Gallium in Cancer Treatment*, Crit. Rev. In Oncology/Hematology, 42:283-296 (2002).
Cox, Merajver, Yoo, Dick, Brewer, Lee and Teknos, *Inhibition of the Growth of Squamous Cell Carcinoma by Tetrathiomolybdate-Induced Copper Supression in a Murine Model*, Arch Otolaryngol Head Neck Surg. 2003; 129:781-785 (2003) 1 page abstract.
Cox, *Structure of an iron-dextran complex*, J. of Pharma & Pharmac, 24:513-517 (1972).
Chu & Devita, *Physicians' Cancer Chemotherapy Drug Manual*, 2003, Jones and Bartlett Publishers, (2003) pp. 12-20.
Degani, *Glycolysis and GLUT1 in Breast Tumors: Markers of Response to Hormonal Therapy*, The American Society of Clinical Oncology, Intn'l J. of Cancer, 107:177-182 (Nov. 2003).2 page summary in asco.org.
Desoize, B., Editor, *Cancer in Metals and Metal Compounds: Part I—Carcinogenesis*, Critical Reviews in Oncology/Hematology, 42:1-3 (2002).

(56) References Cited

OTHER PUBLICATIONS

Desoize, B. Editor, Cancer and Metals and Metal Compounds, Part II—Cancer Treatment, Crit. Rev. In Oncology/Hematology, 42:213-215 (2002).
DEXFERRUM® (Iron Dextran Injection), USP, package insert, (2004).
Easmon *Synthesis, cytotoxicity, and antitumor activity of copper (II) and iron (III) complexes of (4)N-azabicyclo[3.1.2] nonane thiosemicarbazones derived from acyldiazines*, J. Med Chem, Jun. 2001, 44(13); 2164-71, 2 page abstract.
Engels et al, *Hepatitis C Virus Infection and Non-Hodgkin Lymphoma: Results of the NCI-seer Multi-center Case-control Study*, Int. Journal of Cancer, vol. 111, Issue 1, 76-80 (2004) 3 page abstract.
Essner, et al., Advances in FDG PET Probes in Surgical Oncology, Cancer Jour. 8:100-108 (2002).
Galaris, et al., *The Role of Oxidative Stress in Mechanisms of Metal-induced Carcinogenesis*, Critical Reviews in Oncology/Hematology, 42:93-103 (2002).
Gatenby and Gawlinski, the glycolysis phenotype in carcinogenesis and tumor.invasion: insights through mathematical models, Cancer Res., 63(14):3847-54 (Jul,.
Gatenby and Gillies, *Why Do Cancers Have High Aerobic Glycolysis?*, Nature Reviews Cancer, 4 (Nov. 2004).
Geschwind, Ko, Torbenson, Magee and Pedersen, *Novel Therapy for Liver Cancer: Direct Intraarterial Injection of a Potent Inhibitor of ATP Production*, Cancer Research 62, 3909-3913, Jul. 15, 2002.
Hauser & Hauser, *Cancer-Treating Cancer with Insulin Potentiation Therapy*, Beulah Land Press, (2001), pp. 1-414.
Henderson & Hillman, *Characteristics of Iron Dextran Utilization in Man*, Blood, 34(3):357-375 (1969).
Johnson, *An Innovative Drug Delivery Technology*, Magnetics Business & Technology Magazine, (2002).
King, Cancer Combat.
Journal D'Agriculture Pratique, pp. 698-700, 728-729, and 765-766 (1887) (No translation).
Kingston, David, et al,*Paclitaxel analog kills more cancer cells than natural product*, American Chemical Society, Mar. 28, 2004.
Kwok, et al., *The Iron Metabolism of Neoplastic Cells: alterations that facilitate proliferation?*, Crit. Rev. In Oncology/Hematology, 42:65-78 (2002).
LaFontaine; "Comparative Analysis of Copper and Iron Metabolism in Photosynthetic Eukaryotes vs. Yeast and Mammals", Massaro, *Handbook of Copper Pharmacology and Toxicology*, Chapter 30, 481-503, 2002.
Lawrence, *Development and Comparison of Iron Dextran Products*, J. of Pharm. Sci. & Tech., 52(5):190-197(1998).
Lee and Pedersen, *Glucose Metabolism in Cancer*, J. of Biol. Chem. 278(42):41047-41058 (Oct. 2003).
Lodeman, *The Spraying of Plants*, the MacMillan Company, New York, N.Y. (1910).
Marchione, *Hopes in cancer drug dashed*, Milwaukee Journal Sentinel, May 22, 2002.
Markman, M.D. in *Basic Cancer Medicine*, W. B. Saunders Co., p. 103, (1997).
Maschek, et al., *2-deoxy-D-glucose increases the efficacy of adriamycin and paclitaxel in human osteosarcoma and non-small cell lung cancers in vivo*, Cancer Res., 64(1):31-34 (2004).
Masters and Koberle, in *Curing Metastatic Cancer: Lessons from Testicular Germ-Cell Tumours*, Nature Reviews, 3(7) (Jul. 2003).
Mehvar, *Dextrans for targeted and sustained delivery of therapeutic and imaging agents*, J. of Controlled Release, 69:1-25 (2000).
Mehvar, *Recent Trends in the Use of Polysaccharides for Improved Delivery of Therapeutic Agents* Pharmacokinetic and Pharmacodrynamic Perspectives Current Pharmaceutical Biotechnology, 2003, 4, 283-302.
Millardet, *The Discovery of the Bordeaux Mixture* (1885) translated by Schneiderman (1933) p. 13-15.
Millardet, *Notes Sur Les Vignes Americaines et Opuscules Divers Sur le Meme Suhjet*, pp. 56-60 (1881) (No translation).

Moghimi, et al., *Long-Circulating and Target-Specific Nanoparticles: Theory to Practice*, Pharm. Rev., 53(2):283-318 (2001).
Moss, *Questioning Chemotherapy*, Equinox Press, p. 77, (2000).
Moss, *Cancer Therapy*, Equinox Press, p. 316 (1992).
The *Moss Reports Newsletter* (Jul. 4, 2004), Ralph W. Moss, PhD. WeeklyCancerDecisions.com Newsletter #139 Jul. 4, 2004.
Nakakura & Choti, *Management of Hepatocellular Carcinoma*, Oncology, 14(7) (2000).
OncoLink, *Doxirubicin and Paclitaxel Comparable in Treatment of Metastatic Breast Cancer*, Reuters Health, Journal of Clinical Oncology, 2003; 21:588-592.
Pan, et al., *Copper Deficiency Induced by Tetrathiomolybdate Suppresses Tumor Growth and Angiogenesis*, Cancer Res., 62:4854-4859 (2002).
Pedersen et al , "3-Bromopyruvate Slays Hepatoma Cells in Rabbits Without Damaging Normal Tissue", *Inhibiting glycolysis and oxidative phosphorylation, 3-BrPA abolishes cell ATP production*, Reuters News, (Jul. 18, 2002).
Pimentel, David, *CRC Handbook of Pest Management in Agriculture Volume III*, pp. 19-25, 49-59, 70-71, 75-93, 265, 366-369, 494-495, (1980).
Quillin, *Cancer's Sweet Tooth*, Nutrition Science News, (Apr. 2000).
Quillin, *Beating Cancer with Nutrition*, Nutrition Times Press, p. 225 (1998).
Redman, *Phase II Trial of Tetrathiomolybdate in Patients with Advanced Kidney Cancer*, Clin. Cancer Res., 9:1666-1672 (2003).
Rich, *The Red Devil*, Three Rivers Press, (1999), pp. 1-242.
Richardson, *Iron Chelators as therapeutic agents for the Treatment of Cancer*, Crit. Rev. In Oncology/Hematology, 42:267-281 (2002).
Rivenzon-Segal, et. al., *Glycolysis as a metabolic marker in orthotopic breast cancer, monitored by in vivo 13C MRS*, Amer. J. Phys. Endocrinology Metabolism, 283:E623-E630 (2002).
Sagripanti, *DNA Damage Mediated by Metal Ions with Special Reference to Copper and Iron*, Met. Ions Biol. Syst. 36:179-209 (1999).
Sagripanti, et al., *Virus Inactivation by Copper or Iron Ions alone and in the Presence of Peroxide*, Applied and Environ. Microbio, 59:12, 4374-4376 (1993).
Sagripanti, *Metal-based Formulations with High Microbicidal Activity*, Applied and Environ. Microbio, 58:9, 3157-3162 (1992).
Sagripanti and Kraemer, *Site-specific Oxidative DNA Damage at Polyguanosines Produced by Copper Plus Hydrogen Peroxide*, J. of Biol. Chem., 264(3):1729-1734 (1989).
Schiller, et al., *Comparison of Four Chemotherapy Regimens for Advanced Non-Small-Cell Lung Cancer*, The N. Eng. J. of Med., 346(2):92-98 (Jan. 2002).
Schroth et al. "Research Proposal: New Approaches to Controlling Walnut Blight;" 1984 pp. 1-4.
Schroth, Information Disclosure Statement U.S. Appl. No. 07/644,997.
Sledge, et al, *Phase III, Trial of Doxorubicin, paclitaxel, and the combination of doxorubicin and paclitaxel as front-line chemotherapy for metastatic breast cancer: an intergroup trial*, J. of Clinical Oncology, 21 (4):588-592 (Feb. 2003).
Steller, Hermann *Mechanisms and Genes of Cellular Suicide*, Science 267 (5203):1445-1449 (1995).
Stevens, et al., *Body Iron Stores and the Risk of Cancer*, N. Eng. J. of Med., 319(16):1047-1052 (1988).
Teknos, et al., *Anti-Copper Therapy Protects Against Squamous Cell Cancer in Mice*, citing Cox et al, *Inhibition of the Growth of Squamous Cell Carcinoma by Tetrathiomolybdate-Induced Copper Suppression in a Murine Model*, Arch. of. Otolaryngology: Head and Neck Surgery, in OncoLink Cancer News, Reuters, 129:781-785 (2003).
Theophanides, et al., *Copper and Carcinogenesis*, Critical Reviews in Oncology/Hematology, 42:57-64 (2002).
Van Dang et al, The Proc. of the Nat'l Acad. of Sci. 95:1511-1516 (1998).
Van Etten *Administration of Liposomal Agents and Blood Clearance Capacity of the Mononuclear Phagocyte System*, Antimicrobial Agents and Chemotherapy, Jul. 1998, 1677-1681, vol. 42, No. 7.

(56) References Cited

OTHER PUBLICATIONS

Viarengo, "Cellular Responses to Copper in Aquatic Organisms", *Handbook of Copper Pharmacology and Toxicology*, Ed. Massaro, Humana Press, Chapter 25, 417-431, 2002.

Warburg, O. *The Prime Cause and Prevention of Cancer*, Konrad Triltsch, p. 6. (1969).

Warburg, O., *On the Origin of Cancer Cells*, Science 123 (3191): 309-314 (Feb. 1956).

Weinberg, *Human Lactoferrin: a Novel Therapeutic with Board Spectrum Potential*, Pharmacy & Pharmacology, 53 (Oct. 2001).

Weinberg, *Iron and Cancer: a Dangerous Mix*, Iron Disorders Insight, 2(2):11 (1999).

Weinberg, *Development of Clinical Methods of Iron Deprivation for Suppression of Neoplastic and Infectious Diseases*, Cancer Investigation, 17(7):507-513 (1999).

Weinberg, *The Development of Awareness of the Carcinogenic Hazard of Inhaled Iron*, Oncology Res. 11:109-113 (1999).

Weinberg, *Iron Therapy and Cancer*, Kidney Int'l, 55(60):S131-134 (1999).

Weinberg, *The Role of Iron in Cancer*, Euro. J. Cancer Prevention, 5:19-36, (1995).

Weinberg, *Iron in Neoplastic Disease*, Nutrition Cancer, 4(3):223-33 (1993).

Weinberg, *The Development of Awareness of Iron Withholding Defense*, Perspectives in Biology and Medicine, Winter 1993, 36(2): 215-221.

Weinberg, *Iron Loading and Disease Surveillance*, Emerging Infections Diseases, May-Jun. 1999, (5(3).

Wimmer, "Molecular Hardware of Copper Homeostasis in Enderococlus hirae", Massar, *Handbook of Copper Pharmacology and Toxicology*, Chapter 32, Humana Press, 2002, p. 527-542.

Yoshiji, et al., *The Copper Chelating Agent, trientine, suppresses tumor development and angiogenesis in the murine heptatocellular carcinoma cells*, Int'l J. of Cancer, 94:768-773 (2001).

Yoshiji, et al., *The copper chelating agent, Trientine attenuates liver enzymes-altered preneoplastic lesions in rats by angiogenesis suppression*, Oncology Rep., 10(5):1369-73 (2003).

Lu et al., *Hypoxia-inducible Factor I Activation by Aerobic Glycolysis Implicates the Warbug Effect in Carcinogenesis*, J. Biol. Chem., vol. 277, Issue 26, 23111-23115, Jun. 28, 2002, 10 pages.

London, *The Molecular formula and proposed structure of the irondextran complex, IMFERON*, J. of Pharmaceutical Science vol. 39, Issue 7, May 13, 2004, pp. 1838-1846.

RJ Errington, Advanced Practical Inorganic and Metalorganic Chemistry, 1997, pp. 135-136.

Wieczorek, Z. et al, Oncostatic Properties of the Complex of Bivalent Copper with 3-Mercapto-2-Hydroxypropyl Ether of Dextran (C-79), Arch Immunol Ther Exp (Warsz), 1983, vol. 31, No. 5, p. 707-13, 7 pages.

Wieczorek, Z. et al, Anti-infectious Properties of the Complex of Bivalent Copper with 3-mercapto-2-hydroxypropyl of ether dextran (C-79), Arch Immunol Ther Exp (Warsz), 1983, vol. 31, No. 5, p. 701-5, 5 pages.

Spychaj, T et al, Composite Hydrogels of the Polysaccharide/ polyvalent Metal Type, NATO ASI Series, Series 3: High Technology, 1995, vol. 5., p. 211-213, 5 pages.

Jiang, Y. et al, Synthesis and the bio-activities of 2-acetyl-thiophen azine and its new complexes of Fe3+, Cu2+, Zhongguo Yaowu Huaxue Zazhi, 2003, vol. 13, No. 1, p. 12-15, 6 pages.

Kuncheria, J. et al, Antitumor activity of some pyrazolone—copper complexes, Indian Journal of Pharmaceutical Sciences, 1994, vol. 56, No. 2, p. 37-40, 4 pages.

Vasudevachari, M.B., et al, Antiviral activity of lopsome-encapsulated cupric complex of isonicotinic acid hydrazide against avian myeloblastosis virus infection, Indian J Exp Biol, 1985, vol. 23, No. 7, p. 393-6, 4 pages.

Yugiang Huang et al, Preparation on Nanometric CuxFe1—xOFe2O3 for Treatment of Tumor, Journal of Applied Physics, May 15, 2003, 5 pages, vol. 93, No. 10.

High-throughput screening, from Wikipedia, https://en.wikipedia.org/wiki/High-throughput_screening, Oct. 6, 2015.

Micro-encapsulation, from Wikipedia, https://en.wikipedia.org/wiki/Micro-encapsulation, Oct. 9, 2015.

Clostridium botulinum, from Wikipedia,https://en.wikipedia.org/wiki/Cl . . . , Oct. 9, 2015.

\* cited by examiner

CELL LINE: NCI-H23 LUNG
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   708   ±   98 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 239280 | 83933 | 238572 | 83933 | 0 | 35 |
| DIS.COMP. | 0.003 | 327938 | 34095 | 327230 | 34095 | 0 | 14 |
| | 0.01 | 289465 | 62990 | 288757 | 62990 | 0 | 26 |
| | 0.03 | 269840 | 82815 | 269132 | 82815 | 0 | 35 |
| | 0.1 | 273782 | 88132 | 273074 | 88132 | 0 | 37 |
| | 0.3 | 243699 | 73717 | 242991 | 73717 | 0 | 31 |
| | 1 | 338981 | 43708 | 338273 | 43708 | 0 | 18 |
| | 3 | 273100 | 126786 | 272392 | 126786 | 0 | 53 |
| | 10 | 143339 | 64012 | 142631 | 64012 | 40 | 27 |
| BASE | | 297824 | 50646 | 297116 | 50646 | 0 | 21 |
| DOX | 1 µM | 1334 | 246 | 626 | 246 | 100 | 0 |

Fig. 2B

| IC50 >   10  µg/mL |
|---|

| THEORETICAL CALCULATED ABSORBANCE VALUES |
|---|
| IC10  =  214715 |
| IC50  =  119286 |
| IC90  =  23857 |

Fig. 2C

CELL LINE: NCI-H23 LUNG
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]  =  596    ±    198 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 280621 | 45419 | 280026 | 45419 | 0 | 16 |
| DC+B | 0.003 | 293828 | 44679 | 293233 | 44679 | 0 | 16 |
| | 0.01 | 257853 | 62646 | 257257 | 62646 | 8 | 22 |
| | 0.03 | 246812 | 67879 | 246216 | 67879 | 12 | 24 |
| | 0.1 | 298383 | 46767 | 297788 | 46767 | 0 | 17 |
| | 0.3 | 288622 | 28595 | 288026 | 28595 | 9 | 10 |
| | 1 | 217760 | 38288 | 217165 | 38288 | 22 | 14 |
| | 3 | 2942 | 256 | 2347 | 256 | 99 | 0 |
| | 10 | 566 | 185 | -30 | 185 | 100 | 0 |
| BASE | | 254632 | 44431 | 254037 | 44431 | 9 | 16 |
| DOX | 1 µM | 1703 | 429 | 1107 | 429 | 100 | 0 |

Fig. 2E

| IC50 = 1.718 µg/mL |
|---|
| (THEORETICAL IC50 CALCULATED ABSORBANCE VALUE = 140013) |
| CONCENTRATIONS USED FOR REGRESSION 3.000 AND 1.000 µg/mL |
| REGRESSION OUTPUT |
| CONSTANT                           324573<br>STD ERR OF Y EST              27074<br>R SQUARED                                 1<br>NO. OF OBSERVATIONS        16<br>DEGREES OF FREEDOM         14<br><br>X COEFFICENT(S)              -107409<br>STD ERR OF COEF.                6768 |

Fig. 2F

CELL LINE: NCI-H460 LUNG
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   809   ±   298 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 114212 | 21835 | 113403 | 21835 | 0 | 19 |
| DIS.COMP. | 0.003 | 85678 | 43980 | 84869 | 43980 | 25 | 39 |
|  | 0.01 | 79281 | 28129 | 78472 | 28129 | 31 | 25 |
|  | 0.03 | 82290 | 25422 | 81481 | 25422 | 28 | 22 |
|  | 0.1 | 81258 | 32786 | 80449 | 32786 | 29 | 29 |
|  | 0.3 | 79020 | 29100 | 78211 | 29100 | 31 | 26 |
|  | 1 | 62277 | 6501 | 61468 | 6501 | 46 | 6 |
|  | 3 | 10113 | 4953 | 9304 | 4953 | 92 | 4 |
|  | 10 | 1047 | 356 | 238 | 356 | 100 | 0 |
| BASE |  | 80453 | 31751 | 79644 | 31751 | 30 | 28 |
| DOX | 1 µM | 1210 | 207 | 401 | 207 | 100 | 0 |

Fig. 3B

| IC50 = 1.183 µg/mL |
|---|
| (THEORETICAL IC50 CALCULATED ABSORBANCE VALUE = 56701) |
| CONCENTRATIONS USED FOR REGRESSION 3.000 AND 1.000 µg/mL |
| REGRESSION OUTPUT<br><br>CONSTANT                87550<br>STD ERR OF Y EST        5779<br>R SQUARED               1<br>NO. OF OBSERVATIONS     16<br>DEGREES OF FREEDOM      14<br><br>X COEFFICENT(S)         -26082<br>STD ERR OF COEF.        1445 |

Fig. 3C

CELL LINE: NCI-H460 LUNG
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   837   ±   284 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 63961 | 24027 | 63124 | 24027 | 0 | 38 |
| DC+B | 0.003 | 65444 | 19769 | 64607 | 19769 | 0 | 31 |
|  | 0.01 | 67894 | 19699 | 67057 | 19699 | 8 | 31 |
|  | 0.03 | 51046 | 20762 | 50209 | 20762 | 20 | 33 |
|  | 0.1 | 37264 | 14885 | 36427 | 14885 | 42 | 24 |
|  | 0.3 | 5788 | 1720 | 4951 | 1720 | 92 | 3 |
|  | 1 | 641 | 171 | -196 | 171 | 100 | 0 |
|  | 3 | 450 | 181 | -387 | 181 | 100 | 0 |
|  | 10 | 578 | 167 | -260 | 167 | 100 | 0 |
| BASE |  | 92220 | 18472 | 91383 | 18472 | 0 | 29 |
| DOX | 1 µM | 883 | 247 | 46 | 247 | 100 | 0 |

Fig. 3E

| IC50 = 0.131 µg/mL |  |
|---|---|
| (THEORETICAL IC50 CALCULATED ABSORBANCE VALUE = 31562) | |
| CONCENTRATIONS USED FOR REGRESSION 0.300 AND 0.100 µg/mL | |
| REGRESSION OUTPUT | |
| CONSTANT | 52165 |
| STD ERR OF Y EST | 10596 |
| R SQUARED | 1 |
| NO. OF OBSERVATIONS | 16 |
| DEGREES OF FREEDOM | 14 |
| X COEFFICENT(S) | -157381 |
| STD ERR OF COEF. | 26489 |

Fig. 3F

CELL LINE: MCF7 MAMMARY
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   672   ±   83 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 163588 | 68466 | 162916 | 68466 | 0 | 42 |
| DIS.COMP. | 0.003 | 142391 | 71697 | 141719 | 71697 | 13 | 44 |
| | 0.01 | 179067 | 60307 | 178395 | 60307 | 0 | 37 |
| | 0.03 | 124765 | 62644 | 124093 | 62644 | 24 | 38 |
| | 0.1 | 119649 | 57326 | 118977 | 57326 | 27 | 35 |
| | 0.3 | 114224 | 48706 | 113552 | 48706 | 30 | 30 |
| | 1 | 118291 | 34321 | 117618 | 34321 | 28 | 21 |
| | 3 | 58684 | 29044 | 58012 | 29044 | 64 | 18 |
| | 10 | 16646 | 3030 | 15973 | 3030 | 90 | 2 |
| BASE | | 125715 | 61249 | 125043 | 61249 | 23 | 38 |
| DOX | 1 µM | 732 | 60 | 60 | 60 | 100 | 0 |

Fig. 4B

| IC50 = 2.213 µg/mL |
|---|
| (THEORETICAL IC50 CALCULATED ABSORBANCE VALUE = 81458) |
| CONCENTRATIONS USED FOR REGRESSION 3.000 AND 1.000 µg/mL |
| REGRESSION OUTPUT<br><br>CONSTANT                147421<br>STD ERR OF Y EST         31792<br>R SQUARED                      1<br>NO. OF OBSERVATIONS     16<br>DEGREES OF FREEDOM    14<br><br>X COEFFICENT(S)          -29803<br>STD ERR OF COEF.          7948 |

Fig. 4C

CELL LINE: MCF7 MAMMARY
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   1450          ±          1255 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 180297 | 67048 | 178847 | 67048 | 0 | 37 |
| DC+B | 0.003 | 200182 | 40578 | 198732 | 40578 | 0 | 23 |
|  | 0.01 | 202789 | 64075 | 201339 | 64075 | 0 | 36 |
|  | 0.03 | 197598 | 28199 | 196148 | 28199 | 0 | 16 |
|  | 0.1 | 150016 | 66716 | 148567 | 66716 | 17 | 37 |
|  | 0.3 | 195335 | 28074 | 193885 | 28074 | 0 | 16 |
|  | 1 | 86580 | 38955 | 85130 | 38955 | 52 | 22 |
|  | 3 | 1046 | 212 | -404 | 212 | 100 | 0 |
|  | 10 | 482 | 146 | -968 | 146 | 100 | 0 |
| BASE |  | 283739 | 80230 | 282289 | 80230 | 0 | 45 |
| DOX | 1 µM | 555 | 233 | -895 | 233 | 100 | 0 |

Fig. 4E

| IC50 = 0.972 µg/mL |  |
|---|---|
| (THEORETICAL IC50 CALCULATED ABSORBANCE VALUE = 89423) | |
| CONCENTRATIONS USED FOR REGRESSION 1.000 AND 0.300 µg/mL | |
| REGRESSION OUTPUT | |
| CONSTANT | 240494 |
| STD ERR OF Y EST | 33953 |
| R SQUARED | 1 |
| NO. OF OBSERVATIONS | 16 |
| DEGREES OF FREEDOM | 14 |
| X COEFFICENT(S) | -155363 |
| STD ERR OF COEF. | 24252 |

Fig. 4F

CELL LINE: ZR-75-1 MAMMARY
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   592          ±          178 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (μg/mL) | MEAN | SD | | | MEAN | SD |
| CONTROL | - | 108103 | 43069 | 107510 | 43069 | 0 | 40 |
| DIS.COMP. | 0.003 | 132348 | 14569 | 131755 | 14569 | 0 | 14 |
| | 0.01 | 119250 | 30534 | 118658 | 30534 | 0 | 28 |
| | 0.03 | 124791 | 29590 | 124199 | 29590 | 0 | 28 |
| | 0.1 | 113021 | 40121 | 112429 | 40121 | 0 | 37 |
| | 0.3 | 112641 | 21194 | 112049 | 21194 | 0 | 20 |
| | 1 | 94331 | 8863 | 93738 | 8863 | 13 | 8 |
| | 3 | 97565 | 17244 | 96972 | 17244 | 10 | 16 |
| | 10 | 70952 | 24346 | 70359 | 24346 | 35 | 23 |
| BASE | | 127525 | 14303 | 126933 | 14303 | 0 | 13 |
| DOX | 1 μM | 937 | 171 | 345 | 171 | 100 | 0 |

THEORETICAL CALCULATED ABSORBANCE VALUES

CELL LINE: ZR-75-1 MAMMARY
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]  =  655  ±  149 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 76148 | 14755 | 75493 | 14755 | 0 | 20 |
| DC+B | 0.003 | 94190 | 22989 | 93535 | 22989 | 0 | 30 |
| | 0.01 | 102582 | 21922 | 101927 | 21922 | 0 | 29 |
| | 0.03 | 94237 | 25930 | 93582 | 25930 | 0 | 34 |
| | 0.1 | 89610 | 16748 | 88955 | 16748 | 0 | 22 |
| | 0.3 | 89812 | 13449 | 89157 | 13449 | 0 | 18 |
| | 1 | 66568 | 10830 | 65913 | 10830 | 13 | 14 |
| | 3 | 11946 | 1708 | 11291 | 1708 | 85 | 2 |
| | 10 | 663 | 169 | 8 | 169 | 100 | 0 |
| BASE | | 93992 | 23394 | 93337 | 23394 | 0 | 31 |
| DOX | 1 µM | 607 | 175 | -48 | 175 | 100 | 0 |

Fig. 5E

| IC50 = 2.031 µg/mL |
|---|
| (THEORETICAL IC50 CALCULATED ABSORBANCE VALUE = 37746) |
| CONCENTRATIONS USED FOR REGRESSION 3.000 AND 1.000 µg/mL |
| REGRESSION OUTPUT<br><br>CONSTANT 93223<br>STD ERR OF Y EST 7753<br>R SQUARED 1<br>NO. OF OBSERVATIONS 16<br>DEGREES OF FREEDOM 14<br><br>X COEFFICENT(S) -27311<br>STD ERR OF COEF. 1938 |

Fig. 5F

CELL LINE: PC-3 PROSTATE
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]  =  912  ±  286 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 49491 | 15714 | 48579 | 15714 | 0 | 32 |
| DIS.COMP. | 0.003 | 56721 | 19439 | 55808 | 19439 | 0 | 40 |
| | 0.01 | 41732 | 17624 | 40819 | 17624 | 0 | 36 |
| | 0.03 | 57453 | 21988 | 56540 | 21988 | 0 | 45 |
| | 0.1 | 57074 | 24963 | 56161 | 24963 | 16 | 51 |
| | 0.3 | 56819 | 22170 | 55906 | 22170 | 0 | 46 |
| | 1 | 80203 | 19183 | 79290 | 19183 | 0 | 39 |
| | 3 | 90242 | 20098 | 89329 | 20098 | 0 | 41 |
| | 10 | 41161 | 9452 | 40249 | 9452 | 17 | 19 |
| BASE | | 53951 | 15624 | 53039 | 15624 | 0 | 32 |
| DOX | 1 µM | 1801 | 382 | 889 | 382 | 98 | 1 |

THEORETICAL CALCULATED ABSORBANCE VALUES

CELL LINE: PC-3 PROSTATE
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   982         ±         328 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 75060 | 6681 | 74078 | 6681 | 0 | 9 |
| DC+B | 0.003 | 76246 | 12881 | 75263 | 12881 | 0 | 17 |
|  | 0.01 | 76914 | 8723 | 66317 | 28367 | 10 | 38 |
|  | 0.03 | 76769 | 15501 | 75786 | 15501 | 0 | 21 |
|  | 0.1 | 75635 | 6312 | 74653 | 6312 | 0 | 9 |
|  | 0.3 | 75745 | 10158 | 74763 | 10158 | 0 | 14 |
|  | 1 | 60357 | 9393 | 59375 | 9393 | 20 | 13 |
|  | 3 | 8963 | 1479 | 7980 | 1479 | 89 | 2 |
|  | 10 | 844 | 420 | -138 | 420 | 100 | 1 |
| BASE |  | 76812 | 6491 | 75829 | 6491 | 0 | 9 |
| DOX | 1 µM | 1942 | 210 | 960 | 210 | 99 | 0 |

Fig. 6E

| IC50  =  1.869 µg/mL |  |
|---|---|
| (THEORETICAL IC50 CALCULATED ABSORBANCE VALUE = 37039) | |
| CONCENTRATIONS USED FOR REGRESSION 3.000   AND   1.000   µg/mL | |
| REGRESSION OUTPUT | |
| CONSTANT | 85072 |
| STD ERR OF Y EST | 6723 |
| R SQUARED | 1 |
| NO. OF OBSERVATIONS | 16 |
| DEGREES OF FREEDOM | 14 |
| X COEFFICENT(S) | -25697 |
| STD ERR OF COEF. | 1681 |

Fig. 6F

CELL LINE: DLD-1 COLON
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   768    ±    118 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 162684 | 18161 | 161917 | 18161 | 0 | 11 |
| DIS.COMP. | 0.003 | 107941 | 77585 | 107174 | 77585 | 34 | 48 |
| | 0.01 | 117770 | 65709 | 117003 | 65709 | 28 | 41 |
| | 0.03 | 117510 | 55001 | 116742 | 55001 | 28 | 34 |
| | 0.1 | 144989 | 38297 | 144222 | 38297 | 11 | 24 |
| | 0.3 | 100932 | 64511 | 100164 | 64511 | 38 | 40 |
| | 1 | 89095 | 58265 | 88327 | 58265 | 45 | 36 |
| | 3 | 54829 | 19219 | 54062 | 19219 | 67 | 12 |
| | 10 | 9397 | 4807 | 8629 | 4807 | 95 | 3 |
| BASE | | 161024 | 20830 | 160256 | 20830 | 1 | 13 |
| DOX | 1 µM | 1322 | 279 | 554 | 279 | 100 | 0 |

Fig. 7B

| IC50 = 1.430 µg/mL |
|---|
| (THEORETICAL IC50 CALCULATED ABSORBANCE VALUE = 80958) |
| CONCENTRATIONS USED FOR REGRESSION 3.000 AND 1.000 µg/mL |
| REGRESSION OUTPUT |
| CONSTANT 105460<br>STD ERR OF Y EST 43383<br>R SQUARED 0<br>NO. OF OBSERVATIONS 16<br>DEGREES OF FREEDOM 14<br><br>X COEFFICENT(S) -17133<br>STD ERR OF COEF. 10846 |

Fig. 7C

CELL LINE: DLD-1 COLON
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   433   ±   168 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 60191 | 22276 | 59758 | 22276 | 0 | 37 |
| DC+B | 0.003 | 42077 | 20759 | 41644 | 20759 | 30 | 35 |
|  | 0.01 | 70053 | 29529 | 69620 | 29529 | 0 | 49 |
|  | 0.03 | 44268 | 20110 | 43835 | 20110 | 27 | 34 |
|  | 0.1 | 41289 | 25848 | 40857 | 25848 | 32 | 43 |
|  | 0.3 | 18399 | 7678 | 17966 | 7678 | 70 | 13 |
|  | 1 | 7224 | 3177 | 6792 | 3177 | 89 | 5 |
|  | 3 | 564 | 129 | 131 | 129 | 100 | 0 |
|  | 10 | 550 | 328 | 117 | 328 | 100 | 1 |
| BASE |  | 103470 | 32460 | 103037 | 32460 | 0 | 54 |
| DOX | 1 µM | 1481 | 248 | 1049 | 248 | 98 | 0 |

Fig. 7E

| |
|---|
| IC50 = 0.196 µg/mL |
| (THEORETICAL IC50 CALCULATED ABSORBANCE VALUE = 29879) |
| CONCENTRATIONS USED FOR REGRESSION 0.300 AND 0.100 µg/mL |
| REGRESSION OUTPUT |
| CONSTANT                52302<br>STD ERR OF Y EST         19067<br>R SQUARED                    1<br>NO. OF OBSERVATIONS         16<br>DEGREES OF FREEDOM          14<br><br>X COEFFICENT(S)         -114452<br>STD ERR OF COEF.          47667 |

Fig. 7F

CELL LINE: OVCAR-3 OVARIAN
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   793   ±   114 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 21419 | 14475 | 20626 | 14475 | 0 | 70 |
| DIS.COMP. | 0.003 | 19835 | 15417 | 19042 | 15417 | 8 | 75 |
| | 0.01 | 18879 | 12780 | 18086 | 12780 | 12 | 62 |
| | 0.03 | 25350 | 8809 | 24557 | 8809 | 0 | 43 |
| | 0.1 | 25419 | 10790 | 24626 | 10790 | 0 | 52 |
| | 0.3 | 23016 | 8915 | 22223 | 8915 | 0 | 43 |
| | 1 | 17291 | 12124 | 16498 | 12124 | 20 | 59 |
| | 3 | 12085 | 5735 | 11292 | 5735 | 45 | 28 |
| | 10 | 1725 | 634 | 932 | 634 | 95 | 3 |
| BASE | | 25258 | 12252 | 24465 | 12252 | 0 | 59 |
| DOX | 1 µM | 1441 | 207 | 648 | 207 | 97 | 1 |

Fig. 8B

| IC50 = 3.662 µg/mL |
|---|
| (THEORETICAL IC50 CALCULATED ABSORBANCE VALUE = 10313) |
| CONCENTRATIONS USED FOR REGRESSION 10.300 AND 3.000 µg/mL |
| REGRESSION OUTPUT<br><br>CONSTANT                15733<br>STD ERR OF Y EST        4080<br>R SQUARED                   1<br>NO. OF OBSERVATIONS    16<br>DEGREES OF FREEDOM    14<br><br>X COEFFICENT(S)         -1480<br>STD ERR OF COEF.         291 |

Fig. 8C

CELL LINE: OVCAR-3 OVARIAN
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND] = 635 ± 156 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 18870 | 7517 | 18235 | 7517 | 0 | 41 |
| DC+B | 0.003 | 16804 | 4167 | 16169 | 4167 | 11 | 23 |
| | 0.01 | 21353 | 6899 | 20718 | 6899 | 0 | 38 |
| | 0.03 | 19334 | 4315 | 18699 | 4315 | 0 | 24 |
| | 0.1 | 16488 | 5282 | 15853 | 5282 | 13 | 29 |
| | 0.3 | 9722 | 2501 | 9087 | 2501 | 50 | 14 |
| | 1 | 1903 | 510 | 1268 | 510 | 93 | 3 |
| | 3 | 422 | 69 | -214 | 69 | 100 | 0 |
| | 10 | 596 | 105 | -39 | 105 | 100 | 1 |
| BASE | | 17687 | 4190 | 17052 | 4190 | 6 | 23 |
| DOX | 1 µM | 1090 | 233 | 455 | 233 | 98 | 1 |

Fig. 8E

| IC50 = 0.299 µg/mL |
|---|
| (THEORETICAL IC50 CALCULATED ABSORBANCE VALUE = 9118) |
| CONCENTRATIONS USED FOR REGRESSION 0.300 AND 0.100 µg/mL |
| REGRESSION OUTPUT<br><br>CONSTANT　　　　　　　　　　19237<br>STD ERR OF Y EST　　　　　　4133<br>R SQUARED　　　　　　　　　　0<br>NO. OF OBSERVATIONS　　　　16<br>DEGREES OF FREEDOM　　　　14<br><br>X COEFFICENT(S)　　　　　　-33834<br>STD ERR OF COEF.　　　　　10332 |

Fig. 8F

CELL LINE: CAKI-1 RENAL
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   870.000   ±   235.511 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 45398 | 5160 | 44528 | 5160 | 0.0 | 11.6 |
| DIS.COMP. | 0.003 | 42038 | 5884 | 41168 | 5884 | 7.5 | 13.2 |
| | 0.01 | 36374 | 14961 | 35504 | 14961 | 20.3 | 33.6 |
| | 0.03 | 38682 | 9289 | 37812 | 9289 | 15.1 | 20.9 |
| | 0.1 | 35966 | 15199 | 35096 | 15199 | 21.2 | 34.1 |
| | 0.3 | 24042 | 7441 | 23172 | 7441 | 48.0 | 16.7 |
| | 1 | 26367 | 7624 | 25497 | 7624 | 42.7 | 17.1 |
| | 3 | 11765 | 7206 | 10895 | 7206 | 75.5 | 16.2 |
| | 10 | 8181 | 919 | 7311 | 919 | 83.6 | 2.1 |
| BASE | | 42572 | 6530 | 41702 | 6530 | 6.3 | 14.7 |
| DOX | 1 µM | 730 | 195 | -140 | 195 | 100.0 | 0.4 |

Fig. 9B

| IC50 = 1.44 µg/mL |
|---|
| (THEORETICAL IC50 CALCULATED ABSORBANCE VALUE = 22263.938) |
| CONCENTRATIONS USED FOR REGRESSION 3.00 AND 1.00 µg/mL |
| REGRESSION OUTPUT |
| CONSTANT                 3.28E+04<br>STD ERR OF Y EST         7.42E+03<br>R SQUARED                5.25E-01<br>  NO. OF OBSERVATIONS         16<br>  DEGREES OF FREEDOM          14<br><br>X COEFFICENT(S)          -7.30E+03<br>STD ERR OF COEF.          1.85E+03 |

Fig. 9C

CELL LINE: CAKI-1 RENAL
CELLS PLATED: 5.0E+03 CELLS/WELL
TREATMENT DAY 1 POST PLATING, CONTINUOUS EXPOSURE

*TERMINATOR + BASE (60 µg/mL)*

( MEDIA + MTS [BACKGROUND]   =   522   ±   198 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | -  | 24112 | 1386 | 23590 | 1386 | 0 | 6 |
| DC+B | 0.003 | 26995 | 4082 | 26473 | 4082 | 0 | 17 |
|  | 0.01 | 24148 | 3290 | 23626 | 3290 | 0 | 14 |
|  | 0.03 | 24409 | 3976 | 23887 | 3976 | 0 | 17 |
|  | 0.1 | 25371 | 5959 | 24849 | 5959 | 0 | 25 |
|  | 0.3 | 18333 | 3081 | 17811 | 3081 | 24 | 13 |
|  | 1 | 13138 | 4040 | 12616 | 4040 | 47 | 17 |
|  | 3 | 1223 | 261 | 701 | 261 | 97 | 1 |
|  | 10 | 757 | 194 | 235 | 194 | 99 | 1 |
| BASE |  | 27013 | 3311 | 26491 | 3311 | 0 | 14 |
| DOX | 1 µM | 513 | 126 | -9 | 126 | 100 | 1 |

Fig. 9E

| IC50 = 1.138 µg/mL |  |
|---|---|
| (THEORETICAL IC50 CALCULATED ABSORBANCE VALUE = 11795) | |
| CONCENTRATIONS USED FOR REGRESSION 3.000 AND 1.000 µg/mL | |
| REGRESSION OUTPUT | |
| CONSTANT | 18573 |
| STD ERR OF Y EST | 2863 |
| R SQUARED | 1 |
| NO. OF OBSERVATIONS | 16 |
| DEGREES OF FREEDOM | 14 |
| X COEFFICENT(S) | -5957 |
| STD ERR OF COEF. | 716 |

Fig. 9F

CELL LINE: LOX IMVI MELANOMA
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   1902        ±        639 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 243895 | 44414 | 241994 | 44414 | 0 | 18 |
| DIS.COMP. | 0.003 | 258286 | 19215 | 256384 | 19215 | 0 | 8 |
| | 0.01 | 254659 | 36627 | 252757 | 36627 | 0 | 15 |
| | 0.03 | 254844 | 47365 | 252942 | 47365 | 0 | 20 |
| | 0.1 | 266290 | 15708 | 264388 | 15708 | 0 | 6 |
| | 0.3 | 260996 | 45040 | 259094 | 45040 | 0 | 19 |
| | 1 | 290330 | 53822 | 288429 | 53822 | 0 | 22 |
| | 3 | 209898 | 39408 | 207996 | 39408 | 14 | 16 |
| | 10 | 46118 | 11089 | 44216 | 11089 | 82 | 5 |
| BASE | | 242585 | 36793 | 240683 | 36793 | 1 | 15 |
| DOX | 1 µM | 2613 | 906 | 711 | 906 | 100 | 0 |

Fig. 10B

| IC50 = 6.718 µg/mL |
|---|
| (THEORETICAL IC50 CALCULATED ABSORBANCE VALUE = 120997) |
| CONCENTRATIONS USED FOR REGRESSION 10.000 AND 3.000 µg/mL |
| REGRESSION OUTPUT<br><br>CONSTANT 278187<br>STD ERR OF Y EST 28948<br>R SQUARED 1<br>NO. OF OBSERVATIONS 16<br>DEGREES OF FREEDOM 14<br><br>X COEFFICENT(S) -23397<br>STD ERR OF COEF. 2068 |

Fig. 10C

CELL LINE: LOX IMVI MELANOMA
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   789   ±   398 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 285056 | 33838 | 213002 | 135019 | 0 | 63 |
| DC+B | 0.003 | 288418 | 15624 | 215524 | 134163 | 0 | 63 |
|  | 0.01 | 268852 | 46465 | 200850 | 130503 | 6 | 61 |
|  | 0.03 | 247485 | 26154 | 184824 | 116676 | 13 | 55 |
|  | 0.1 | 257474 | 29499 | 192316 | 121767 | 10 | 57 |
|  | 0.3 | 190485 | 32458 | 142075 | 92346 | 33 | 43 |
|  | 1 | 34952 | 6888 | 25424 | 17195 | 88 | 8 |
|  | 3 | 1591 | 700 | 404 | 945 | 100 | 0 |
|  | 10 | 1029 | 259 | -17 | 524 | 100 | 0 |
| BASE |  | 306550 | 29632 | 229123 | 144098 | 0 | 68 |
| DOX | 1 µM | 2221 | 293 | 877 | 1058 | 100 | 0 |

Fig. 10E

| IC50 = 0.513 µg/mL |  |
|---|---|
| (THEORETICAL IC50 CALCULATED ABSORBANCE VALUE = 106501) | |
| CONCENTRATIONS USED FOR REGRESSION 1.000 AND 0.300 µg/mL | |
| REGRESSION OUTPUT | |
| CONSTANT | 192068 |
| STD ERR OF Y EST | 66421 |
| R SQUARED | 0 |
| NO. OF OBSERVATIONS | 16 |
| DEGREES OF FREEDOM | 14 |
| X COEFFICENT(S) | -166643 |
| STD ERR OF COEF. | 47443 |

Fig. 10F

CELL LINE: SNB-75 CNS
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   672   ±   302 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 48412 | 19367 | 47739 | 19367 | 0 | 41 |
| DIS.COMP. | 0.003 | 48690 | 12158 | 48018 | 12158 | 0 | 25 |
| | 0.01 | 36743 | 8449 | 36071 | 8449 | 24 | 18 |
| | 0.03 | 43415 | 15428 | 42743 | 15428 | 10 | 32 |
| | 0.1 | 46415 | 12022 | 45743 | 12022 | 4 | 25 |
| | 0.3 | 46134 | 10910 | 45462 | 10910 | 5 | 23 |
| | 1 | 23478 | 12579 | 22806 | 12579 | 52 | 26 |
| | 3 | 7921 | 1545 | 7249 | 1545 | 85 | 3 |
| | 10 | 809 | 123 | 137 | 123 | 100 | 0 |
| BASE | | 58868 | 20011 | 58196 | 20011 | 0 | 42 |
| DOX | 1 µM | 1288 | 302 | 615 | 302 | 99 | 1 |

Fig. 11B

| IC50 = 0.895 µg/mL |
|---|
| (THEORETICAL IC50 CALCULATED ABSORBANCE VALUE = 23870) |
| CONCENTRATIONS USED FOR REGRESSION 1.000 AND 0.300 µg/mL |
| REGRESSION OUTPUT <br><br> CONSTANT 56348 <br> STD ERR OF Y EST 12549 <br> R SQUARED 1 <br> NO. OF OBSERVATIONS 16 <br> DEGREES OF FREEDOM 14 <br><br> X COEFFICENT(S) -36287 <br> STD ERR OF COEF. 8964 |

Fig. 11C

CELL LINE: SNB-75 CNS
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   591   ±   131 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 76631 | 13201 | 76040 | 13201 | 0 | 17 |
| DC+B | 0.003 | 84352 | 17247 | 83761 | 17247 | 0 | 23 |
|  | 0.01 | 76032 | 9649 | 75441 | 9649 | 1 | 13 |
|  | 0.03 | 43393 | 18208 | 42802 | 18208 | 44 | 24 |
|  | 0.1 | 38209 | 12752 | 37618 | 12752 | 51 | 17 |
|  | 0.3 | 19327 | 30859 | 18736 | 30859 | 75 | 41 |
|  | 1 | 793 | 204 | 202 | 204 | 100 | 0 |
|  | 3 | 257 | 73 | -334 | 73 | 100 | 0 |
|  | 10 | 452 | 119 | -139 | 119 | 100 | 0 |
| BASE |  | 59124 | 15254 | 58533 | 15254 | 23 | 20 |
| DOX | 1 µM | 1006 | 169 | 415 | 169 | 99 | 0 |

Fig. 11E

| IC50 = 0.095 µg/mL |  |
|---|---|
| (THEORETICAL IC50 CALCULATED ABSORBANCE VALUE = 38020) | |
| CONCENTRATIONS USED FOR REGRESSION 0.100 AND 0.030 µg/mL | |
| REGRESSION OUTPUT | |
| CONSTANT | 45023 |
| STD ERR OF Y EST | 15719 |
| R SQUARED | 0 |
| NO. OF OBSERVATIONS | 16 |
| DEGREES OF FREEDOM | 14 |
| X COEFFICENT(S) | -74055 |
| STD ERR OF COEF. | 112276 |

Fig. 11F

TOXICITY VALUES (Tritiated Thymidine Incorporation)

| CONC. (µg/mL) | 0 | 0.32 | 1 | 3.2 | 10 | 32 | 100 |
|---|---|---|---|---|---|---|---|
| SAMPLE 1 | 187251 | 238620 | 247533 | 147690 | 4875 | 7905 | 100 |
| SAMPLE 2 | 215975 | 249276 | 208674 | 168000 | 6001 | 4214 | 44 |
| SAMPLE 3 | 251706 | 243978 | 228104 | 157458 | 5483 | 6214 | 67 |
| MEAN | 218311 | 243958 | 228104 | 157716 | 5453 | 6111 | 70 |
| STD. DEV. | 14.8 | 2.4 | 8.9 | 4.7 | 0.3 | 0.8 | 0.0 |
| MEAN % INH. | 0 | 0 | 0 | 27.8 | 97.5 | 97.2 | 100 |

Fig. 12B

| IC50 (µg/mL) = 5.87 |
|---|

Fig. 12C

TOXICITY VALUES (Tritiated Thymidine Incorporation)

| CONC. (µg/mL) | 1000 | 320 | 100 | 32 | 10 | 3.2 | 1 | 0.32 | 0.1 | 0.032 | 0.01 | 0.0032 | 0 |
|---|---|---|---|---|---|---|---|---|---|---|---|---|---|
| SAMPLE 1 | 44 | 52 | 36 | 40 | 540 | 336208 | 468933 | 470659 | 484041 | 482276 | 478360 | 520558 | 522374 |
| SAMPLE 2 | 264 | 480 | 1281 | 184 | 1974 | 361141 | 451751 | 479896 | 490045 | 485336 | 476935 | 521223 | 509600 |
| MEAN | 154 | 265 | 659 | 12 | 1257 | 348675 | 460342 | 475278 | 487043 | 483806 | 477148 | 520891 | 515987 |
| MEAN % INH. | 100 | 99.9 | 99.9 | 99.9 | 99.9 | 32.4 | 10.8 | 7.9 | 5.6 | 6.2 | 7.5 | 0 | 0 |

| CELL LINE | IC50 (µg/mL) DISCLOSED COMPOSITION ONLY | IC50 (µg/mL) DISCLOSED COMP. + BASE (60 µg/mL) |
|---|---|---|
| NCI-H23 LUNG | >10 | 1.718 |
| NCI-H460 LUNG | 1.183 | 0.131 |
| MCF7 MAMMARY | 2.213 | 0.972 |
| ZR-75-1 MAMMARY | >10 | 2.031 |
| PC-3 PROSTATE | >10 | 1.869 |
| DLD-1 COLON | 1.430 | 0.196 |
| OVCAR-3 OVARIAN | 3.662 | 0.299 |
| CAKI-1 RENAL | 1.440 | 1.138 |
| LOX IMVI MELANOMA | 6.718 | 0.513 |
| SNB-75 CNS | 0.895 | 0.095 |
| CEM-SS LEUKEMIC (#1) | 5.87 | - |
| CEM-SS LEUKEMIC (#2) | 4.975 | - |

Fig. 14

ELEMENTAL IRON DERIVED FROM IRON DEXTRAN IN MONKEY PLASMA

| CONTROL NUMBER | ID/DAY | TIME | ANALYTE/LIMIT | VALUES | UNITS |
|---|---|---|---|---|---|
| 413223 | AD51,DAY1 | PRE | IRON | 0.0 | MG/ML |
| 413223 | AD51,DAY1 | PRE | RL | 0.1 | |
| 413224 | AN3B,DAY1 | PRE | IRON | 0.0 | MG/ML |
| 413224 | AN3B,DAY1 | PRE | RL | 0.1 | |
| 413225 | AD51,DAY1 | POST | IRON | 6.8 | MG/ML |
| 413225 | AD51,DAY1 | POST | RL | 0.1 | |
| 413226 | AH3B,DAY1 | POST | IRON | 11.2 | MG/ML |
| 413226 | AH3B,DAY1 | POST | RL | 0.1 | |
| 413227 | AD51,DAY1 | 10 MIN | IRON | 7.1 | MG/ML |
| 413227 | AD51,DAY1 | 10 MIN | RL | 0.1 | |
| 413228 | AH3B,DAY1 | 10 MIN | IRON | 11.8 | MG/ML |
| 413228 | AH3B,DAY1 | 10 MIN | RL | 0.1 | |
| 413229 | AD51,DAY2 | 24 HR | IRON | 4.7 | MG/ML |
| 413229 | AD51,DAY2 | 24 HR | RL | 0.1 | |
| 413230 | AH3B,DAY2 | 24 HR | IRON | 7.0 | MG/ML |
| 413230 | AH3B,DAY2 | 24 HR | RL | 0.1 | |
| 413231 | AD51,DAY3 | 48 HR | IRON | 3.2 | MG/ML |
| 413231 | AD51,DAY3 | 48 HR | RL | 0.1 | |
| 413232 | AH3B,DAY3 | 48 HR | IRON | 6.4 | MG/ML |
| 413232 | AH3B,DAY3 | 48 HR | RL | 0.1 | |
| 413233 | AD51,DAY4 | 72 HR | IRON | 1.6 | MG/ML |
| 413233 | AD51,DAY4 | 72 HR | RL | 0.1 | |
| 413234 | AH3B,DAY4 | 72 HR | IRON | 5.5 | MG/ML |
| 413234 | AH3B,DAY4 | 72 HR | RL | 0.1 | |

Fig. 15A

ELEMENTAL IRON DERIVED FROM IRON DEXTRAN IN MONKEY PLASMA (continued)

| CONTROL NUMBER | ID/DAY | TIME | ANALYTE/ LIMIT | VALUES | UNITS |
|---|---|---|---|---|---|
| 413235 | AD51,DAY5 | 96 HR | IRON | 0.7 | MG/ML |
| 413235 | AD51,DAY5 | 96 HR | RL | 0.1 | |
| 413236 | AH3B,DAY5 | 96 HR | IRON | 3.9 | MG/ML |
| 413236 | AH3B,DAY5 | 96 HR | RL | 0.1 | |
| 413237 | AD51,DAY6 | 120 HR | IRON | 0.1 | MG/ML |
| 413237 | AD51,DAY6 | 120 HR | RL | 0.1 | |
| 413238 | AH3B,DAY6 | 120 HR | IRON | 2.6 | MG/ML |
| 413238 | AH3B,DAY6 | 120 HR | RL | 0.1 | |
| 413239 | AD51,DAY7 | N/A | IRON | 0.0 | MG/ML |
| 413239 | AD51,DAY7 | N/A | RL | 0.1 | |
| 413240 | AH3B,DAY7 | N/A | IRON | 1.4 | MG/ML |
| 413240 | AH3B,DAY7 | N/A | RL | 0.1 | |
| 413241 | AD51,DAY8 | N/A | IRON | 0.0 | MG/ML |
| 413241 | AD51,DAY8 | N/A | RL | 0.1 | |
| 413242 | AH3B,DAY8 | N/A | IRON | 0.6 | MG/ML |
| 413242 | AH3B,DAY8 | N/A | RL | 0.1 | |
| 413243 | AH3B,DAY9 | N/A | IRON | 0.0 | MG/ML |
| 413243 | AH3B,DAY9 | N/A | RL | 0.1 | |
| 413244 | AD51,DAY9 | N/A | IRON | 0.0 | MG/ML |
| 413244 | AD51,DAY9 | N/A | RL | 0.1 | |
| 413245 | AH3B,DAY10 | N/A | IRON | 0.0 | MG/ML |
| 413245 | AH3B,DAY10 | N/A | RL | 0.1 | |
| 413246 | AD51,DAY10 | N/A | IRON | 0.0 | MG/ML |
| 413246 | AD51,DAY10 | N/A | RL | 0.1 | |

Fig. 15B

ELEMENTAL IRON DERIVED FROM IRON DEXTRAN IN MONKEY PLASMA (concluded)

| CONTROL NUMBER | ID/DAY | TIME | ANALYTE/ LIMIT | VALUES | UNITS |
|---|---|---|---|---|---|
| 413247 | AD51,DAY15 | N/A | IRON | 0.0 | MG/ML |
| 413247 | AD51,DAY15 | N/A | RL | 0.1 | |
| 413248 | AH38,DAY38 | N/A | IRON | 0.0 | MG/ML |
| 413248 | AH3B,DAY38 | N/A | RL | 0.1 | |
| 413249 | AD51,DAY22 | N/A | IRON | 0.0 | MG/ML |
| 413249 | AD51,DAY22 | N/A | RL | 0.1 | |
| 413250 | AH3B,DAY22 | N/A | IRON | 0.0 | MG/ML |
| 413250 | AH3B,DAY22 | N/A | RL | 0.1 | |

KEY

| | | |
|---|---|---|
| AD51 | = | Monkey administered 400mg equivalent of elemental iron per kg of body weight |
| AH3B | = | Monkey administered 500mg equivalent of elemental iron per kg of body weight |
| RL | = | Reporting Limit |
| TIME | = | When samples were taken after intravenous infusion |
| PRE | = | pretreatment levels |
| POST | = | directly after infusion |
| 10 MIN | = | 10 minutes after infusion |

Fig. 15C

*SINGLE DOSE ADMINISTRATION*

ELEMENTAL IRON DERIVED FROM IRON DEXTRAN IN MONKEY PLASMA

| GROUP NUMBER | NUMBER OF ANIMALS | TREATMENT ADMINISTRATION | | | | OBSERVATION PERIOD |
| --- | --- | --- | --- | --- | --- | --- |
| | | SUBSTANCE | DOSE LEVEL | ROUTE | DOSING REGIMEN | |
| 1 | 1 | IRON DEXTRAN COMPLEX | 400 MG ELEMENTAL IRON/ KG | IV | DAY 1 3 HOUR INFUSION 1 MIN/ML | 10 DAYS |
| 2 | 1 | | 500 MG ELEMENTAL IRON/ KG | | | |

Fig. 16

|   | 1 | 2 | 3 | 4 | 5 | 6 |
|---|---|---|---|---|---|---|
| A |   |   |   |   |   | Media Control (Blank) |
| B | Media Control (Blank) | Cell Control | Cell Control | Cell Control | Cell Control | Cell Control |
| C | Media Control (Blank) |   | Drug 1 Toxicity Control 0.2 µM | Drug 1 Toxicity Control 0.2 µM | Drug 1 Toxicity Control 0.2 µM | Drug 1 Toxicity Control 0.2 µM |
| D | Media Control (Blank) |   | Drug 1 Toxicity Control 0.63 µM | Drug 1 Toxicity Control 0.63 µM | Drug 1 Toxicity Control 0.63 µM | Drug 1 Toxicity Control 0.63 µM |
| E | Media Control (Blank) |   | Drug 1 Toxicity Control 2 µM | Drug 1 Toxicity Control 2 µM | Drug 1 Toxicity Control 2 µM | Drug 1 Toxicity Control 2 µM |
| F | Media Control (Blank) |   | Drug 1 Toxicity Control 6.3 µM | Drug 1 Toxicity Control 6.3 µM | Drug 1 Toxicity Control 6.3 µM | Drug 1 Toxicity Control 6.3 µM |
| G | Media Control (Blank) |   | Drug 1 Toxicity Control 20 µM | Drug 1 Toxicity Control 20 µM | Drug 1 Toxicity Control 20 µM | Drug 1 Toxicity Control 20 µM |
| H |   |   |   |   |   | Media Control (Blank) |

STANDARDIZED 5-2 CELL LINE ANTIVIRAL EVALUATION 96-WELL PLATE FORMAT FOR THE ASSESSMENT OF CELL NUMBERS.

Fig. 17A

|   | 7 | 8 | 9 | 10 | 11 | 12 |
|---|---|---|---|---|---|---|
| A | Media Control (Blank) | | | | | |
| B | Cell Control | Cell Control | Cell Control | Cell Control | Cell Control | Media Control (Blank) |
| C | Drug 2 Toxicity Control 0.2 µM | Drug 2 Toxicity Control 0.2 µM | Drug 2 Toxicity Control 0.2 µM | Drug 2 Toxicity Control 0.2 µM | | Media Control (Blank) |
| D | Drug 2 Toxicity Control 0.63 µM | Drug 2 Toxicity Control 0.63 µM | Drug 2 Toxicity Control 0.63 µM | Drug 2 Toxicity Control 0.63 µM | | Media Control (Blank) |
| E | Drug 2 Toxicity Control 2 µM | Drug 2 Toxicity Control 2 µM | Drug 2 Toxicity Control 2 µM | Drug 2 Toxicity Control 2 µM | | Media Control (Blank) |
| F | Drug 2 Toxicity Control 6.3 µM | Drug 2 Toxicity Control 6.3 µM | Drug 2 Toxicity Control 6.3 µM | Drug 2 Toxicity Control 6.3 µM | | Media Control (Blank) |
| G | Drug 2 Toxicity Control 20 µM | Drug 2 Toxicity Control 20µM | Drug 2 Toxicity Control 20 µM | Drug 2 Toxicity Control 20 µM | | Media Control (Blank) |
| H | Media Control (Blank) | | | | | |

STANDARDIZED 5-2 CELL LINE ANTIVIRAL EVALUATION 96-WELL PLATE FORMAT FOR THE ASSESSMENT OF CELL NUMBERS.

Fig. 17B

|   | 1 | 2 | 3 | 4 | 5 | 6 |
|---|---|---|---|---|---|---|
| A |   |   |   |   |   |   |
| B |   |   |   |   |   |   |
| C | Media Control (Blank) | Virus Control | Drug 1 Antiviral Efficacy 0.2 µM | Drug 1 Antiviral Efficacy 0.2 µM | Drug 1 Antiviral Efficacy 0.2 µM | Drug 1 Antiviral Efficacy 0.2 µM |
| D | Media Control (Blank) | Virus Control | Drug 1 Antiviral Efficacy 0.63 µM | Drug 1 Antiviral Efficacy 0.63 µM | Drug 1 Antiviral Efficacy 0.63 µM | Drug 1 Antiviral Efficacy 0.63 µM |
| E | Media Control (Blank) | Virus Control | Drug 1 Antiviral Efficacy 2 µM | Drug 1 Antiviral Efficacy 2 µM | Drug 1 Antiviral Efficacy 2 µM | Drug 1 Antiviral Efficacy 2 µM |
| F | Media Control (Blank) | Virus Control | Drug 1 Antiviral Efficacy 6.3 µM | Drug 1 Antiviral Efficacy 6.3 µM | Drug 1 Antiviral Efficacy 6.3 µM | Drug 1 Antiviral Efficacy 6.3 µM |
| G | Media Control (Blank) | Virus Control | Drug 1 Antiviral Efficacy 20 µM | Drug 1 Antiviral Efficacy 20 µM | Drug 1 Antiviral Efficacy 20 µM | Drug 1 Antiviral Efficacy 20 µM |
| H |   |   |   |   |   |   |

STANDARDIZED 5-2 CELL LINE ANTIVIRAL EVALUATION 96-WELL PLATE FORMAT FOR THE DETERMINATION OF ANTIVIRAL ACTIVITY.

Fig. 18A

|   | 7 | 8 | 9 | 10 | 11 | 12 |
|---|---|---|---|---|---|---|
| A |   |   |   |   |   |   |
| B |   |   |   |   |   |   |
| C | Drug 2 Antiviral Efficacy 0.2 µM | Drug 2 Antiviral Efficacy 0.2 µM | Drug 2 Antiviral Efficacy 0.2 µM | Drug 2 Antiviral Efficacy 0.2 µM | Virus Control | Media Control (Blank) |
| D | Drug 2 Antiviral Efficacy 0.63 µM | Drug 2 Antiviral Efficacy 0.63 µM | Drug 2 Antiviral Efficacy 0.63 µM | Drug 2 Antiviral Efficacy 0.63 µM | Virus Control | Media Control (Blank) |
| E | Drug 2 Antiviral Efficacy 2 µM | Drug 2 Antiviral Efficacy 2 µM | Drug 2 Antiviral Efficacy 2 µM | Drug 2 Antiviral Efficacy 2 µM | Virus Control | Media Control (Blank) |
| F | Drug 2 Antiviral Efficacy 6.3 µM | Drug 2 Antiviral Efficacy 6.3 µM | Drug 2 Antiviral Efficacy 6.3 µM | Drug 2 Antiviral Efficacy 6.3 µM | Virus Control | Media Control (Blank) |
| G | Drug 2 Antiviral Efficacy 20 µM | Drug 2 Antiviral Efficacy 20 µM | Drug 2 Antiviral Efficacy 20 µM | Drug 2 Antiviral Efficacy 20 µM | Virus Control | Media Control (Blank) |
| H |   |   |   |   |   |   |

STANDARDIZED 5-2 CELL LINE ANTIVIRAL EVALUATION 96-WELL PLATE FORMAT FOR THE DETERMINATION OF ANTIVIRAL ACTIVITY.

Fig. 18B

PLATE: 2  DRUG: Composition #4

HCV IN VITRO ANTIVIRAL SCREEN
LUCIFERASE-BASED ANTIVIRAL EVALUATION

Cell numbers

| | 1 | 2 | 3 | 4 | 5 | 6 | 7 | 8 | 9 | 10 | 11 | 12 |
|---|---|---|---|---|---|---|---|---|---|---|---|---|
| A | 3.3E+06 | 3.4E+06 | 3.4E+06 | 3.5E+06 | 2.8E+06 | 3.4E+06 | 3.6E+06 | | | | | |
| B | 3.6E+06 | 7.0E+06 | 6.5E+06 | 6.8E+06 | 6.3E+06 | 6.0E+06 | 6.3E+06 | 6.2E+06 | 6.7E+06 | 5.5E+06 | 6.7E+06 | 3.6E+06 |
| C | 3.5E+06 | | 5.8E+06 | 6.0E+06 | 5.1E+06 | 5.5E+06 | | | | | | 3.5E+06 |
| D | 3.5E+06 | | 5.8E+06 | 5.5E+06 | 5.4E+06 | 5.5E+06 | | | | | | 3.6E+06 |
| E | 3.4E+06 | | 5.2E+06 | 5.3E+06 | 5.2E+06 | 5.1E+06 | | | | | | 3.5E+06 |
| F | 3.5E+06 | | 1.8E+06 | 3.9E+06 | 3.6E+06 | 3.5E+06 | | | | | | 3.6E+06 |
| G | 3.6E+06 | | 3.2E+06 | 3.2E+06 | 3.0E+06 | 3.1E+06 | | | | | | 3.6E+06 |
| H | 3.1E+06 | 3.2E+06 | 3.4E+06 | 3.2E+06 | 3.1E+06 | 3.4E+06 | 3.6E+06 | | | | | |

BOLD – highest drug conc          values shown are optical densities

Fig. 19A

LUCIFERASE

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C |   | 0.03680 | 0.02560 | 0.01720 | 0.01850 | 0.01630 |   |   |   |    | 0.03720 |    |
| D |   | 0.03380 | 0.01990 | 0.01190 | 0.00510 | 0.00890 |   |   |   |    | 0.03320 |    |
| E |   | 0.03440 | 0.01090 | 0.00570 | 0.00660 | 0.00670 |   |   |   |    | 0.03150 |    |
| F |   | 0.03010 | 0.00060 | 0.00040 | 0.00060 | 0.00040 |   |   |   |    | 0.02570 |    |
| G |   | 0.02660 | 0.00040 | 0.00020 | 0.00040 | 0.00030 |   |   |   |    | 0.02770 |    |
| H |   |   |   |   |   |   |   |   |   |    |    |    |

LUMINSENCE

VIRUS CONTROL = 0.0317
CV VIRUS CONTROL = 12.9%
CELL CONTROL = 2.9E+06
CV CELL CONTROL = 15.1%

BOLD – HIGHEST DRUG CONC    VALUES SHOWN ARE LUCIFERASE

VIRUS    HCV RNA REPLICONS    PROJECT #  --        SPONSOR    SUPERFOX
STRAIN   CON-1                PASSAGE    27        TEST DATE  9/19/2003
CELLS    HUH-LUC/NEO ET       OPERATOR   JW        DATE READ  9/22/2003

| PARAMETER | 50% | 90% |
|---|---|---|
| TC (µg/ml) | 6.5216 | 13.245 |
| IC (µg/ml) | 0.84 | --- |
| TI (THERAPEUTIC INDEX) | 7.764 | --- |

Fig. 19B

| VALUES OF COLUMNS | ROW ON PLATE | CONC. (µg/ml) | ANTIVIRAL TEST VALUES ||| CYTOTOXICITY VALUES |||
|---|---|---|---|---|---|---|---|---|
| | | | MEAN LUC | SD LUC | % CONTROL LUC | MEAN O.D. | SD O.D. | % CONTROL VIABILITY |
| 1 THROUGH 5 (LEFT SIDE OF PLATE) | | 0 | 3.170E-02 | 4.094E-03 | 100% | 2.9E+05 | 4.09E-03 | 100% |
| | C | 0.50 | 1.940E-02 | 4.231E-03 | 61% | 2.6E+05 | 3.85E+05 | 92% |
| | D | 1.58 | 1.145E-02 | 5.283E-03 | 35% | 2.2E+05 | 1.68E+05 | 75% |
| | E | 5.00 | 7.475E-03 | 2.327E-03 | 24% | 1.8E+06 | 8.33E+04 | 55% |
| | F | 15.81 | 5.000E-04 | 1.555E-04 | 2% | -9.1E+04 | 9.60E+05 | 0% |
| | HIGH G | 50.00 | 3.250E-04 | 9.574E-05 | 1% | -5.4E+04 | 9.62E+04 | 0% |

Fig. 19C

HCV RNA REPLICON
LUCIFERASE-BASED ANTIVIRAL EVALUATION

CELL NUMBERS

| | 1 | 2 | 3 | 4 | 5 | 6 | 7 | 8 | 9 | 10 |
|---|---|---|---|---|---|---|---|---|---|---|
| A | | | | | 3.4E+06 | 3.6E+06 | 3.3E+06 | 3.2E+06 | 3.3E+06 | 3.4E+06 |
| B | 3.6E+06 | 7.0E+06 | 6.5E+06 | 6.8E+06 | 6.3E+06 | 6.0E+06 | 6.2E+06 | 6.7E+06 | 6.7E+06 | 3.6E+06 |
| C | 3.5E+06 | | | | | 5.2E+06 | 5.5E+06 | 5.5E+06 | 5.1E+06 | 3.5E+06 |
| D | 3.5E+06 | | | | | 5.1E+06 | 5.5E+06 | 5.1E+06 | 5.3E+06 | 3.6E+06 |
| E | 3.4E+06 | | | | | 5.0E+06 | 4.9E+06 | 5.0E+06 | 5.0E+06 | 3.5E+06 |
| F | 3.5E+06 | | | | | 3.7E+06 | 3.6E+06 | 3.6E+06 | 6.5E+06 | 3.6E+06 |
| G | 3.6E+06 | | | | | 2.2E+06 | 3.2E+06 | 3.2E+06 | 3.3E+06 | 3.6E+06 |
| H | 3.4E+06 | | | | 3.6E+06 | 3.2E+06 | 3.3E+06 | 3.8E+06 | 3.1E+06 | 3.5E+06 |

11
12

BOLD – HIGHEST DRUG CONC    VALUES SHOWN ARE OPTICAL DENSITIES

Fig. 20A

LUCIFERASE

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C | 0.0368 |   |   |   |   |   | 0.0187 | 0.0197 | 0.0212 | 0.0189 | 0.0372 |   |
| D | 0.0338 |   |   |   |   |   | 0.0080 | 0.0079 | 0.0084 | 0.0143 | 0.0332 |   |
| E | 0.0344 |   |   |   |   |   | 0.0075 | 0.0054 | 0.0105 | 0.0120 | 0.0315 |   |
| F | 0.0301 |   |   |   |   |   | 0.0005 | 0.0005 | 0.0007 | 0.0006 | 0.0257 |   |
| G | 0.0266 |   |   |   |   |   | 0.0004 | 0.0003 | 0.0007 | 0.0006 | 0.0277 |   |
| H |   |   |   |   |   |   |   |   |   |    |    |    |

BOLD – HIGHEST DRUG CONC    VALUES SHOWN ARE LUCIFERASE LUMINSENCE

VIRUS CONTROL = 0.0317   VIRUS HCV RNA REPLICONS   PROJECT 27   SPONSOR SUPERFOX
CV VIRUS CONTROL = 12.9%   STRAIN CON-1   PASSAGE   TEST DATE 9/19/2003
CELL CONTROL = 2.9E+05   CELLS HUH-LUC/NEO ET   OPERATOR JW   DATE READ 9/22/2003
CV CELL CONTROL = 15.1%

| PARAMETER | 50% | 90% |
|---|---|---|
| TC (μg/ml) | 6.2333 | 19.156 |
| IC (μg/ml) | 0.77 | ---- |
| TI (THERAPEUTIC INDEX) | 8.095 | ---- |

Fig. 20B

| VALUES OF COLUMNS | ROW ON PLATE | CONC. (µg/ml) | ANTIVIRAL TEST VALUES | | | CYTOTOXICITY VALUES | | |
|---|---|---|---|---|---|---|---|---|
| | | | MEAN LUC | SD LUC | % CONTROL LUC | MEAN O.D. | SD O.D. | % CONTROL VIABILITY |
| 7 through 12 (right side of plate) | C | 0 | 3.17E-02 | 4.09E-03 | 100% | 2.9E+06 | 4.31E+05 | 100% |
| | D | 0.50 | 1.95E-02 | 1.14E-03 | 62% | 1.8E+06 | 2.17E+05 | 64% |
| | E | 1.58 | 9.65E-03 | 3.11E-03 | 30% | 2.0E+05 | 2.04E+05 | 70% |
| | F | 5.00 | 8.85E-03 | 2.95E-03 | 28% | 1.7E+05 | 4.81E+04 | 59% |
| | | 15.81 | 5.75E-04 | 9.57E-05 | 2% | 3.5E+05 | 1.08E+05 | 12% |
| | high G | 50.00 | 5.00E-04 | 1.83E-04 | 2% | -2.5E+05 | 5.11E+05 | 0% |

Fig. 20C

PLATE: 2    HCV IN VITRO ANTIVIRAL SCREEN    DRUG: IFNa
LUCIFERASE-BASED ANTIVIRAL EVALUATION

CELL NUMBERS

| | 1 | 2 | 3 | 4 | 5 | 6 | 7 | 8 | 9 | 10 | 11 | 12 |
|---|---|---|---|---|---|---|---|---|---|---|---|---|
| A | 3.6E+06 | 3.4E+06 | 3.4E+06 | 3.5E+06 | 3.5E+06 | 3.4E+06 | 3.6E+06 | | | | | |
| B | 3.6E+06 | 7.8E+06 | 7.5E+06 | 6.8E+06 | 7.1E+06 | 7.2E+06 | 7.1E+06 | 6.7E+06 | 6.7E+06 | 7.2E+06 | 7.3E+06 | 3.6E+06 |
| C | 3.6E+06 | | 6.8E+06 | 6.9E+06 | 6.8E+06 | 6.7E+06 | | | | | | 3.6E+06 |
| D | 3.6E+06 | | 6.6E+06 | 6.9E+06 | 6.7E+06 | 6.1E+06 | | | | | | 3.6E+06 |
| E | 3.6E+06 | | 7.1E+06 | 6.4E+06 | 6.5E+06 | 6.7E+06 | | | | | | 3.6E+06 |
| F | 3.7E+06 | | 8.2E+06 | 5.8E+06 | 6.4E+06 | 6.5E+06 | | | | | | 3.6E+06 |
| G | 3.6E+06 | | 5.2E+06 | 8.2E+06 | 5.3E+06 | 6.8E+06 | | | | | | 3.6E+06 |
| H | 3.6E+06 | 3.5E+06 | 3.4E+06 | 3.5E+06 | 3.4E+06 | 3.5E+06 | 3.6E+06 | | | | | |

BOLD – HIGHEST DRUG CONC    VALUES SHOWN ARE OPTICAL DENSITIES

Fig. 21A

LUCIFERASE

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | | 0.02000 | 0.01880 | 0.01680 | 0.01790 | 0.01610 | | | | | 0.02840 | |
| D | | 0.02370 | 0.01180 | 0.00960 | 0.00940 | 0.00820 | | | | | 0.02930 | |
| E | | 0.02830 | 0.00510 | 0.00200 | 0.00230 | 0.00270 | | | | | 0.03130 | |
| F | | 0.02220 | 0.00130 | 0.00080 | 0.00100 | 0.00100 | | | | | 0.02590 | |
| G | | 0.02570 | 0.00060 | 0.00030 | 0.00050 | 0.00050 | | | | | 0.02740 | |
| H | | | | | | | | | | | | |

VIRUS CONTROL = 0.0262
CV VIRUS CONTROL = 13.2%
CELL CONTROL = 3.6E+06
CV CELL CONTROL = 9.7%

BOLD – HIGHEST DRUG CONC    VALUES SHOWN ARE LUCIFERASE LUMINSENCE

VIRUS    HCV RNA REPLICONS    PROJECT        SPONSOR: SUPERFOX
STRAIN   CON-1                PASSAGE   27   TEST DATE  9/19/2003
CELLS    HUH-LUC/NEO ET       OPERATOR  JW   DATE READ  9/22/2003

| PARAMETER | 50% | 90% |
|---|---|---|
| TC (μg/ml) | >5.000 | >5.000 |
| IC (μg/ml) | 0.10 | 0.63 |
| TI (THERAPEUTIC INDEX) | 50.00 | 7.937 |

Fig. 21B

| VALUES OF COLUMNS | ROW ON PLATE | CONC. (µg/ml) | ANTIVIRAL TEST VALUES ||||  CYTOTOXICITY VALUES |||
|---|---|---|---|---|---|---|---|---|
| | | | MEAN LUC | SD LUC | % CONTROL LUC | MEAN O.D. | SD O.D. | % CONTROL VIABILITY |
| 1 THROUGH 5 (LEFT SIDE OF PLATE) | C | 0 | 2.622E-02 | 3.453E-03 | 100% | 3.6E+06 | 3.45E-03 | 100% |
| | D | 0.05 | 1.740E-02 | 1.192E-03 | 66% | 3.3E+06 | 9.46E+04 | 93% |
| | E | 0.15 | 9.750E-03 | 1.500E-03 | 37% | 3.1E+06 | 3.15E+05 | 87% |
| | F | 0.50 | 3.025E-03 | 1.413E-03 | 12% | 3.3E+05 | 3.24E+05 | 93% |
| | G | 1.58 | 1.025E-03 | 2.062E-04 | 4% | 3.3E+06 | 1.01E+06 | 91% |
| | HIGH G | 5.00 | 4.750E-04 | 1.258E-04 | 2% | 2.8E+05 | 1.44E+06 | 77% |

Fig. 21C

PLATE:     HCV RNA REPLICON     DRUG: RBV
LUCIFERASE-BASED ANTIVIRAL EVALUATION

CELL NUMBERS

| | 1 | 2 | 3 | 4 | 5 | 6 | 7 | 8 | 9 | 10 | 11 | 12 |
|---|---|---|---|---|---|---|---|---|---|---|---|---|
| A | | | | | | 3.4E+06 | 3.6E+06 | 3.6E+06 | 3.6E+06 | 3.3E+06 | 3.3E+06 | 3.4E+06 |
| B | 3.6E+06 | 7.8E+06 | 7.5E+06 | 6.8E+06 | 7.1E+06 | 7.2E+06 | 7.1E+06 | 6.7E+06 | 6.7E+06 | 7.2E+06 | 7.3E+06 | 3.6E+06 |
| C | 3.6E+06 | | | | | | 6.0E+06 | 6.2E+06 | 6.2E+06 | 6.2E+06 | | 3.6E+06 |
| D | 3.6E+06 | | | | | | 4.7E+06 | 4.8E+06 | 5.6E+06 | 5.4E+06 | | 3.6E+06 |
| E | 3.6E+06 | | | | | | 4.4E+06 | 4.1E+06 | 4.3E+06 | 4.4E+06 | | 3.6E+06 |
| F | 3.7E+06 | | | | | | 4.2E+06 | 4.0E+06 | 3.8E+06 | 4.1E+06 | | 3.6E+06 |
| G | 3.6E+06 | | | | | | 2.8E+06 | 2.8E+06 | 3.9E+06 | 4.7E+06 | | 3.6E+06 |
| H | | | | | | 3.5E+06 | 3.6E+06 | 3.5E+06 | | 3.4E+06 | 3.6E+06 | 3.5+06 |

BOLD – HIGHEST DRUG CONC     VALUES SHOWN ARE OPTICAL DENSITIES

Fig. 22A

LUCIFERASE

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | 0.0200 | | | | | | 0.0142 | 0.0161 | 0.0160 | 0.0157 | 0.0284 | |
| D | 0.0237 | | | | | | 0.0063 | 0.0067 | 0.0055 | 0.0109 | 0.0293 | |
| E | 0.0283 | | | | | | 0.0012 | 0.0008 | 0.0012 | 0.0014 | 0.0313 | |
| F | 0.0222 | | | | | | 0.0005 | 0.0005 | 0.0004 | 0.0009 | 0.0259 | |
| G | 0.0257 | | | | | | 0.0003 | 0.0005 | 0.0006 | 0.0009 | 0.0274 | |
| H | | | | | | | | | | | | |

VIRUS CONTROL = 0.0262
CV VIRUS CONTROL = 13.2%
CELL CONTROL = 3.6E+06
CV CELL CONTROL = 9.7%

BOLD – HIGHEST DRUG CONC      VALUES SHOWN ARE LUCIFERASE LUMINSENCE

VIRUS STRAIN: HCV RNA REPLICONS CON-1
CELLS: HUH-LUC/NEO ET
PROJECT SPONSOR
PASSAGE 27
OPERATOR JW
SUPERFOX
TEST DATE 9/19/2003
DATE READ 9/22/2003

| PARAMETER | 50% | 90% |
|---|---|---|
| TC (µg/ml) | 5.3654 | 82.493 |
| IC (µg/ml) | --- | --- |
| TI (THERAPEUTIC INDEX) | --- | --- |

Fig. 22B

| VALUES OF COLUMNS | ROW ON PLATE | CONC. (µg/ml) | ANTIVIRAL TEST VALUES ||| CYTOTOXICITY VALUES |||
|---|---|---|---|---|---|---|---|---|
| | | | MEAN LUC | SD LUC | % CONTROL LUC | MEAN O.D. | SD O.D. | % CONTROL VIABILITY |
| 7 THROUGH 12 (RIGHT SIDE OF PLATE) | C | 0 | 2.62E-02 | 3.45E-03 | 100% | 3.6E+06 | 3.46E+05 | 100% |
| | D | 2.00 | 1.55E-02 | 8.83E-04 | 59% | 2.6E+06 | 1.06E+05 | 74% |
| | E | 6.32 | 7.35E-03 | 2.42E-03 | 28% | 1.6E+06 | 4.27E+05 | 46% |
| | F | 20.00 | 1.15E-03 | 2.52E-04 | 4% | 9.5E+05 | 1.53E+05 | 27% |
| | HIGH G | 63.25 | 5.75E-04 | 2.22E-04 | 2% | 4.6E+05 | 1.44E+05 | 13% |
| | | 200.00 | 5.75E-04 | 2.50E-04 | 2% | 8.4E+03 | 9.18E+05 | 0% |

Fig. 22C

96-WELL TISSUE CULTURE PLATE FORMAT FOR HBV DRUG SCREENING

|   | 1 | 2 | 3 | 4 | 5 | 6 | 7 | 8 | 9 | 10 | 11 | 12 |
|---|---|---|---|---|---|---|---|---|---|----|----|----|
| A | Media | Media | Media | Media | Media | Media | Media | Media | Media | Media | Media | Media |
| B | Media | Cells + Drug 1 100μM | Cells + Drug 1 100μM | Cells + Drug 1 100μM | Cells + Drug 2 100μM | Cells + Drug 2 100μM | Cells + Drug 2 100μM | Cells + Drug 3 100μM | Cells + Drug 3 100μM | Cells + Drug 3 100μM | VC | Media |
| C | Media | Cells + Drug 1 32 μM | Cells + Drug 1 32 μM | Cells + Drug 1 32 μM | Cells + Drug 2 32 μM | Cells + Drug 2 32 μM | Cells + Drug 2 32 μM | Cells + Drug 3 32 μM | Cells + Drug 3 32 μM | Cells + Drug 3 32 μM | VC | Media |
| D | Media | Cells + Drug 1 10 μM | Cells + Drug 1 10 μM | Cells + Drug 1 10 μM | Cells + Drug 2 10 μM | Cells + Drug 2 10 μM | Cells + Drug 2 10 μM | Cells + Drug 3 10 μM | Cells + Drug 3 10 μM | Cells + Drug 3 10 μM | VC | Media |
| E | Media | Cells + Drug 1 3.2 μM | Cells + Drug 1 3.2 μM | Cells + Drug 1 3.2 μM | Cells + Drug 2 3.2 μM | Cells + Drug 2 3.2 μM | Cells + Drug 2 3.2 μM | Cells + Drug 3 3.2 μM | Cells + Drug 3 3.2 μM | Cells + Drug 3 3.2 μM | VC | Media |
| F | Media | Cells + Drug 1 1 μM | Cells + Drug 1 1 μM | Cells + Drug 1 1 μM | Cells + Drug 2 1 μM | Cells + Drug 2 1 μM | Cells + Drug 2 1 μM | Cells + Drug 3 1 μM | Cells + Drug 3 1 μM | Cells + Drug 3 1 μM | VC | Media |
| G | Media | Cells + Drug 1 320nM | Cells + Drug 1 320nM | Cells + Drug 1 320nM | Cells + Drug 2 320nM | Cells + Drug 2 320nM | Cells + Drug 2 320nM | Cells + Drug 3 320nM | Cells + Drug 3 320nM | Cells + Drug 3 320nM | VC | Media |
| H | Media | Media | Media | Media | Media | Media | Media | Media | Media | Media | Media | Media |

VC = VIRUS CONTROL = CELLS ALONE WITHOUT DRUGS.

96-WELL TISSUE CULTURE PLATE FORMAT FOR BVDV DRUG SCREENING

| | 1 | 2 | 3 | 4 | 5 | 6 | 7 | 8 | 9 | 10 | 11 | 12 |
|---|---|---|---|---|---|---|---|---|---|---|---|---|
| A | Media | Media | Media | Media | Media | Media | Blank | Blank | Blank | Blank | Blank | Blank |
| B | Cells + Drug 1 0.32 µM | Cell Control | Cells + Virus + Drug 1 0.32 µM | | | Cells + Drug 1 0.32 µM | Cells + Drug 2 0.32 µM | Blank | Cells + Virus + Drug 2 0.32 µM | | Cell Control | Cells + Drug 2 0.32 µM |
| C | Cells + Drug 1 1 µM | Cell Control | Cells + Virus + Drug 1 1 µM | | | Cells + Drug 1 1 µM | Cells + Drug 2 1 µM | | Cells + Virus + Drug 2 1 µM | | Cell Control | Cells + Drug 2 1 µM |
| D | Cells + Drug 1 3.2 µM | Cell Control | Cells + Virus + Drug 1 3.2 µM | | | Cells + Drug 1 3.2 µM | Cells + Drug 2 3.2 µM | | Cells + Virus + Drug 2 3.2 µM | | Cell Control | Cells + Drug 2 3.2 µM |
| E | Media Drug 1 10 µM | Virus Control | Cells + Virus + Drug 1 10 µM | | | Cells + Drug 1 10 µM | Cells + Drug 2 10 µM | | Cells + Virus + Drug 2 10 µM | | Cell Control | Cells + Drug 2 10 µM |
| F | Cells + Drug 1 32 µM | Virus Control | Cells + Virus + Drug 1 32 µM | | | Cells + Drug 1 32 µM | Cells + Drug 2 32 µM | | Cells + Virus + Drug 2 32 µM | | Cell Control | Cells + Drug 2 32 µM |
| G | Cells + Drug 1 100 µM | Virus Control | Cells + Virus + Drug 1 100 µM | | | Cells + Drug 1 100 µM | Cells + Drug 2 100 µM | | Cells + Virus + Drug 2 100 µM | | Cell Control | Cells + Drug 2 100 µM |
| H | Drug 1 100 µM + Media | Drug 1 32 µM + Media | Drug 1 10 µM + Media | Drug 1 3.2 µM + Media | Drug 1 1 µM + Media | Drug 1 0.32 µM + Media | Drug 2 100 µM + Media | Drug 2 32 µM + Media | Drug 2 10 µM + Media | Drug 2 3.2 µM + Media | Drug 2 1 µM + Media | Drug 2 0.32 µM + Media |

VC = VIRUS CONTROL = CELL

EFFECT OF COMPOSITION ON VIRUS PRODUCTION IN HepG2 2.15 CELLS

| | DNA COPY NUMBER (per 3 µl) | | | | | |
|---|---|---|---|---|---|---|
| CONC (µg/ml) | 100 | 31.6 | 10 | 3.16 | 1 | 0.316 | 0 |
| SAMPLE 1 | 5.9 | 828.0 | 9864.7 | 13925.1 | 17055.5 | 21377.4 | |
| SAMPLE 2 | 6.9 | 448.9 | 10462.4 | 15349.5 | 14360.7 | 20087.9 | |
| SAMPLE 3 | 6.3 | 501.4 | 7715.0 | 12606.6 | 18034.6 | 21396.5 | |
| MEAN | 6.4 | 592.7 | 9347.4 | 13960.4 | 16483.6 | 20953.9 | 17714.0 |
| % VC | 0.0 | 3.3 | 52.8 | 78.8 | 93.1 | 118.3 | 100.0 |

IC50 (µg/ml) = 11.2

| | TOXICITY VALUES (XTT – O.D. @ 450/650 nm) | | | | | |
|---|---|---|---|---|---|---|
| CONC (µg/ml) | 100 | 61.6 | 10 | 3.16 | 1 | 0.316 | 0 |
| SAMPLE 1 | 0.131 | 1.257 | 1.309 | 1.333 | 1.348 | 1.413 | |
| SAMPLE 2 | 0.127 | 1.247 | 1.294 | 1.324 | 1.361 | 1.363 | |
| SAMPLE 3 | 0.127 | 1.209 | 1.325 | 1.355 | 1.342 | 1.439 | |
| MEAN | 0.128 | 1.238 | 1.309 | 1.337 | 1.350 | 1.405 | 1.425 |
| % CC | 9.0 | 86.9 | 91.9 | 93.8 | 94.8 | 98.6 | 100.0 |

EFFECT OF 3TC ON VIRUS PRODUCTION IN HepG2 2.15 CELLS

| CONC (μM) | 1 | 0.32 | 0.1 | 0.032 | 0.01 | 0/0032 | 0 |
|---|---|---|---|---|---|---|---|
| SAMPLE 1 | 2867.0 | 2566.2 | 2476.3 | 4049.5 | 6339.3 | 14134.0 | |
| SAMPLE 2 | 2337.0 | 2661.1 | 3119.3 | 4543.6 | 8147.4 | 9541.7 | |
| SAMPLE 3 | 2150.8 | 2243.9 | 2197.9 | 3920.2 | 7093.8 | 12932.8 | |
| MEAN | 2451.6 | 2490.4 | 2597.8 | 4171.1 | 7193.5 | 12202.9 | 17714.0 |
| % VC | 13.8 | 14.1 | 14.7 | 23.5 | 40.6 | 68.9 | 100.0 |

DNA COPY NUMBER (per 3 μl)

| CONC (μM) | 1 | 0.32 | 0.1 | 0.032 | 0.01 | 0.0032 | 0 |
|---|---|---|---|---|---|---|---|
| SAMPLE 1 | 1.394 | 1.489 | 1.314 | 1.330 | 1.388 | 1.372 | |
| SAMPLE 2 | 1.357 | 1.336 | 1.323 | 1.331 | 1.388 | 1.378 | |
| SAMPLE 3 | 1.423 | 1.549 | 1.315 | 1.323 | 1.352 | 1.477 | |
| MEAN | 1.391 | 1.458 | 1.317 | 1.328 | 1.376 | 1.409 | 1.425 |
| % CC | 97.6 | 102.3 | 92.4 | 93.2 | 96.6 | 98.9 | 100.0 |

TOXICITY VALUES (XTT – O.D. @ 450/650 nm)

EFFECT OF BASE VIRUS PRODUCTION IN HepG2 2.15 CELLS

| CONC (μg/ml) | 6.00 E ± 01 | 3.00E ± 01 | 1.50E ± 01 | 5.00E ± 00 |
|---|---|---|---|---|
| SAMPLE 1 | 160968.6 | 77149.1 | 118158.0 | 89503.8 |
| SAMPLE 2 | 92577.7 | 82394.7 | 86701.8 | 106390.2 |
| SAMPLE 3 | 117866.4 | 79521.4 | 86814.3 | 90977.7 |
| MEAN | 123804.2 | 79688.4 | 97228.0 | 95623.9 |
| % VC | 164.6 | 105.9 | 129.3 | 127.1 |

75218.3
100.0

| CONC (μg/ml) | 6.00 E ± 01 | 3.00E ± 01 | 1.50E ± 01 | 5.00E ± 00 |
|---|---|---|---|---|
| SAMPLE 1 | 1.273 | 1.272 | 1.235 | 1.275 |
| SAMPLE 2 | 1.257 | 1.265 | 1.228 | 1.249 |
| SAMPLE 3 | 1.302 | 1.228 | 1.250 | 1.251 |
| MEAN | 1.277 | 1.255 | 1.238 | 1.256 |
| % CC | 100.8 | 99.1 | 97.7 | 99.3 |

EFFECT OF COMPOSITION WITH 5 µg/ml BASE
ON VIRUS PRODUCTION IN HepG2 2.15 CELLS

| DNA COPY NUMBER (per 3µl) | | | | |
|---|---|---|---|---|
| CONC (µg/ml) | 1.00E+01 | 3.16E+00 | 1.00E+00 | 0 |
| SAMPLE 1 | 44854.9 | 41617.1 | 56281.7 | |
| SAMPLE 2 | 33691.7 | 40753.2 | 65844.7 | |
| SAMPLE 3 | 33416.1 | 55544.6 | 61513.6 | |
| MEAN | 37320.9 | 45971.6 | 61213.3 | 53267.8 |
| % VC | 70.1 | 86.3 | 114.9 | 100.0 |

IC50 (µg/ml) = >10

| TOXICITY VALUES (XTT – O.D. @ 450/650 nm) | | | | |
|---|---|---|---|---|
| CONC (µg/ml) | 1.00E+01 | 3.16E+00 | 1.00E+00 | 0 |
| SAMPLE 1 | 1.218 | 1.252 | 1.302 | |
| SAMPLE 2 | 1.247 | 1.233 | 1.279 | |
| SAMPLE 3 | 1.265 | 1.254 | 1.287 | |
| MEAN | 1.243 | 1.246 | 1.289 | 1.259 |
| % CC | 98.8 | 99.0 | 102.4 | 100.0 |

EFFECT OF COMPOSITION WITH 15 μg/ml BASE
ON VIRUS PRODUCTION IN HepG2 2.15 CELLS

DNA COPY NUMBER (per 3μl)

| CONC (μg/ml) | 1.00E+01 | 3.16E+00 | 1.00E+00 | 0 |
|---|---|---|---|---|
| SAMPLE 1 | 4,752.67 | 42627.9 | 35571.7 | |
| SAMPLE 2 | 29233.7 | 47639.9 | 35748.6 | |
| SAMPLE 3 | 48591.1 | 47911.9 | 49803.9 | |
| MEAN | 38912.4 | 46059.9 | 40374.7 | 53267.8 |
| % VC | 73.1 | 86.5 | 75.8 | 100.0 |

TOXICITY VALUES (XTT – O.D. @ 450/650 nm)

| CONC (μg/ml) | 1.00E+01 | 3.16E+00 | 1.00E+00 | 0 |
|---|---|---|---|---|
| SAMPLE 1 | 1.289 | 1.284 | 1.307 | |
| SAMPLE 2 | 1.216 | 1.280 | 1.233 | |
| SAMPLE 3 | 1.230 | 1.238 | 1.226 | |
| MEAN | 1.245 | 1.267 | 1.255 | 1.259 |
| % CC | 98.9 | 100.7 | 99.7 | 100.0 |

EFFECT OF COMPOSITION WITH 30 µg/ml BASE
ON VIRUS PRODUCTION IN HepG2 2.15 CELLS

| | DNA COPY NUMBER (per 3µl) | | | |
|---|---|---|---|---|
| CONC (µg/ml) | 1.00E+01 | 3.16E+00 | 1.00E+00 | 0 |
| SAMPLE 1 | 43524.0 | 85362.6 | 40085.5 | |
| SAMPLE 2 | 55516.7 | 46875.0 | 49541.9 | |
| SAMPLE 3 | 47614.6 | 52647.5 | 54847.7 | |
| MEAN | 48885.1 | 61628.4 | 48158.4 | 53267.8 |
| % VC | 91.8 | 115.7 | 90.4 | 100.0 |

| | TOXICITY VALUES (XTT – O.D. @ 450/650 nm) | | | |
|---|---|---|---|---|
| CONC (µg/ml) | 1.00E+01 | 3.16E+00 | 1.00E+00 | 0 |
| SAMPLE 1 | 1.266 | 1.287 | 1.262 | |
| SAMPLE 2 | 1.254 | 1.270 | 1.245 | |
| SAMPLE 3 | 1.259 | 1.289 | 1.241 | |
| MEAN | 1.260 | 1.282 | 1.249 | 1.259 |
| % CC | 100.1 | 101.8 | 99.2 | 100.0 |

EFFECT OF COMPOSITION WITH 60 μg/ml BASE
ON VIRUS PRODUCTION IN HepG2 2.15 CELLS

| DNA COPY NUMBER (per 3μl) | | | | | |
|---|---|---|---|---|---|
| CONC (μg/ml) | 1.00E+01 | 3.16E+00 | 1.00E+00 | | 0 |
| SAMPLE 1 | 37540.5 | 62736.4 | 64796.4 | | |
| SAMPLE 2 | 60252.4 | 57108.7 | 54260.4 | | |
| SAMPLE 3 | 45315.0 | 77992.4 | 43662.3 | | |
| MEAN | 47702.6 | 65945.8 | 54239.7 | | 53267.8 |
| % VC | 89.6 | 123.8 | 101.8 | | 100.0 |

| TOXICITY VALUES (XTT – O.D. @ 450/650 nm) | | | | | |
|---|---|---|---|---|---|
| CONC (μg/ml) | 1.00E+01 | 3.16E+00 | 1.00E+00 | | 0 |
| SAMPLE 1 | 1.318 | 1.321 | 1.288 | | |
| SAMPLE 2 | 1.257 | 1.245 | 1.296 | | |
| SAMPLE 3 | 1.270 | 1.267 | 1.219 | | |
| MEAN | 1.282 | 1.278 | 1.268 | | 1.259 |
| % CC | 101.8 | 101.5 | 100.7 | | 100.0 |

EFFECT OF COMPOSITION ON VIRUS PRODUCTION IN HepG 2.2.15 CELLS

| DNA COPY NUMBER (per 3μl) | | | | |
|---|---|---|---|---|
| CONC (μM) | 1.00E+01 | 3.16E+00 | 1.00E+00 | 0 |
| SAMPLE 1 | 78252.8 | 62279.6 | 61585.4 | |
| SAMPLE 2 | 69508.6 | 71840.2 | 68642.4 | |
| SAMPLE 3 | 88014.0 | 76533.7 | 81013.2 | |
| MEAN | 78591.8 | 70217.8 | 70413.6 | 75218.3 |
| % VC | 104.5 | 93.4 | 93.6 | 100.0 |

| TOXICITY VALUES (XTT – O.D. @ 450/650 nm) | | | | |
|---|---|---|---|---|
| CONC (μM) | 1.00E+01 | 3.16E+00 | 1.00E+00 | 0 |
| SAMPLE 1 | 1.285 | 1.337 | 1.297 | |
| SAMPLE 2 | 1.272 | 1.277 | 1.254 | |
| SAMPLE 3 | 1.243 | 1.274 | 1.248 | |
| MEAN | 1.267 | 1.296 | 1.266 | 1.267 |
| % CC | 100.0 | 102.3 | 99.9 | 100.0 |

EFFECT OF 3TC ON VIRUS PRODUCTION IN HepG2 2.15 CELLS

DNA COPY NUMBER (per 3 μl)

| CONC (μM) | 1 | 0.32 | 0.1 | 0.032 | 0.01 | 0.0032 | 0 |
|---|---|---|---|---|---|---|---|
| SAMPLE 1 | 5071.9 | 7739.9 | 7205.2 | 12648.5 | 17569.0 | 53809.6 | |
| SAMPLE 2 | 4226.9 | 9565.2 | 9317.8 | 8933.6 | 17342.0 | 24093.2 | |
| SAMPLE 3 | 4585.4 | 5280.4 | 6408.2 | 13059.9 | 16682.7 | 40809.5 | |
| MEAN | 4628.0 | 7528.5 | 7643.7 | 11547.3 | 17197.9 | 39570.8 | 53267.8 |
| % VC | 8.7 | 14.1 | 14.3 | 21.7 | 32.3 | 74.3 | 100.0 |

TOXICITY VALUES (XTT – O.D. @ 450/650 nm)

| CONC (μM) | 1 | 0.32 | 0.1 | 0.032 | 0.01 | 0.0032 | 0 |
|---|---|---|---|---|---|---|---|
| SAMPLE 1 | 1.253 | 1.221 | 1.187 | 1.193 | 1.241 | 1.231 | |
| SAMPLE 2 | 1.222 | 1.203 | 1.213 | 1.198 | 1.203 | 1.240 | |
| SAMPLE 3 | 1.267 | 1.240 | 1.199 | 1.207 | 1.223 | 1.235 | |
| MEAN | 1.247 | 1.221 | 1.200 | 1.199 | 1.222 | 1.235 | 1.259 |
| % CC | 99.1 | 97.0 | 95.3 | 95.3 | 97.1 | 98.1 | 100.0 |

EFFECT OF 3TC ON VIRUS PRODUCTION IN HepG2 2.15 CELLS

| CONC (μM) | 1 | 0.32 | 0.1 | 0.032 | 0.01 | 0.0032 | 0 |
|---|---|---|---|---|---|---|---|
| SAMPLE 1 | 14769.6 | 14668.0 | 16297.0 | 21073.4 | 35583.3 | 55483.0 | |
| SAMPLE 2 | 13040.9 | 12534.6 | 14610.2 | 28292.7 | 36579.8 | 64766.3 | |
| SAMPLE 3 | 12587.3 | 9441.9 | 18726.4 | 18209.6 | 35828.8 | 79070.3 | |
| MEAN | 13465.9 | 12214.8 | 16544.5 | 22525.2 | 35997.3 | 66439.9 | 75218.3 |
| % VC | 17.9 | 16.2 | 22.0 | 29.9 | 47.9 | 88.3 | 100.0 |

DNA COPY NUMBER (per 3 μl)

IC50 (μM) = 0.0096

| CONC (μM) | 1 | 0.32 | 0.1 | 0.032 | 0.01 | 0.0032 | 0 |
|---|---|---|---|---|---|---|---|
| SAMPLE 1 | 1.222 | 1.186 | 1.205 | 1.244 | 1.192 | 1.249 | |
| SAMPLE 2 | 1.222 | 1.227 | 1.214 | 1.245 | 1.193 | 1.209 | |
| SAMPLE 3 | 1.264 | 1.236 | 1.224 | 1.247 | 1.225 | 1.199 | |
| MEAN | 1.236 | 1.216 | 1.214 | 1.245 | 1.203 | 1.219 | 1.267 |
| % CC | 97.6 | 96.0 | 95.8 | 98.3 | 95.0 | 96.2 | 100.0 |

TOXICITY VALUES (XTT – O.D. @ 450/650 nm)

EFFECT OF COMPOSITION –HP WITH BASE (200 μg/ml) ON VIRUS PRODUCTION IN HepG2 2.15 CELLS

| CONC (μg/ml) | DNA COPY NUMBER (per 3 μl) | | | | | |
|---|---|---|---|---|---|---|
| | 100 | 31.6 | 10 | 3.16 | 1 | 0.316 | 0 |
| SAMPLE 1 | 930.4 | 4455.3 | 9609.3 | 14263.1 | 11436.4 | 10444.7 | |
| SAMPLE 2 | 448.4 | 6236.0 | 10104.2 | 25694.9 | 18789.6 | 13517.3 | |
| SAMPLE 3 | 405.6 | 4406.5 | 13302.8 | 21471.1 | 12653.1 | 16829.6 | |
| MEAN | 594.8 | 5032.6 | 11005.4 | 20476.4 | 14293.0 | 13597.2 | 12207.8 |
| % VC | 4.9 | 41.2 | 90.2 | 167.7 | 117.1 | 111.4 | 100.0 |

| CONC (μg/ml) | TOXICITY VALUES (XTT – O.D. @ 450/650 nm) | | | | | |
|---|---|---|---|---|---|---|
| | 100 | 31.6 | 10 | 3.16 | 1 | 0.316 | 0 |
| SAMPLE 1 | 0.087 | 0.521 | 1.299 | 1.395 | 1.439 | 1.447 | |
| SAMPLE 2 | 0.090 | 0.490 | 1.259 | 1.333 | 1.452 | 1.509 | |
| SAMPLE 3 | 0.062 | 0.562 | 1.265 | 1.337 | 1.413 | 1.462 | |
| MEAN | 0.086 | 0.524 | 1.274 | 1.355 | 1.435 | 1.473 | 1.449 |
| % CC | 6.0 | 36.2 | 67.9 | 93.5 | 99.0 | 101.6 | 100.0 |

EFFECT OF 3TC ON VIRUS PRODUCTION IN HepG2 2.15 CELLS

| CONC (μM) | 1 | 0.32 | 0.1 | 0.032 | 0.01 | 0.0032 | 0 |
|---|---|---|---|---|---|---|---|
| SAMPLE 1 | 1850.2 | 2041.5 | 1894.8 | 5141.5 | 7962.3 | 9723.3 | |
| SAMPLE 2 | 1851.3 | 2200.4 | 2653.5 | 6686.7 | 10605.8 | 12596.2 | |
| SAMPLE 3 | 1308.1 | 1772.3 | 2602.3 | 5652.6 | 11822.9 | 8448.6 | |
| MEAN | 1669.9 | 2004.7 | 2383.5 | 5826.9 | 10130.4 | 10256.0 | 12207.8 |
| % VC | 13.7 | 16.4 | 19.5 | 47.7 | 83.0 | 84.0 | 100.0 |

DNA COPY NUMBER (per 3 μl)

| CONC (μM) | 1 | 0.32 | 0.1 | 0.032 | 0.01 | 0.0032 | 0 |
|---|---|---|---|---|---|---|---|
| SAMPLE 1 | 1.483 | 1.453 | 1.400 | 1.435 | 1.407 | 1.489 | |
| SAMPLE 2 | 1.534 | 1.443 | 1.427 | 1.403 | 1.405 | 1.456 | |
| SAMPLE 3 | 1.494 | 1.406 | 1.421 | 1.393 | 1.382 | 1.444 | |
| MEAN | 1.504 | 1.434 | 1.416 | 1.411 | 1.396 | 1.463 | 1.449 |
| % CC | 103.8 | 99.0 | 97.7 | 97.4 | 96.5 | 101.0 | 100.0 |

TOXICITY VALUES (XTT – O.D. @ 450/650 nm)

EFFECT OF COMPOSITION #4 ON VIRUS PRODUCTION IN HepG2 2.15 CELLS

| CONC (µg/ml) | 100 | 31.6 | 10 | 3.16 | 1 | 0.316 | 0 |
|---|---|---|---|---|---|---|---|
| | | | DNA COPY NUMBER (per 3 µl) | | | | |
| SAMPLE 1 | 34.5 | 1283.3 | 54014.7 | 51735.0 | 26956.5 | 20268.4 | |
| SAMPLE 2 | 100.9 | 3658.1 | 32635.6 | 43596.4 | 98391.0 | 40391.8 | |
| SAMPLE 3 | 35.3 | 6001.7 | 47553.0 | 65249.1 | 67485.0 | 29409.2 | |
| MEAN | 56.9 | 3647.7 | 44734.4 | 53526.8 | 64277.5 | 30023.1 | 54975.9 |
| % VC | 0.1 | 6.6 | 81.4 | 97.4 | 116.9 | 54.6 | 100.0 |

| CONC (µg/ml) | 100 | 31.6 | 10 | 3.16 | 1 | 0.316 | 0 |
|---|---|---|---|---|---|---|---|
| | | | TOXICITY VALUES (XTT – O.D. @ 450/650 nm) | | | | |
| SAMPLE 1 | 0.091 | 1.024 | 1.101 | 1.260 | 1.170 | 1.208 | |
| SAMPLE 2 | 0.100 | 1.034 | 1.078 | 1.306 | 1.273 | 1.206 | |
| SAMPLE 3 | 0.107 | 1.076 | 1.080 | 1.282 | 1.247 | 1.291 | |
| MEAN | 0.099 | 1.045 | 1.086 | 1.283 | 1.230 | 1.235 | 1.474 |
| % CC | 6.7 | 70.9 | 73.7 | 87.0 | 83.4 | 83.8 | 100.0 |

EFFECT OF 3TC ON VIRUS PRODUCTION IN HepG2 2.15 CELLS

| CONC (µM) | 1 | 0.32 | 0.1 | 0.032 | 0.01 | 0.0032 | 0 |
|---|---|---|---|---|---|---|---|
| SAMPLE 1 | 8703.3 | 13891.4 | 13537.0 | 24756.1 | 95296.9 | 49701.7 | |
| SAMPLE 2 | 14569.5 | 18900.7 | 16300.0 | 17830.7 | 36946.4 | 86606.0 | |
| SAMPLE 3 | 5434.8 | 11398.7 | 8572.2 | 22501.2 | 40973.7 | 31768.2 | |
| MEAN | 9569.2 | 14730.3 | 12803.0 | 21696.0 | 57739.0 | 56025.3 | 54975.9 |
| % VC | 17.4 | 26.8 | 23.3 | 39.5 | 105.0 | 101.9 | 100.0 |

DNA COPY NUMBER (per 3 µl)

| CONC (µM) | 1 | 0.32 | 0.1 | 0.032 | 0.01 | 0.0032 | 0 |
|---|---|---|---|---|---|---|---|
| SAMPLE 1 | 1.502 | 1.467 | 1.480 | 1.485 | 1.509 | 1.419 | |
| SAMPLE 2 | 1.467 | 1.439 | 1.418 | 1.507 | 1.450 | 1.414 | |
| SAMPLE 3 | 1.503 | 1.448 | 1.426 | 1.495 | 1.494 | 1.419 | |
| MEAN | 1.491 | 1.451 | 1.441 | 1.496 | 1.484 | 1.417 | 1.474 |
| % CC | 101.1 | 98.5 | 97.8 | 101.5 | 100.7 | 96.2 | 100.0 |

TOXICITY VALUES (XTT – O.D. @ 450/650 nm)

EFFECT OF 3TC ON VIRUS PRODUCTION IN HepG2 2.15 CELLS

| CONC (μM) | 1 | 0.32 | 0.1 | 0.032 | 0.01 | 0.0032 | 0 |
|---|---|---|---|---|---|---|---|
| SAMPLE 1 | 14642.3 | 16341.7 | 12241.0 | 33856.8 | 70145.7 | 29409.2 | |
| SAMPLE 2 | 12876.3 | 11430.3 | 17929.7 | 17820.3 | 27002.9 | 22211.1 | |
| SAMPLE 3 | 9395.0 | 18733.6 | 8988.2 | 31365.6 | 43624.5 | 50365.7 | |
| MEAN | 12304.5 | 15501.9 | 13053.0 | 27680.9 | 46924.4 | 33995.3 | 54975.9 |
| % VC | 22.4 | 28.2 | 23.7 | 50.4 | 85.4 | 61.8 | 100.0 |

DNA COPY NUMBER (per 3 μl)

IC50 (μM) = 0.0329

| CONC (μM) | 1 | 0.32 | 0.1 | 0.032 | 0.01 | 0.0032 | 0 |
|---|---|---|---|---|---|---|---|
| SAMPLE 1 | 1.441 | 1.292 | 1.209 | 1.337 | 1.437 | 1.390 | |
| SAMPLE 2 | 1.441 | 1.325 | 1.194 | 1.385 | 1.458 | 1.420 | |
| SAMPLE 3 | 1.462 | 1.406 | 1.231 | 1.411 | 1.469 | 1.484 | |
| MEAN | 1.448 | 1.341 | 1.211 | 1.378 | 1.455 | 1.431 | 1.474 |
| % CC | 98.2 | 91.0 | 82.2 | 93.5 | 98.7 | 97.1 | 100.0 |

TOXICITY VALUES (XTT – O.D. @ 450/650 nm)

PLATE W2U                    IN VITRO ANTIVIRAL RESULTS         DRUG: AVS COMPOSITION
DRUG COMPOSITION                    XTT ASSAY                   TAI:>0.42        SI: ----

| | 1 | 2 | 3 | 4 | 5 | 6 | 7 | 8 | 9 | 10 | 11 | 12 |
|---|---|---|---|---|---|---|---|---|---|---|---|---|
| | | | reagent background | | | | | | plastic background | | | |
| A | 0.371 | 0.395 | 0.359 | 0.357 | 0.356 | 0.355 | 0.016 | 0.016 | 0.015 | 0.017 | 0.017 | 0.017 |
| | tox | cc/vc | drug COMPOSITION experimental | | | tox | | | | | cc/vc | |
| B | 1.988 | 1.778 | 0.849 | 0.947 | 0.931 | 1.670 | | | | | 1.808 | |
| C | 0.995 | 1.732 | 0.495 | 0.458 | 0.719 | 0.926 | | | | | 1.762 | |
| D | 0.333 | 1.720 | 0.278 | 0.276 | 0.276 | 0.271 | | | | | 1.801 | |
| E | 0.288 | 0.971 | 0.282 | 0.283 | 0.281 | 0.280 | | | | | 0.746 | |
| F | 0.297 | 0.747 | 0.285 | 0.283 | 0.287 | 0.280 | | | | | 0.984 | |
| G | 0.295 | 0.859 | 0.300 | 0.290 | 0.304 | 0.290 | | | | | 0.658 | |
| | | | color/metric background | | | | | | | | | |
| H | 0.304 | 0.288 | 0.282 | 0.292 | 0.265 | 0.287 | | | | | | | lox – cell toxicity    cc – cell control    vc – virus control    BOLD – highest drug conc    values shown are optical densities VIRUS   BVDV           PASSAGE -                PROJECT #
CELLS   MDBK           PASSAGE -                SPONSOR       VICTOR
                       OPERATOR  JYW            TEST DATE     05/09/03
                                                DATE READ     05/14/03

Fig. 40A

| | |
|---|---|
| REAGENT | 0.360 |
| VIRUS CONTROL | 0.468 |
| CELL CONTROL | 1.407 |
| DIFFERENTIAL | 0.939 |

| DRUG COMPOSITION | 25% | 50% | 95% |
|---|---|---|---|
| TC (µg/ml) | 0.65 | 0.97 | 3.01 |
| IC (µg/ml) | --- | --- | --- |
| ANTIVIRAL INDEX (AI) | --- | --- | --- |

| DRUG COMPOSITION | | ANTIVIRAL TEST VALUES | | CYTOTOXICITY TEST VALUES | | COLOR/METRIC CONTROL |
|---|---|---|---|---|---|---|
| ROW ON PLATE | CONC. (µ/ml) | MEAN O.D. | % RED. IN VIRAL CPE | MEAN O.D. | % CELL VIABILITY | |
| low B | 0.32 | 0.155 | 17% | 1.543 | 100% | -073 |
| C | 1 | -.195 | 0% | 0.676 | 48% | -075 |
| D | 3.2 | -.483 | 0% | 0.011 | 1% | -068 |
| E | 10 | -.468 | 0% | 0.003 | 0% | -078 |
| F | 32 | -.471 | 0% | 0.001 | 0% | -072 |
| high G | 100 | -.475 | 0% | -012 | 0% | -055 |

Fig. 40B

PLATE W2U  IN VITRO ANTIVIRAL RESULTS  DRUG: AVS IFN ALPHA
DRUG IFN ALPHA  XTT ASSAY  TAI:>7.24  SI: >1.37

| | 1 | 2 | 3 | 4 | 5 | 6 | 7 | 8 | 9 | 10 | 11 | 12 |
|---|---|---|---|---|---|---|---|---|---|---|---|---|
| | | | reagent background | | | | | | plastic background | | | |
| A | 0.371 | 0.395 | 0.359 | 0.357 | 0.356 | 0.355 | 0.016 | 0.016 | 0.015 | 0.017 | 0.017 | 0.017 |
| | | cc/vc | | | | | lox | drug IFN ALPHA experimental | | | cc/vc | lox |
| B | | 1.778 | | | | | 1.790 | 0.664 | 0.630 | 0.834 | 1.808 | 1.984 |
| C | | 1.732 | | | | | 1.709 | 0.769 | 0.851 | 0.934 | 1.762 | 2.081 |
| D | | 1.720 | | | | | 1.658 | 0.545 | 0.848 | 0.499 | 1.801 | 2.101 |
| E | | 0.971 | | | | | 1.705 | 0.480 | 0.456 | 0.591 | 0.746 | 2.096 |
| F | | 0.747 | | | | | 1.762 | 0.681 | 0.737 | 0.708 | 0.984 | 2.120 |
| G | | 0.859 | | | | | 1.951 | 1.194 | 1.707 | 1.492 | 0.658 | 2.019 |
| | | | | | | | | | colorimetric background | | | |
| H | | | | | | | 0.351 | 0.360 | 0.361 | 0.364 | 0.367 | 0.383 | lox – cell toxicity    cc – cell control    vc – virus control    BOLD – highest drug conc    values shown are optical densities VIRUS  BVDV  PASSAGE -  PROJECT #  VICTOR
CELLS  MDBK  PASSAGE –  SPONSOR  VICTOR
              OPERATOR  JYW  TEST DATE  05/09/03
                             DATE READ  05/14/03

Fig. 41A

| | | 25% | 50% | 95% |
|---|---|---|---|---|
| REAGENT | 0.360 | DRUG IFN ALPHA | | | |
| VIRUS CONTROL | 0.468 | TC (IU) | 100.00 | 100.00 | 100.00 |
| CELL CONTROL | 1.407 | IC (IU) | 48.40 | 73.10 | ---- |
| DIFFERENTIAL | 0.939 | ANTIVIRAL INDEX (AI) | 2.07 | 1.37 | ---- |

| DRUG IFN ALPHA | | ANTIVIRAL TEST VALUES | | CYTOTOXICITY TEST VALUES | | COLOR/METRIC CONTROL |
|---|---|---|---|---|---|---|
| ROW ON PLATE | CONC. (IU) | MEAN O.D. | % RED. IN CPE | MEAN O.D. | % CELL VIABILITY | |
| low  B | 0.32 | -.142 | 0% | 1.504 | 100% | 0.024 |
| C | 1 | 0.016 | 2% | 1.528 | 100% | 0.008 |
| D | 3.2 | -.202 | 0% | 1.515 | 100% | 0.005 |
| E | 10 | -.321 | 0% | 1.539 | 100% | 0.002 |
| F | 32 | -.120 | 0% | 1.581 | 100% | 0.001 |
| high  G | 100 | 0.646 | 69% | 1.635 | 100% | -.009 |

Fig. 41B

PLATE W49                          IN VITRO ANTIVIRAL RESULTS        DRUG: AVS COMPOSITION_#4
DRUG COMPOSITION_#4                      XTT ASSAY                   TAI: 22.76          SI: 3.82

|   | 1 | 2 | 3 | 4 | 5 | 6 | 7 | 8 | 9 | 10 | 11 | 12 |
|---|---|---|---|---|---|---|---|---|---|----|----|----|
|   |   |   | reagent background | | | | | | plastic background | | | |
| A | 0.151 | 0.157 | 0.159 | 0.152 | 0.162 | 0.158 | 0.002 | 0.002 | 0.002 | 0.002 | 0.002 | 0.002 |
|   | lox | cc/vc | drug COMPOSITION_#4 experimental | | | lox | | | | | cc/vc | |
| B | 1.456 | 1.061 | 0.169 | 0.293 | 0.196 | 1.254 | | | | | 1.302 | |
| C | 1.570 | 1.291 | 0.327 | 0.367 | 0.246 | 1.601 | | | | | 1.210 | |
| D | 1.338 | 1.205 | 0.453 | 0.845 | 1.177 | 1.540 | | | | | 1.260 | |
| E | 0.775 | 0.190 | 1.083 | 1.105 | 1.265 | 1.136 | | | | | 0.425 | |
| F | 0.155 | 0.194 | 0.144 | 0.144 | 0.143 | 0.146 | | | | | 0.224 | |
| G | 0.159 | 0.193 | 0.146 | 0.152 | 0.148 | 0.152 | | | | | 0.225 | |
|   |   |   |   | colorimetric background | | | | | | | | |
| H | 0.153 | 0.159 | 0.158 | 0.157 | 0.158 | 0.155 | | | | | | | lox – cell toxicity    cc – cell control    vc – virus control    BOLD – highest drug conc    values shown are optical densities VIRUS    BVDV           PASSAGE -                   PROJECT #
CELLS    MDBK           PASSAGE –                   SPONSOR        VICTOR
                        OPERATOR  JYW               TEST DATE      BUCKWOLD
                                                                   06/24/03
                                                    DATE READ      06/30/03

Fig. 42A

| | | | |
|---|---|---|---|
| REAGENT | 0.157 | | |
| VIRUS CONTROL | 0.085 | | |
| CELL CONTROL | 1.065 | | |
| DIFFERENTIAL | 0.980 | | |

| DRUG COMPOSITION #4 | 25% | 50% | 95% |
|---|---|---|---|
| TC (μg/ml) | 10.00 | 17.30 | 30.50 |
| IC (μg/ml) | 1.50 | 2.62 | ----- |
| ANTIVIRAL INDEX (AI) | 6.69 | 6.62 | ----- |

| COMPOSITION_#4 | | ANTIVIRAL TEST VALUES | | CYTOTOXICITY TEST VALUES | | |
|---|---|---|---|---|---|---|
| ROW ON PLATE | CONC. (μg/ml) | MEAN O.D. | % RED. IN VIRAL CPE | MEAN O.D. | % CELL VIABILITY | COLORIMETRIC CONTROL |
| low B | 0.32 | -.021 | 0% | 1.201 | 100% | -.002 |
| C | 1 | 0.069 | 7% | 1.427 | 100% | 0.002 |
| D | 3.2 | 0.582 | 59% | 1.282 | 100% | 0.001 |
| E | 10 | 0.907 | 93% | 0.797 | 75% | 0.002 |
| F | 32 | -.101 | 0% | -.009 | 0% | 0.003 |
| high G | 100 | -.089 | 0% | 0.003 | 0% | -.004 |

Fig. 42B

PLATE W47  
DRUG IFN

IN VITRO ANTIVIRAL RESULTS  
XTT ASSAY

DRUG: AVS IFN  
TAI:>36.47  SI: >8.68

|   | 1 | 2 | 3 | 4 | 5 | 6 | 7 | 8 | 9 | 10 | 11 | 12 |
|---|---|---|---|---|---|---|---|---|---|---|---|---|
|   |   |   | reagent background | | | | | | plastic background | | | |
| A | 0.246 | 0.229 | 0.233 | 0.224 | 0.234 | 0.235 | 0.018 | 0.017 | 0.018 | 0.016 | 0.017 | 0.017 |
|   |   | cc/vc | | | | | lox | drug IFN ALPHA experimental | | | cc/vc | lox |
| B |   | 1.629 | | | | | 1.646 | 0.357 | 0.334 | 0.353 | 1.485 | 1.396 |
| C |   | 1.634 | | | | | 1.704 | 0.337 | 0.348 | 0.312 | 1.704 | 1.570 |
| D |   | 1.558 | | | | | 1.607 | 0.492 | 0.456 | 0.412 | 1.568 | 1.564 |
| E |   | 0.310 | | | | | 1.591 | 0.948 | 1.010 | 0.856 | 0.596 | 1.603 |
| F |   | 0.319 | | | | | 1.595 | 1.404 | 1.398 | 1.504 | 0.377 | 1.703 |
| G |   | 0.324 | | | | | 1.671 | 1.685 | 1.732 | 1.666 | 0.355 | 1.507 |
|   |   |   |   |   |   |   |   |   | colorimetric background | | | |
| H |   |   |   |   |   |   | 0.241 | 0.246 | 0.248 | 0.245 | 0.254 | 0.264 | lox – cell toxicity    cc – cell control    vc – virus control    BOLD – highest drug conc    values shown are optical densities

VIRUS   BVDV  
CELLS   MDBK

PASSAGE -  
PASSAGE –  
OPERATOR  JYW

PROJECT #  
SPONSOR        VICTOR  
TEST DATE      BUCKWOLD  
DATE READ      06/24/03  
               06/30/03

Fig. 43A

| REAGENT | 0.234 |
| --- | --- |
| VIRUS CONTROL | 0.147 |
| CELL CONTROL | 1.363 |
| DIFFERENTIAL | 1.216 |

| DRUG IFNA | 25% | 50% | 95% |
| --- | --- | --- | --- |
| TC (IU) | 100% | 100% | 100% |
| IC (IU) | 5.66 | 11.50 | 66.60 |
| ANTIVIRAL INDEX (AI) | 17.68 | 8.68 | 1.50 |

| DRUG IFNA | | ANTIVIRAL TEST VALUES | | CYTOTOXICITY TEST VALUES | | |
| --- | --- | --- | --- | --- | --- | --- |
| ROW ON PLATE | CONC. (IU) | MEAN O.D. | % RED. IN CPE | MEAN O.D. | % CELL VIABILITY | COLOR/METRIC CONTROL |
| low B | 0.32 | -.063 | 0% | 1.256 | 92% | 0.031 |
| C | 1 | -.069 | 0% | 1.383 | 100% | 0.021 |
| D | 3.2 | 0.062 | 5% | 1.341 | 98% | 0.011 |
| E | 10 | 0.544 | 45% | 1.350 | 99% | 0.014 |
| F | 32 | 1.043 | 86% | 1.404 | 100% | 0.012 |
| high G | 100 | 1.307 | 100% | 1.349 | 99% | 0.007 |

Fig. 43B

| 100 | 31.6 | 10 | 3.16 | 1 | 0.316 | 0 |
|---|---|---|---|---|---|---|
|  |  |  |  |  |  |  |
|  |  |  |  |  |  |  |
|  |  |  |  |  |  |  |
|  |  |  |  |  |  |  |

| TOXICITY VALUES (XTT – O.D. @ 450/650 nm) |  |  |  |  |  |  |
|---|---|---|---|---|---|---|
| CONC (µg/ml) | 100.00 | 31.60 | 10.00 | 3.16 | 1.00 | 0.32 | 0.00 |
| SAMPLE 1 | 0.0828 | 0.1687 | 1.0120 | 1.2871 | 1.2620 | 1.2415 | 1.2700 |
| SAMPLE 2 | 0.0856 | 0.2397 | 0.9995 | 1.1237 | 1.3391 | 1.3123 | 1.2388 |
| SAMPLE 3 |  |  |  |  |  |  | 1.2853 |
| SAMPLE 4 |  |  |  |  |  |  | 1.3747 |
| MEAN | 0.0842 | 0.2042 | 1.0058 | 1.2054 | 1.3006 | 1.2769 | 1.2922 |
| % CC | 6.5160 | 15.8025 | 77.8324 | 93.2828 | 100.6462 | 98.8160 | 100.0000 |

| 25 | 27 | 23 | 25 | 24 | 28 | 27 | 31 | 27 | 28 | 25 |
|---|---|---|---|---|---|---|---|---|---|---|
| 25 | 2373 | 31021 | 29188 | 29463 | 28916 | 28035 | 29160 | 55203 | 2391 | 26 |
| 29 | 1676 | 32754 | 30303 | 31284 | 31460 | 34551 | 29490 | 27904 | 1753 | 23 |
| 23 | 1687 | 32540 | 31757 | 30992 | 29051 | 33468 | 31727 | 28512 | 1763 | 22 |
| 27 | 1649 | 33218 | 30876 | 31906 | 30559 | 33374 | 31372 | 28565 | 1763 | 23 |
| 25 | 1637 | 32388 | 30674 | 29768 | 30934 | 33973 | 30161 | 29435 | 1704 | 23 |
| 24 | 1596 | 28220 | 28512 | 27670 | 26752 | 29106 | 27156 | 26230 | 1649 | 23 |
| 25 | 27983 | | | | | | | | | |
|  | 28220 | | | | | | | | | |
|  | 29024 | | | | | | | | | |
|  | 29768 | | | | | | | | | |
|  | 29243 | | | | | | | | | |
|  | 26132 | | | | | | | | | |
| 23 | 23 | 22 | 22 | 22 | 23 | 22 | 21 | 22 | 22 | 22 | media me 1705.3
media S. 57.0
mean +2 1819.4
mean -2 1591.3

Fig. 45A above values – mean media blank

| blank | blank | blank | blank | blank | blank | blank | blank | blank | blank |
|---|---|---|---|---|---|---|---|---|---|
| blank | 667.7 | 26777.7 | 29315.7 | 27482.7 | 27757.7 | 27210.7 | 26329.7 | 27454.67 | 53497.7 | 68.5.7 |
| blank | -29.3 | 26514.7 | 31048.7 | 28597.7 | 29578.7 | 29754.7 | 32845.7 | 27784.67 | 26198.7 | 47.7 |
| blank | -18.3 | 27318.7 | 30834.7 | 30051.7 | 29286.7 | 27345.7 | 31762.7 | 30021.67 | 26806.7 | 57.7 |
| blank | -56.3 | 28062.7 | 31512.7 | 29170.7 | 30200.7 | 28853.7 | 31668.7 | 29666.67 | 26859.7 | 57.7 |
| blank | -68.3 | 27537.7 | 30682.7 | 28968.7 | 28062.7 | 29228.7 | 32267.7 | 28455.67 | 27729.7 | -1.3 |
| blank | -109.3 | 24426.7 | 26514.7 | 26806.7 | 25964.7 | 25046.7 | 27400.7 | 25450.67 | 24524.7 | -56.3 |
| blank | blank | blank | blank | blank | blank | blank | blank | blank | blank | blank | bacteria     26371.3
bacteria S   1657.4

Fig. 45B

% inhibition

| Conc: μg/ml | drug only | | | | | | | |
|---|---|---|---|---|---|---|---|---|
| 1.0 | 97.5 | 0.4 | -11.2 | -4.2 | -5.3 | -3.2 | 0.2 | -4.1 |
| 1.0 | 100.1 | -0.5 | -17.7 | -8.4 | -12.2 | -12.8 | -24.6 | -5.4 |
| 10.0 | 100.1 | -3.6 | -16.9 | -14.0 | -11.1 | -3.7 | -20.4 | -13.8 |
| 10.0 | 100.2 | -6.4 | -19.5 | -10.6 | -14.5 | -9.4 | -20.1 | -12.5 |
| 60.0 | 100.3 | -4.4 | -16.3 | -9.8 | -6.4 | -10.8 | -22.4 | -7.9 |
| 60.0 | 100.4 | 7.4 | -0.5 | -1.7 | 1.5 | 5.0 | -3.9 | 3.5 |

Fig. 46

| Base (μg/ml) | EC$_{50}$(μg/ml) | IC$_{50}$(μg/ml) | SI$_{60}$ |
|---|---|---|---|
| 0 | 0.33 | 7.22 | 22 |
| 25 | 0.64 | 8.46 | 13 |
| 50 | 0.18 | 6.87 | 38 |
| 100 | 0.73 | 6.89 | 9.4 |
| 200 | 0.65 | 6.14 | 9.4 |

Fig. 47

Fig. 48A  HCV RNA REPLICON LUCIFERASE-BASED ANTIVIRAL EVALUATION

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B | 2073210 | 14677013 | 14264177 | 15503969 | 14603986 | 2178598 | 2129268 | 2023616 | 1995192 | 2120365 | 2036336 | 2150 |
| C | 2142409 |   |   |   |   | 13652945 | 15412688 | 15616771 | 13457561 | 15697443 | 14110404 | 2073 |
| D | 2171175 |   |   |   |   |   | 14387065 | 16721829 | 15536298 | 16788494 |   | 2002 |
| E | 2093917 |   |   |   |   |   | 15730585 | 17353988 | 16864494 | 19024156 |   | 1992 |
| F | 1921297 |   |   |   |   |   | 17552108 | 15573770 | 14939612 | 17957098 |   | 2136 |
| G | 2213144 |   |   |   |   |   | 18579410 | 15982694 | 14746282 | 14739557 |   | 2034 |
| H |   |   |   |   |   |   | 3275213 | 3016283 | 3593713 | 3526846 |   | 1946 |
|   |   |   |   |   |   | 1941361 | 2059326 | 2151354 | 2043985 | 2205484 | 2187454 | 2157 |

BOLD – highest drug conc    values shown are optical densities

Fig. 48B
Luciferase

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B |   |   |   |   |   |   |   |   |   |   |   |   |
| C |   | 267,8000 |   |   |   |   | 224,1000 | 228,7000 | 273,7000 | 250,1000 | 250,0000 | 250,1000 |
| D |   | 277,7000 |   |   |   |   | 174,8000 | 183,5000 | 161,7000 | 149,800 | 243,4000 |   |
| E |   | 302,8000 |   |   |   |   | 135,7000 | 128,0000 | 93,7000 | 112,2000 | 256,1000 |   |
| F |   | 316,5000 |   |   |   |   | 76,3000 | 56,8000 | 83,9000 | 67,5000 | 296,6000 |   |
| G |   | 294,0000 |   |   |   |   | 1,8000 | 1,3000 | 2,9000 | 6,2000 | 280,7000 |   |
| H |   |   |   |   |   |   |   |   |   |   |   |   |

BOLD – highest drug conc    values shown are Luciferase luminsence

VIRUS        HCV RNA REPLICONS
STRAIN       CON-1
CELLS        Huh-Luc/Neo ET

VIRUS CONTROL =        270,0700            PASSAGE         25
CV VIRUS CONTROL =     9,0%                CV CELL CONTROL =    4,5%
CELL CONTROL =         1,3E+07

| Parameter | 50% | 90% |
|---|---|---|
| Cytotoxicity = IC (µg/ml) | 7.2176 | 14.422 |
| Antiviral Activity = EC (µg/ml) | 0.33 | --- |
| Selectivity Index = SI (IC/EC) | 21.87 | --- |

Fig. 49

| VALUES OF COLUMNS | ROW ON PLATE | CONC. (µg/ml) | ANTIVIRAL TEST VALUES | | | CYTOTOXICITY VALUES | | |
|---|---|---|---|---|---|---|---|---|
| | | | MEAN LUC | SD LUC | % CONTROL LUC | MEAN O.O. | SD O.O. | % CONTROL VIABILITY |
| 7 through 12 (right side of plate) | C | 0 | 2.77E+02 | 2.45E+01 | 100% | 1.3E+07 | 5.86E+05 | 100% |
| | D | 0.03 | 2.46E+02 | 2.35E+01 | 68% | 1.4E+07 | 1.72E+05 | 110% |
| | E | 0.13 | 1.67E+02 | 1.40E+01 | 01% | 1.4E+07 | 1.99E+05 | 100% |
| | F | 0.64 | 1.17E+02 | 1.65E+01 | 42% | 1.2E+07 | 5.51E+05 | 90% |
| | | 3.20 | 7.11E+01 | 1.17E+01 | 25% | 1.3E+07 | 4.41E+05 | 97% |
| | High G | 16.00 | 2.75E+00 | 1.77E+00 | 1% | 5.7E+05 | 2.20E+05 | 4% |

Fig. 50

Fig. 52A    HCV RNA REPLICON LUCIFERASE-BASED ANTIVIRAL EVALUATION

Call numbers

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   | 2049868 | 2144638 | 2090437 | 2136030 | 2200774 | 210287 | 224178 |
| B | 2285902 | 12087235 | 12820794 | 13521435 |   | 13091944 | 14306314 | 11573040 | 12764144 | 12784144 |   | 2193100 |
| C | 2050910 |   |   |   |   |   | 12503798 | 1244350 | 12821804 | 12680592 |   | 200529 |
| D | 2159220 |   |   |   |   |   | 14753021 | 14197272 | 14579332 | 14201435 |   | 218542 |
| E | 2094188 |   |   |   |   |   | 12640874 | 11882548 | 12288063 | 12297423 |   | 2125904 |
| F | 212620 |   |   |   |   |   | 12596487 | 11422906 | 11811547 | 10924319 |   | 2066355 |
| G | 2170737 |   |   |   |   |   | 3097175 | 3113802 | 2805528 | 2762716 |   | 203822 |
| H |   |   |   |   |   | 2032097 | 1944088 | 2081542 | 2140332 | 2108273 | 2154321 | 2204230 |

BOLD – highest drug conc    values shown are optical densities
Luciferase

Fig. 52B

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C |   | 96.6000 |   |   |   |   | 108.8000 | 83.8000 | 107.4000 | 101.1000 | 102.9000 |   |
| D |   | 132.6000 |   |   |   |   | 71.2000 | 68.3000 | 66.9000 | 57.3000 | 126.0000 |   |
| E |   | 115.7000 |   |   |   |   | 41.7000 | 42.4000 | 40.0000 | 44.4000 | 108.2000 |   |
| F |   | 133.9000 |   |   |   |   | 25.8000 | 19.4000 | 21.7000 | 24.2000 | 141.1000 |   |
| G |   | 153.2000 |   |   |   |   | 0.1000 | 0.0000 | 0.7000 | 1.8000 | 115.1000 |   |
| H |   |   |   |   |   |   |   |   |   |    |    |    |

BOLD – highest drug conc    values shown are Luciferase luminsence
VIRUS    HCV RNA REPLICONS    PROJECT # --
STRAIN   CON-1                PASSAGE 25
CELLS    ET                   CV CELL CONTROL = 6.3%

VIRUS CONTROL = 122.3300
CV VIRUS CONTROL = 6.3%
CELL CONTROL

| Parameter | 50% | 90% |
|---|---|---|
| Cytotoxicity = IC (µg/ml) | 6.8732 | 16.369 |
| Antiviral Activity = EC (µg/ml) | 0.18 | --- |
| Selectivity Index = SI (IC/EC) | 38.18 | --- |

Fig. 53

| VALUES OF COLUMNS | ROW ON PLATE | CONC. (µg/ml) | ANTIVIRAL TEST VALUES | | | CYTOTOXICITY VALUES | | |
|---|---|---|---|---|---|---|---|---|
| | | | MEAN LUC | SD LUC | % CONTROL LUC | MEAN O.O. | SD O.O. | % CONTROL VIABILITY |
| 7 through 12 +n bvc 1,(right side of plate) | C | 0 | 1.22E+02 | 1.81E+01 | 100% | 1.1E+07 | 6.87E+05 | 100% |
| | D | 0.03 | 9.97E+01 | 1.10E+01 | 82% | 1.0E+07 | 1.72E+05 | 96% |
| | E | 0.13 | 6.59E+01 | 6.02E+00 | 54% | 1.2E+07 | 2.04E+05 | 113% |
| | F | 0.04 | 4.21E+01 | 1.82E+00 | 34% | 1.0E+07 | 3.10E+05 | 93% |
| | high G | 3.20 | .28E+01 | 2.81E+00 | 19% | 9.6E+05 | 7.08E+05 | 88% |
| | | 16.00 | 6.50E-01 | 0.27E+01 | 1% | 8.6E+05 | .86E+05 | 8% |

Fig. 54

Fig. 56A
HCV RNA REPLICON LUCIFERASE-BASED ANTIVIRAL EVALUATION

Cell numbers

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   | 2065165 | 2181837 | 2165641 | 2127211 | 2117211 | 2110479 | 2126417 |
| B | 2205484 | 15586300 | 16166425 | 18412973 | 15893525 | 16072533 | 16006133 | 16393528 | 16204289 | 14877013 | 18711764 | 2181302 |
| C | 2264578 |   |   |   |   |   | 16635670 | 16716057 | 15792140 | 17470192 |   | 2188838 |
| D | 2142124 |   |   |   |   |   | 16870370 | 17790676 | 16188039 | 15969188 |   | 2038699 |
| E | 2082930 |   |   |   |   |   | 16948835 | 16678640 | 16310709 | 15521251 |   | 2174734 |
| F | 2059501 |   |   |   |   |   | 15712722 | 15202231 | 14483876 | 13551704 |   | 2049608 |
| G | 2022475 |   |   |   |   |   | 3149339 | 2811146 | 3348007 | 2710606 |   | 2018639 |
| H |   |   |   |   |   | 2044551 | 2096909 | 2024800 | 2092107 | 2101586 | 2098362 | 2175662 |

BOLD – HIGHEST DRUG CONC VALUES SHOWN ARE OPTICAL DENSITIES

Fig. 56B
LUCIFERASE

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C |   | 259.8000 |   |   |   |   |   | 214.1000 | 196.6000 | 218.6000 | 224.4000 | 205.5000 |
| D |   | 258.9000 |   |   |   |   |   | 195.0000 | 166.6000 | 194.8000 | 155.0000 | 190.8000 |
| E |   | 282.4000 |   |   |   |   |   | 130.5000 | 112.4000 | 130.0000 | 112.3000 | 250.8000 |
| F |   | 206.1000 |   |   |   |   |   | 74.3000 | 68.2000 | 73.1000 | 58.5000 | 199.6000 |
| G |   | 238.4000 |   |   |   |   |   | 1.8000 | 1.5000 | 2.0000 | 4.7000 | 253.9000 |
| H |   |   |   |   |   |   |   |   |   |    |    |    |

BOLD – HIGHEST DRUG CONC
VIRUS CONTROL = 234.4000
CV VIRUS CONTROL = 13.4%
CELL CONTROL = 1.4E+07

VALUES SHOWN ARE LUCIFERASE LUMINSENCE
VIRUS          HCV RNA REPLICONS
STRAIN         CON-1
CELLS          HUH-LUC/NEO ET

PASSAGE        25
CV CELL CONTROL = 7.2%

| Parameter | 50% | 90% |
|---|---|---|
| Cytotoxicity = IC (µg/ml) | 6.8864 | 14.820 |
| Antiviral Activity = EC (µg/ml) | 0.73 | --- |
| Selectivity Index = SI (IC/EC) | 8.433 | --- |

Fig. 57

| VALUES OF COLUMNS | ROW ON PLATE | CONC. (µg/ml) | ANTIVIRAL TEST VALUES | | | CYTOTOXICITY VALUES | | |
|---|---|---|---|---|---|---|---|---|
| | | | MEAN LUC | BD LUC | % CONTROL LUC | MEAN O.O. | SD O.O. | % CONTROL VIABILITY |
| 7 through 12 (right side of plate) | C | 0 | 2.34E+02 | 3.14E+01 | 100% | 1.4E+07 | 1.01E+06 | 100% |
| | D | .03 | 2.13E+02 | 1.20E+01 | 91% | 1.5E+07 | 6.68E+05 | 103% |
| | E | 0.13 | 1.78E+02 | 2.02E+01 | 76% | 1.5E+07 | 8.15E+05 | 104% |
| | F | 0.64 | 1.21E+02 | 1.03E+01 | 52% | 1.4E+07 | 7.78E+05 | 98% |
| | | 3.20 | 6.85E+01 | 7.19E+00 | 29% | 1.3E+07 | 9.36E+05 | 90% |
| | high G | 16.00 | 2.66E+00 | 1.44E+00 | 1% | 9.1E+05 | 2.96E+05 | 6% |

HCV RNA REPLICON LUCIFERASE-BASED ANTIVIRAL EVALUATION

Cell numbers

| | 1 | 2 | 3 | 4 | 5 | 6 | 7 | 8 | 9 | 10 | 11 | 12 |
|---|---|---|---|---|---|---|---|---|---|---|---|---|
| A | | | | | | | 2185973 | 217613 | 2151689 | 2134759 | 2169959 | 2132034 | 2174831 |
| B | 2171564 | 17375782 | 17202958 | 17438344 | 17024562 | 17460350 | 16879190 | 16841036 | 17501364 | 16277815 | 17057540 | 2234280 |
| C | 2227805 | | | | | | 17255058 | 15945528 | 16638528 | 17295112 | | 2217147 |
| D | 2176786 | | | | | | 17673810 | 17090648 | 17187694 | 17072574 | | 2178892 |
| E | 2150113 | | | | | | 15641675 | 16136798 | 15861966 | 15937656 | | 2130674 |
| F | 2078638 | | | | | | 14741794 | 14365993 | 13489423 | 14875370 | | 2180609 |
| G | 2100820 | | | | | | 2578071 | 2593187 | 2447397 | 2531048 | | 2029977 |
| H | | | | | | 2059063 | 2084409 | 2141509 | 2154801 | 2133584 | 2185036 | 2153746 |

BOLD – HIGHEST DRUG CONC    VALUES SHOWN ARE OPTICAL DENSITIES

LUCIFERASE

Fig. 60B

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | | 296.1000 | | | | | 252.9000 | 228.8000 | 290.7000 | 259.9000 | 252.6000 | |
| D | | 278.0000 | | | | | 171.1000 | 186.7000 | 218.8000 | 218.500 | 254.1000 | |
| E | | 283.0000 | | | | | 131.5000 | 147.4000 | 154.5000 | 119.5000 | 242.1000 | |
| F | | 298.0000 | | | | | 77.0000 | 71.6000 | 88.4000 | 84.0000 | 257.3000 | |
| G | | 352.0000 | | | | | 1.7000 | 2.2000 | 4.7000 | 5.3000 | 241.3000 | |
| H | | | | | | | | | | | | |

BOLD – HIGHEST DRUG CONC    VALUES SHOWN ARE LUCIFERASE LUMINSENCE

| | | |
|---|---|---|
| VIRUS CONTROL = | 275.5900 | VIRUS  HCV RNA REPLICONS |
| CV VIRUS CONTROL = | 12.4% | STRAIN CON-1 |
| CELL CONTROL = | 1.5E+07 | CELLS  HUH-LUC/NEO ET   CV CELL CONTROL =  2.5% |

| Parameter | 50% | 90% |
|---|---|---|
| Cytotoxicity = IC (µg/ml) | 6.1415 | 13.873 |
| Antiviral Activity = EC (µg/ml) | 0.05 | --- |
| Selectivity Index = SI (IC/EC) | 9.448 | --- |

Fig. 61

| VALUES OF COLUMNS | ROW ON PLATE | CONC. (µg/ml) | ANTIVIRAL TEST VALUES ||| CYTOTOXICITY VALUES |||
|---|---|---|---|---|---|---|---|---|
| | | | MEAN LUC | SD LUC | % CONTROL LUC | MEAN O.O. | SD O.O. | % CONTROL VIABILITY |
| 7 through 12 (right side of plate) | C | 0 | 2.78E+02 | 3.41E+01 | 100% | 1.5E+07 | 3.78E+05 | 100% |
| | D | 0.03 | 2.58E+02 | 2.55E+01 | 94% | 1.5E+07 | 6.34E+05 | 98% |
| | E | 0.13 | 1.00E+02 | 2.38E+01 | 72% | 1.5E+07 | 2.83E+05 | 101% |
| | F | 0.64 | 1.38E+02 | 1.58E+01 | 50% | 1.4E+07 | 2.05E+05 | 92% |
| | | 3.20 | 8.03E+01 | 7.36E+00 | 29% | 1.2E+07 | 6.24E+05 | 82% |
| high | G | 16.00 | 3.53E+00 | 1.70E+01 | 1% | 3.0E+0? | 6.56E+04 | 3% |

Fig. 62

Activity of compound #236 Spiked with 4 µg/ml #25 and 0.8 µg/ml #4 against HIV-1 clinical isolates in fresh human PBMC's

| Virus Isolate | #236 spiked w/ #25 & #4 | | | AZT | | | Dextran Sulfate | | |
|---|---|---|---|---|---|---|---|---|---|
| | IC50 (µg/ml) | TC50 (µg/ml) | TI | IC50 (nM) | TC50 (nM) | TI | IC50 (µg/ml) | TC50 (µg/ml) | TI |
| ROJO | <0.005 | 18.0 | >3600 | 0.7 | >1000 | >1429 | -- | -- | -- |
| MDR 769 | 0.009 | 20.5 | 2278 | -- | -- | -- | 2.56 | >100 | >39.1 |
| G910.6.2.3 | <0.005 | 20.5 | >4100 | -- | -- | -- | 0.36 | >100 | >278 |
| 52-52 | <0.005 | 20.5 | >4100 | -- | -- | -- | 0.25 | >100 | >400 |
| 52-52 | <0.005 | 18.0 | >3600 | 106.9 | >1000 | >9.4 | -- | -- | -- |
| TEKI | <0.005 | 18.0 | >3600 | 8.21 | >1000 | >121.8 | -- | -- | -- |
| BR/92/026 | <0.005 | 18.0 | >3600 | 1.4 | >1000 | >714.3 | -- | -- | -- |

Fig. 64

Comparison of Virus Controls with and without the #25 and #4 Spike

| Virus Isolate | Average Virus Control With Spike (cpm) | Average Virus Control With Spike (cpm) | % Reduction in Virus due to Spike |
|---|---|---|---|
| ROJO | 21418 | 871 | 95.9 |
| MDR 769 | 2345 | 1063 | 54.7 |
| G910.6.2.3 | 5917 | 2996 | 49.4 |
| 52-52 | 8953 | 2444 | 72.7 |
| 52-52 | 8303 | 2026 | 75.6 |
| TEKI | 16551 | 7452 | 55.0 |
| BR/92/026 | 17331 | 3334 | 80.8 |

INHIBITION OF HIV-1 ROJO REPLICATION IN PBMC
BY COMPOUND #236 WITH 4 µg/ml COMPOUND #25 AND 0.8 µg/ml COMPOUND #4

| CONC (µg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| SAMPLE 1 | 30053 | 11179 | 222 | 300 | 424 | 3615 | 212 | 288 | 641 | 252 |
| SAMPLE 2 | 23462 | 775 | 7343 | 739 | 3813 | 556 | 5013 | 2609 | 317 | 180 |
| SAMPLE 3 | 10739 | 3774 | 310 | 607 | 300 | 490 | 2305 | 274 | 1281 | 252 |
| MEAN | 21418.0 | 5242.7 | 2825.0 | 548.7 | 1512.3 | 1553.7 | 2510.0 | 1057.0 | 739.7 | 228.0 |
| %VC | 100.0 | 24.5 | 12.3 | 2.6 | 7.1 | 7.3 | 11.7 | 4.9 | 3.5 | 1.1 |

Fig. 66B

| CONC (µg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| SAMPLE 1 | 128798.6 | 140629.0 | 136450.5 | 143153.3 | 137954.2 | 143156.9 | 132858.0 | 105653.5 | 82402.6 | |
| SAMPLE 2 | 128599.8 | 118852.8 | 136044.0 | 128201.8 | 136861.2 | 141349.0 | 125359.2 | 108655.2 | 79570.1 | 261.4 |
| SAMPLE 3 | 148002.5 | 134150.4 | 130734.0 | 137910.2 | 141843.6 | 143580.1 | 130729.7 | 103405.7 | 65999.5 | 269.3 |
| MEAN | 135133.7 | 131220.7 | 135086.2 | 138421.8 | 138856.3 | 142688.6 | 129649.0 | 105904.8 | 75990.7 | 236.6 |
| %CC | 100.0 | 97.1 | 100.0 | 101.0 | 102.8 | 105.8 | 95.9 | 78.4 | 56.2 | 0.2 |

INHIBITION OF HIV-1 ROJO REPLICATION IN PBMC BY AZT CONTROL

| CONC (nM) | 0.00 | 0.1010 | 0.3200 | 1.000 | 3.160 | 10.00 | 31.82 | 100.00 | 316.20 | 1000.00 |
|---|---|---|---|---|---|---|---|---|---|---|
| SAMPLE 1 | 30053 | 4144 | 28402 | 12344 | 5487 | 9011 | 377 | 198 | 330 | 190 |
| SAMPLE 2 | 23462 | 25089 | 19258 | 2636 | 9004 | 3589 | 620 | 190 | 168 | 168 |
| SAMPLE 3 | 10739 | 19146 | 16642 | 2599 | 9691 | 354 | 258 | 300 | 300 | 242 |
| MEAN | 21418.0 | 16119.7 | 21434.0 | 5859.7 | 8080.7 | 4318.0 | 418.3 | 229.3 | 266.0 | 200.0 |
| %VC | 100.0 | 75.3 | 100.1 | 27.4 | 37.6 | 20.2 | 2.0 | 1.1 | 1.2 | 0.9 |

Fig. 69B

TOXICITY VALUES (THYMIDINE UPTAKE (CPM))

| CONC (nM) | 0.00 | 0.1010 | 0.3200 | 1.000 | 3.160 | 10.00 | 31.62 | 100.00 | 316.20 | 1000.00 |
|---|---|---|---|---|---|---|---|---|---|---|
| SAMPLE 1 | 128798.6 | 130512.0 | 143585.0 | 160628.0 | 176377.0 | 132452.0 | 128041.0 | 107554.0 | 79975.0 | 104895.0 |
| SAMPLE 2 | 128599.8 | 136075.0 | 165458.0 | 104326.0 | 128243.0 | 122506.0 | 278.0 | 97411.0 | 114861.0 | 80940.0 |
| SAMPLE 3 | 148002.5 | 119478.0 | 130595.0 | 117965.0 | 96872.0 | 106556.0 | 98342.0 | 109383.0 | 82864.0 | 82369.0 |
| MEAN | 135133.7 | 128688.3 | 146546.0 | 127639.7 | 133830.7 | 120504.7 | 75553.7 | 104776.0 | 92566.7 | 89334.7 |
| %CC | 100.0 | 95.2 | 108.4 | 94.5 | 99.0 | 88.2 | 55.9 | 77.5 | 68.5 | 66.1 |

INHIBITION OF HIV-1 ROJO REPLICATION IN PBMC BY COMPOUND #236 WITH 4 μg/ml COMPOUND #25 AND 0.8 μg/ml COMPOUND #4

| CONC (μg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| SAMPLE 1 | 1961 | 1713 | 1920 | 1493 | 1449 | 2056 | 878 | 785 | 231 | 180 |
| SAMPLE 2 | 2005 | 1071 | 450 | 849 | 1090 | 659 | 688 | 829 | 295 | 231 |
| SAMPLE 3 | 3070 | 1278 | 702 | 1361 | 922 | 1632 | 578 | 1045 | 519 | 216 |
| MEAN | 2345.3 | 1354.0 | 1024.0 | 1234.3 | 1153.7 | 1449.0 | 714.7 | 886.3 | 348.3 | 209.0 |
| %VC | 100.0 | 57.7 | 43.7 | 52.6 | 49.2 | 61.8 | 30.5 | 37.8 | 14.9 | 8.9 |

Fig. 72B

| CONC (μg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| SAMPLE 1 | 128798.6 | 140629.0 | 138480.5 | 143153.3 | 137954.2 | 143156.9 | 132858.0 | 105653.5 | 82402.6 | 185.0 |
| SAMPLE 2 | 114086.4 | 118882.8 | 136044.0 | 128201.8 | 136661.2 | 141349.0 | 125359.2 | 108655.2 | 79570.1 | 261.4 |
| SAMPLE 3 | 110182.8 | 134150.4 | 130734.0 | 137910.2 | 141843.6 | 143560.1 | 130729.7 | 103405.7 | 65999.5 | 269. |
| MEAN | 117689.3 | 131220.7 | 135086.2 | 136421.8 | 138886.3 | 142688.6 | 129649.0 | 105904.8 | 75990.7 | 238.6 |
| %CC | 100.0 | 111.5 | 114.8 | 115.9 | 118.0 | 121.2 | 110.2 | 90.0 | 6.6 | 0.2 |

TOXICITY VALUES (THYMIDINE UPTAKE (CPM))

Fig. 75A
INHIBITION OF HIV-1 MDR REPLICATION IN PBMC BY DEXTRAN SULFATE CONTROL

| CONC (µg/ml) | RT VALUES (CPM) | | | | | | | |
|---|---|---|---|---|---|---|---|---|
| | 0.00 | 0.0100 | 0.0320 | 0.101 | 0.320 | 1.00 | 3.16 | 10.00 | 31.62 | 100.00 |
| SAMPLE 1 | 1961 | 2101 | 2397 | 1691 | 1888 | 1676 | 1499 | 762 | 403 | 288 |
| SAMPLE 2 | 2006 | 2826 | 2974 | 2193 | 2038 | 1506 | 1174 | 586 | 418 | 359 |
| SAMPLE 3 | 3070 | 3011 | 2027 | 2319 | 1432 | 1617 | 561 | 681 | 469 | 374 |
| MEAN | 2345.3 | 2646.0 | 2466.0 | 2067.7 | 1779.3 | 1599.7 | 1078.0 | 676.3 | 430.0 | 339.7 |
| %VC | 100.0 | 112.8 | 105.1 | 88.2 | 75.9 | 68.2 | 48.0 | 28.8 | 18.3 | 14.5 |

Fig. 75B

| CONC (µg/ml) | TOXICITY VALUES (THYMIDINE UPTAKE (CPM)) | | | | | | | |
|---|---|---|---|---|---|---|---|---|
| | 0.00 | 0.0100 | 0.0320 | 0.101 | 0.320 | 1.00 | 3.16 | 10.00 | 31.62 | 100.00 |
| SAMPLE 1 | 128798.6 | 112637.0 | 100000.6 | 110051.2 | 117448.8 | 129012.8 | 115722.6 | 105502.6 | 113566.6 | 123618.8 |
| SAMPLE 2 | 114086.4 | 114123.8 | 111911.8 | 122434.2 | 131352.2 | 117167.4 | 110507.8 | 107314.2 | 110475.4 | 131567.8 |
| SAMPLE 3 | 110182.8 | 113521.8 | 112259.0 | 113265.6 | 127331.4 | 116953.2 | 119954.8 | 108235.4 | 112574.0 | 142906.4 |
| MEAN | 117689.3 | 113427.5 | 108057.1 | 115250.3 | 125377.5 | 121044.5 | 115395.0 | 107017.4 | 112205.3 | 132697.6 |
| %CC | 100.0 | 96.4 | 91.8 | 97.9 | 106.5 | 102.7 | 98.1 | 90.9 | 95.3 | 112.8 |

INHIBITION OF HIV-1 G910.6.2.3 REPLICATION IN PBMC
BY COMPOUND #236 WITH 4 µg/ml COMPOUND #25 AND 0.8 µg/ml COMPOUND #4

| CONC (µg/ml) | \ | \ | \ | \ | \ | \ | \ | \ | \ |
|---|---|---|---|---|---|---|---|---|---|
| | 0.00 | 0.005 | 0.02 | 0.05 | 0.18 | 0.50 | 1.58 | 5.00 | 15.81 | 50.00 |

| | 0.00 | 0.005 | 0.02 | 0.05 | 0.18 | 0.50 | 1.58 | 5.00 | 15.81 | 50.00 |
|---|---|---|---|---|---|---|---|---|---|---|
| SAMPLE 1 | 4824 | 716 | 3087 | 1295 | 2517 | 2291 | 212 | 1614 | 281 | 166 |
| SAMPLE 2 | 5349 | 1758 | 2873 | 1420 | 2064 | 1522 | 688 | 490 | 360 | 166 |
| SAMPLE 3 | 7577 | 1765 | 1337 | 600 | 1625 | 768 | 256 | 1369 | 317 | 159 |
| MEAN | 5916.7 | 1413.0 | 2432.3 | 1105.0 | 2068.7 | 1527.0 | 385.3 | 1157.7 | 319.3 | 163.7 |
| %VC | 100.0 | 23.9 | 41.1 | 16.7 | 35.0 | 25.8 | 6.5 | 19.6 | 5.4 | 2.8 |

RT Values (cpm)

Fig. 78B

TOXICITY VALUES (Thymidine Uptake (CPM))

| CONC (µg/ml) | 0.00 | 0.005 | 0.02 | 0.05 | 0.16 | 0.50 | 1.5? | 5.00 | 15.81 | 50.00 |
|---|---|---|---|---|---|---|---|---|---|---|
| SAMPLE 1 | 128798.6 | 140629.0 | 138480.5 | 143153.3 | 137954.2 | 143156.9 | 132858.0 | 105653.5 | 82402.6 | 185.0 |
| SAMPLE 2 | 114086.4 | 118882.8 | 136044.0 | 128201.6 | 136861.2 | 141349.0 | 125359.2 | 108655.2 | 79570.1 | 261.4 |
| SAMPLE 3 | 110182.8 | 134150.4 | 130734.0 | 137910.2 | 141843.6 | 143560.1 | 130729.7 | 103405.7 | 65999.5 | 269.3 |
| MEAN | 117689.3 | 131220.7 | 135086.2 | 136421.8 | 138886.3 | 142688.6 | 129649.0 | 105904.8 | 75990.7 | 238.6 |
| %CC | 100.0 | 111.5 | 114.8 | 115.9 | 118.0 | 121.2 | 110.2 | 90.0 | 64.6 | 0.2 |

Fig. 79

| IC50 (µg/ml) = <0.00500 | TC50 (µg/ml) = 20.5 | TI = >4100.00 |
|---|---|---|

INHIBITION OF HIV-1 G910.6.2.3 REPLICATION IN PBMC BY DEXTRAN SULFATE CONTROL

Fig. 81A

| | | | | | RT Values (cpm) | | | | | |
|---|---|---|---|---|---|---|---|---|---|---|
| CONC (μg/ml) | 0.00 | 0.0100 | 0.0320 | 0.101 | 0.320 | 1.00 | 3.16 | 10.00 | 31.62 | 100.00 |
| SAMPLE 1 | 4824 | 3655 | 3655 | 2939 | 2370 | 1831 | 1263 | 344 | 234 | 132 |
| SAMPLE 2 | 5349 | 4683 | 4632 | 3574 | 3463 | 3123 | 1093 | 527 | 176 | 66 |
| SAMPLE 3 | 7577 | 5231 | 4062 | 5435 | 3153 | 2961 | 1181 | 483 | 190 | 95 |
| MEAN | 5916.7 | 4523.0 | 4116.3 | 3882.7 | 2995.3 | 2638.3 | 1179.0 | 451.3 | 200.0 | 97.7 |
| %VC | 100.0 | 76.4 | 69.6 | 67.3 | 50.6 | 44.6 | 19.9 | 7.6 | 3.4 | 1.7 |

Fig. 81B

| | | | | | TOXICITY VALUES (Thymidine Uptake (CPM)) | | | | | |
|---|---|---|---|---|---|---|---|---|---|---|
| CONC (μg/ml) | 0.00 | 0.0100 | 0.0320 | 0.101 | 0.320 | 1.00 | 3.16 | 10.00 | 31.62 | 100.00 |
| SAMPLE 1 | 128798.6 | 112637.0 | 100000.6 | 110051.2 | 117448.8 | 129012.8 | 115722.6 | 105602.6 | 113566.6 | 123618.6 |
| SAMPLE 2 | 114086.4 | 114123.8 | 11911.8 | 122434.2 | 131352.2 | 117167.4 | 110507.6 | 107314.2 | 110475.4 | 131587.6 |
| SAMPLE 3 | 110182.8 | 113521.5 | 122259.0 | 113265.6 | 127331.4 | 116953.2 | 119954.8 | 108235.4 | 112574.0 | 142906.4 |
| MEAN | 117689.3 | 113427.5 | 106057.1 | 115250.3 | 125377.5 | 121044.5 | 115392.0 | 107017.4 | 112205.3 | 132697.? |
| %CC | 100.0 | 96.4 | 91.8 | 97.9 | 108 | 102.9 | 98.1 | 90.9 | 95.3 | 112.8 |

Fig. 82

| IC50 (μg/ml) = 0.36 | TC50 (μg/ml) = >100.0 | TI = >277.78 |

Fig. 84A

INHIBITION OF HIV-1 52-52 REPLICATION IN PBMC
BY COMPOUND #236 WITH 4 µg/ml COMPOUND #25 AND 0.8 µg/ml COMPOUND #4

| CONC (µg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| | | | | RT Values (cpm) | | | | | | |
| SAMPLE 1 | 7844 | 2829 | 1351 | 1668 | 1295 | 1471 | 1141 | 872 | 410 | 281 |
| SAMPLE 2 | 8928 | 2378 | 2393 | 1800 | 1507 | 1529 | 1185 | 720 | 346 | 360 |
| SAMPLE 3 | 10087 | 1817 | 2445 | 1595 | 2064 | 1237 | 498 | 901 | 267 | 267 |
| MEAN | 8953.0 | 2341.3 | 2063.0 | 1687.7 | 1622.0 | 1412.3 | 941.3 | 831.0 | 341.0 | 302.7 |
| %VC | 100.0 | 26.2 | 23.0 | 18.9 | 18.1 | 15.8 | 10.5 | 9.3 | 3.8 | 3.4 |

Fig. 84B

| CONC (µg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| | | | | TOXICITY VALUES (Thymidine Uptake (CPM)) | | | | | | |
| SAMPLE 1 | 128798.5 | 140629.0 | 138480.5 | 143153.3 | 137954.2 | 143156.9 | 132958.0 | 105653.5 | 82402.6 | 185.0 |
| SAMPLE 2 | 114086.4 | 118882.8 | 136044.0 | 128201.8 | 136861.2 | 141349.0 | 125359.2 | 108655.2 | 79570.1 | 261.4 |
| SAMPLE 3 | 110182.8 | 134150.4 | 130734.0 | 137910.2 | 141843.6 | 143560.1 | 130729.7 | 103405.7 | 65999.5 | 269.3 |
| MEAN | 117689.3 | 131220.7 | 135086.2 | 136421.8 | 138886.3 | 142688.6 | 129649.0 | 105904.8 | 75990.7 | 238.8 |
| %CC | 100.0 | 111.5 | 114.8 | 115.9 | 118.0 | 121.2 | 110.2 | 90.0 | 64.6 | 0.2 |

INHIBITION OF HIV-1 52-52 REPLICATION IN PBMC
BY DEXTRAN SULFATE CONTROL

| | RT Values (cpm) | | | | | | | | |
|---|---|---|---|---|---|---|---|---|---|
| CONC (μg/ml) | 0.00 | 0.0100 | 0.0320 | 0.101 | 0.320 | 1.00 | 3.18 | 10.00 | 31.62 | 100.00 |
| SAMPLE 1 | 7844 | 5853 | 4402 | 4741 | 4423 | 3773 | 1122 | 586 | 381 | 264 |
| SAMPLE 2 | 8928 | 6845 | 6793 | 4867 | 5004 | 2688 | 1248 | 469 | 307 | 381 |
| SAMPLE 3 | 10087 | 8059 | 6541 | 5354 | 3603 | 1595 | 1233 | 535 | 330 | 205 |
| MEAN | 8953.0 | 6919.0 | 5912.0 | 4987.3 | 4343.3 | 2685.3 | 1201.0 | 530.0 | 339.3 | 283.3 |
| %VC | 100.0 | 77.3 | 66.0 | 55.7 | 48 | 30.0 | 13.4 | 5.9 | 3.8 | 3.2 |

Fig. 87B

| | TOXICITY VALUES (Thymidine Uptake (CPM)) | | | | | | | | |
|---|---|---|---|---|---|---|---|---|---|
| CONC (μg/ml) | 0.00 | 0.0100 | 0.0320 | 0.101 | 0.320 | 1.00 | 3.16 | 10.00 | 31.62 | 100.00 |
| SAMPLE 1 | 128798.6 | 112637.0 | 100000.6 | 110051.2 | 117448.8 | 129012.8 | 115722.6 | 105502.6 | 113566.6 | 123618.6 |
| SAMPLE 2 | 114086.4 | 114123.8 | 111911.8 | 122434.2 | 131352.2 | 117167.4 | 110507.6 | 107314.2 | 110475.4 | 131567.8 |
| SAMPLE 3 | 110182.8 | 113521.8 | 122259.0 | 113265.6 | 127331.4 | 116953.2 | 119954.8 | 108235.4 | 112574.0 | 142906.4 |
| MEAN | 117689.3 | 113427.5 | 108057.1 | 115250.3 | 125377.5 | 121044.5 | 115395.0 | 107017.4 | 112205.3 | 132697.6 |
| %CC | 100.0 | 96.4 | 91.8 | 97.9 | 108.5 | 102 | 98.1 | 90 | 95.3 | 112.8 |

INHIBITION OF HIV-1 52-52 REPLICATION IN PBMC
BY COMPOUND #236 WITH 4 μg/ml COMPOUND #25 AND 0.8 μg/ml COMPOUND #4

| CONC (μg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| SAMPLE 1 | 6570 | 1152 | 1484 | 1120 | 1434 | 1910 | 959 | 395 | 216 | 223 |
| SAMPLE 2 | 9613 | 1418 | 1448 | 1178 | 1112 | 1595 | 1098 | 389 | 259 | 252 |
| SAMPLE 3 | 8725 | 3043 | 2223 | 1749 | 1112 | 1632 | 1112 | 865 | 317 | 331 |
| MEAN | 8302.7 | 1871.0 | 1718.3 | 1349.0 | 1219.3 | 1712.3 | 1056.3 | 550.0 | 264.0 | 268.7 |
| %VC | 100.0 | 22.5 | 20.7 | 18.2 | 14.7 | 20.6 | 12.7 | 8.6 | 3.2 | 3.2 |

RT Values (cpm)

Fig. 90B

| CONC (μg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| SAMPLE 1 | 128798.6 | 140629.0 | 138480.5 | 143153.3 | 137954.2 | 143156.9 | 132858.0 | 105653.5 | 82402.6 | 185.0 |
| SAMPLE 2 | 128599.8 | 118882.8 | 136044.0 | 128201.8 | 136861.2 | 141349.0 | 125559.2 | 108655.2 | 79570.1 | 261.4 |
| SAMPLE 3 | 148002.5 | 134150.4 | 130734.0 | 137910.2 | 141843.8 | 143560.1 | 130729.7 | 103405.7 | 65999.5 | 269.3 |
| MEAN | 135133.7 | 131220.7 | 135085.2 | 136421.8 | 138886.3 | 142688.6 | 129649.0 | 105904.8 | 75990.7 | 238.6 |
| %CC | 100.0 | 97.1 | 100.0 | 101.0 | 102.8 | 105.6 | 95.9 | 78.4 | 56.2 | 0.2 |

TOXICITY VALUES (Thymidine Uptake (CPM))

Fig. 91

| IC50 (μg/ml) = <0.00500 | TC50 (μg/ml) = 18.0 | TI = >3600.00 |
|---|---|---|

Fig. 93A

INHIBITION OF HIV-1 52-52 REPLICATION IN PBMC BY AZT CONTROL

| CONC (nM) | | | | | RT Values (cpm) | | | | |
|---|---|---|---|---|---|---|---|---|---|
| | 0.00 | 0.1010 | 0.3200 | 1.000 | 3.160 | 10.00 | 31.62 | 100.00 | 316.20 | 1000.00 |
| SAMPLE 1 | 5570 | 7318 | 6319 | 6868 | 7142 | 4999 | 4970 | 3457 | 2329 | 425 |
| SAMPLE 2 | 9613 | 7163 | 7496 | 7438 | 5805 | 7230 | 4366 | 5092 | 3384 | 2600 |
| SAMPLE 3 | 8725 | 10472 | 8369 | 7068 | 7186 | 7799 | 4741 | 4168 | 2461 | 3128 |
| MEAN | 8302.7 | 8317.7 | 7394.7 | 7124.7 | 6711.0 | 6676.0 | 4699.0 | 4239.0 | 2724.7 | 2051.0 |
| %VC | 100.0 | 100.2 | 89.1 | 85.8 | 80.8 | 80.4 | 56.6 | 51.1 | 32.8 | 24.7 |

Fig. 93B

| CONC (nM) | | | | | TOXICITY VALUES (Thymidine Uptake (CPM)) | | | | |
|---|---|---|---|---|---|---|---|---|---|
| | 0.00 | 0.1010 | 0.3200 | 1.000 | 3.160 | 10.00 | 31.62 | 100.00 | 316.20 | 1000.00 |
| SAMPLE 1 | 128798.6 | 130512.0 | 143585.0 | 160628.0 | 176377.0 | 132452.0 | 128041.0 | 107554.0 | 79975.0 | 104695.0 |
| SAMPLE 2 | 128599.8 | 136075.0 | 165458.0 | 104325.0 | 128243.0 | 122506.0 | 278.0 | 97411.0 | 114861.0 | 80940.0 |
| SAMPLE 3 | 148002.5 | 119478.0 | 130595.0 | 117965.0 | 96872.0 | 106556.0 | 98342.0 | 109363.0 | 82884.0 | 82369.0 |
| MEAN | 135133.7 | 128688.3 | 146546.0 | 127839.7 | 133830.7 | 120504.7 | 75553.7 | 104776.0 | 92566.7 | 89334.7 |
| %CC | 100.0 | 95.2 | 108.4 | 94.5 | 99.0 | 89.2 | 55 | 77.5 | 68.5 | 66.1 |

INHIBITION OF HIV-1 TEKI REPLICATION IN PBMC
BY COMPOUND #236 WITH 4 µg/ml COMPOUND #25 AND 0.8 µg/ml COMPOUND #4

| CONC (µg/ml) | 0.00 | 0.005 | 0.02 | 0.05 | 0.16 | 0.50 | 1.58 | 5.00 | 15.21 | 50.00 |
|---|---|---|---|---|---|---|---|---|---|---|
| SAMPLE 1 | 18509 | 5954 | 8038 | 6287 | 7935 | 4706 | 6448 | 2313 | 1146 | 86 |
| SAMPLE 2 | 13857 | 5806 | 4868 | 3535 | 3388 | 3915 | 2803 | 1751 | 1038 | 101 |
| SAMPLE 3 | 17286 | 8939 | 4993 | 4150 | 5738 | 6727 | 2664 | 2565 | 1427 | 151 |
| MEAN | 16550.7 | 6899.7 | 5986.3 | 4657.3 | 5687.0 | 5116.0 | 3971.7 | 2209.7 | 1203.7 | 112.7 |
| %VC | 100.0 | 41.7 | 36.0 | 28.1 | 34.4 | 30.9 | 24.0 | 13.4 | 7.3 | 0.7 |

Fig. 96B

TOXICITY VALUES (Thymidine Uptake (CPM))

| CONC (µg/ml) | 0.00 | 0.005 | 0.02 | 0.05 | 0.16 | 0.50 | 1.58 | 5.00 | 15.81 | 50.00 |
|---|---|---|---|---|---|---|---|---|---|---|
| SAMPLE 1 | 128798.6 | 140629.0 | 138480.5 | 143153.3 | 137954.2 | 143156.9 | 132858.0 | 105653.5 | 82402.6 | 185.0 |
| SAMPLE 2 | 128599.8 | 118882.8 | 136044.0 | 128201.8 | 136881.2 | 141349.0 | 125359.2 | 108855.2 | 79570.1 | 261.2 |
| SAMPLE 3 | 148002.5 | 134150.4 | 130734.0 | 137910.2 | 141843.6 | 143560.1 | 130729.7 | 103405.7 | 65999.5 | 269.3 |
| MEAN | 135133.7 | 131220.7 | 135086.2 | 136421.8 | 138886.3 | 142688.6 | 129649.0 | 105904.8 | 75990.7 | 238.8 |
| %CC | 100.0 | 97.1 | 100.0 | 101.0 | 102.8 | 105.6 | 95.9 | 78.4 | 56.2 | 0.2 |

INHIBITION OF HIV-1 TEKI REPLICATION IN PBMC BY AZT CONTROL

| CONC (nM) | 0.00 | 0.1010 | 0.3200 | 1.000 | 3.160 | 10.00 | 31.62 | 100.00 | 316.20 | 1000.00 |
|---|---|---|---|---|---|---|---|---|---|---|
| | | | | RT Values (cpm) | | | | | | |
| SAMPLE 1 | 18509 | 16575 | 12057 | 12292 | 14081 | 9404 | 2113 | 1139 | 608 | 249 |
| SAMPLE 2 | 13857 | 12857 | 15960 | 14570 | 11058 | 7038 | 2930 | 1773 | 344 | 198 |
| SAMPLE 3 | 17286 | 14827 | 17701 | 15509 | 14126 | 5412 | 2895 | 798 | 557 | 125 |
| MEAN | 16550.7 | 14753.0 | 15239.3 | 14123.7 | 13088.3 | 7284.7 | 2646.0 | 1236.7 | 503.0 | 190.7 |
| %VC | 100.0 | 89.1 | 92.1 | 85.3 | 79.1 | 44.0 | 18.0 | 7.5 | 3.0 | 1.2 |

Fig. 99B

| CONC (nM) | 0.00 | 0.1010 | 0.3200 | 1.000 | 3.160 | 10.00 | 31.62 | 100.00 | 316.20 | 1000.00 |
|---|---|---|---|---|---|---|---|---|---|---|
| | | | | TOXICITY VALUES (Thymidine Uptake (CPM)) | | | | | | |
| SAMPLE 1 | 128798.6 | 130512.0 | 143585.0 | 160628.0 | 176377.0 | 132452.0 | 128041.0 | 107554.0 | 79975.0 | 104695.0 |
| SAMPLE 2 | 128599.8 | 136075.0 | 165458.0 | 104326.0 | 128243.0 | 122508.0 | 278.0 | 97411.0 | 114861.0 | 80940.0 |
| SAMPLE 3 | 148002.5 | 119478.0 | 130595.0 | 117965.0 | 96872.0 | 106556.0 | 98342.0 | 109363.0 | 82884.0 | 82369.0 |
| MEAN | 135133.7 | 128688.3 | 146546.0 | 127639.7 | 133830.7 | 120504.7 | 75553.7 | 104776.0 | 92566.7 | 89334.7 |
| %CC | 100.0 | 95.2 | 108.4 | 94.5 | 99.0 | 89.2 | 55.9 | 77.5 | 68.5 | 66.1 |

Fig. 100

| IC50 (nM) = 8.21 | TC50 (nM) = >1000.0 | TI = >121.80 |
|---|---|---|

Fig. 102A

INHIBITION OF HIV-1 BR/92/026 REPLICATION IN PBMC
BY COMPOUND #236 WITH 4 μg/ml COMPOUND #25 AND 0.8 μg/ml COMPOUND #4

| CONC (μg/ml) | RT Values (cpm) | | | | | | | | |
|---|---|---|---|---|---|---|---|---|---|
| | 0.00 | 0.005 | 0.02 | 0.05 | 0.16 | 0.50 | 1.58 | 5.00 | 15.81 | 50.00 |
| SAMPLE 1 | 18768 | 3331 | 2607 | 3037 | 2649 | 1749 | 995 | 735 | 216 | 166 |
| SAMPLE 2 | 13939 | 2282 | 2585 | 1742 | 1281 | 1829 | 1354 | 1052 | 156 | 216 |
| SAMPLE 3 | 19287 | 3641 | 2888 | 2554 | 235? | 1778 | 1171 | 778 | 375 | 245 |
| MEAN | 17331.3 | 3084.7 | 2693.3 | 2444.3 | 2095.3 | 1785.3 | 1173.3 | 855.0 | 252.3 | 209.0 |
| %VC | 100.0 | 17.8 | 15.5 | 14.1 | 12.1 | 10.3 | 6.7 | 4.9 | 1.5 | 1.2 |

Fig. 102B

| CONC (μg/ml) | TOXICITY VALUES (Thymidine Uptake (CPM)) | | | | | | | | |
|---|---|---|---|---|---|---|---|---|---|
| | 0.00 | 0.005 | 0.02 | 0.05 | 0.16 | 0.50 | 1.58 | 5.00 | 15.81 | 50.00 |
| SAMPLE 1 | 128796.6 | 140629.0 | 138480.5 | 143153.3 | 137954.2 | 143156.9 | 132858.0 | 105653.5 | 82402.6 | 185.0 |
| SAMPLE 2 | 128599.8 | 118882.8 | 136044.0 | 128201.8 | 136861.2 | 141349.0 | 125359.2 | 108655.2 | 79570.1 | 261.2 |
| SAMPLE 3 | 148002.5 | 134150.4 | 130734.0 | 137910.2 | 141843.6 | 143560.1 | 130729.7 | 103405.7 | 65999.5 | 269.3 |
| MEAN | 135133.7 | 131220.7 | 135086.2 | 136421.8 | 138886.3 | 142688.6 | 129649.0 | 105904.8 | 75990.7 | 238.6 |
| %CC | 100.0 | 97.1 | 100.0 | 101.0 | 102.8 | 105.6 | 95.9 | 78.4 | 56.2 | 0.2 |

Fig. 105A INHIBITION OF HIV-1 BR/92/026 REPLICATION IN PBMC BY AZT CONTROL

| CONC (nM) | 0.00 | 0.1010 | 0.3200 | 1.000 | 3.180 | 10.00 | 31.62 | 100.00 | 316.20 | 1000.00 |
|---|---|---|---|---|---|---|---|---|---|---|
| | | | | | RT Values (cpm) | | | | | |
| SAMPLE 1 | 18768 | 11228 | 12339 | 9028 | 5155 | 2791 | 546 | 330 | 256 | 286 |
| SAMPLE 2 | 13939 | 15561 | 10220 | 10313 | 4150 | 1469 | 458 | 432 | 271 | 242 |
| SAMPLE 3 | 19287 | 15512 | 16649 | 11265 | 5391 | 613 | 354 | 308 | 256 | 154 |
| MEAN | 17331.3 | 14133.7 | 13069.3 | 10201.3 | 4898.7 | 1624.3 | 452.7 | 356.7 | 281.0 | 227.3 |
| %VC | 100.0 | 81.5 | 75.4 | 58.9 | 28.3 | 9.4 | 2.6 | 2.1 | 1.5 | 1.3 |

Fig. 105B

| CONC (nM) | 0.00 | 0.1010 | 0.3200 | 1.000 | 3.160 | 10.00 | 31.62 | 100.00 | 316.20 | 1000.00 |
|---|---|---|---|---|---|---|---|---|---|---|
| | | | | TOXICITY VALUES (Thymidine Uptake (CPM)) | | | | | | |
| SAMPLE 1 | 128798.6 | 130512.0 | 143585.0 | 160628.0 | 176377.0 | 132452.0 | 128041.0 | 107554.0 | 79975.0 | 104695.0 |
| SAMPLE 2 | 128599.8 | 136075.0 | 165458.0 | 104326.0 | 128243.0 | 122506.0 | 278.0 | 97411.0 | 114861.0 | 80940.0 |
| SAMPLE 3 | 148002.5 | 119478.0 | 130595.0 | 117965.0 | 96872.0 | 106556.0 | 98342.0 | 109363.0 | 82884.0 | 82369.0 |
| MEAN | 135133.7 | 128688.3 | 146546.0 | 127639.7 | 133830.7 | 120504.7 | 75553.7 | 104776.0 | 92566.7 | 89334.7 |
| %CC | 100.0 | 95.2 | 108.4 | 94.5 | 99.0 | 89.2 | 55.9 | 77.5 | 68.5 | 66.1 |

COMPOSITIONS AND METHODS OF USE FOR TREATMENT OF MAMMALIAN DISEASES

RELATED APPLICATIONS

This application is a continuation-in-part of application Ser. No. 10/888,576 filed Jul. 9, 2004 for Anti Tumor Compositions and Methods of Use and Claims, now U.S. Pat. No. 7,449,196 B1 issued Nov. 11, 2008, priority under 35 U.S.C. 120 therefrom. This application is also based in part upon provisional application No. 60/598,179 filed on Aug. 2, 2004 for Compositions and Method of Treatment of Viral Ailments and upon provisional application No. 60/666,135, filed on Mar. 29, 2005 for Compositions For Use With Microbe and Vector-borne Diseases and Methods of Use, and claims benefit under 35 U.S.C. 119(e) therefrom.

TECHNICAL FIELD

The present disclosure relates to pharmaceutical compositions, methods of use and methods of manufacture. These compositions are useful for the treatment of a wide variety of ailments and infections in mammals including cancer, viral infections such as hepatitis or HIV, infectious viral disease such as Ebola, microbe-borne conditions, malaria, and smallpox and other diseases caused by infectious microorganisms, including bacteria.

BACKGROUND

All patents, scientific articles, and other documents mentioned herein are incorporated by reference as if reproduced in full below. Cancer is the rapid and uncontrolled proliferation of new cells within a body, and is a leading cause of death in animals, including humans. This proliferation far exceeds the normal level of apoptosis, the physiological process essential to normal development and homeostasis of multicellular organisms. (Stellar, Science 267:1445-1449 (1995)).

Chemotherapy, often used in conjunction with radiation treatments and surgery, is a standard cancer treatment used today. Chemotherapy is generally understood to mean medications or drugs that destroy cancer cells. Presently, there are over one hundred drugs used in various combinations to treat cancer. (The American Cancer Society, *Consumers Guide to Cancer Drugs*, Jones and Bartlett Publishers, (2000)). "All these drugs have one characteristic in common. They work because they're poisons." (Moss, *Questioning Chemotherapy*, Equinox Press, pg. 77, (2000)). Chemotherapeutic agents are highly toxic and typically have narrow therapeutic indices. These agents exhibit little specificity for malignant cells, and they cannot discriminate effectively between normal and malignant cells. Consequently, all cells and tissues, and especially rapidly proliferating cells, such as the bone marrow cells, the spermatogonia, and the gastrointestinal crypt epithelium cells, are very vulnerable. (Baquiran, *Cancer Chemotherapy Handbook*, Lippincott, pg. 85 (2001)). Moreover, the side effects of chemotherapy can be horrific, as is well known to those of skill in the art and to those unfortunate enough to have the art practiced upon them. (The American Cancer Society, *Consumers Guide to Cancer Drugs*, Jones and Bartlett Publishers, (2000)). See also, (Baquiran, *Cancer Chemotherapy Handbook*, Lippincott, p 85 (2001)); (Chu & Devita, *Physicians' Cancer Chemotherapy Drug Manual*, 2003, Jones and Bartlett Publishers, (2003)); (Lance Armstrong, *It's Not About the Bike*, Berkley Publishing, (2000)), (King, King and Pearlroth, *Cancer Combat*, Bantam Books, (1998)); (Rich, *The Red Devil*, Three Rivers Press, (1999)); and (Marchione, *Hopes in cancer drug dashed*, Milwaukee Journal Sentinel, May 22, (2002)). Current cancer treatments including chemotherapy do not generally work well with solid tumors. (Moss, *Questioning Chemotherapy*, Updated Edition, Equinox Press, 2000:18) and (Masters and Koberle, in *Curing Metastatic Cancer: Lessons from Testicular Germ-Cell Tumours*, Nature Reviews, 3(7) (July 2003)).

Resistance can develop to chemotherapeutic agents, causing the agents to work for some types of cancer, but not for others, or not work at all. Resistance has been demonstrated to every single chemotherapeutic agent ever developed. This resistance may be innate, acquired or emergent resistance. (Chu & Devita; *Physicians' Cancer Chemotherapy Drug Manual*, 2003, Jones and Bartlett Pub. (2003)). In addition, it has been commonly assumed that combining chemotherapeutic agents will result in regimens with superior response rates. However, a study demonstrated that chemotherapy agents, used either in sequence or in combination for metastatic breast cancer, provided equivalent results with regard to survival and quality of life was measured. (Sledge, et al., *Phase III, Trial of Doxorubicin, paclitaxel, and the combination of doxorubicin and paclitaxel as front-line chemotherapy for metastatic breast cancer: an intergroup trial*, J. of Clin. Oncology, 21 (4):588-592 (February 2003)).

Additionally, a study utilizing four of the newer chemotherapy regimens and drugs produced a two-year survival rate of 11% and substantial toxicity. The response and survival rate did not differ significantly amongst the four groups treated with the different regimens for advanced non-small-cell lung cancer. (Schiller, et al., *Comparison of Four Chemotherapy Regimens for Advanced Non-Small-Cell Lung Cancer*, The N. Eng. J. of Med., 346(2):92-98 (January 2002)).

Cancer cells are well known to have a higher glucose uptake and metabolism, and the resulting enhanced glycolysis can serve as an indication of a malignant transformation. (Mehvar, *Dextrans for targeted and sustained delivery of therapeutic and imaging agents*, J. of Controlled Release, 69:1-25 (2000)); (Essner, et al., *Advances in FDG PET Probes in Surgical Oncology*, Cancer Jour. 8:100-108 (2002)). Cancer cells utilize and metabolize glucose at high rates, (even in the presence of high oxygen concentrations) forming mostly lactate. (Warburg, O., *On The Origin of Cancer Cells*, Science 123 (3191): 309-314 (February 1956)). Lactate, therefore, is detected in cancer cells at much higher levels than in the corresponding normal tissues. (Rivenzon-Segal, et. al., *Glycolysis as a metabolic marker in orthotopic breast cancer, monitored by in vivo 13C MRS*, Amer. J. Phys. Endocrinology Metabolism, 283: E623-E630 (2002); See also, (Lee and Pedersen, *Glucose Metabolism in Cancer*, J. of Biol. Chem. 278 (42):41047-41058 (October 2003)); (Gatenby and Gawlinski, *The glycolysis phenotype in carcinogenesis and tumor invasion: insights through mathematical models*, Cancer Res., 63(14):3847-54 (July 2003)); (Degani, *The American Society of Clinical Oncology*, Intn'l J. of Cancer, 107:177-182 (November 2003)); (Warburg, O. *The Prime Cause and Prevention of Cancer*, Konrad Triltsch, p 6. (1969)). Glucose typically enters most cells by facilitated diffusion through one of a family of glucose transporters. (Katzung, *Basic & Clinical Pharmacology*, McGraw Hill Co. Inc., pg. 715 (2001)). Glucose forms that are incompatible with these transporters can be taken in by phagocytosis, also known as endocytosis, either by a cell of the phagocytic system or a cell associated with a tissue. The phagocytic system, also known as the reticuloendothelial system ("RES"), or the mononuclear phagocyte system ("MPS"), is a diffuse system, which includes the fixed macrophages of tissues, liver, spleen, lymph nodes and bone marrow, along with the fibroblastic reticular cells of hemotopoietic tissues.

Glucose initiates, promotes, drives and amplifies the growth and metastasis of tumor cells. Anaerobic glycolosis favored by tumor cells, is a very inefficient and primitive process to produce ATP, requiring prodigious amounts of glucose. Thus, the scientific community is currently working on ways to deprive tumor cells of glucose. (Van Dang et al, The Proc. of the Nat'l Acad. of Sci. 95:1511-1516 (1998)). (Pedersen, *Inhibiting glycolysis and oxidative phosphorylation, 3-BrPA abolishes cell ATP production*, Reuters News, (Jul. 18, 2002)). An in vivo murine study on xenograft models of human osteosarcoma and non-small cell lung cancer found that the glycolytic inhibitor 2-deoxy-D-glucose in combination with adriamycin or paxlitaxel, resulted in significant slower tumor growth. (Maschek, et al., *2-deoxy-D-glucose increases the efficacy of adriamycin and paclitaxel in human osteosarcoma and non-small cell lung cancers in vivo*, Cancer Res., 64(1):31-34 (2004)). In addition, positive clinical results have been found with the anti-cachexia drug, hydrazine sulfate, which inhibits neoglucogenesis. (Moss, *Cancer Therapy*, Equinox Press, p 316 (1992)). Many dietary modifications directed at depriving cancer cells of glucose have also been studied. (Quillin, *Beating Cancer with Nutrition*, Nutrition Times Press, p 225 (1998)); (Quillin, *Cancer's Sweet Tooth*, Nutrition Science News, (April 2000)); and (Hauser & Hauser, *Cancer-Treating Cancer with Insulin Potentiation Therapy*, Beulah Land Press, (2001)).

Copper (Cu), is an essential trace element, and necessary for life in organisms ranging from bacteria to mammals. Copper promotes and is an essential co-factor for angiogenesis, a requirement for the growth of cancer, especially solid tumors. (Brewer, *Handbook of Copper Pharmacology and Toxicology*, Humana Press, Chap. 27, (2002)); (Brem, *Angiogenesis and Cancer Control: From Concept to Therapeutic Trial*, Cancer Control Jour., 6 (5):436-458 (1999). Since angiogenesis is generally not required in adults, the inhibition of angiogenesis through copper removal, copper reduction therapy, or copper withholding, has been explored as a possible mechanism for inhibiting further tumor growth. (Brewer, supra); See, also U.S. Pat. No. 6,703,050 of Brewer et al. Tumors of many types have a great need for copper and sequester copper, because copper is an essential cofactor for angiogenesis and proliferation. (Brewer, *Copper Control as an Antiangiogenic Anticancer Therapy: Lessons from Treating Wilson's Disease*, Exp. Bio. and Med., 226(7):665-673 (2001)). Because of this avidity for copper, and effects of copper promoting tumor initiation, growth and metastasis, the scientific community continues to develop methods and pharmaceuticals of withholding copper from tumor cells. (Brem, supra); (Brewer, supra); (Brewer, et al., *Treatment of Metastatic Cancer with Tetrathiomolybdate, an Anticopper, Antiangiogenesis Agent: Phase I Study*, Clin. Cancer Res., 6:1-10 (2000)); (Redman, *Phase II Trial of Tetrathiomolybdate in Patients with Advanced Kidney Cancer*, Clin. Cancer Res., 9:1666-1672 (2003)); (Pan, et al., *Copper Deficiency Induced by Tetrathiomolybdate Suppresses Tumor Growth and Angiogenesis*, Cancer Res., 62:4854-4859 (2002)); (Teknos, et al., *Inhibition of the Growth of Squamous Cell Carcinoma by Tetrathiomolybdate-Induced Copper Suppression in a Murine Model*, Arch. of Otolaryngology: Head And Neck Surgery, Oncolink Cancer News, Reuters, 129: 781-785 (2003)); (Yoshiji, et al., *The Copper Chelating Agent, trientine, suppresses tumor development and angiogenesis in the murine heptatocellular carcinoma cells*, Int'l J. of Cancer, 94:768-773 (December 2001); (Yoshiji, et al., *The copper chelating agent, Trientine attenuates liver enzymes-altered preneoplastic lesions in rats by angiogenesis suppression*, Oncology Rep., 10(5):1369-73 (2003)); (Brem, et al., *Penicillamine and Reduction of Copper for Angiosuppressive Therapy of Adults with Newly Diagnosed Glioblastoma*, H. Lee Moffitt Cancer Center & Research Inst., (1999)); (Sagripanti and Kraemer, *Site-specific Oxidative DNA Damage at Polyguanosines Produced by Copper Plus Hydrogen Peroxide*, J. of Biol. Chem., 264(3):1729-1734 (1989)).

Copper may also promote cancer growth in ways such as damaging DNA. (Sagripanti, supra (1999)). The destructive activity of copper in a cell includes binding to DNA, cleaving DNA, in the presence of reducants and hydrogen peroxides, non-specific disruption of cellular function, and the generation of free hydroxyl radicals through Haber-Weiss reactions. (Theophanides, et al., *Copper and Carcinogenesis*, Critical Reviews In Oncology/Hematology, 42:57-64 (2002)). Copper also plays a role in the formation of reactive oxygen species ("ROS"). (Sagripanti, *DNA Damage Mediated by Metal Ions with Special Reference to Copper and Iron*, Met. Ions Biol. Syst. 36:179-209(1999)).

The use of copper has also been disclosed for the treatment of cancer in a number of U.S. Patents as well: U.S. Pat. No. 4,952,607 discloses copper complexes exhibiting super oxide dismutase-like activity in mammalian cells; U.S. Pat. No. 5,124,351 discloses the use of copper chelate of nitrilotriacetic acid or a copper chelate of bis-thiosemicarbazone; U.S. Pat. No. 5,632,982 discloses the use of copper chelates in conjunction with a surface membrane protein receptor internalizing agent, particularly TNF for use against target cells; and U.S. Pat. No. 6,706,759 discloses the use of dithiocarbamate derivatives and copper.

It is also known that a quantitative difference exists between cancer cells and normal cells with respect to iron requirements, because enhanced acquisition of iron initiates, promotes, and amplifies the growth, and metastasis, of tumor cells. Iron is an essential transition metal for a large number of biological processes ranging from oxygen transport through DNA synthesis and electron transport. Iron is also involved in carcinogenic mechanisms, which include the generation of DNA damaging reactive oxygen species, and the suppression of host cell defenses. (Desoize, B., Editor, *Cancer in Metals and Metal Compounds: Part I—Carcinogenesis*, Critical Reviews In Oncology/Hematology, 42:1-3 (2002)); (Galaris, et al., *The Role of Oxidative Stress in Mechanisms of Metal-induced Carcinogenesis*, Critical Reviews In Oncology/Hematology, 42:93-103 (2002)); (Weinberg, *Cancer and Iron: a Dangerous Mix*, Iron Disorders Insight, 2(2):11 (1999)); (Weinberg, *The Development of Awareness of the Carcinogenic Hazard of Inhaled Iron*, Oncology Res. 11:109-113 (1999)); (Weinberg, *Iron Therapy and Cancer*, Kidney Int'l, 55(60): S131-134 (1999)); (Weinberg, *The Role of Iron in Cancer*, Euro. J. Cancer Prevention, 5:19-36, (1996)); (Weinberg, *Iron in Neoplastic Disease*, Nutrition Cancer, 4(3):223-33 (1993)); (Stevens, et al., *Body Iron Stores and the Risk of Cancer*, N. Eng. J. of Med., 319(16):1047-1052 (1988)).

A number of pharmaceuticals have been developed to control and restrict the supply of iron to tumor cells using different approaches, including intracellular iron-chelating agents for withdrawal of the metal, use of gallium salts to interfere with iron uptake, and utilization of monoclonal antibodies to transferrin receptors on tumors to block the uptake of iron. For example, U.S. Pat. No. 6,589,96, incorporated herein in its entirety, teaches the use of iron chelators as chemotherapeutic agents against cancer to deprive cancer cells of iron. See also, (Kwok, et al., *The Iron Metabolism of Neoplastic Cells: alterations that facilitate proliferation?*, Crit. Rev. In Oncology/Hematology, 42:65-78 (2002), discloses tumor cells express high levels of the transferrin receptor 1 (TFR1) and internalize iron (Fe) from transferrin (TF) at a tremendous rate.); (Desoize, B. Editor, *Cancer and Metals and Metal Compounds, Part II—Cancer Treatment*, Crit. Rev. In Oncology/Hematology, 42:213-215 (2002)); (Collery, et al., *Gallium in Cancer Treatment*, Crit. Rev. In Oncology/Hematology, 42:283-296 (2002)); (Weinberg, *Development of Clinical Methods of Iron Deprivation for Suppression of Neoplastic and Infectious Diseases*, Cancer Investigation, 17(7):507-513 (1999)); (Weinberg, *Human Lactoferrin: a Novel Therapeutic with Board Spectrum Potential*, Pharmacy & Pharmacology, 53 (October 2001)); (Richardson, *Iron Chelators as therapeutic agents for the Treatment of Cancer*, Crit. Rev. In Oncology/Hematology, 42:267-281 (2002)).

When an iron dextran complex is administered to the blood system, the cellular toxicity of iron is blocked by the dextran sheath or shell in doses above or below the rate of clearance of the RES system. (Lawrence, *Development and Comparison of Iron Dextran Products*, J. of Pharm. Sci. & Tech., 52(5):190-197(1998)); (Cox, *Structure of an iron-dextran complex*, J. of Pharma & Pharmac, 24:513-517 (1972)); (Henderson & Hillman, *Characteristics of Iron Dextran Utilization in Man*, Blood, 34(3):357-375 (1969)); U.S. Pat. No. 5,624,668). Iron dextran can remain in the plasma and traffic throughout the body for weeks inertly, while being removed from the plasma by the phagocytic system and cancer cells.

Copper and iron are essential micronutrients for all organisms because of their function as co-factors in enzymes that catalyze redox reactions in fundamental metabolic processes. (Massaro, editor, *Handbook of Copper Pharmacology and Toxicity*, Humana Press, 2002, Chapter 30, p 481). Studies have shown synergistic interactions between iron and copper, which result in a significant increase in utilization of iron as compared to the utilization found with iron only compounds. (Massaro, Chap. 30, supra). To bind iron to the plasma protein transferrin, oxidation is required from $Fe^{2+}$ to $Fe^{3+}$. The oxidation may be mediated by multicopper ferroxidases, hephaestin or ceruloplasmin. Hephaestin may act together with Ferroportin1 at the surface of enterocytes to oxidize $Fe^{2+}$ to $Fe^{3+}$ prior to export into blood plasma for loading onto transferrin. An additional important role of ceruloplasmin is the mobilization of iron from tissues such as the liver where ceruloplasmin is synthesized. The ceruloplasmin can contain six copper atoms, is secreted from the liver, and can carry at least 95% of total serum copper for delivery to tissues. In addition, ceruloplasmin, via its ferroxidase activity, mediates iron release from the liver, also for delivery to tissues. Thus, both copper and iron support the hematopoietic system, especially red blood cell formation. Each is essential for the formation of red blood cells.

The American Cancer Society report, *Cancer Facts and Figures* 2003, discloses that "cancer is a group of diseases characterized by uncontrolled growth and spread of abnormal cells. About 1,334,100 new cancer cases are expected to be diagnosed in the United States in 2003, with 556,500 cancer deaths expected in 2003." The present invention includes, but is not limited to, the treatment of these cancers disclosed in *Cancer Facts and Figures* 2003, page 4, supra, such as, Oral Cavity and Pharynx, Digestive System, Respiratory System, Bones and Joints, Soft Tissue, Skin, Breast, Genital System, Urinary System, Eye and Orbit, Brain and Other Nervous System, Endocrine System, Lymphoma, Multiple Myeloma, Leukemia, and Other Unspecified Primary Sites. Treatment with the present invention also includes basal and squamous cell skin cancers and in situ carcinomas, Hyper Proliferative Disorders, myelodysplasia disorders and Plasma Cell Dyscrasias, which is characterized by an increase in plasma cells in the bone marrow, or uncommonly, other tissue. A description of these clinical abnormalities is disclosed by Markman, M. D. in *Basic Cancer Medicine*, W. B. Saunders Co., p. 103, (1997).

It would be advantageous to develop an effective chemotherapeutic agent which employs biocompatible materials, materials which feed every cell in the body, to effectuate cell death, at minimum, prevent cancer cell replication, and avoid classic and numerous deadly chemotherapeutic side effects. Such a therapeutic agent would avoid the issues of tissue resistance and lack of specificity that are caused by many pharmaceuticals, thereby destroying or disabling many previously unmanageable cancers without debilitating or killing the patient.

With respect to viral diseases, Hepatitis is a prime example. Hepatitis, generally, is caused by viral infections and may include a number of different strains. Hepatitis C is the most common strain and the most blood-borne infection and one of the most important causes of chronic liver disease in the United States. Hepatitis C virus ("HCV") is a disease causing inflammation of the liver. HCV is a single-stranded RNA virus of the family Flaviviridae and genus *hepacivirus* and has at least 6 major genotypes and more than 50 subtypes of HCV. Hepatitis C is the leading cause of liver transplantation in the United States as well as 15 percent of acute viral hepatitis, 60 to 70 percent of chronic hepatitis, and up to 50 percent of cirrhosis, end-stage liver disease, and liver viruses, including heptocellular carcinoma. The U.S. Center for Disease Control and Prevention reports that approximately 1.8 percent of the U.S. population, or 3.9 million Americans, have been infected with HCV, and of those, most cases are undiagnosed. Globally, the World Health Organization estimates that 170 million persons, which equates to approximately 3 percent of the world's population, are chronically infected with HCV, and additionally 3 to 4 million persons are newly infected each year.

The course of hepatitis C infection can be accelerated by the immunodeficiency associated with HIV infection, and thereby increasing the incidence of cirrhosis. Co-infection with the hepatitis B virus ("HBV") also has been associated with increased severity of chronic hepatitis C, and accelerated progression to cirrhosis. In addition, HBV co-infection seems to enhance the risk of hepatocellular carcinoma development. (See, for example, eMedicine.Com, Inc for co-infection information).

Hepatitis A is caused by the hepatitis A virus ("HAV"), a nonenveloped, positive stranded RNA virus of the genus *hepatovirus* of the family Picornavirus. HAV interferes with the liver's functions while replicating in hepatocytes. As a consequence of pathological damage, the liver becomes inflamed. HAV has been found to be the major cause of infectious hepatitis.

Hepatitis B is caused by the hepatitis B virus ("HBV"), an enveloped virus containing a 42 nm partially double stranded, circular DNA genome, and classified within the family Hepadnavirus. Hepatitis B is a serious and common infectious disease of the liver, affecting millions of people throughout the world. HBV is believed to be the major cause of serum hepatitis. The hepatitis delta virus ("HDV") was shown to rely on HBV for transmission because it used the hepatitis B surface antigen (HBsAg) as its own virion coat. The antigen resembles hepatitis B core antigen ("HbcAg") in its subcellular localization. Its presence was always associated with HBV infection, but it rarely coexisted with HBcAg. HDV infection can be acquired either as a co-infection with HBV or as a superinfection of persons with chronic HBV infection. Persons with HBV-HDV co-infection may have more severe acute disease and a higher risk of fulminant hepatitis (2%-20%) as compared with those infected with HBV alone. However, chronic HBV infection appears to occur less frequently in persons with HBV-HDV co-infection. Chronic HBV carriers who acquire HDV superinfection usually develop chronic HDV infection. In long-term studies of chronic HBV carriers with HDV superinfection, 70%-80% have developed evidence of chronic liver diseases with cirrhosis compared with 15%-30% of patients with chronic HBV infection alone.

Hepatitis E is caused by the hepatitis E virus ("HEV"), a nonenveloped, spherical, positive-stranded RNA virus. Several different strains have been isolated, partially characterized and molecularly cloned (1990-92). Although originally classified within the family of Caliciviruses, they are now unclassified. HEV causes self-limited acute viral hepatitis in adults aged 1540. Symptomatic HEV infection is uncommon in children; although HEV infection is frequent in children, it is mostly asymptomatic and anicteric.

Vaccines exist to protect against hepatitis A and hepatitis B. Hepatitis D, caused by a defective virus, is harmless without HBV. Both hepatitis A and hepatitis E are self-limited and, in most cases, will cease after a period of time. Hepatitis C, however, is neither defective nor self-limiting, and no vaccine currently exists to prevent against infection.

Some patients with typical signs and symptoms of acute viral hepatitis do not have serologic markers of any of these types of viral hepatitis and can be classified as having non-ABCDE hepatitis. Recently, new viruses have been discovered in patients with non-ABCDE hepatitis.

Current treatment options for people with chronic hepatitis, particularly hepatitis C, usually combine lifestyle changes with a strict drug regimen. Because of the metabolizing role of the liver, diet most likely plays an important role in influencing the rate of progression of the disease. A diseased liver in a person infected with hepatitis C can particularly be affected by an excess of certain products, including sodium, fat, and especially alcohol, which lowers the effectiveness of medications. Due to the failure of many conventional treatments and the severity of the side effects associated with the drug regimens, some people infected with hepatitis C turn to alternative therapies, which can include the use of herbals and botanicals, relaxation, and spiritual healing.

Interferons are the mainstay of conventional drug therapy hepatitis C. Interferon is a naturally occurring glycoprotein that is secreted by cells in response to viral infections. Interferons bind to specific receptors on the cell surface initiating intracellular signaling via a complex cascade of protein-protein interactions leading to rapid activation of gene transcription. Interferon-stimulated genes modulate many biological effects including the inhibition of viral replication in infected cells, inhibition of cell proliferation, and immunomodulation. Various recombinant forms of interferon alpha, and interferon alpha-2b, and a recombinant non-naturally occurring type I interferon are approved to treat chronic viral hepatitis C. However, interferon is known to cause both physical and psychological side effects, such as, irritability, depression, anxiety, and suicidal behavior; decrease in the number of white blood cells and platelets; heart problems, body organ problems, which can result in autoimmune disease, including systemic lupus erythematosus. Flu-like side effects are also common. Interferon is often pegylated, by linking the polyethylene glycol ("PEG") to the interferon molecule via a stable amide bond to lysine, as protection from immune system destruction and provide a longer residence time in the body. Ribavirin is often combined with an interferon for treatment of hepatitis and is believed to have some effect in preventing the multiplication of viruses.

Infectious diseases kill over 10 million people each year, more than 90 percent of whom are located in the developing world. Malaria, and other vector-borne diseases, infects an approximately one billion people worldwide. Those figures are now expected to increase as malaria is undergoing a resurgence based on factors such as the emergence of drug-resistant strains of the parasite, the appearance of parasite-carrying mosquitoes that are resistant to insecticides, environmental changes, and an increased population.

Most anti-infective malarial drugs interfere with aspects of protozoan metabolism that differ significantly from the human host. The *Plasmodium* species of the malaria parasite infect humans. *P. falciparum* parasites causes the most lethal form of malaria in humans and is the most common species. Other species, including *P. vivax, P. ovale* and *P. malariae*, may cause less virulent types of the disease. Mosquitoes inject the parasites, also known as sporozoites, into subcutaneous mammal tissue, or occasionally directly into the bloodstream. The parasitic sporozoites then travel to the liver, where the sporozoites are believed to pass through several hepatocytes before invasion. Parasitic development then begins. A co-receptor on the sporozoites mediates invasion. The co-receptor, thrombospondin, binds, via certain domains, specifically to heparin sulphate proteoglycans on hepatocytes in the region in apposition to sinusoidal endothelium and Kuppfer cells. Each sporozoite develops into tens of thousands of merozoites once inside the hepatocyte, which can each invade an erythrocyte (or red blood cell "RBC") upon release from the liver. *Plasmodium* infects host erythrocytes during the phase of their life cycle that gives rise to the symptoms of malaria. The parasite has a 48-hour cycle of invasion, growth and release from an infected erythrocyte. During this cycle, the parasite induces a large increase in the permeability of the host red blood cell membrane, allowing the parasite to garner nutrients from the host bloodstream, and to discharge waste products. The malaria parasite degrades up to 80% of the hemoglobin in the host cell. This degradation occurs in lysosomal food vacuoles and involves, at minimum, aspartic proteases (plasmepsins), the cysteine protease falcipain 2, and many additional peptidases including a metallopeptidase. The results include a release of large amounts of Fe(II) heme, which is rapidly oxidized to Fe(III) hematin and sequestered as an inert pigment called hemozoin that comprises a structured lattice of aggregated heme dimers.

Parasite survival within its host requires several metabolic adaptations that render it susceptible to chemotherapeutic attack and some drug targets can be targeted to functions of distinct organellar structures. Quinoline, aryl alcohol antimalarial-drugs, and the artemisinins and other antimalarial peroxides are concentrated in food vacuoles and are believed to exert their activity through interaction with heme. Quinolines are believed to disrupt or prevent effective formation of haemozoin by binding to heme through an alternate stacking of their planar aromatic structures, which results in heme-mediated toxicity to the parasite, and may involve inducing lipid peroxidation. The artemisinins can undergo oxidoreductive cleavage of their peroxide bond in the food vacuole, most likely through interaction with Fe(II) heme. These interactions are believed to generate fatal free radical-induced damage to the parasite. However, the exact mechanisms of generation and mechanisms of parasite death are unknown.

However, resistance is developing many commonly distributed drugs, in particular the less expensive types. Additionally, in practice, the costs of treating malaria patients with most anti-malarial-infected drug may not be affordable for most communities or households in countries, which may already have widespread resistance to commonly available, inexpensive drugs.

It would be advantageous to develop an effective agent which employs biocompatible materials to have an anti-malarial-treatment which simultaneously kills the protozoa, supports the production of red blood cells, white blood cells, platelets, addresses the widespread iron deficiency and anemia, and supplies carbohydrates, and is composed of biological materials which are native to the body, and nourishes every normal cell.

Ebola Hemorrhagic Fever, commonly referred to as "Ebola," is one of the most lethal viruses to infect humans and nonhuman primates. Caused by the Ebola virus, this infectious disease is named for the river in Zaire where it was first discovered in 1976. Since its discovery, different strains of the virus have caused epidemics with 50 to 90 percent mortality rates.

The Ebola virus is a member of the negative-stranded RNA virus family Filoviridae, similar to the Marburg virus, a related but less-fatal hemorrhagic disease. The particles are pleomorphic, however the basic structure is long and filamentous, essentially bacilliform and the viruses often takes on a "U" shape. The particles can be up to 14,000 nm in length and average 80 nm in diameter. The Ebola virus consists of an outer lipid membrane embedded with glycoproteins, and an inner viral capsid which surrounds the viral RNA. The viral genome consists of a single negative strand of RNA that is non-infectious itself, non-polyadenylated, with a linear arrangement of genes. The whole virion, that is, the complete viral particle consisting of RNA surrounded by a protein shell, constitutes the infective form of a virus. See, for example, the web sites of the United States Center for Disease Control ("CDC").

The virus enters a cell via an unknown mechanism, and the virus transcribes its RNA and replicates in the cytoplasm of the infected cell. As the infection progresses, the cytoplasm of the infected cell develops "prominent inclusion bodies" that contain the viral nucleocapsid, which can become highly structured. The virus then assembles, and buds off the host cell, and obtains its lipoprotein coat from the outer membrane of the infected cell.

Four different strains of Ebola are known to exist, three of which cause disease in humans. Named for their site of outbreak, they are Ebola-Zaire (90% fatality rate), Ebola-Sudan (50% fatality rate), and Ebola-Ivory Coast (one case reported; patient survived). The fourth, Ebola-Reston, has caused disease in nonhuman primates, but not in humans. Confirmed cases of Ebola Hemorrhagic Fever have been reported in several African countries as well as, in England where a laboratory worker became ill as a result of an accidental needle-stick. The Ebola-Reston virus caused severe illness and death in monkeys imported to research facilities in the United States and Italy; several research workers became infected with the virus during these outbreaks, but did not become ill. Ebola typically appears in sporadic outbreaks, usually spread within a health-care setting through the inadequate sterilization of needles. It is likely that sporadic, isolated cases occur as well (like Ebola-Ivory Coast), but go unrecognized and unreported. The natural reservoir of the Ebola virus remains unknown.

Little is known about the pathogenesis of filoviruses. It is known, however, that Ebola attacks cells important to the function of lymphatic tissues. The virus can be found in fibroblastic reticular cells ("FRC") among the loose connective tissue under the skin and in the FRC conduit in lymph nodes. This allows Ebola to rapidly enter the blood and leads to disruption of lymphocyte homing at high endothelial venules. See the Stanford University website on filoviruses. Due to the nature of the hemorraghic fever, little is known about the host immune response to infection. Antibodies that are produced primarily attack the surface glycoproteins of the virus. It is known that patients who die usually have not developed a significant immune response to the virus at the time of death. See. For example, the website of the United Sates Center for Disease Control. Anti-Ebola antibodies have been found in domestic guinea pigs, but there is no evidence of its transmission to humans. See, the Canadian Office of Laboratory Safety website.

Diagnosing Ebola in an individual who has been infected only a few days is difficult because early symptoms, such as red eyes and a skin rash, are nonspecific to the virus and are seen in other patients with diseases that occur much more frequently. Antigen-capture enzyme-linked immunosorbent assay (ELISA) testing, IgM ELISA, polymerase chain reaction (PCR), and virus isolation can be used to diagnose a case of Ebola HF within a few days of the onset of symptoms. Persons tested later in the course of the disease, or after recovery, can be tested for IgM and IgG antibodies. The disease can also be diagnosed retrospectively in deceased patients by using virus isolation, immunohistochemistry testing, or PCR.

No known cure for Ebola has thus far been successful. Present treatments are directed at maintaining renal function and electrolyte balance; and combating hemorrhage and shock; transfusion of convalescent serum may also be beneficial. Standard antiviral therapies, including interferon, which boosts the immune system, and ribavarin, an antiviral drug, have not been shown to be effective against the Ebola virus. See, the Canadian Office of Laboratory Safety website. The longer a patient can be kept alive, the greater the chance of recovery because more time is provided for the development of a natural immune response. To date, there are no vaccines for Ebola approved for use in humans.

Investigators at the Vaccine Research Center (VRC), in conjunction with the US Army Medical Research Institute for Infectious Diseases (USAMRIID), and the Centers for Disease Control and Prevention (CDC), have developed a potentially effective vaccine strategy for Ebola virus infection in non-human primates. In 2003, the VRC initiated the first human trial of a DNA vaccine designed to prevent Ebola infection. If this DNA vaccine, which contains three genes from the Ebola virus, proves to be safe in humans, a vaccine could be available in the future as part of a long-term preventive to protect health care workers, military personnel, and primary responders to a possible bioterrorism attack.

Smallpox is said to represent "both the zenith and nadir of human achievement". Once the cause of the death and disfigurement of millions, it is the only disease to be successfully eradicated through a concerted and extensive effort that transcended political and ideological boundaries. Because of these efforts, no documented, naturally occurring case of this once high-mortality infection has occurred since Oct. 26, 1977. (The last naturally occurring case was an unvaccinated hospital cook in Somalia.) Smallpox was officially declared eradicated by the World Health Organization (WHO) in 1980. In spite of this, or perhaps because of this, more than two decades after its eradication, smallpox is once again a very real threat.

Officially, smallpox exists only for research purposes in two locations: the Centers for Disease Control and Prevention, Atlanta, Ga., United States and the Russian State Centre for Research on Virology and Biotechnology, Koltsovo, Novosibirsk Region, Russian Federation. The extent of clandestine stockpiles in other parts of the world remains unknown. There are concerns, however, that terrorists or rogue states may unleash the virus as one of the most devastating potential biological weapons ever conceived. As a biological weapon, smallpox could be spread in aerosol form, since smallpox is spread person to person by respiratory secretions (airborne droplets) from an infected person coughing or through direct contact with infected skin lesions.

Poxviruses, characterized by a brick-shape, are the largest animal viruses visible with a light microscope and are larger than some bacteria. Smallpox is caused by the variola virus, a member of the genus *Orthopoxvirus*, subfamily Chordopoxyirinae of the family Poxyiridae. Other members of the genus include cowpox, camelpox, and monkeypox. The virion contains DNA-dependant RNA polymerase; this enzyme is required because the virus replicates in the cytoplasm and does not have access to the cellular RNA polymerase located in the nucleus. Poxviruses are the only viruses known to be able to replicate in cell cytoplasm without need of a nucleus.

Two main forms of smallpox exist: variola major and variola minor. While showing similar lesions, the disease takes a much milder course in the less-common variola minor, which has a case-fatality rate of about one percent. Comparatively, variola major is fatal in approximately thirty percent of all cases. There are also two rare forms of smallpox: hemorrhagic and malignant. In the former, invariably fatal form, the rash is accompanied by hemorrhaging into the mucous membranes and the skin. Malignant smallpox is characterized by lesions that did not develop to the pustular stage, remaining soft and flat. It is also almost invariably fatal.

Viral penetration is usually attained through the respiratory tract and local lymph nodes, and is followed by the virus entering the blood (primary viremia). After penetrating the cell and uncoating, the virion DNA-dependant RNA polymerase synthesizes early mRNA, which is translated into early nonstructural proteins—mainly enzymes required for subsequent steps in viral replication. The viral DNA is replicated in typical semiconservative fashion, after which late structural proteins are synthesized that will form the progeny virions. The virions are assembled and acquire their envelopes by budding from the cell membrane as they are released from the cell. Internal organs are infected; then the virus reenters the blood (secondary viremia) and spreads to the skin. These events occur during the incubation period, when the patient is still appears well. The incubation period of smallpox can range from 7 to 17 days, and most commonly between 12 and 14 days. During this period, there is no evidence of viral shedding; the person looks and feels healthy and cannot infect others.

Existing vaccines have proven efficacy but also have a high incidence of adverse side effects; this risk is sufficiently high that vaccination is not warranted if there is no or little real risk of exposure. It is estimated that one person in every million vaccinated will die of side effects, which include eczema vaccinatum, progressive vaccinia, generalized vaccinia, and postvaccinial encephalitis. Prevention is the only effective way to deal with smallpox, for there are currently no known antiviral treatments for people infected with the virus.

Variola, prior to eradication, carried a mortality rate of 30% in unvaccinated persons. Researchers estimate that vaccinated individuals retain immunity for approximately 10 years, although the duration never has been evaluated fully. Vaccination of the general population in the United States ceased after 1980.

SUMMARY OF THE INVENTION

This disclosure relates to a Composition having medicinal properties for use with mammalian diseases such as anti-cancer properties and methods of use, anti-viral properties and methods of use, anti-protozoan properties and methods of use, and anti-bacterial properties and methods of use in mammals. A chemical Composition for use as a pharmaceutical of a biologically acceptable copper compound and may include other components such as iron, which is transported to afflicted cells in a pharmaceutical acceptable carrier. For example, the compound may be formed of a core of at least biologically acceptable copper compound which may be encapsulated with a sheath that surrounds or coats the copper compound core and prevents immediate chemical interaction of the core with the surrounding environment. The Composition is combined with a pharmaceutically acceptable carrier for administration to patients and may be used alone or in conjunction with conventional treatments.

Also disclosed is a method for treating diseases by administering the Composition having a biologically acceptable copper compound core, with a sheath encapsulating the copper compound core, and a pharmaceutical carrier to the patient. The patient is monitored regularly to determine the level and/or presence of the disease. The Composition may be re-administered at intervals determined to be medically necessary by the physician, based on the results of the monitoring.

Without limitation, these and other objects, features, and advantages of the present invention, will become apparent to those with skill in the art after review of the following detailed description of the disclosed embodiments and the appended drawings and claims.

BRIEF DESCRIPTION OF THE DRAWINGS

FIG. 2B is a chart of NCI-H23 lung cells dose response with control, the Composition alone, Base Compound alone and doxorubicin alone.

FIG. 2C is a chart of NCI-H23 lung cells with the Composition alone, with the $IC_{50}$ value.

FIG. 2E is a chart of NCI-H23 lung cells with control, the Composition plus Base Compound, Base Compound alone and doxorubicin alone.

FIG. 2F is a chart of NCI-H23 lung cells with the Composition plus Base Compound, with the $IC_{50}$ value.

FIG. 3B is a chart of NCI-H460 lung cells with control, the Composition alone, Base Compound alone, and doxorubicin alone.

FIG. 3C is a chart of NCI-H460 lung cells with the Composition along, with the $IC_{50}$ value.

FIG. 3E is a chart of NCI-H460 lung cells dose response with control, the Composition plus Base Compound, Base Compound alone and doxorubicin alone.

FIG. 3F is a chart of NCI-H460 lung cells with the Composition plus Base Compound, with the $IC_{50}$ value.

FIG. 4B is a chart of MCF7 mammary cells dose response with control, the Composition alone, Base Compound alone and doxorubicin alone.

FIG. 4C is a chart of MCF7 mammary cells with the Composition alone, with the $IC_{50}$ value.

FIG. 4E is a chart of MCF7 mammary cells with control, the Composition plus Base Compound, Base Compound alone and doxorubicin alone.

FIG. 4F is a chart of MCF7 mammary cells with the Composition plus Base Compound, with the $IC_{50}$ value.

FIG. 5B is a chart of ZR-75-1 mammary cells dose response with control, the Composition alone, Base Compound alone and doxorubicin alone.

FIG. 5C is a chart of ZR-75-1 mammary cells with the Composition alone, with the $IC_{50}$ value.

FIG. 5E is a chart of ZR-75-1 mammary cells alone with control, the Composition plus Base Compound, Base Compound alone and doxorubicin alone.

FIG. 5F is a chart of ZR-75-1 mammary cells with the Composition plus Base Compound, with the $IC_{50}$ value.

FIG. 6B is a chart of PC-3 prostate cells dose response with control, the Composition alone, Base Compound alone and doxorubicin alone.

FIG. 6C is a chart of PC-3 prostate cells with the Composition alone, with the $IC_{50}$ value.

FIG. 6E is a chart of PC-3 prostate cells with control, the Composition plus Base Compound, Base Compound alone and doxorubicin alone.

FIG. 6F is a chart of PC-3 prostate cells with the Composition plus Base Compound, with the $IC_{50}$ value.

FIG. 7B is a chart of DLD-1 colon cells dose response with control, the Composition alone, Base Compound alone and doxorubicin alone.

FIG. 7C is a chart of DLD-1 colon cells with the Composition alone, with the $IC_{50}$ value.

FIG. 7E is a chart of DLD-1 colon cells with control, the Composition plus Base Compound, Base Compound alone and doxorubicin alone.

FIG. 7F is a chart of DLD-1 colon cells with the Composition plus Base Compound, with the $IC_{50}$ value.

FIG. 8B is a chart of OVCAR-3 ovarian cells dose response with control, the Composition alone, Base Compound alone and doxorubicin alone.

FIG. 8C is a chart of OVCAR-3 ovarian cells with the Composition alone, with the $IC_{50}$ value.

FIG. 8E is a chart of OVCAR-3 ovarian cells with control, the Composition plus Base Compound, Base Compound alone and doxorubicin alone.

FIG. 8F is a chart of OVCAR-3 ovarian cells with the Composition plus Base Compound, with the $IC_{50}$ value.

FIG. 9B is a chart of CAKI-1 renal cells dose response with control, the Composition alone, Base Compound alone and doxorubicin alone.

FIG. 9C is a chart of CAKI-1 renal cells with the Composition alone, with the $IC_{50}$ value.

FIG. 9E is a chart of CAKI-1 renal cells with control, the Composition plus Base Compound, Base Compound alone and doxorubicin alone.

FIG. 9F is a chart of CAKI-1 renal cells with the Composition plus Base Compound, with the $IC_{50}$ value.

FIG. 10B is a chart of LOX IMVI melanoma cells dose response with control, the Composition alone, Base Compound alone and doxorubicin alone.

FIG. 10C is a chart of LOX IMVI melanoma cells with the Composition alone, with the $IC_{50}$ value.

FIG. 10E is a chart of LOX IMVI melanoma cells with control, the Composition plus Base Compound, Base Compound alone and doxorubicin alone.

FIG. 10F is a chart of LOX IMVI melanoma cells with the Composition plus Base Compound, with the $IC_{50}$ value.

FIG. 11B is a chart of SBN-75 CSN cells dose response with control, the Composition alone, Base Compound alone and doxorubicin alone.

FIG. 11C is a chart of SBN-75 CNS cells with the Composition alone, with the $IC_{50}$ value.

FIG. 11E is a chart of SBN-75 CNS cells with control, the Composition plus Base Compound, Base Compound alone and doxorubicin alone.

FIG. 11F is a chart of SBN-75 CNS cells with the Composition plus Base Compound, with the $IC_{50}$ value.

FIG. 12B is a chart of the assayed toxicity values of the CEM-SS Leukemic cells data.

FIG. 12C provides the $IC_{50}$ of the CEM-SS Leukemic cells data.

FIG. 13B shows assayed toxicity values of the CEM-SS Leukemic cell data.

FIG. 13C provides the $IC_{50}$ of the CEM-SS Leukemic cell data.

FIG. 14 is a table of the cell lines used and the results of this disclosure.

FIGS. 15 A, B, and C are portions of a table on the concentration of the equivalent of elemental iron, which was derived from iron dextran, found in the monkey plasma over time.

FIG. 16 is a table of the single dose administrations of elemental iron, which was derived from iron dextran, found in the monkey plasma over time.

FIG. 17A is a table of the 96-well plate format for standardized 5-2 cell line antiviral evaluation.

FIG. 17B also is a table of the 96-well plate format for standardized 5-2 cell line antiviral evaluation.

FIG. 18A is a table of the standardized 5-2 cell line antiviral evaluation 96 well plate format for anti viral evaluation.

FIG. 18B also is a table of the standardized 5-2 cell line antiviral evaluation 96 well plate format for anti viral evaluation.

FIGS. 19A, 19B, 19C and 19D show results of in vitro antiviral screen of the Composition 4 on HCV using luciferase based evaluations.

FIGS. 20A, 20B, 20C and 20D show results of in vitro antiviral screen of the Composition HP on HCV RNA replicon using luciferase based evaluations.

FIGS. 21A, 21B, 21C and 21D show results of in vitro antiviral screen of the human interferon on alpha 2b on HCV using luciferase based evaluations.

FIGS. 22A, 22B, 22C and 22D show results of in vitro antiviral screen of ribavirin on HCV using luciferase based evaluations.

FIG. 23 is a table of the standardized 5-2 cell line antiviral evaluation 96 well plate format for anti viral HBV evaluation.

FIG. 24 is a table of the standardized 5-2 cell line antiviral evaluation 96 well plate format for anti viral BVDV evaluation.

FIGS. 25A and 25B show results of in vitro antiviral screen of the Composition on virus production in HepG2.15 cells.

FIGS. 26A and 26B show results of in vitro antiviral screen of the 3TC on virus production in HepG2.15 cells.

FIGS. 27A and 27B show results of in vitro antiviral screen of the Base Compound on virus production in HepG2.15 cells.

FIGS. 28A and 28B show results of in vitro antiviral screen of the Composition and the Base Compound on virus production in HepG2.15 cells.

FIGS. 29A and 29B show results of in vitro antiviral screen of the Composition and the Base Compound on virus production in HepG2.15 cells.

FIGS. 30A and 30B show results of in vitro antiviral screen of the Composition and the Base Compound on virus production in HepG2.15 cells.

FIGS. 31A and 31B show results of in vitro antiviral screen of the Composition and the Base Compound on virus production in HepG2.15 cells.

FIGS. 32A and 32B show results of in vitro antiviral screen of the Composition on virus production in HepG2.15 cells.

FIGS. 33A and 33B show results of in vitro antiviral screen of the 3TC on virus production in HepG2.15 cells.

FIGS. 34A and 34B show results of in vitro antiviral screen of the 3TC on virus production in HepG2.15 cells.

FIGS. 36A and 36B show results of in vitro antiviral screen of the 3TC on virus production in HepG2.15 cells.

FIGS. 37A and 37B show results of in vitro antiviral screen of the Composition 4 on virus production in HepG2.15 cells.

FIGS. 38A and 38B show results of in vitro antiviral screen of the 3TC on virus production in HepG2.15 cells.

FIGS. 39A and 39B show results of in vitro antiviral screen of the 3TC on virus production in HepG2.15 cells.

FIGS. 40A, 40B and 40C show results of in vitro antiviral screen of the Composition and the XTT Assay on virus production in HepG2.15 cells.

FIGS. 41A, 41B and 41C show results of in vitro antiviral screen of the interferon alpha 2b and the XTT Assay on virus production in HepG2.15 cells.

FIGS. 42A, 42B and 42C show results of in vitro antiviral screen of the Composition 4 and the XTT Assay on virus production in HepG2.15 cells.

FIGS. 43A, 43B and 43C show results of in vitro antiviral screen of the interferon alpha 2b and the XTT Assay on virus production in HepG2.15 cells.

FIGS. 44A and 44B show results of antiviral screen of the cynmolgous monkey primary hepatocyte cytotoxicity evaluation experiment.

FIG. 45A and FIG. 45B show a table of experimental results of an in vitro activity of the Composition with *mycobacterium tubercolois* where 10 μg/ml of the Composition kills 90 percent of the *bacillus*.

FIG. 46 shows the percentage of the inhibition of the *mycobacterium tubercolois bacillus* with respect to the concentration of the Composition.

FIG. 47 shows a table of Composition concentration used in conjunction with the Base.

FIGS. 48A and 48B show HCV RNA replicon luciferase-based antiviral evaluation.

FIG. 49 shows a table of parameters for the HCV RNA replicon luciferase-based antiviral evaluation.

FIG. 50 shows the anti-viral test values of the HCV RNA replicon luciferase-based antiviral evaluation.

FIGS. 52A and 52B show HCV RNA replicon luciferase-based antiviral evaluation for a second plate.

FIG. 53 shows a table of parameters for the HCV RNA replicon luciferase-based antiviral evaluation for the data of FIGS. 52A and 52B.

FIG. 54 shows the anti-viral test values of the HCV RNA replicon luciferase-based antiviral evaluation for the second plate.

FIGS. 56A and 56B show HCV RNA replicon luciferase-based antiviral evaluation for a third plate.

FIG. 57 shows a table of parameters for the HCV RNA replicon luciferase-based antiviral evaluation for the data of FIGS. 56A and 56B.

FIG. 58 shows the anti-viral test values of the HCV RNA replicon luciferase-based antiviral evaluation for the third plate.

FIGS. 60A and 60B show HCV RNA replicon luciferase-based antiviral evaluation for a fourth plate.

FIG. 61 shows a table of parameters for the HCV RNA replicon luciferase-based antiviral evaluation for the data of FIGS. 60A and 60B.

FIG. 62 shows the anti-viral test values of the HCV RNA replicon luciferase-based antiviral evaluation for the second plate.

FIG. 64 shows activity of compound #236 spiked with 4 ug/ml #25 and 0.8 ug/ml #4 against HIV-1 clinical isolates in fresh human PBMC's.

FIG. 65 is a comparison of virus controls with and without the #25 and #4 spike.

FIGS. 66A and 66B show inhibition of HIV-1 ROJO replication in PBMC by compound #236 with 4 ug/ml compound #25 and 0.8 ug/ml compound #4.

FIG. 67 shows the evaluation of the data in FIGS. 66A and 66B.

FIG. 68 is a chart of the inhibition of HIV-1 ROJO replication in PBMC by compound #236 with 4 ug/ml compound #25 and 0.8 ug/mil compound #4.

FIGS. 69A and 69B are the data of inhibition of HIV-1 ROJO replication in PBMC by AZT control.

FIG. 70 shows the evaluation of the data in FIGS. 69A and 69B.

FIG. 71 is a graph of the inhibition of HIV-1 ROJO replication in PBMC by AZT control.

FIGS. 72A and 72B show the inhibition of HIV-1 ROJO replication in PBMC by compound #236 with 4 ug/ml compound #25 and 0.8 ug/ml compound #4.

FIG. 73 shows the evaluation of the data in FIGS. 72A and 72B.

FIG. 74 is a graph of the inhibition of HIV-1 ROJO replication in PBMC by compound #236 with 4 ug/ml compound #25 and 0.8 ug/ml compound #4.

FIGS. 75A and 75B show the data showing the inhibition of HIV-1 MDR replication in PBMC by dextran sulfate control.

FIG. 76 shows the evaluation of the data in FIGS. 75A and 75B.

Figure 77:
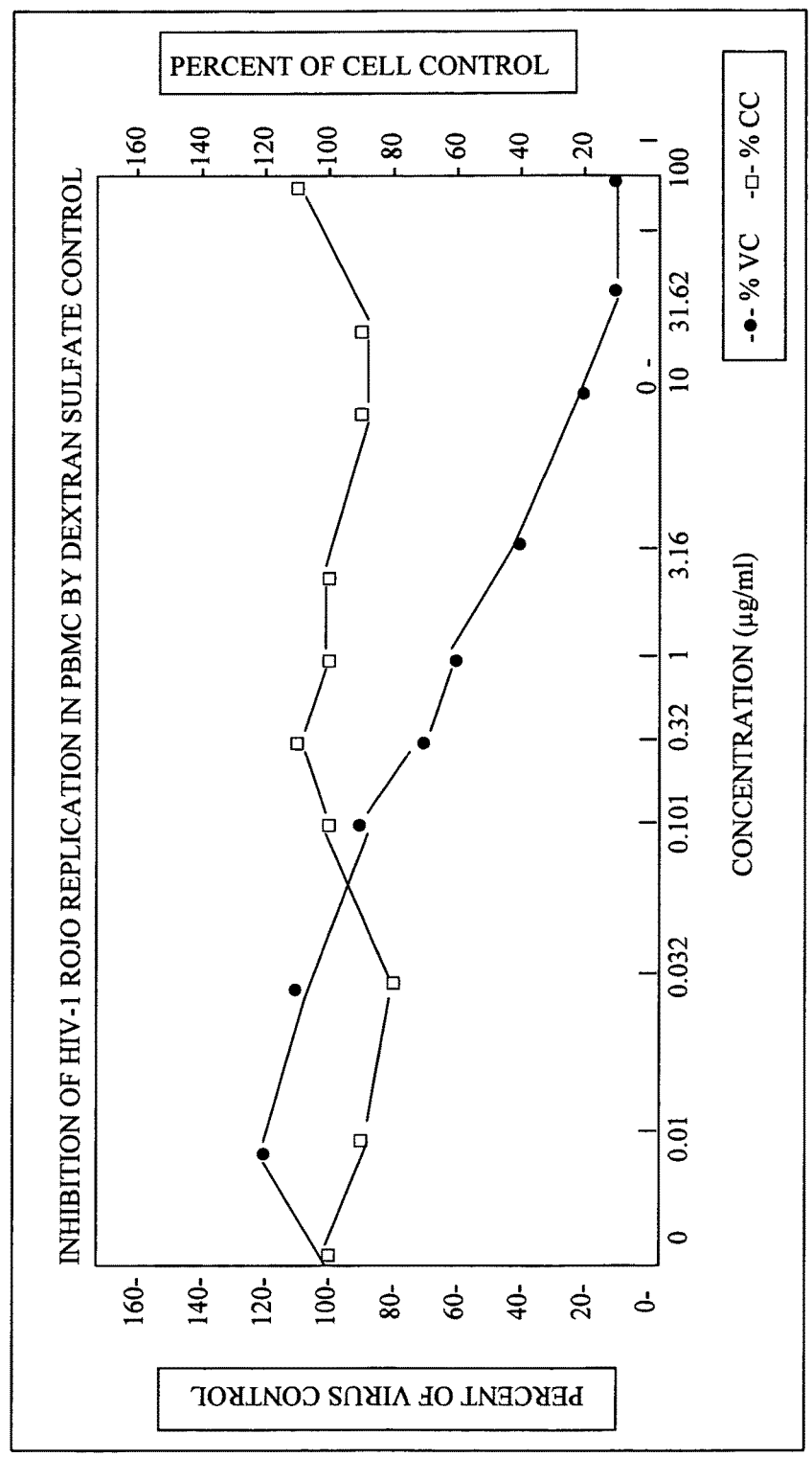

FIG. 77 is a graph of the inhibition of HIV-1 ROJO replication in PBMC by dextran sulfate control.

FIGS. 78A and 78B are charts of the inhibition of HIV-1 G910.6.2.3 replication in PBMC by compound #236 with 4 ug/ml compound #25 and 0.8 ug/ml compound #4.

FIG. 79 shows the evaluation of the data in FIGS. 78A and 78B.

Figure 80:
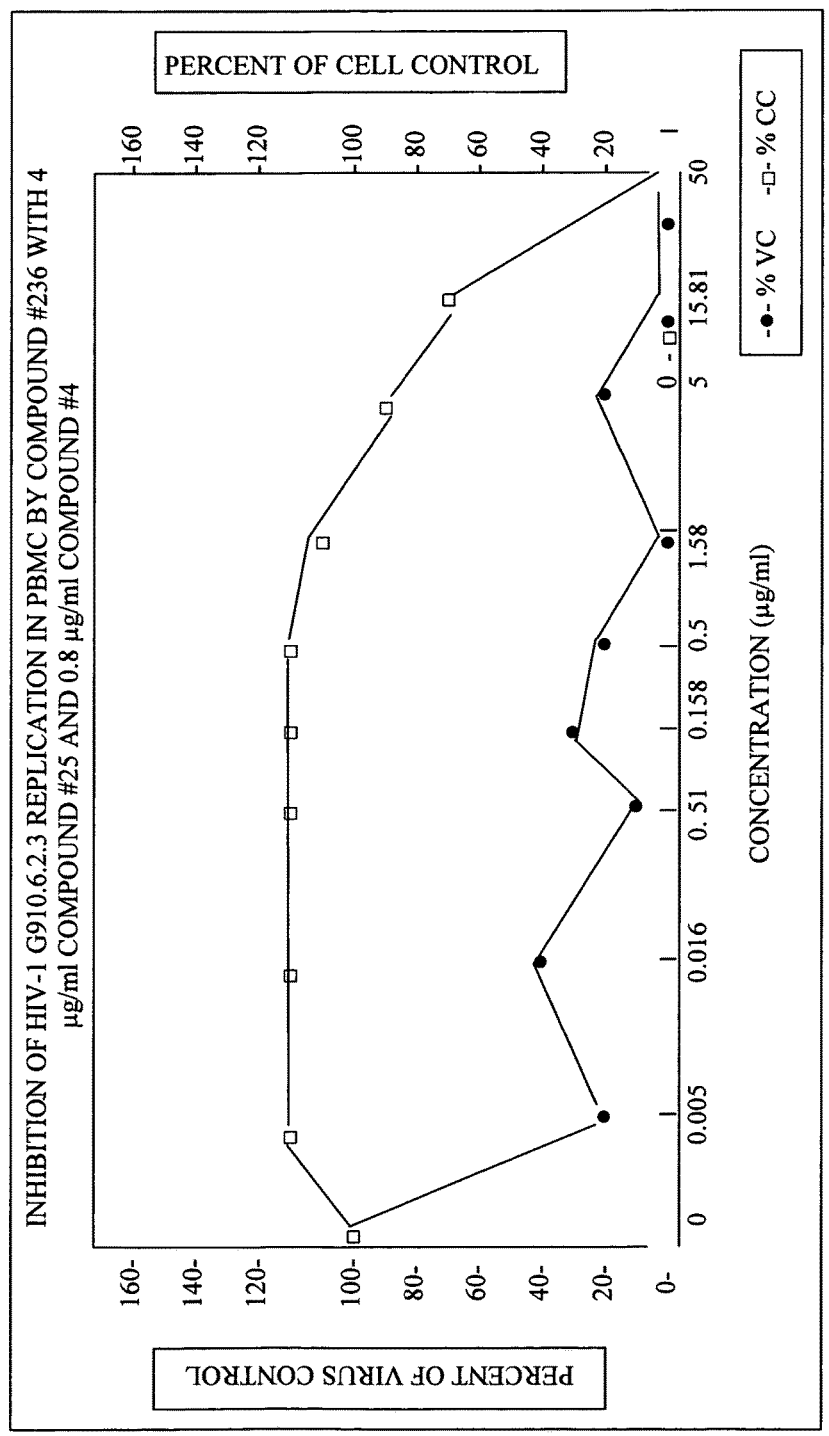

FIG. 80 is a graph of the inhibition of HIV-1 g 910.6.2.3 replication in PBMC by compound #236 with 4 ug/ml compound #25 and 0.8 ug/ml compound #4.

FIGS. 81A and 81B are the data for the inhibition of HIV-1 G910.6.2.3 replication in PBMC by dextran sulfate control.

FIG. 82 shows the evaluation of the data in FIGS. 81A and 81B.

Figure 83:
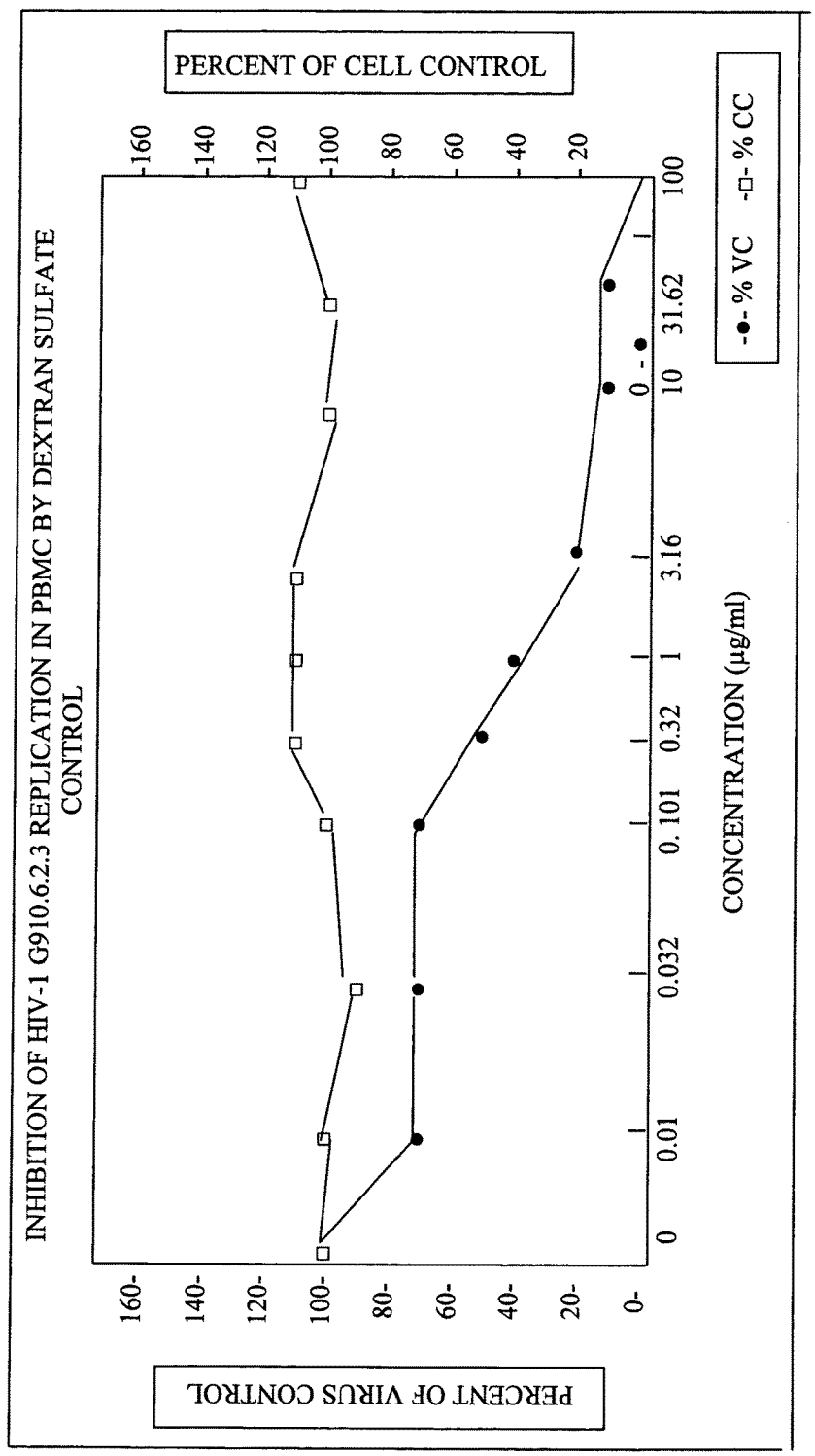

FIG. 83 is a graph of the inhibition of HIV-1 G910.6.2.3 replication in PBMC by dextran sulfate control.

FIGS. 84A and 84B show the inhibition of HIV-1 52-52 replication in PBMC by compound #236 with 4 ug/ml compound #25 and 0.8 ug/ml compound #4.

FIG. 85 shows the evaluation of the data in FIGS. 84A and 84B.

Figure 86:
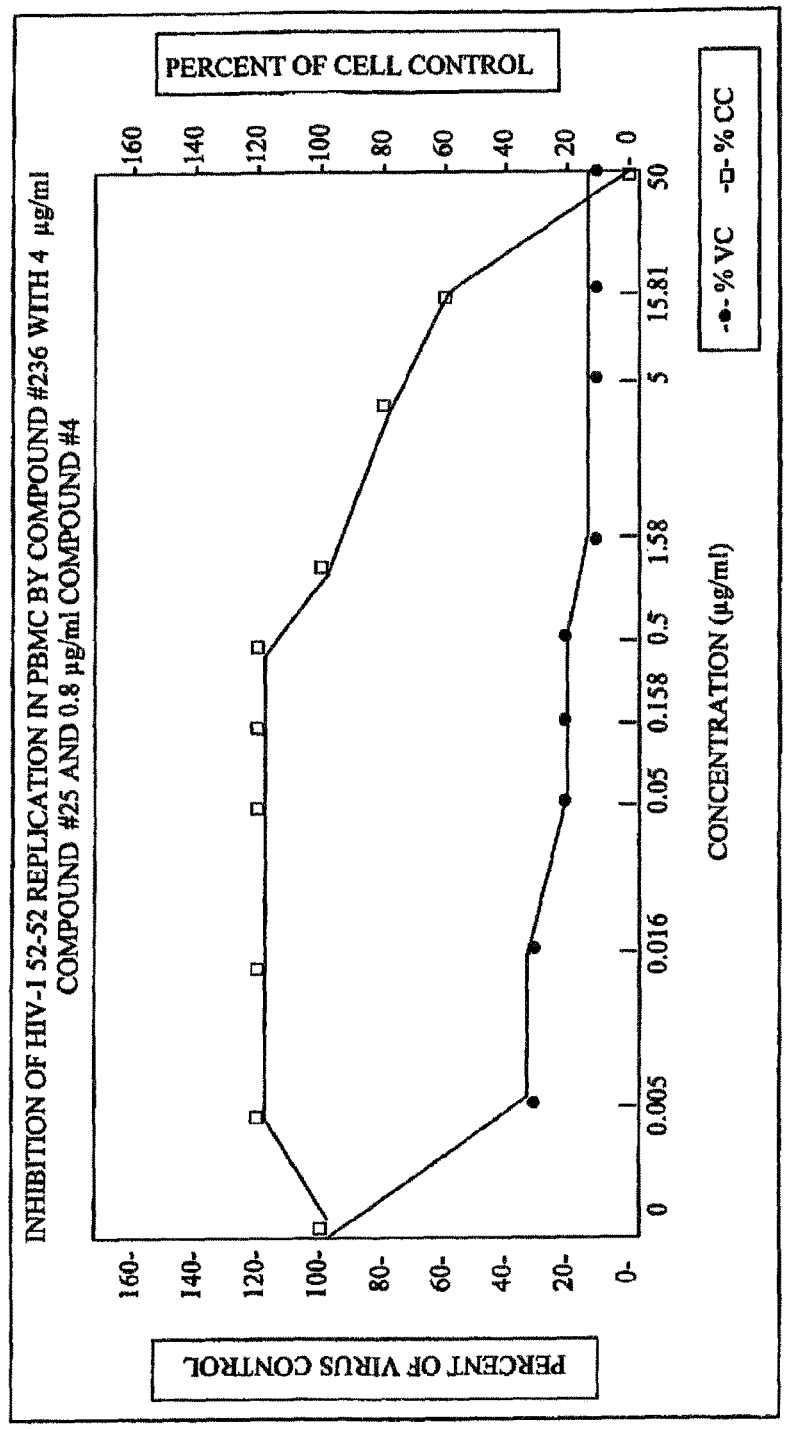

FIG. 86 is the graph of the inhibition of HIV-1 52-52 replication in PBMC by compound #236 with 4 ug/ml compound #25 and 0.8 ug/ml compound #4.

FIGS. 87A and 87B are charts of the inhibition of HIV-1 52-52 replication in PBMC by dextran sulfate control.

FIG. 88 shows the evaluation of the data in FIGS. 87A and 87B.

Figure 89:
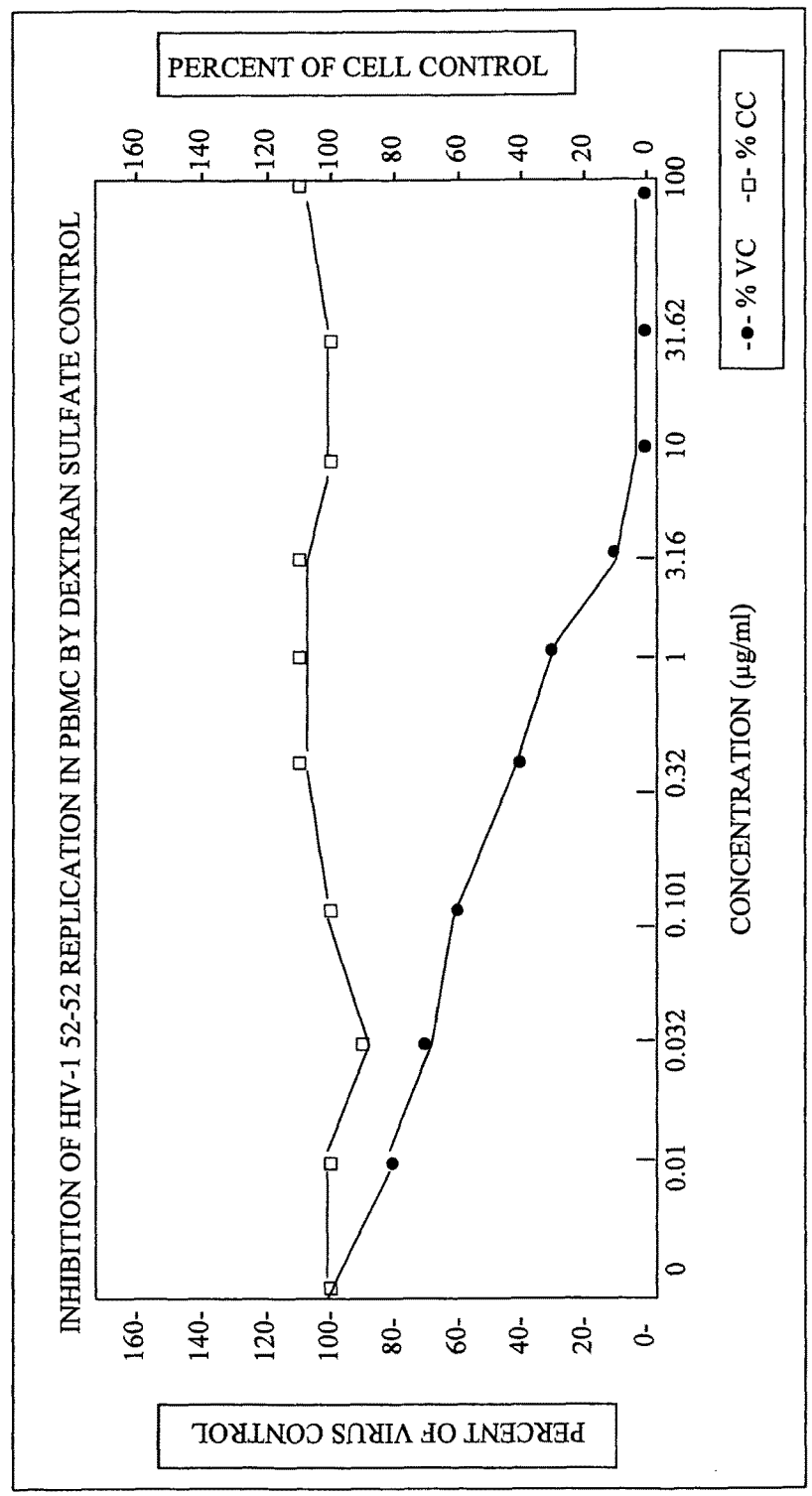

FIG. 89 is a graph of the inhibition of HIV-1 52-52 replication in PBMC by dextran sulfate control.

FIGS. 90A and 90B is the inhibition of HIV-1 52-52 replication in PBMC by compound #236 with 4 ug/ml compound #25 and 0.8 ug/ml compound #4.

FIG. 91 shows the evaluation of the data in FIGS. 90A and 90B.

Figure 92:
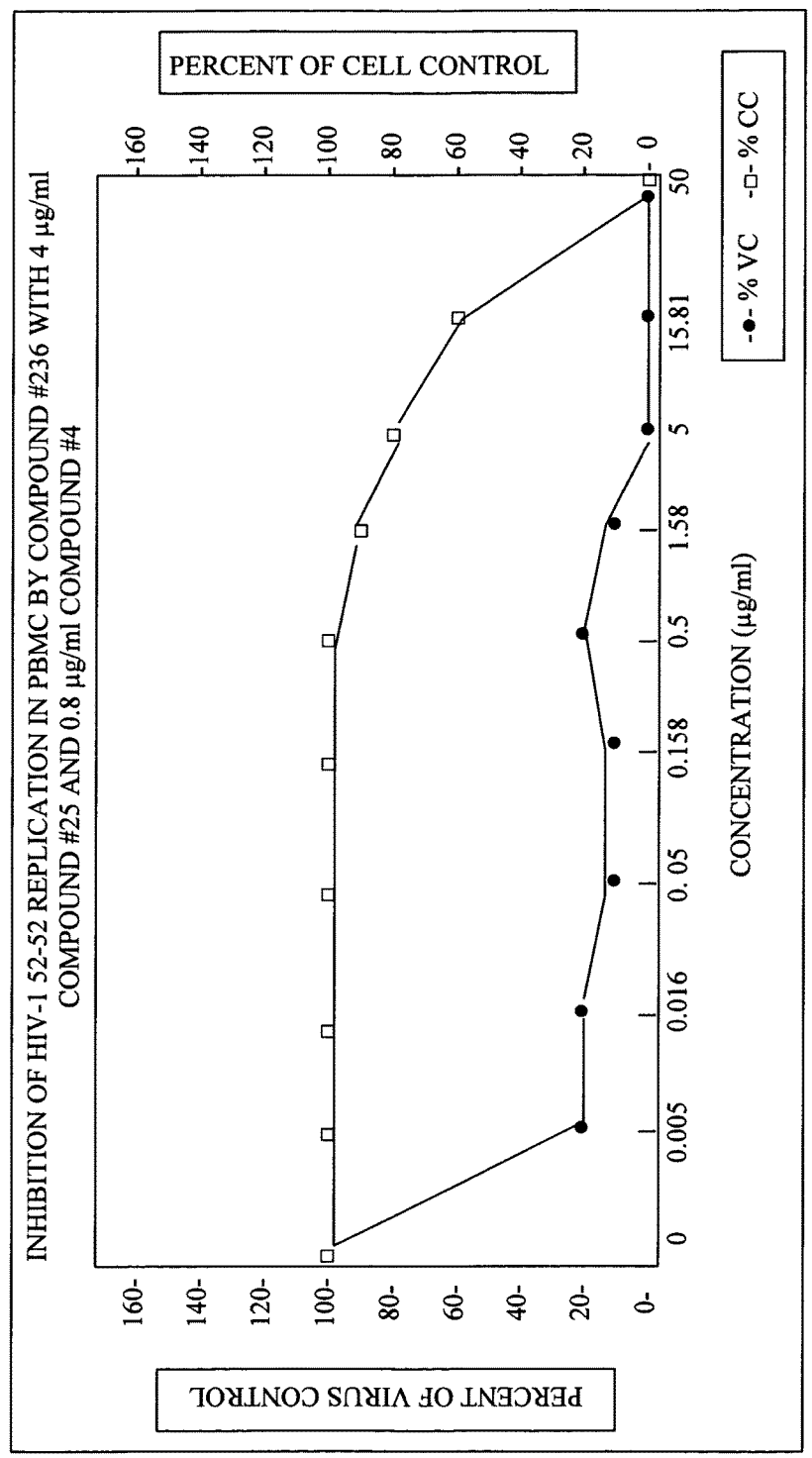

FIG. 92 is a chart of the inhibition of HIV-1 52-52 replication in PBMC by compound #236 with 4 ug/ml compound #25 and 0.8 ug/ml compound #4.

FIGS. 93A and 93B are charts of the inhibition of HIV-1 52-52 replication in PBMC by AZT control.

FIG. 94 shows the evaluation of the data in FIGS. 93A and 93B.

Figure 95:
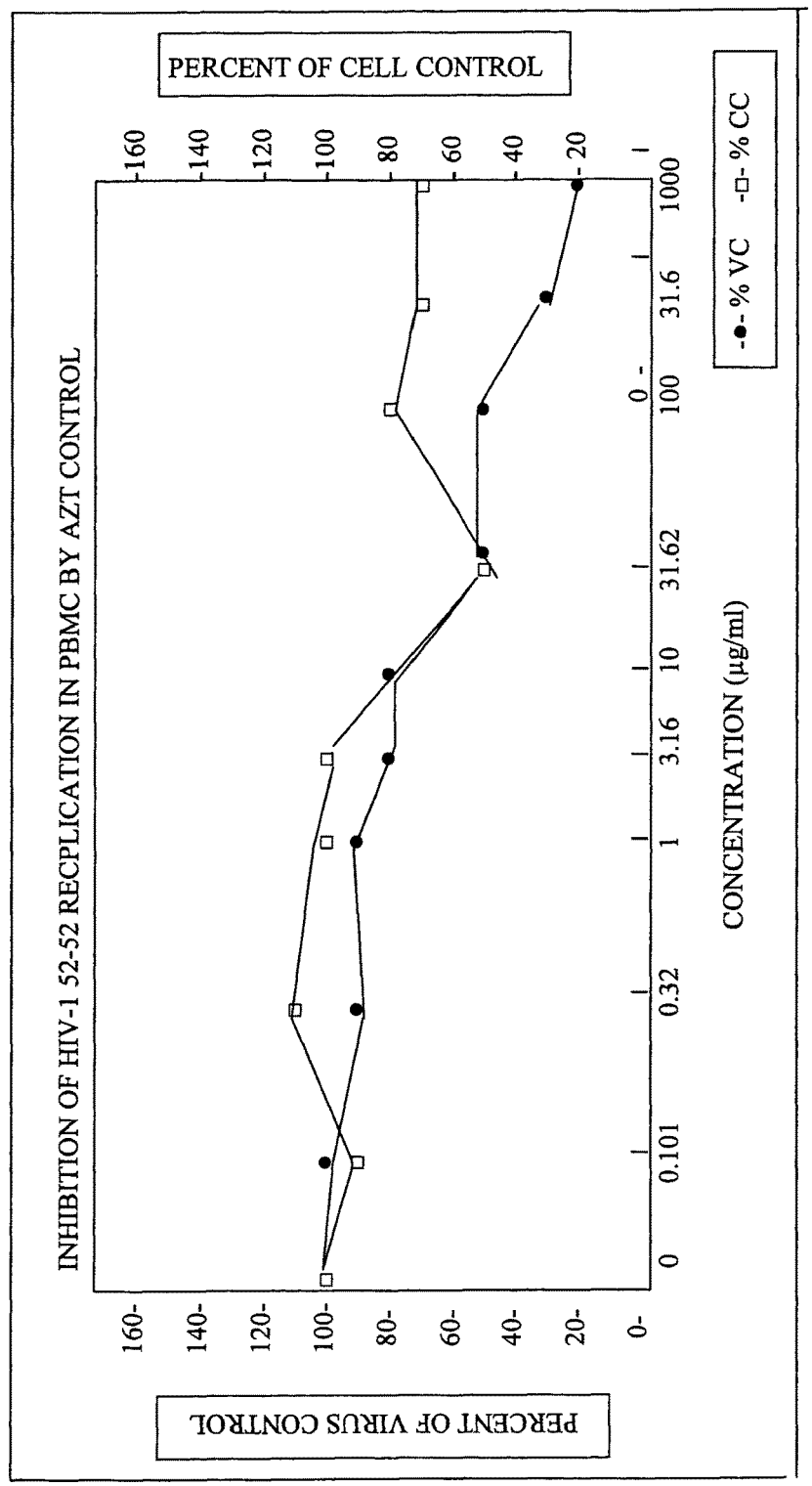

FIG. 95 is a graph of the inhibition of HIV-1 52-52 replication in PBMC by AZT control.

FIGS. 96A and 96B are the data on inhibition of HIV-1 TEKI replication in PBMC by compound #236 with 4 ug/ml compound #25 and 0.8 ug/ml compound #4.

FIG. 97 shows the evaluation of the data in FIGS. 96A and 96B.

Figure 98:
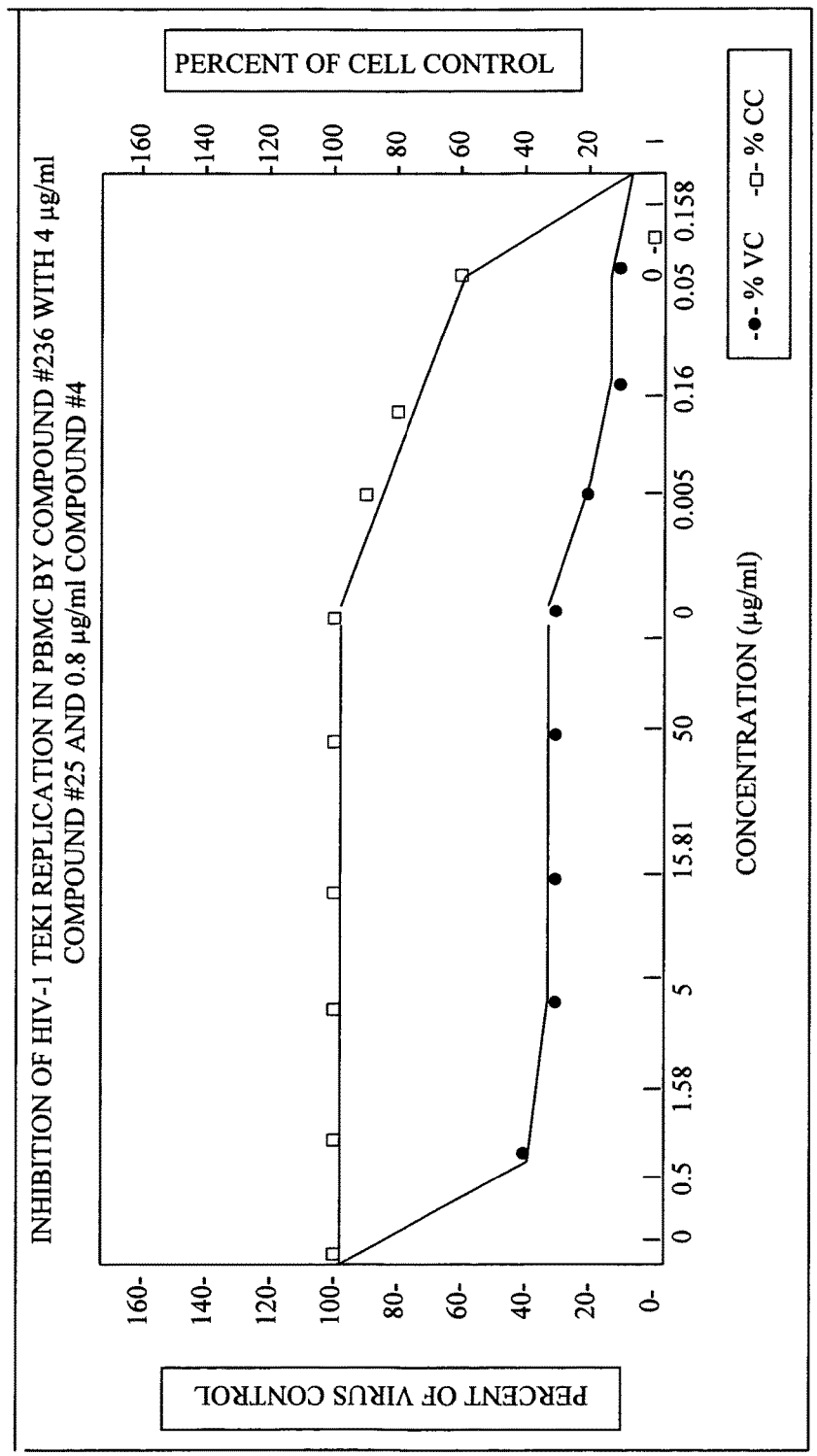

FIG. 98 is a graph of the inhibition of HIV-1 TEKI replication in PBMC by compound #236 with 4 ug/ml compound #25 and 0.8 ug/ml compound #4.

FIGS. 99A and 99B are the data of the inhibition of HIV-1 TEKI replication in PBMC by AZT control.

FIG. 100 shows the evaluation of the data in FIGS. 99A and 99B.

Figure 101:
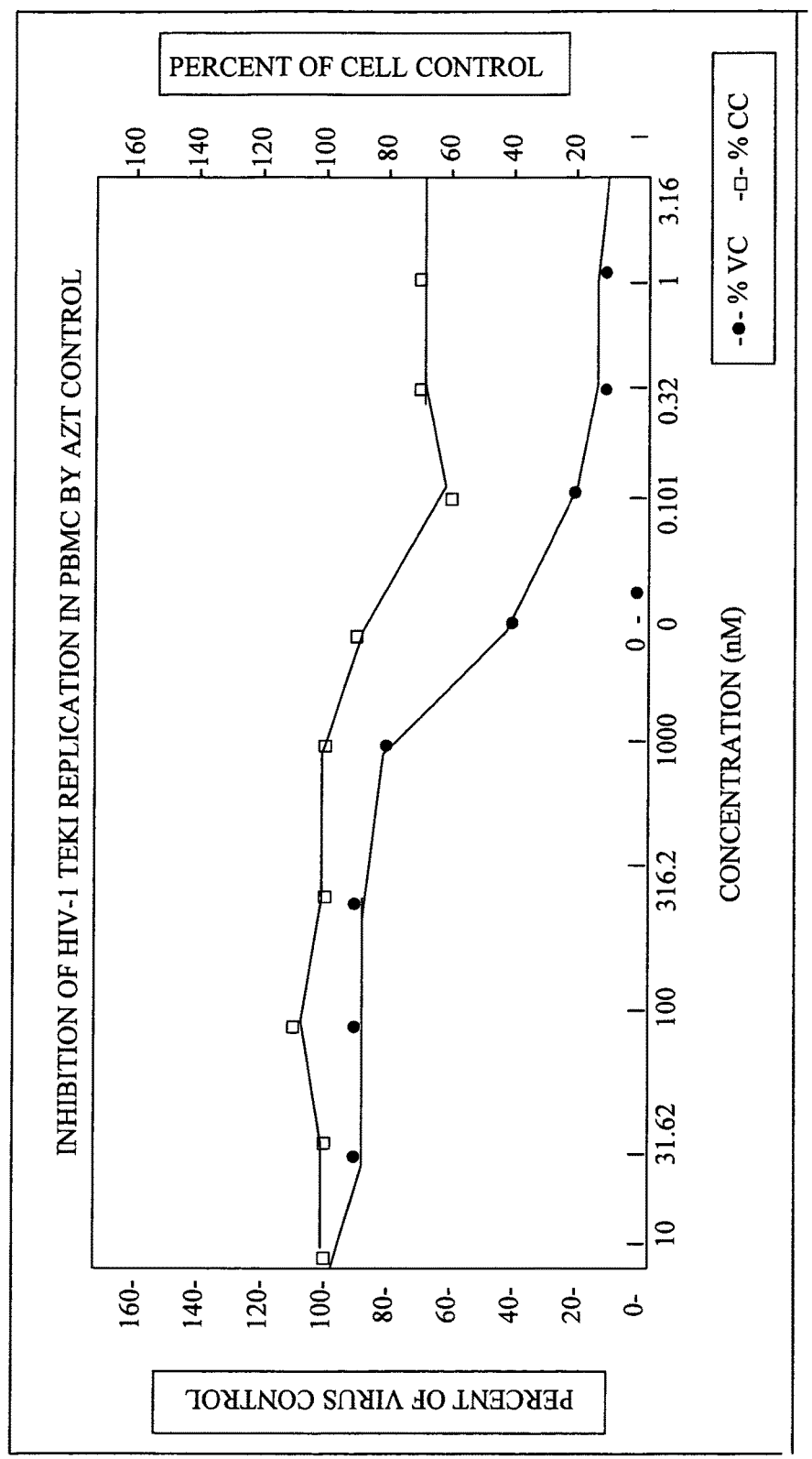

FIG. 101 is a graph showing the inhibition of HIV-1 TEKI replication in PBMC by AZT control.

FIGS. 102A and 102B are the data of the inhibition of HIV-1 BR/92/026 replication in PBMC by compound #236 with 4 ug/ml compound #25 and 0.8 ug/ml compound.

FIG. 103 shows the evaluation of the data in FIGS. 102A and 102B.

Figure 104:
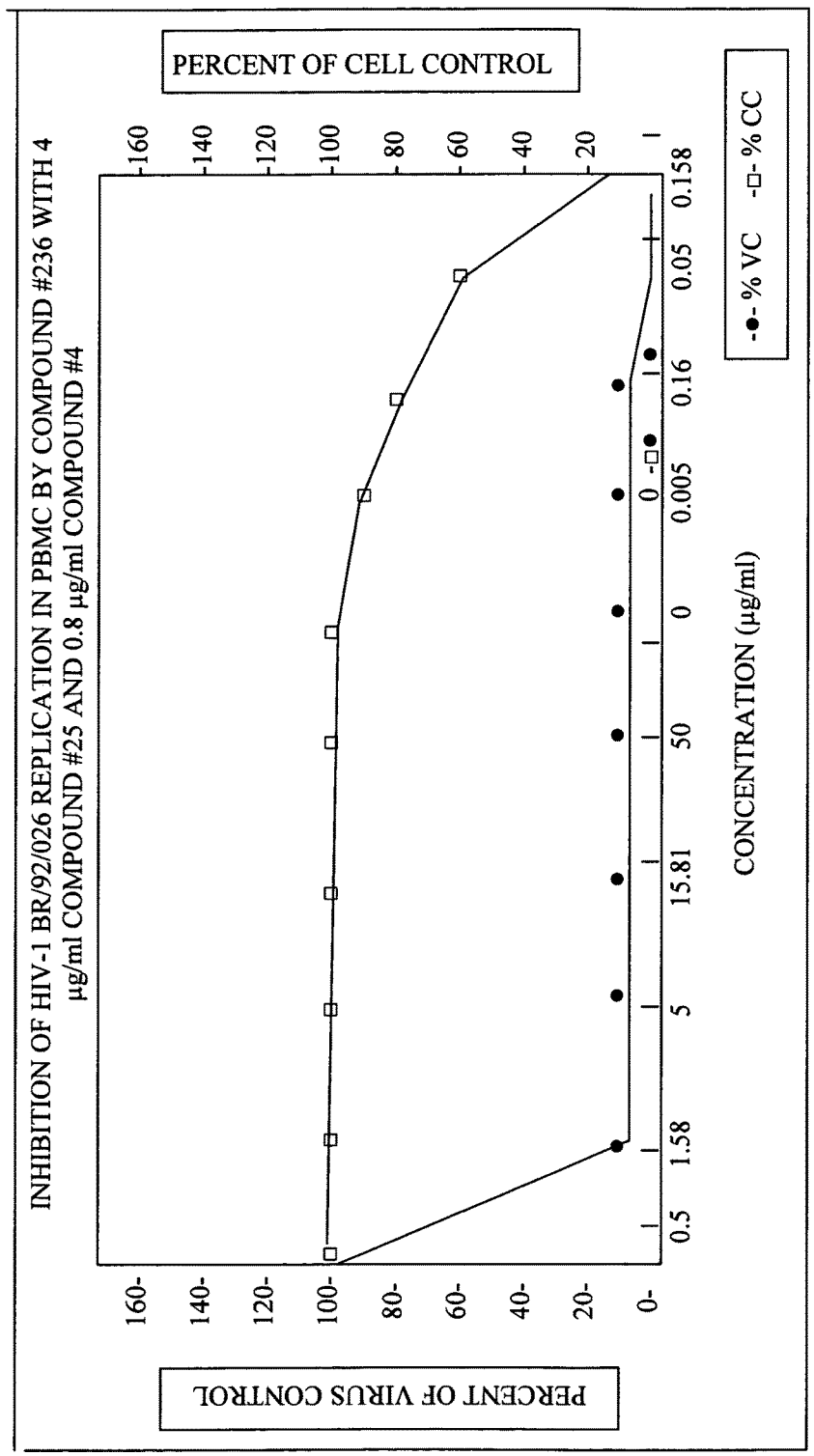

FIG. 104 is a graph of the inhibition of HIV-1 BR/92/026 replication in PBMC by compound #236 with 4 ug/ml compound #25 and 0.8 ug/ml compound #4.

FIGS. 105A and 105B are the data of the inhibition of HIV-1 BR/92/026 replication in PBMC by AZT control.

FIG. 106 shows the evaluation of the data in FIGS. 105A and 105B.

Figure 107:
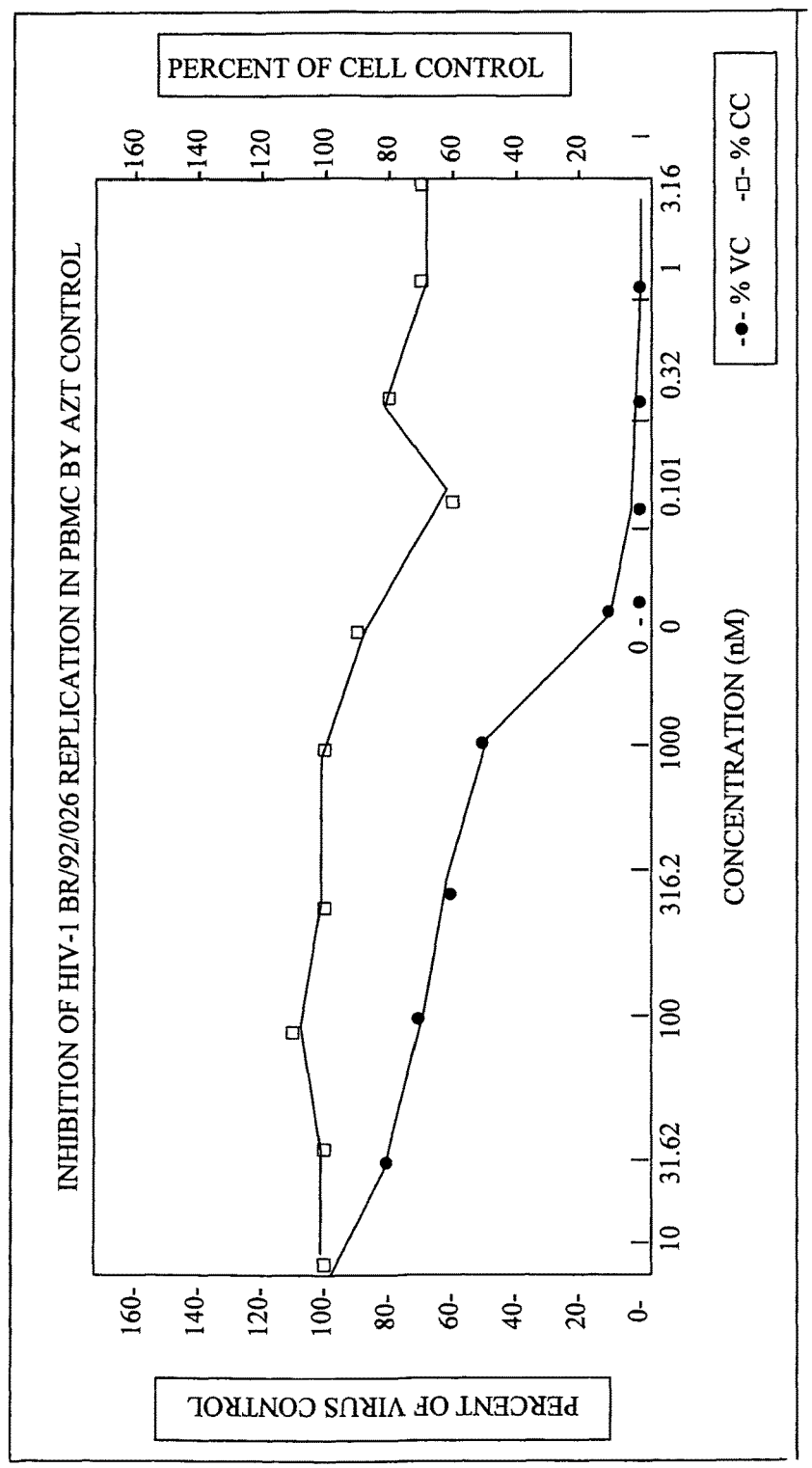

FIG. 107 is a graph of the inhibition of HIV-1 BR/92/026 replication in PBMC by AZT Control.

DETAILED DESCRIPTION

This disclosure relates to a Composition which may be used in the treatment of a number of mammalian diseases. For example, the Composition can selectively exploit chemical variations and requirements between normal cells and cancer cells to inhibit and/or prevent the proliferation of cancerous cells in mammals. Most cancer treatments are unfocused and detrimentally affect healthy cells as well as cancerous cells in contact with the treatment because of a lack of specificity in traditional treatments. The ability of the disclosed Composition to exploit these chemical differences and requirements, and target cancer cells focuses the therapeutic agent to the desired cells and limits effects on healthy cells of a mammal. The disclosed chemical Composition, therefore, provides a chemotherapeutic that is less toxic with reduced side effects. This disclosure relates to the addition of glucose, copper and iron compounds to cancer cells, cell proliferating diseases (such as pre-cancerous cells, psoriasis, and so on), hyper proliferative disorders, myelodysplasia disorders, plasma cell dyscrasias, solid tumors, liquid tumors, and metastatic diseases to shrink tumors by killing tumor cells and/or arresting their growth. The Composition employs agents, which have been shown to be effective anti-cancer agents in the Examples below, although recurrently the subject of research with respect to the withholding, restricting, limiting and modulating intended to block initiation, promotion, and growth of tumors and metastasis of cancer cells.

The disclosed Composition my also be employed as an antiviral agent which may be used to diminish or destroy viruses present in mammals. Such viruses may include, inter alia, hepatitis strains, for example, hepatitis C, hepatitis A, hepatitis B, hepatitis D, and hepatitis E, as well as other infective viruses, virus infected cells and viral diseases, such as small pox, its strains and related diseases, such as monkey pox, cowpox, and camel pox; as well as other infective viruses, virus infected cells and viral diseases, such as HIV/AIDS, hepatitis, and Ebola. Such viruses may include, inter alia, the strains of the Ebola virus, including Ebola-Zaire, Ebola-Sudan, and Ebola-Ivory Coast, and Ebola-Reston and Marburg viruses, as well as other infective viruses, virus infected cells and viral diseases, such as small pox, hepatitis, and HIV. The disclosed composition can be effective as potent viricide, and without being bound to a particular theory or mechanism, it is believed that the viricidal action functions as described above to disrupt the viral DNA and rupture the viral envelope. The disclosed Composition is also effective and may be used as a pharmaceutical to treat intracellular pathogens, such as bacteria or protozoans, any pathogen having a cell structure or cell wall, and/or any pathogen which has an intracellular life cycle in part, such as tuberculosis in mammals.

This disclosure also relates to a Composition which can inhibit and/or prevent vector- and microbe-borne diseases in mammals, and would typically be administered to mammals. The disclosed Composition can lower or eliminate the parasitic load of a mammal infected with a vector- or microbe-borne disease, which may include, for example, diseases are caused by microbes, both aerobic and anaerobic, such as protozoa, helminthes (parasitic worms), bacteria, including gram positive and gram negative (such as spirochetes), fungi (including fungi causing systemic infections) and viruses. These microbes often carry for life-threatening diseases which continue to claim lives on a large scale in many locales throughout the world, especially in developing countries. The life cycle of many microbes involves an insect vector and a vertebrate host. Other types, such as *giardia lambia*, may be contracted though poor or contaminated water sources. A lack of potable, fresh water and a continual presence of disease-carrying vectors is particularly problematic in developing areas. The disclosed Composition is effective in lowering and/or eliminating the presence of protozoans, such as, for example, *Plasmodium, Trichomonas, Entamoeba, Leishmania*, and the like, by rupturing the protozoan and cells infected with protozoans. Bacteria cells, such as staph or anaerobic mycoplasma, fungal cells, viruses and other microbes may also be eliminated and/or their numbers effectively limited and lowered by destroying the microbes' outer layer and rupturing the host cell. The disclosed Composition can be administered as a treatment for malaria, and other diseases caused by microbes, in a pharmaceutically acceptable, physiologically beneficial, and cost-efficient manner. The cost of many pharmaceuticals is often the determining factor for treatments in developing countries and an effective and cost-efficient pharmaceutical, such as the disclosed Composition, can provide treatment and disease relief in those areas.

The Composition is comprised of, at least, nanoparticles of a fixed copper compound core, or a fixed copper-iron compound core, or a combination of the two. These cores may be encapsulated, coated, adsorbed, complexed, or the like, with a protective sheath or jacket which also functions to target cancer cells. This sheath or jacket may be any combination of materials, such as a glucose or liposome, and, optionally, the resulting glucose encapsulated core may be coated with liposomes. In another embodiment, the core may be encapsulated with dextran alone or any glucose or combination of sugar-based substances. Alternatively, a liposome encapsulated core may then be coated with an outer dextran sheath.

As transition metals, copper and iron can generate reactive oxygen species including hydroxyl radicals. It is widely recognized that transition metals, including $Cu^+$, $Fe^{2+}$, $Sn^{3+}$, $Co^{2+}$ and $Ni^{2+}$, have been demonstrated to cause catalysis of free-radical reactions in biological systems. Therefore, cancer cells can be destroyed by digestion and fragmentation, which can be achieved by oxidation by copper or iron, and/or catalyzed free-radical chemical reactions. The $Cu^{2+}$ associates with the guanine-cytosine base pairs of DNA to cause local free-radical damage to the DNA that is characteristic of attack by hydroxyl ion. Copper is a promoter of free-radical damage to lipids, proteins, and especially to DNA and its base pairs. (Aruoma, *Copper ion-dependent damage to the base pairs in DNA in the presence of hydrogen peroxide*, Biochem. Jour., 273: 601-4(1991)). In addition to the generation of oxygen species, the transitional metals, copper and iron, may be limiting nutrients to the growth and replication of cancer cells in mammals, as has been demonstrated in many in vitro, mammalian studies.

Suitable copper compounds for use as the core are any biologically acceptable copper compounds which include, but are not limited to, any fixed coppers including, cupric hydroxide, copper oxide, copper oxychloride, cupric carbonate basic, copper sulfate, copper sulfate basic, cuprous oxide, cupric hydroxide-iron hydroxide, copper-iron oxide, cupric citrate, cupric glycinate, cupric gluconate, cupric phosphate, cuprobam, cupric salicylite, indigo copper, cupro-cupric sulfate, cuprous sulfate, cuprous sulfate hemihydrite, any of the natural copper containing minerals such as cupric sulfate basic, the minerals brochantite, langite, malachite, azurite, cheesylite, cornetite, dihydyrite, libethenite, phosphorochalcite, pseudolibethenite, pseudo-malachite, tagilite, antlerite, covellite, marshite, cuprite, chalcocite, Rogojski's salt, brochantite, hydrocyanite, chalcanthtite, and the like, or any copper minerals occurring in nature such as nantokite or dolerophane and so on. See also, for examples of copper compounds, Merck's Manual 13$^{th}$ ed., Merck & Co. 2001, and Hawley's Condensed Chemical Dictionary 14$^{th}$ ed., John Wiley & Sons, Inc. 2001. Copper hydroxide, a fixed copper, is a preferred compound to form the core. In another embodiment, the core may also be composed of cupric hydroxide-iron hydroxide to provide a synergistic effect, which enhances the cellular toxicity of both the copper and iron. In one embodiment, any biocompatible form of copper compound that can cause catalysis of free-radical reactions in biological systems may be used as a core metal for the disclosed Composition. A biologically acceptable copper compound as defined herein is a copper compound, which may be used with and within a biological system with little or no detrimental effect, i.e. it does not appreciably alter or appreciably affect in any adverse way, the biological system into which it is introduced.

In a further embodiment, a combination of copper oxide, copper hydroxide-iron hydroxide or another of the fixed coppers and iron, may be used as a core to provide synergistic effects of the combination. Any biocompatible iron compound may be used in conjunction with the copper core, including without limitation, for example, $Fe^{3+}$, and its salts, iron hydroxide, iron oxyhydroxide, iron oxide, iron glucose, ferric citrate, Ferritin, ferrous fumarate, ferrous sulfate, and the like, to iron load the biological environment, including iron-saturated human holotransferrin.

Experiments on metabolic clearance rates done on cynomolgus monkeys (species *Macaca fascicularis*) have shown the safe use of large dosages of elemental iron derived from iron dextran. (All experiments were preformed in compliance with the Animal Welfare Act and Regulations.) Dosages of 400 mg and 500 mg of elemental iron, derived from iron dextran, per kg of body weight were safely administered to the cynomolgus monkeys by intravenous infusion. The iron dextran showed a protracted plasma residence time which functions as a decoy for the phagocytic system to redistribute the disclosed Composition to the plasma with few negative side effects. The administered iron dextran remained in the monkey plasma for at least 120 hours, at milligram levels. Single dosages of iron dextran were also separately administered to monkeys, with few negative side effects, i.e. abdominal swelling. (See, U.S. application Ser. No. 10/888,576 incorporated herein in its entirety.) The monkey model clears the iron dextran from the system much more very rapidly, as compared to humans, because of a higher metabolic rate. Therefore, a longer plasma residence time is anticipated in humans, as has been shown in research, such as, for example, Henderson & Hillman, (1969).

The nanoparticles of the disclosed Composition preferably can be encapsulated, surrounded, complexed, or adsorbed by, and bound to, at least one sheath or coat that is preferably composed of a sugar substance, such as a glucose, a saccharide, a polysaccharide e.g. starch, cellulose, dextrans, alginides, chitosan, pectin, hyaluronic acid, pullulan (a bacterial polysaccharide), dextran, carboxyalkyl dextran, carboxyalkyl cellulose and the like. These dextrans can include, for example, those disclosed by Mehvar, supra (2000); and *Recent Trends in the Use of Polysaccharides for Improve Delivery of Therapeutic Agents: Pharmacokinetic and Pharmacodynamic Perspectives*, Curr. Pharm. Biotech. 4:283-302 (2003), and liposomes coated with dextran as disclosed by Moghimi, et al., *Long-Circulating and Target-Specific Nanoparticles: Theory to Practice*, Pharm. Rev., 53(2):283-318 (2001)) both of which are incorporated herein in their entirety. The sheath encoats, or encapsulates, the disclosed Composition's core and prevents chemical interaction of the core with the surrounding environment, blocking the degradation of the core and the emanation of the copper and/or iron from the copper compound, and/or the copper-iron compound from the core. The thickness of the sheath may be varied, if desired, by those skilled in the art. Because the sheath is composed primarily of a substance that is not necessarily recognized by the body as foreign matter, the body is less likely to develop a resistance to the Composition. In one embodiment, the sheath can be composed of dextran, also known as macrose, a high molecular weight polysaccharide. Dextran is an ideal candidate for use as a sheath because it is often administered to mammals as a blood plasma substitute or expander, is generally not rejected by the mammalian system, and can remain in the plasma for an extended period of time. Other biocompatible materials for the formation of a polymeric shell, sheath, or jacket can include proteins, polypeptides, oligopeptides, polynucleotides, polysacchrides, lipids and so on. Additional sheath materials include, for example, those of U.S. Pat. Nos. 6,096,331; and 6,506,405, incorporated herein in their entirety. Alternatively, combinations of two or more of the above named materials may be used to form the sheath.

In another embodiment, the disclosed Composition can be sheathed or encapsulated with a liposome coat. This liposome coat may be the sole sheath encapsulating the core, or may be a second coat over one, or a combination, of the above named materials. PEG liposome polymer coatings have been shown to reduce phagocytic system uptake and provide long residence time according to research by the Alza Corporation, *Delivery Times, Issues and Opportunities*, Vol 2 (1), incorporated herein in its entirety. Residence time in the plasma can be extended to periods of at least several days to weeks after IV injection without releasing the encapsulated drug, which would lower the administration frequency of the drug. See, e.g., U.S. Pat. No. 6,465,008; U.S. Pat. Pub. US2002/017271181; U.S. Pat. Pub. US2001/005118381; each of which is incorporated herein in its entirety.

Alternatively, the core may be transported to cell-specific sites with the use of targeting agents or markers which may target cancer cells, cell proliferating diseases (such as pre-cancerous cells, psoriasis, and so on), solid tumors, liquid tumors, and metastatic diseases. Any targeting agent or marker which can medicinally utilized within a biological system may be employed to actively transport the core to the specific site of the cancer cells (See, for example, R. C. Juliano, Targeted Drug Delivery, Handbook of Experimental Pharmacology, Vol. 100, Ed. Born, G. V. R. et al., Springer Verlag). For example, a binding molecule to a cancerous cell surface site or cell surface receptor, surfactant, a ligand, an antibody, proteins, peptides, enzymes, specific chemical compounds, and so on, may be used as targeting agents or markers to target cancer cells. These targeting agents or markers may be used instead of, or in conjunction with, at least one sheath encapsulating the core.

For one example, a binding molecule to a hepatocyte cell surface site or cell surface receptor, surfactant, a ligand, an antibody, proteins, peptides, enzymes, specific chemical compounds, and so on, may be used as targeting agents or markers to target infected cells. These targeting agents or markers may be used instead of, or in conjunction with, at least one sheath encapsulating the core.

In another example, with respect to Ebola, targeting agents which are specific to conserved locations, such as, EBOV glycoprotein, which is the only protein known to be on the Ebola virion surface, and conserved helicase, protease, polymerase, and untranslated regions of the viral RNA. All of these are involved in critical stages of viral replication and therefore may be logical locations for targeting agents. The Ebola envelope glycoproteins has been mapped, and conserved locations may be used as targets. The toxicity of these viral envelope glycoproteins plays a significant role in the human disease as full-length envelope glycoproteins induce toxic effects in vivo by affecting blood vessels.

In yet another example, targeting agents which are specific to conserved locations, such as hepatitis C envelope protein E2 which includes a binding site for a receptor expressed on hepatocytes and B lymphocytes (CD-81), and highly conserved hepatitis C virus-specific helicase, protease, polymerase, and untranslated regions at both ends of the viral RNA, 5'-UTR and 3'-UTR. All of these are involved in critical stages of viral replication and therefore may be logical locations for targeting agents. It has also been found that cell surface heparan sulfate proteoglycans ("HSPG") play an important role in mediating HCV envelope-target cell interaction, which can be inhibited with heparin and liver-derived highly sulfated heparan sulfate in a dose-dependent manner. The docking of E2 to cellular HSPG may be the initial step in the interaction between HCV and the cell surface resulting in receptor-mediated entry and initiation of infection. (Barth, H. et al., *Cellular Binding of Hepatitis C Virus Envelope Glycoprotein E2 Requires Cell Surface Heparan Sulfate*, J. Biol. Chem., 278:42, 41003-41012 (2003)), therefore a targeting agent specific to this site may block the cell surface receptor and prevent cellular infection. Likewise, the CD81 binding site for E2 has been localized within the large extracellular loop domain, and amino acid residues essential for this interaction have been identified and may be an ideal location for specific targeting agents. (Roccasecca, R., et al. *Binding of the Hepatitis C Virus E2 Glycoprotein to CD81 Is Strain Specific and Is Modulated by a Complex Interplay between Hypervariable Regions 1 and 2*, Jour. of Virology, 77:3, 1856-1867 (2003)).

For example, a binding molecule to a red blood cell surface site or cell surface receptor, surfactant, a ligand, an antibody, proteins, peptides, enzymes, specific chemical compounds, and so on, may be used as targeting agents or markers to target malarial-infected cells. These targeting agents or markers may be used instead of, or in conjunction with, at least one sheath encapsulating the core.

In a corresponding smallpox example, targeting agents which are specific to conserved locations, such as, envelope glycoproteins, and conserved helicase, protease, polymerase, and untranslated regions of the viral RNA. All of these are involved in critical stages of viral replication and therefore may be logical locations for targeting agents.

The nanoparticle size of the entire disclosed Composition may be approximately 1 nm to approximately 10,000 nm. In a more preferred embodiment, the particle size may be approximately 15 nm to approximately 500 nm. A most preferred embodiment for particle size is approximately 20 nm to approximately 200 nm.

Empty liposomes, which are devoid of drugs, may be co-administered or administered before, during, or after the Composition itself to the patient, to function as a decoy, placebo carrier, or redistribution agent with respect to the phagocytic system and allow the Composition to remain in the plasma for an extended period of time. The empty liposome decoys, or placebo carriers, occupy the phagocytic system and also redistribute the disclosed composition away from clearance by cells in the liver and in the spleen and thus concentrate the disclosed composition in the plasma for an extended period of time. Biocompatible materials used for polymeric shells may also be employed as decoys, alone or in combination with liposomes.

Iron dextran is also an exemplary example of a biocompatible iron compound which iron loads tissues through at least two different pathways, and works advantageously with the disclosed Composition as a redistribution agent. The first is phagocytosis by cancer cells through an extended human plasma residence time. The second is increasing the transferrin saturation through processing of the iron dextran through the phagocytic system. The intra-cellular metabolism of iron dextran within a tumor cell increases the acidity of the environment, which further promotes the breakdown of the disclosed Composition. For the purposes of this patent application, phagocytosis and endocytosis are defined as the uptake of material, including particulate materials, into a cell by the formation of a membrane vesicle, and are used herein as equivalent terms.

In one embodiment, the disclosed composition plus iron dextran plus empty liposomes may be added to the total parenteral nutrition ("TPN") for the cancer patient. The disclosed composition includes essential trace elements of copper, and may include iron, as well as glucose, and/or liposomes, which are fats, to contribute to the patient's bodily requirements. Thus the Composition also provides an important contribution to the total parenteral nutrition of the patient.

In yet another embodiment, the Composition may be used with insulin potentiation therapy ("IPT"), with or without iron dextran, to promote the ingestion of these agents of the invention into the tumor cell. (Hauser & Hauser, *Cancer-Treating Cancer with Insulin Potentiation Therapy*, Beulah Land Press, p 267 (2001)). In addition, other insulin potentiators may be added to amplify the effects of the Composition to activate latently infected resting memory lymphocytes and other latently infected cells, including those in sanctuary sites.

Without being limited, held, or bound to any particular theory or mechanism of action, it is believed that the Composition, the redistribution agents, i.e., iron dextran with or without empty liposomes, enters the system, traffics throughout the body as an inert entity, and is removed from the plasma by the phagocytic system and/or cancer cells. The Composition functions as a prodrug, it is inert in the plasma and active intracellularly within cancer cells. The Composition can remain in the mammal's plasma for a period of many days, depending on the dosage levels, when used with a redistribution agent or placebo carrier. (It is known that iron-dextran can remain in the plasma for weeks, especially when doses are administered above the clearance rate of the phagocyte system. The processing of the iron dextran by the phagocytic system is rate limited to a daily maximum amount, leaving the balance for future use.) The sheath may not be immediately recognized as foreign matter by the phagocytic system because it is a sugar-based substance and is not rejected by the mammalian system, allowing the Composition to remain in circulation of the mammal for a longer period than most therapeutics, making it more likely to come into contact with target cells and providing more efficacy with fewer doses than traditional chemotherapeutic agents. The Composition circulates, via any biological pathway, throughout the body and may contact any cell type. For the most part, the phagocytic system takes up the Composition, as do cancer cells which have a high affinity to phagocytize molecules necessary for proliferation, such as sugars. Normal, healthy cells generally have very little interaction with the Composition. The Composition that is taken up by the phagocytic system is processed, to a large degree, through the liver in hepatocytes that store glucose, iron, and copper and are later released through their appropriate protein carriers to feed and nurture cells of the body. Since sugars, copper, and iron are bodily requirements, well known to the phagocytic system, the phagocytic system is able to process, transport, store, or eliminate them with little toxicity, while the Composition kills cancer cells and simultaneously feeds and nourishes cells in the body.

When the Composition is phagocytized by cancer cells, or enters the cells by other means, the Composition is exposed to the cells' acidic environment, including lactic acid, caused by the anaerobic glycolysis process which is common to cancer cells. Any iron dextran that may be present in the cell also contributes to the acidity of the environment during the breakdown of the iron dextran compound. The sugar sheath is metabolized and the core of the disclosed Composition breaks down under acidic conditions, generating at least free ions, free radicals, and reactive oxygen species ("ROS"). The free radicals taken together with the free transition metal ions have cytotoxic effects on the cells and generate DNA-damaging free radicals and ROS. The free radicals and ROS prevent replication of the cell and, eventually, cause cell death. In contrast, normal healthy cells generally process glucose aerobically, without lactic acid production. Therefore, if phagocytized by normal cells, the sheath is not readily broken down and the metal core remains safely encapsulated in the sheath, which buffers the cellular toxicity of the core.

The Composition is ideally suited as a treatment of malaria, and similar microbe-borne diseases because of the Composition is processed through the liver as are the *Plasmodium* as part of their life cycle within a host mammal. Once a mammal is infected, the sporozoite stage of the *Plasmodium* infect the mammal's liver where they reproduce asexually. The sporozoite in the liver mature into schizonts, which later rupture and release merozoites. Therefore, the Composition will be in contact with, and lower and/or eliminate, the parasitic load in the liver since both the Composition and the sporozoites must process through the host mammal's liver. After this initial replication in the liver, the parasites undergo asexual multiplication in the erythrocytes. This multiplication produces merozoites which infect red blood cells. The ring stage trophozoites mature into schizonts, which rupture releasing merozoites into the blood stream of the host. (Some parasites differentiate into sexual erythrocytic stages.) "Blood stage" parasites are responsible for the clinical manifestations of the disease.

While in the blood, i.e. during the blood stage, *Plasmodium* actively ferments glucose as a primary source of energy. The metabolic process of glycolysis converts glucose to lactate, and *Plasmodium* uses essentially the same process as is found in other organisms. *Plasmodium*, and other parasites, exhibit a high rate of glycolysis and utilize up to 75 times more glucose than uninfected erythrocytes. Approximately 85% of that glucose utilized by *Plasmodium* is converted to lactate. The high lactate dehydrogenase ("LDH") activity is believed to function in the regeneration of $NAD^+$ from NADH which is produced earlier in the glycolytic pathway by glyceraldehyde-3-phophate dehydrogenase. The net result of glycolysis is to produce ATP. Therefore, the infected cells have a natural affinity to sugar sheath of the Composition, and uptake the Composition rapidly to continue its glycolytic process.

Some of the glycolytic intermediates may be used for synthetic purposes. Aerobic metabolism also involves the catabolism of pyruvate, which is a glycolysis intermediate preceding lactate, to carbon dioxide and hydrogen atoms via the tricarboxylic acid cycle. The hydrogen atoms are captured by the reduction of $NAD^+$ to NADH. Electrons from the captured hydrogen are fed into a chain of electron carriers and ultimately transferred to molecular oxygen to form water. ATP is generated by capturing energy during electron transport by the oxidative phosphorylation process. While in the blood, *Plasmodium* do not exhibit a complete tricarboxylic acid cycle, except in a glucose-poor host environment. Therefore, the Composition will come in contact with and interact with an over whelming majority of malarial-infected cells, which all have an affinity for glucose.

Some species of *Plasmodium* are known to persist in the liver for long periods of time and cause relapses by invading the bloodstream weeks, or even years later. Therefore, preventative administration of the Composition may also be useful in non-symptomatic mammals located in high-risk areas.

When the Composition is phagocytized by malarial-infected cells, or enters the cells by other means, the Composition is exposed to the cells' acidic environment, including lactic acid, caused by the anaerobic glycolysis process which is common to malarial-infected cells. Any iron dextran that may be present in the cell also contributes to the acidity of the environment during the breakdown of the iron dextran compound. The sugar sheath is metabolized and the core of the disclosed Composition breaks down under acidic conditions, generating at least free ions, free radicals, and reactive oxygen species ("ROS"), including hydrogen peroxide compounds. The free radicals taken together with the free transition metal ions have cytotoxic effects on the cells and generate DNA-damaging free radicals and ROS. The free radicals and ROS prevent replication of the cell and, eventually, cause cell death. In contrast, normal healthy cells generally process glucose aerobically, without lactic acid production. Therefore, if phagocytized by normal cells, the sheath is not readily broken down and the metal core remains safely encapsulated in the sheath, which buffers the cellular toxicity of the core.

Copper is well known to those skilled in the art as a potent viricide. In vitro testing has shown that copper with hydrogen peroxide kills surrogate models of virtually every microorganism afflicting mammals. (See, Sagripanti, et al., *Virus Inactivation by Copper or Iron Ions alone and in the Presence of Peroxide*, Applied and Environ. Microbio, 59:12, 4374-4376 (1993); Sagripanti, *Metal-based Formulations with High Microbicidal Activity*, Applied and Environ. Microbio, 58:9, 3157-3162 (1992)). The disclosed composition has also been shown effective as a potent viricide, and without being bound to a particular theory or mechanism, it is believed that the viricidal action functions as described above to disrupt the viral DNA and rupture the viral envelope. The disclosed Composition can be useful to destroy those viruses known to cause cancer, such as, for example, HBV and HCV for hepatocellular carcinoma, HPV for cervical cancer, EBV (Epstein-Barr virus) for Burkitt's lymphoma, and HTLV 1 for a form of leukemia. Thus the disclosed composition, with or without the addition of the iron-dextran base, is active in the pre-cancerous stages, before the cells become fully transformed. The disclosed composition may advantageously traffic throughout the body, including the central nervous system and brain.

The administration of iron compositions and/or iron dextran compositions may be combined with the disclosed Composition to provide synergistic reactions between the copper and iron for enhanced cellular toxicity. The synergy between copper and iron is known in the art, and has been described in the literature, see, for example, U.S. Pat. No. 5,202,353, incorporated herein in its entirety, which discloses use of the synergistic affects of copper compositions and iron compositions for use as fungicides and bactericides. The iron compositions and/or iron dextran compositions may also be administered to redistribute the disclosed Composition and allow the Composition a longer residence time in the patient's plasma. Far higher dosages of iron dextran may be employed, than that of elemental iron salts, for a greater cytotoxicity, and a protracted residence plasma time. The greater the iron level, the greater the synergistic cytotoxicity of the Composition. Because it is well known in the art that the phagocytic system removes the smaller particles from the plasma circulation first, the combination of the iron dextran with a smaller diameter than the Composition allows a protracted plasma residence time. The diameters of the iron dextran and the core of the disclosed Composition may be varied to manipulate the plasma time of these particles as desired. In one embodiment, the iron dextran can be administered above the clearance level of the phagocyte system, which can serve as a decoy, placebo carrier, or redistribution agent to allow the Composition to remain in the plasma for an extended period of time. (See, Henderson & Hillman, *Characteristics of Iron Dextran Utilization in Man*, Blood, 34(3):357-375(1969)). This use of iron dextran at a dose above the rate of clearance of the phagocyte system, to allow the disclosed Composition to remain in the plasma for an extended period of time, is known in the art as a redistribution (away from the liver and spleen to the plasma). Generally, smaller doses of iron dextran (50-500 mg) are cleared within approximately 3 days, larger doses of iron dextran (>500 mg), however, are cleared at a constant rate of 10-20 mg/hr and are typically associated with increased plasma concentration of iron dextran for as long as 3 weeks. Other agents which may serve as decoys for the phagocytic system to redistribute the disclosed Composition to the plasma include, without limitation, pullulan, dextran sulfate, empty liposomes, and those taught by U.S. Pat. Nos. 6,506,405, and 6,096,331 incorporated herein in their entirety.

Experiments on metabolic clearance rates done on cynomolgus monkeys (species *Macaca fascicularis*) have shown the safe use of large dosages of elemental iron derived from iron dextran. (All experiments were preformed in compliance with the Animal Welfare Act and Regulations.) Dosages of 400 mg and 500 mg of elemental iron, derived from iron dextran, per kg of body weight were safely administered to the cynomolgus monkeys by intravenous infusion. The iron dextran showed a protracted plasma residence time which functions as a decoy for the phagocytic system to redistribute the disclosed Composition to the plasma with few negative side effects. As shown in FIGS. 15A, B and C, the administered iron dextran remained in the monkey plasma for at least 120 hours, at milligram levels. Single dosages of iron dextran were also separately administered to monkeys, as shown in FIG. 16, with few negative side effects, i.e. abdominal swelling. The monkey model clears the iron dextran from the system much more very rapidly, as compared to humans, because of a higher metabolic rate. Therefore, a longer plasma residence time is anticipated in humans, as has been shown in research, such as, for example, Henderson & Hillman, (1969).

The side effects of the Composition, with or without the addition of an iron dextran compound, are far fewer than the well-known side effects of the standardly administered chemotherapy, although the disclosed Composition can be used in conjunction with additional therapeutic agents. The disclosed Composition and iron dextran have breakdown byproducts of copper and iron, which support the bioproduction of red blood cells, white blood cells and platelets. Because the Composition supports the hemopoietic system, its use limits or eliminates the well-known devastating fatigue, risk of infection, and the adverse effects of cytotoxic chemotherapy on the bone marrow (and other quickly growing cells) that are standardly caused by commonly used chemotherapy agents. In addition, the use of ancillary medications such as colony stimulating factors to accelerate bone marrow recovery and erythropoietin, a colony stimulating growth factor for red blood cells for the prevention of severe myelosuppression, and their severe side effects can be restricted. Since the need for the use of these drugs can be restricted, the quality of life of the patient may be improved.

For diagnostic purposes, the Composition may be labeled with magnetic targeted carriers to allow imaging of the cancer cells and provide information to determine further medical treatments, including targeting tumors with external magnets. (Johnson, *An Innovative Drug Delivery Technology*, Magnetics Business & Technology Magazine, (2002)). A wide variety of other labels may be employed, such as radionuclides, fluors, enzymes, enzyme substrates, enzyme co-factors, enzyme inhibitors, ligands (particularly haptens), etc., and are well known to those skilled in the art.

Since the disclosed composition, iron dextran, and empty liposomes are all formed of biocompatible materials, all may be administered over an extended period of time as compared to other chemotherapeutic agents. The effective dose or effective amount can vary subject to the evaluation of those of skill in the art in relation to the particular type of cancer, the regimen of administration, the body weight of the subject, the aggressiveness of the cell growth and the degree in which the subject has been negatively affected by prior chemotherapy. In general, a therapeutically effective amount is that which decreases, or at minimum prevents further growth, of a primary or metastatic tumor.

The disclosed Composition can be administered to a patient as a pharmaceutical composition in combination with a pharmaceutical carrier. A pharmaceutical carrier can be any compatible, non-toxic substance suitable for delivery of the Composition to the patient that is medically acceptable. Sterile water, alcohol, fats, waxes, and inert solids may be included in the carrier. Pharmaceutically accepted adjuvants (buffering agents, dispersing agent) may also be incorporated into the pharmaceutical compound. In one embodiment, the Composition may be combined with sterile water, or deinozed water and free dextran, dextran free of drug, to form a sterile colloidal suspension.

The disclosed Composition may be administered to a patient in a variety of ways, such as oral, intravenous, subcutaneous, intraperitoneal, intrathecal, intramuscular, intracranial, inhalational, topical, transdermal, suppository (rectal), pessary (vaginal) or an implantable polymer disclosed composition saturated depot or wafer, such as, for example, a Giladel Wafer®. Preferably, the pharmaceutical compound may be administered parenterally, e.g., subcutaneously, intramuscularly or intravenously. Thus, the disclosed Composition may include a solution dissolved in an acceptable carrier, preferably an aqueous carrier, for parenteral administration. A variety of aqueous carriers can be used, e.g., water, buffered water, 0.4% saline, 0.3% glycine and the like. These solutions are sterile and generally free of particulate matter. These compounds may be sterilized by conventional, well-known sterilization techniques. The Composition may contain pharmaceutically acceptable auxiliary substances as required to approximate physiological conditions such as pH adjusting and buffering agents, and if necessary for sensitive patients, toxicity adjusting agents and the like, for example sodium acetate, sodium chloride, potassium chloride, calcium chloride, sodium lactate, etc. The concentration of the disclosed Composition in these formulations can vary widely, e.g., from less than about 0.1 mg to about 5 mg, ranging to as much as 10 mg or 15 mg or more of the equivalent of elemental copper derived from the Composition per ml of carrier. The preferred concentration of the disclosed Composition is approximately 5 mg of the equivalent of elemental copper derived from the Composition per ml of carrier, and will be selected primarily based on fluid volumes, viscosities, etc., in accordance with the particular mode of administration selected. The preferred pH range for use with the disclosed Composition is between approximately 7 and approximately 8.5, and the more preferred pH range is between approximately 7.5 and approximately 8.0.

Actual methods for preparing parenterally administerable compounds and adjustments necessary for administration to patients, typically mammals, will be known or apparent to those skilled in the art and are described in more detail in, for example, *Remington's Pharmaceutical Science: The Science and Practice of Pharmacy*, 20$^{th}$ Ed., Lippincott, Williams & Wilkins; (2000), which is incorporated herein by reference.

It will be appreciated that the disclosed Composition addresses the very pressing problem of targeting cancer therapy for specificity, while greatly limiting or eliminating the horrendous side effects of chemotherapy. Moreover, the disclosed Composition, especially when used with iron dextran, can overcome the difficulties of drug resistance. The disclosed composition may be employed with or without the iron dextran loading, to accomplish highly effective treatment against solid tumors, liquid tumors (blood), as well as metastatic cancers, while providing an agent that is cost effective because low dosages produce high activity and results. The disclosed Composition is designed to be administered by itself as a chemotherapeutic agent, with iron dextran, and/or in conjunction with conventional cancer therapies. Most importantly, the Composition's highly targeted and highly efficient cell kill rate can save innumerable lives at a cost effective rate that can be made available to any medical facility. For example, the disclosed Composition is very well suited to treat hepatocellular carcinoma, with or without iron loading. Hepatocellular carcinoma ("HCC") is the most common, primary cancer of the liver, and causes over 550,000 deaths annually, worldwide. Heretofore, no significantly effective treatments existed for HCC. (Nakakura & Choti, *Management of Hepatocellular Carcinoma*, Oncology, 14(7) (2000)). The disclosed Composition, however, may be introduced to the blood stream, and traffic through the hepatic artery to expose the normal hepatocytes and the cancerous hepatocytes to the Composition. The hepatocytes breakdown the dextran to use or store glucose as glycogen, and may also store copper and iron that is derived from the Composition. Thus, the HCC cell is subject to the cytotoxicity caused by the disclosed Composition. Any excess copper that is not stored, may be excreted through the biliary, and other bodily systems. Copper and iron from the hepatocytes are bound to the respective protein carriers, which include transferrin and ceruloplamin to feed the cells of the patient's body.

It may also be appreciated that the disclosed Composition addresses the very pressing problem of malaria therapy which provides efficient and safe treatment while remaining cost-accessible to developing areas which typically suffer the highest rates of vector and microbe borne diseases. The disclosed composition may be employed with or without the iron dextran loading, to accomplish highly effective treatment against malaria, other parasitic diseases of a protozoan, bacterial, fungal or viral origin. The disclosed Composition is designed to be administered by itself as an anti-malarial agent, with iron dextran, and/or in conjunction with conventional therapies. Most importantly, the Composition is highly efficient and high targeted towards affected cells, which can save innumerable lives at a cost effective rate that can be made available to any medical facility around the world. Since the life cycle of the malarial protozoan reproduces in the host's liver within 48 hours, and the Composition must be processed through the liver, the Composition will limit and/or eliminate the microbes before the infection can advance to further stages. Any excess copper that is not stored, may be excreted through the biliary, and other bodily systems. Copper and iron from the hepatocytes of the liver are bound to the respective protein carriers, which include transferrin and ceruloplamin to feed the cells of the patient's body.

The following examples are intended to illustrate but not limit the invention. While they are typical of those that might be used, other procedures known to those skilled in the art may alternatively be used.

EXAMPLES

Example 1

An in vitro human tumor screen was used to evaluate anti-proliferative effects of the disclosed Composition and the Composition in combination with the Base Compound of iron dextran. Human tumor cell lines representing models of cancers with the greatest incidence, greatest increase of incidence, the greatest mortality, or cancers that are highly resistant to treatment were selected. The testing was conducted using standard tissue culture techniques that are well known in the art and the $^3$H-thymidine assay for analysis.

Experimental Design.

This experiment was designed to evaluate the anti-proliferative and cytotoxic effects of the disclosed Composition alone, and in combination with Base Compound, and doxorubicin, also known by its trade name Adriamycin, as a positive control which is a mainstay in the treatment of many cancers used in combination with various chemotherapies (See, Chu and Devita, *Cancer Chemotherapy Drug Manual* 2003, Jones and Bartlett Publishers, pg 138-139. (2003)) on the human tumor cell lines CAK-1 renal, DLD-1 colon, LOX IMVI melanoma, MCF7 mammary, NCI-H23 lung, NCI-H460 lung, OVCAR-3 ovarian, PC-3 prostate, SNB-75 CNS, ZR-75-1 mammary, and CEM-SS leukemic cells. See, FIG. 14. For all experiments, the cells were harvested, centrifuged to remove the media, and suspended in fresh complete medium. Samples were taken to determine cell density. All cell counts were determined with a Coulter Model $Z_1$ cell counter (Beckman Coulter, Inc. Fullerton, Calif.) and viability was measured with propidium iodide staining followed by analysis on a Coulter EPICS XL flow cytometer (Beckman Coulter, Inc. Fullerton, Calif.). All cell lines were each plated at $5 \times 10^3$ cells per well in complete medium. The following day, the cells were dosed with 8 dilutions of the Composition alone and the Composition in combination with the Base Compound of iron dextran (60 µg/mL, which is the equivalent of elemental iron derived from iron dextran). All iron dextran amounts are measured as the approximate equivalent of elemental iron derived from the iron dextran. The Base Compound of iron dextran was also run alone as a control. The plates were analyzed on Day 4 after the initiation of treatment.

The Composition was formed as follows: An inorganic copper salt, 4.854 g of copper nitrate (99.999%), was dissolved in 20 ml deionized water (Molecular Biology Reagent from Sigma-Aldrich), or distilled water could also be used. This solution was refluxed for approximately two hours. The copper salt solution was reacted with 2 g of oxidized dextran or 2 g of hydrogenated dextran at low temperature. (Clinical grade dextran, D4751 with an average molecular weight of 64,000-78,000, was purchased from Sigma-Aldrich.) This solution was refluxed for 1 hour before adding 0.2 ml of 0.5 M NaOH in the solution. After refluxing the solution for another two hours, it was divided in half. Half of the solution was combined with 2 g of oxidized dextran, and 40 ml of water were added, and followed by a two-hour refluxing step. The second half of the solution was combined with hydrogenated dextran, 40 ml of water were added, and followed by a two-hour refluxing step. The solutions were then each combined with 0.1 ml of 0.5 NaOH, and the reflux was continued for an additional two hours. The solutions were allowed to cool to room temperature. The resulting solution of a $Cu(OH)_2$-dextran nanoparticles were precipitated in a controlled manner, wherein each $Cu(OH)_2$ nanoparticle is covered by dextran molecules by adding 120 cc of 0.25 M NaOH to the final solutions. The water content of the solutions was evaporated in a vacuum to increase the copper concentration in the solutions. The precipitates with large particles were centrifuged to prepare the aqueous solutions of $Cu(OH)_2$-dextran nanoparticles. The final copper concentration in the solutions was typically approximately 5 mg/ml and the final pH ranges from approximately 7.5 to approximately 8.5, and was assayed by atomic absorption spectrometry and/or inductive coupled plasma spectrometry. The particle size of the $Cu(OH)_2$-dextran nanoparticles was determined by laser light scattering. The particle size for oxidized dextran was in the range of approximately 150 nm to approximately 200 nm and for hydrogenated dextran was in the range of approximately 20 nm to approximately 50 nm. After determining the particle size, the solutions were tested for free copper ions using a copper electrode. The copper specific electrode was calibrated with four known copper concentrations solutions. These concentrations were as follows: 0.1 moles/liter, 0.01 moles/liter, 0.001 moles/liter and 0.0002 moles/liter (~1 ppm). The millivolt readings of four standard Cu2+ solutions were, respectively:

| Cu2+ Conc. | mV |
|---|---|
| 0.1 M | 239 |
| 0.01 M | 206 |
| 0.001 M | 175 |
| 0.0002 M (1 ppm) | 163 |

The mV reading for these copper solutions was typically less than 130 mV, which suggest that free Cu2+ concentration in solutions is less than 1 ppm, and often lower than the level of detection. (As a point of reference, the Environmental Protection Agency allows 1.3 ppm of copper in drinking water, see, for example, a website of the United States Environmental Protection Agency on safe water, and possible contaminants of drinking water, including copper.) The colloidal suspensions of the disclosed Composition in all samples had little free copper detected, typically approximately below the levels of detection of 1 ppm. The copper hydroxide solution prepared using oxidized dextran had a pH of 8.5. The solution formed with hydrogenated dextran exhibited no free copper ions, typically below the levels of detection of 1 ppm.

Preparation of Copper Hydroxide-Iron Hydroxide Nanoparticles (a) Preparation of Sample 1

A copper salt, 2.428 g, of Cu nitrate (99.999% pure, Alfa Aesar, catalog #10699) was combined with 0.2 g of $FeCl_3$, $6H_2O$ (purity 97-102%, Alfa Aesar, Catalog #12497), and 4.0 g of hydrogenated dextran. These components were dissolved in 70 ml of deionized water (Molecular Biology Reagent from Sigma-Aldrich). This solution was then refluxed for approximately 3 hrs. The solution was allowed to cool before adding 92.8 cc of 0.25M NaOH (Fisher ACS, catalog # S318-3) into the solution. The final pH of the solution was 8.5. After 6 days, pH decreased to 6.85, and 1.7 cc of 0.25M NaOH solution was added to adjust the pH to 8.5. Analysis of the copper and iron concentration in solution was done by atomic absorption spectrometry ("AA") and/inductive coupled plasma spectrometry ("ICP"). The solution was syringe filtered, and the dark green solution was stored in sterile vials. Iron oxyhydroxide may also be employed as a substitute for iron hydroxide in this or any sample.

(b) Preparation of Sample 2

The copper salt, 2.428 g, of Cu nitrate (99.999% pure, Alfa Aesar, catalog #10699) was combined with 0.4 g of $FeCl_3$, $6H_2O$ (purity 97-102%, Alfa Aesar, Catalog #12497), and 4.2 g of hydrogenated dextran. These components were dissolved in 75 ml of deionized water (Molecular Biology Reagent from Sigma-Aldrich). This solution was refluxed for approximately 3 hrs. The solution was allowed to cool before adding 102.2 cc of 0.25M NaOH (Fisher ACS, catalog # S318-3) in the solution. The final pH of the solution was 8.5. After 6 days, pH decreased to 7.4, and 1.6 cc of 0.25M NaOH solution was added to adjust the pH to 8.5. Analysis of the copper and iron concentration in solution was done by AA and/ICP. The solution was centrifuged, and the dark green solution with slight haze was stored in sterile vials.

(c) Preparation of Sample 3

The copper salt, 2.428 g, of Cu nitrate (99.999% pure, Alfa Aesar, catalog #10699) was combined with 0.2 g of $FeCl_3$, $6H_2O$ (purity 97-102%, Alfa Aesar, Catalog #12497), 1.2 g of hydrogenated dextran, and 2.8 g dextran (MW=15,000). These components were dissolved in 70 ml of deionized water (Molecular Biology Reagent from Sigma-Aldrich). This solution was refluxed for approximately 3 hrs. The solution was allowed to cool before adding 83.2 cc of 0.25M NaOH (Fisher ACS, catalog # S318-3) into the solution. The final pH of the solution was 8.5. After 6 days, pH decreased to 7.64, and 0.6 cc of 0.25M NaOH solution was added to adjust the pH to 8.5. Analysis of the copper and iron concentration in solution was done by M and/ICP. The solution was centrifuged, and the dark green solution was stored in sterile vials.

Experimental Design I

Cell Lines and Standard Agents

The cell lines were propagated using standard tissue culture procedures and seeded in microtiter plates prior to dosing. The control groups included a Base Compound (60 µg/mL) only treatment, complete medium control, and positive control (doxorubicin, 1 µM). For each concentration level of the Composition, eight replicates of each cell line were treated.

Cell Culture

The cell lines used in the following Examples are listed below in Chart 1. The Composition was tested on the listed solid tumors, and liquid tumors, but may be effectively used for any type of cancers. The cell lines were propagated under sterile conditions and incubated at 37° C. in HEPA-filtered $CO_2$ tissue culture incubators with 5% $CO_2$ and 95% humidity. Each cell line was sub-cultured weekly to bi-weekly or more frequently for use in experiments.

$^3$H (Tritiated)-Thymidine Assay

Anticellular effects of the compounds on the tumor lines were assessed with the $^3$H-thymidine DNA incorporation assay. Tritiated-thymidine was purchased as a 1 mCi stock and diluted 1:25 in media. One day prior to harvest, 25 µL (1 µCi) of the diluted $^3$H-thymidine was added to each well, and the plates were incubated overnight. The following morning the cells were harvested onto glass fiber filters using a Skatron cell harvester (Molecular Devices Corporation, Sunnyvale Calif.). The filters were then placed in scintillation vials and scintillation cocktail was added (Beckman Coulter, Inc. Fullerton, Calif.). The vials were then read on a Beckman LS6000IC liquid scintillation counter (Beckman Coulter, Inc. Fullerton, Calif.) and the data were reported as counts per minute (CPM). The data were transferred into Lotus 123 for processing.

For all cell lines, the cells were harvested, centrifuged to remove the media, and suspended in fresh complete medium. Samples were taken to determine cell density. The cell count was determined with a Coulter Model $Z_1$ cell counter (Beckman Coulter, Inc. Fullerton, Calif.) and cell viability was measured with propidium iodide staining. Analysis was then conducted on a Coulter EPICS XL flow cytometer (Beckman Coulter, Inc. Fullerton, Calif.). The cell lines were each plated at 5×10$^3$ cells per well in complete medium. On the second day, the cells were washed with 8 dilutions of the disclosed Composition alone, or in combination with the Base Compound at the concentration of 60 µg/mL. A control was run by washing cells with only the Base Compound. On day 4 after the initial treatment, the plates were analyzed. The results were summarized below:

TABLE 1

| Cell Line | $IC_{50}$ (µg/mL) Composition | $IC_{50}$ (µg/mL) Composition and Base Compound (60 µg/mL) |
|---|---|---|
| CAKI-1 renal | 1.440 | 1.138 |
| DLD-1 colon | 1.430 | 0.196 |
| NCI-H23 lung | >10 | 1.718 |
| NCI-H 460 lung | 1.183 | 0.131 |
| LOX IMVI melanoma | 6.718 | 0.513 |
| MCF7 mammary | 2.213 | 0.972 |
| OVCAR-3 ovarian | 3.662 | 0.299 |
| PC-3 prostate | >10 | 1.869 |
| SNB-75 CNS | 0.895 | 0.095 |
| ZR-75-1 mammary | >10 | 2.031 |
| CEM-SS Leukemic 1 | 5.87 | |
| CEM-SS Leukemic 2 | 4.975 | |

The experiments, described below, performed on tumor cells lines are presented with results in Table 1, with the exception of the HT29 human colon adenocarcinoma cells. The Composition plus the Base Compound at 60 µg/ml resulted in 100% cell kill, with the exception of the CAKI-1 renal line, which resulted in 99% cell kill. Moreover, the further addition of increased base compound to composition increases the cytotoxicity, if necessary. In three cell lines that were resistant to Composition alone, up to 10 µg/ml, namely NCI-H23 lung, ZR-75-1 mammary and PC-3 prostate, resistance was completely overcome with the addition of Base Compound to the Composition, at 60 µg/ml, resulting in 100% cell kill. For all cell lines that were exposed to the Base Compound, the $IC_{50}$ was lowered significantly by the synergistic, ctyotoxic effects of the Base Compound in combination with the disclosed Composition, demonstrating enhanced cell kill with the addition of Base Compound. For all the cell lines that were exposed to the Base Compound, Composition with the Base Compound equaled or exceeded the cell kill of doxorubicin, a mainstay chemotherapeutic drug in the treatment of breast cancer and other cancers, which is well known to have many severe side effects.

Example 2

Figure 1:
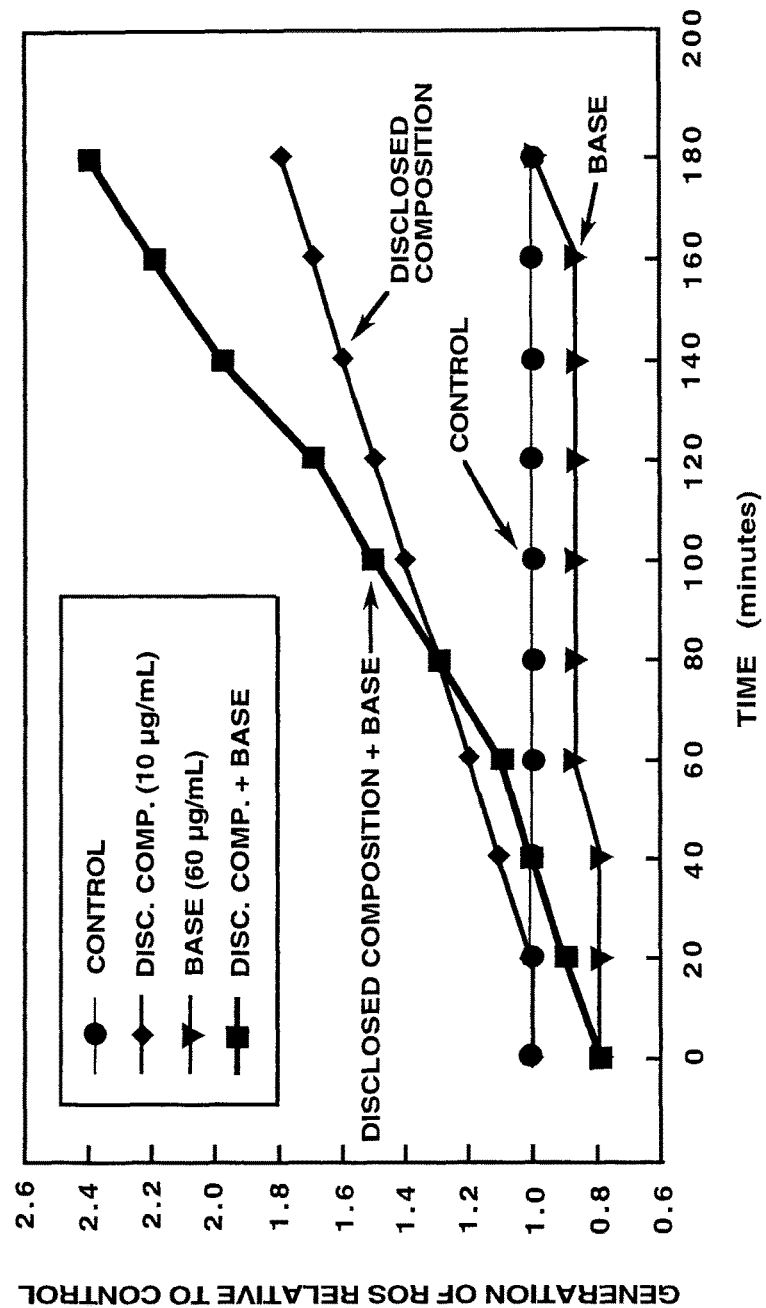
FIG. 1 is a graph of the release of ROS by HT29 human-colon adenocarcinoma cells by iron dextran alone and the Composition alone and in combination after 24 hours pre-incubation.

FIG. 1 the Release of ROS (Reactive Oxygen Species) by HT29 Human Colon Adenocarcinoma Cell Line after 24-Hr Incubation.

The data were obtained after a 24 hour incubation of HT29 cells with 10 µg/mL of the disclosed Composition, 60 µg/mL of the Composition plus Base Compound, and 60 µg/mL of the iron dextran Base Compound alone. The assay depends on a non-fluorescent substrate added to wells in which cells are growing. Where ROS are present, the substrate is broken down to form a fluorescent product. The data in FIG. 1 demonstrates that the Composition produces ROS above the level of the control of fresh medium and the Base Compound. The data further demonstrates an increased production of ROS with the disclosed Composition in combination with the Base Compound, above that of the disclosed Composition or the Base Compound alone. The combination of the disclosed Composition and the Base Compound generates a significant amount of ROS, as do radiation treatments for cancer patients, which is generally believed to exert its cytotoxic effect by the generation of DNA damaging free radicals. The combination of the disclosed Composition and the Base Compound can be used in conjunction with radiation treatment can increase the amount of cancer killing free radicals generated by radiation and exert increased cell-kill over radiation alone. This is known in the art as a radio sensitizer, compounds which amplify and potentiate the cytotoxic effect of radiation.

Example 3

Figure 2A:
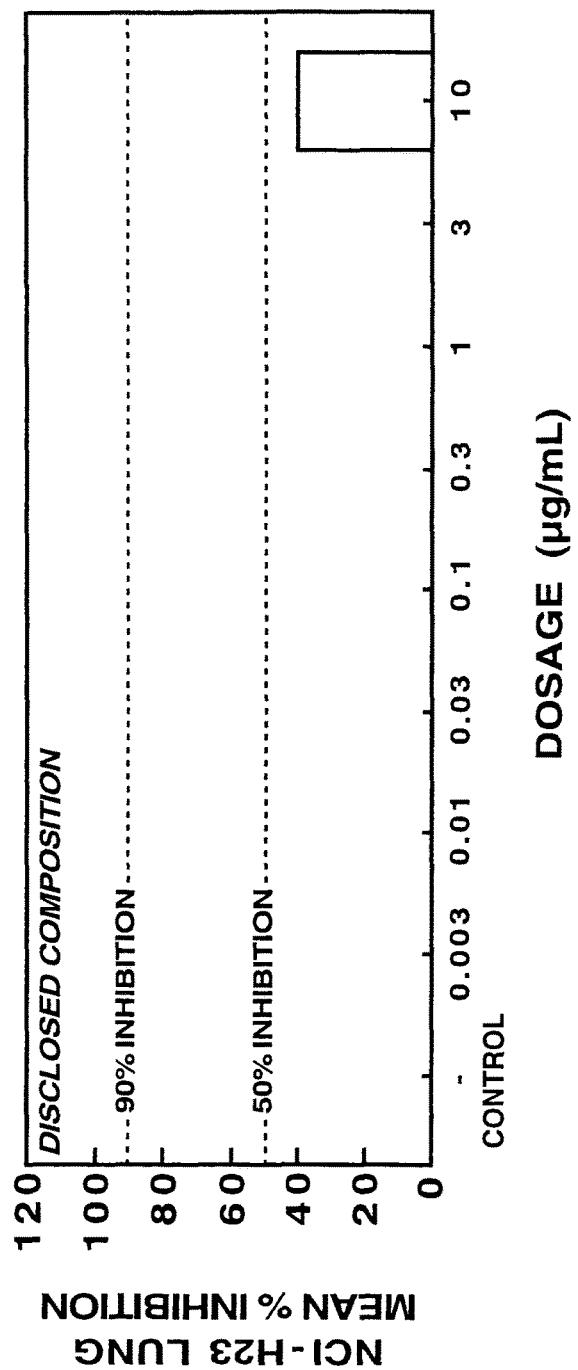
FIG. 2A is a graph of the concentration of the Composition alone plotted against NCI-H23 lung cells mean percent inhibition.

FIG. 2A discloses a graph of the mean inhibitory concentration of the disclosed Composition against the NCI-H23 lung cells. The inhibitory concentration 50 ("$IC_{50}$") is defined as the concentration of the employed composition or compound that is inhibitory or effective on 50%, or more, of the cells used in an experimental procedure. The disclosed Composition has a highly effective $IC_{50}$ level of approximately 10 µg/ml when applied to NCI-H23 lung cells. FIG. 2B provides the absorbance values of the disclosed Composition, the Base Compound, doxorubicin, and a control for the NCI-H23 Lung cells in both media and MTS reagent (Promega, Madison Wis., U.S.). The MTS reagent is a tetrazolium salt that it is converted to a colored compound of formazan when applied to live cells, with the emission of light at approximately 490 nm. The disclosed Composition inhibited forty percent of the cultured NCI-H23 Lung cells at a dosage 10 µg/mL. Although doxorubicin exhibited a high inhibitory effect, it is also known to have many detrimental side effects when used in vivo, which the disclosed Composition will not cause. The absorbance value units are also given and some background absorbance was assumed to have occurred, and typically ranges between 0.2-0.4 units after 4 hours of incubation. FIG. 2C discloses the expected theoretical absorbance levels of the disclosed Composition for varying IC levels.

Figure 2D:
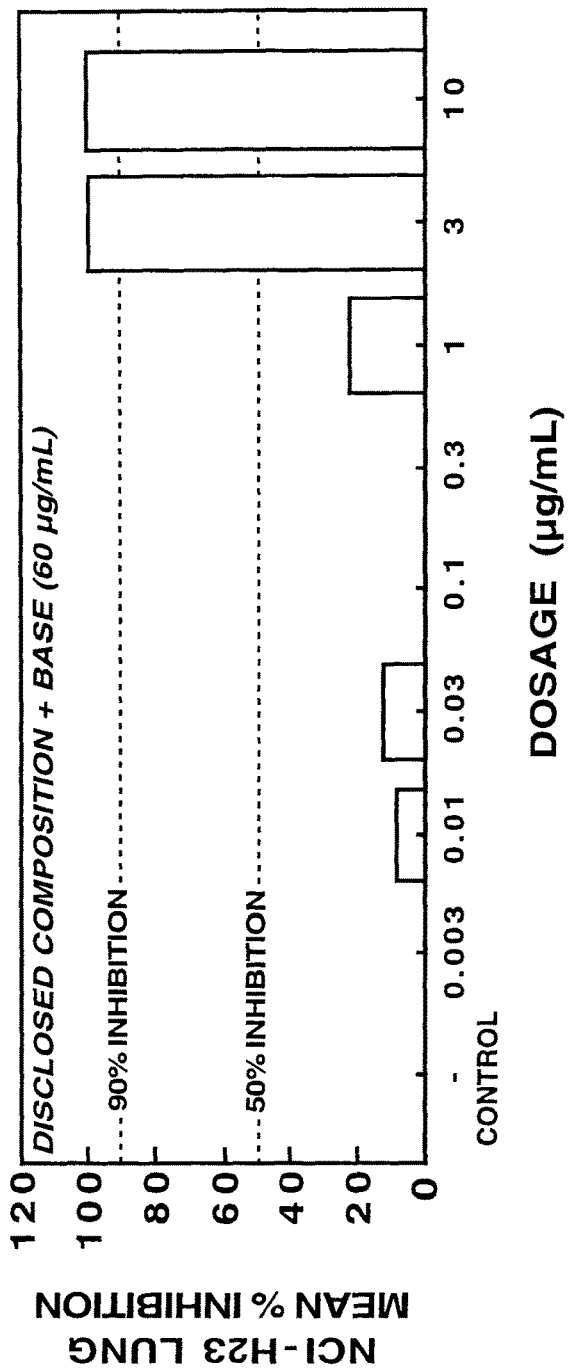
FIG. 2D is a graph of the concentration of the Composition plus Base Compound plotted against NCI-H23 lung cells mean % inhibition.

As shown in FIG. 2D, the NCI-H23 lung cells showed little or no resistance to both the 3 µg/mL and 10 µg/mL dosages of the Composition with the addition of the Base Compound. This combination of the Composition with the addition of the Base Compound resulted in over a 99-100% inhibition of the cells in vitro, which equals that of doxirubicin. The concentration of the Composition together with the Base Compound was 60 µg/mL. FIG. 2E shows the absorbance values and inhibition percentages of the Composition plus Base Compound combination, which demonstrated 100% inhibition of the NCI-H23 lung cells at the low dosage of 10 µg/mL. FIG. 2F show the statistical results of the regression output for the experiments.

Example 4

Figure 3A:
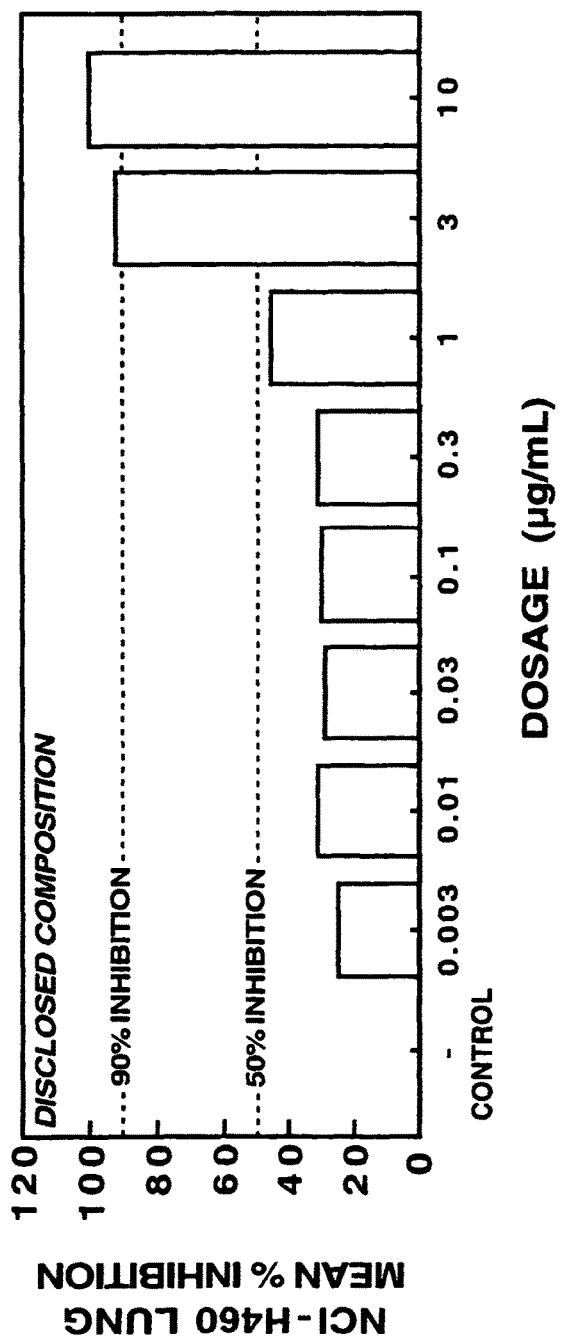
FIG. 3A is a graph of the concentration of the Composition alone plotted against NCI-H460 lung cells mean % inhibition.

FIG. 3A shows over 90% inhibition of NCI-H460 lung cells with the high activity and cytotoxicity of the disclosed Composition at a 10 µg/mL concentration. The disclosed Composition was also highly effective at a 3 µg/mL concentration with a 90% inhibition rate and nearly 50% inhibition of the cells at only a 1 µg/mL concentration. The disclosed Composition also exhibited significant inhibition percentages at very low dosages. FIG. 3B provides the absorbance value units from the varying dosages, as shown, as well as the inhibition percentages for the different dosages, which were very high. FIG. 3C discloses the $IC_{50}$ at a low dosage of 1.183 µg/mL of the Composition, and the statistical analysis of the regression output.

Figure 3D:
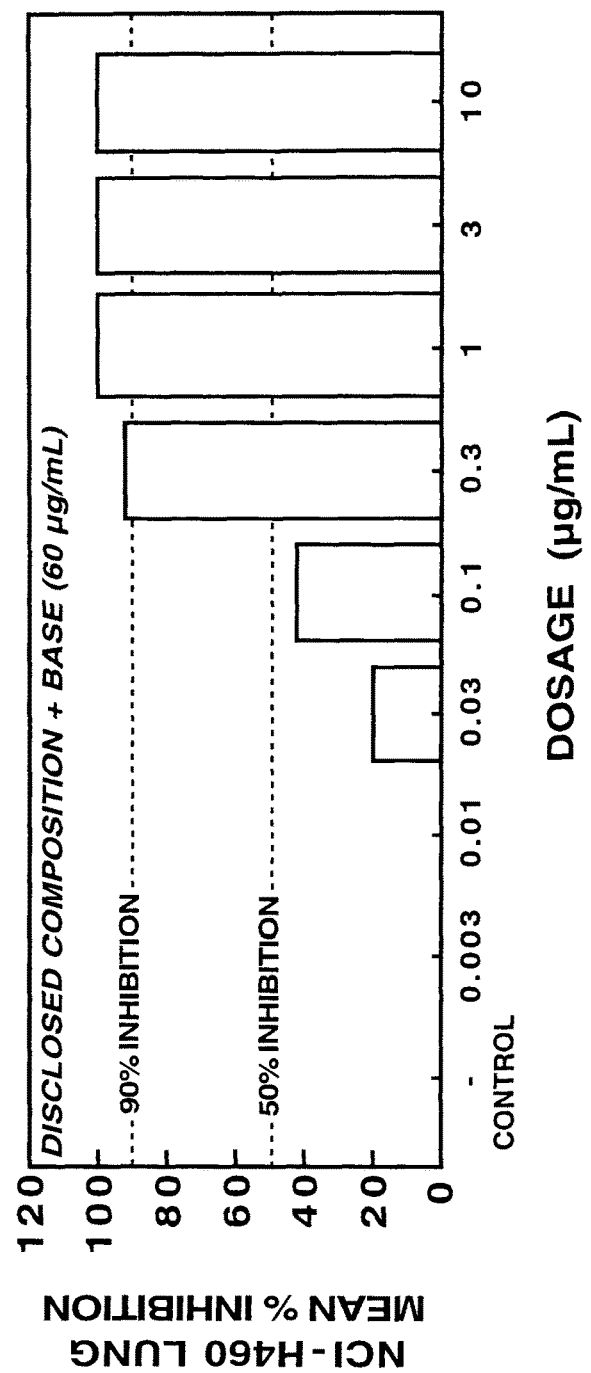
FIG. 3D is a graph of the concentration of the Composition plus Base Compound plotted against NCI-H460 lung cells mean percent inhibition.

This example examines the effect of toxicity of the Composition plus the Base Compound against NCI-H460 lung cells. The results of these tests are shown in FIGS. 3D, 3E and 3F. FIG. 3D shows an enhanced cell kill of the NCI-H460 lung cells where the Base Compound is added to the disclosed Composition, as compared to the results of the Composition itself. As shown in FIG. 3A, 10 µg/ml of the Composition were applied for a resulting 100% cell kill. Where the Base Compound was added to the Composition, 1 µg/ml of Composition plus Base Compound resulted in a 100% cell kill, as shown in FIG. 3D. The concentration of Composition plus Base Compound was a very efficient 0.131 µg/ml resulting in an $IC_{50}$ inhibition, and by contrast, the concentration of the Composition alone was 1.183 µg/ml to resulting in an $IC_{50}$ inhibition of the experimental cells. FIG. 3E discloses the absorbance value units from the varying dosages, as shown, as well as the inhibition percentages for the different dosages, which were very high. The combination of the Composition with the Base Compound was shown to be highly effective in its toxic activity against NCI-H460 Lung cells.

Example 5

Figure 4A:
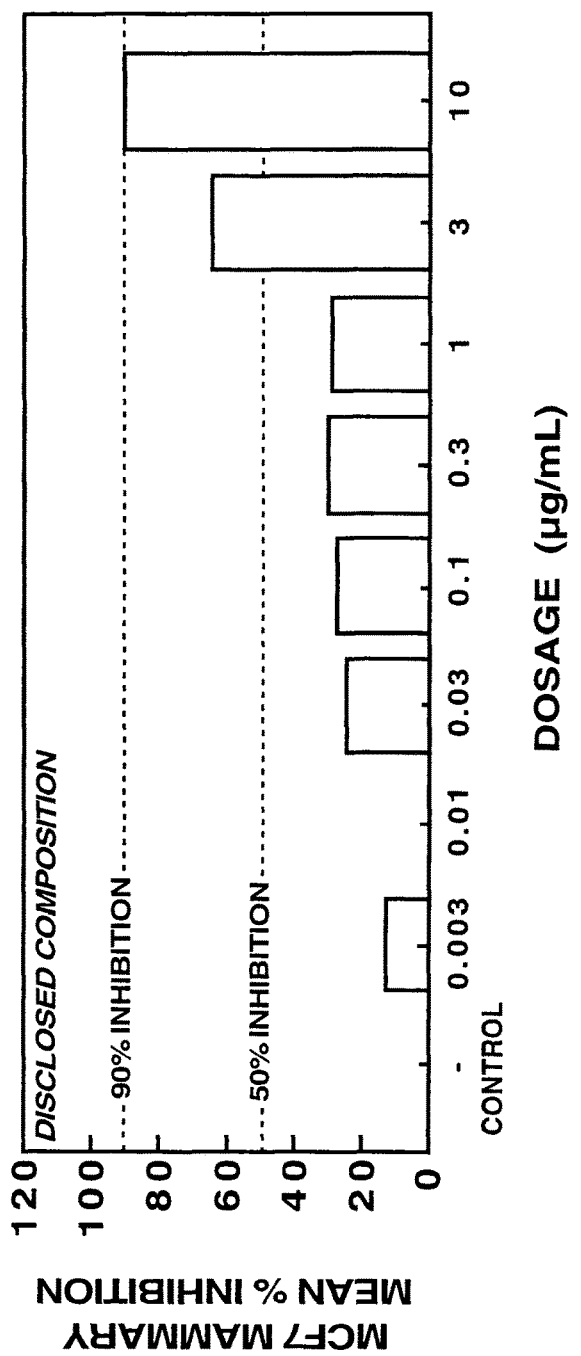
FIG. 4A is a graph of the concentration of the Composition alone plotted against MCF7 mammary cells mean percent inhibition.

This example examines the effect of toxicity of the Composition alone against MCF7 mammary cells. FIG. 4A shows the very high activity of the disclosed Composition against MCF7 mammary cells. The Composition exhibited over 90% inhibition of the cells at 10 µg/mL, and over 60% inhibition at 3 µg/mL. FIG. 4B provides the absorbance values for disclosed Composition, plus the media and MTS. FIG. 4C provides the calculated $IC_{50}$ of 2.213 µg/mL, and the regression output for 3.000 and 1.000 concentrations.

Figure 4D:
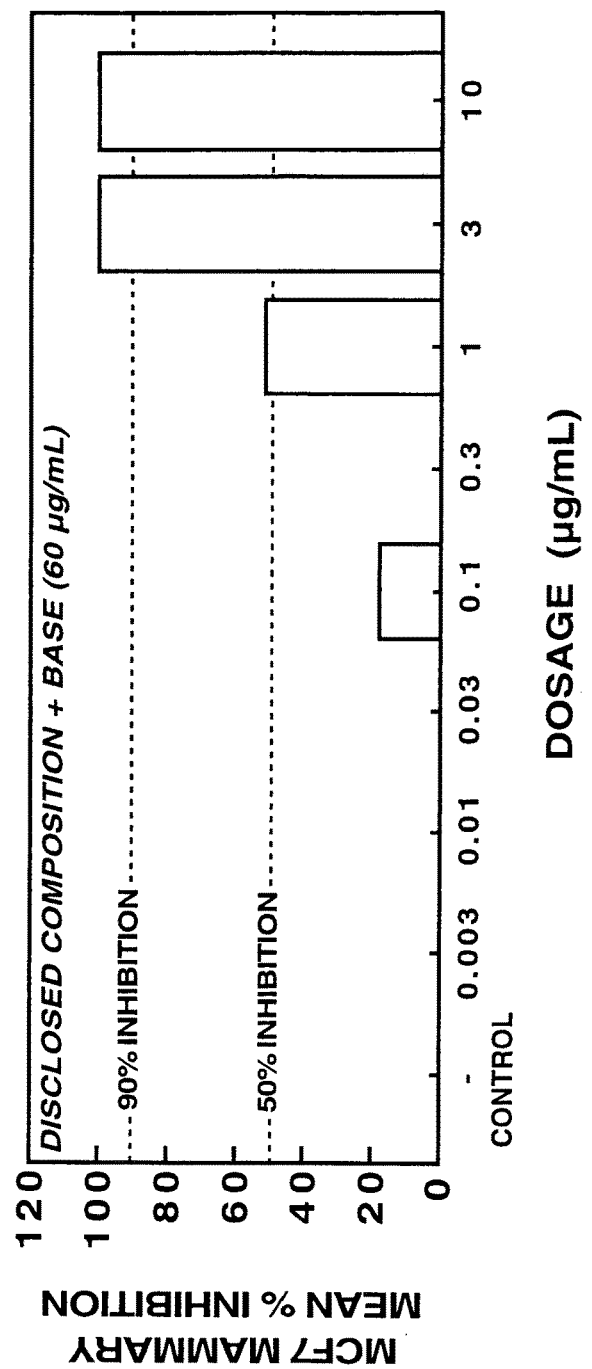
FIG. 4D is a graph of the concentration of the Composition plus Base Compound plotted against MCF7 mammary cells mean % inhibition.

FIGS. 4D, 4E and 4F examine the effect of toxicity of the Composition in combination with the Base Compound against MCF7 mammary cells. These tests show an enhanced cell kill with the addition of the Base Compound to this cell line, as compared to the disclosed Composition only, as shown in FIGS. 4A, 4B, and 4C. FIG. 4A shows that 10 µg/ml were required for 90% cell kill. When tested in combination with the Base Compound, only 3 µg/ml of the Composition is required for 100% of cell kill, which lowered the $IC_{50}$ to 0.972 µg/ml for the same cell line.

Example 6

Figure 5A:
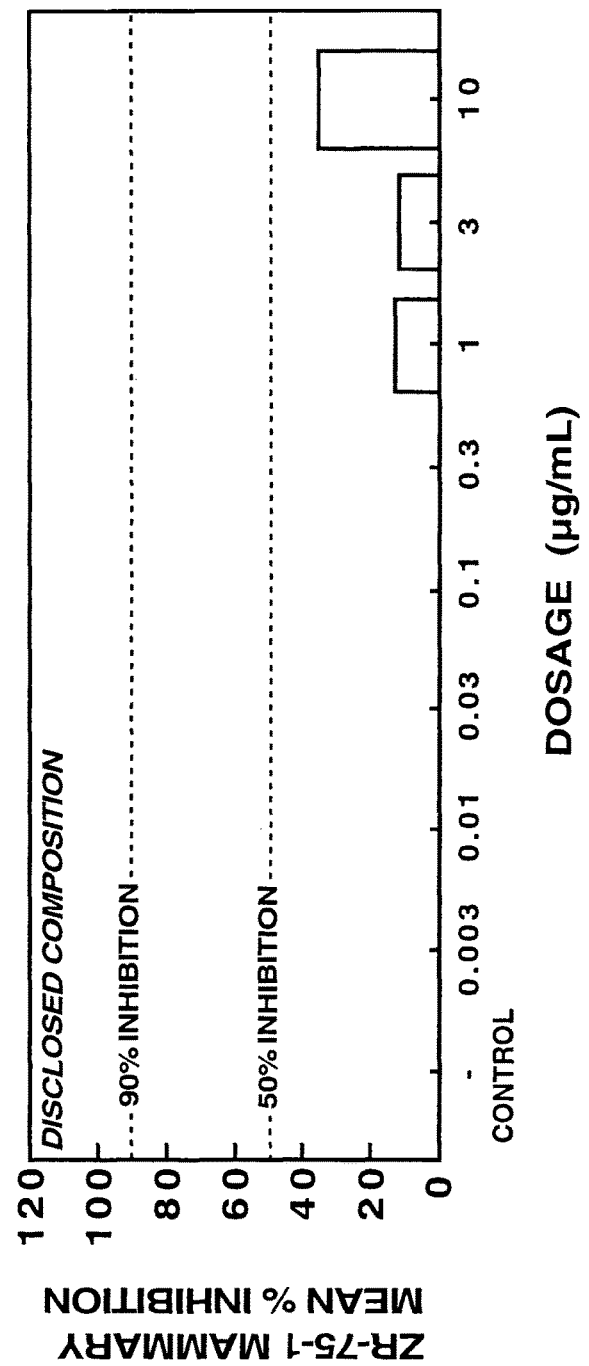
FIG. 5A is a graph of the concentration of the Composition alone plotted against ZR-75-1 mammary cells mean percent inhibition.

FIG. 5A graphs the effect of toxicity of the disclosed Composition against ZR-75-1 mammary cells. These tests showed an approximately 35% inhibition at 10 µg/mL of the ZR-75-1 mammary cells. This cell line showed resistance to the Composition at concentrations up to approximately 10 µg/ml. The absorbance values and inhibition percentages are shown in FIGS. 5B and 5C.

Figure 5D:
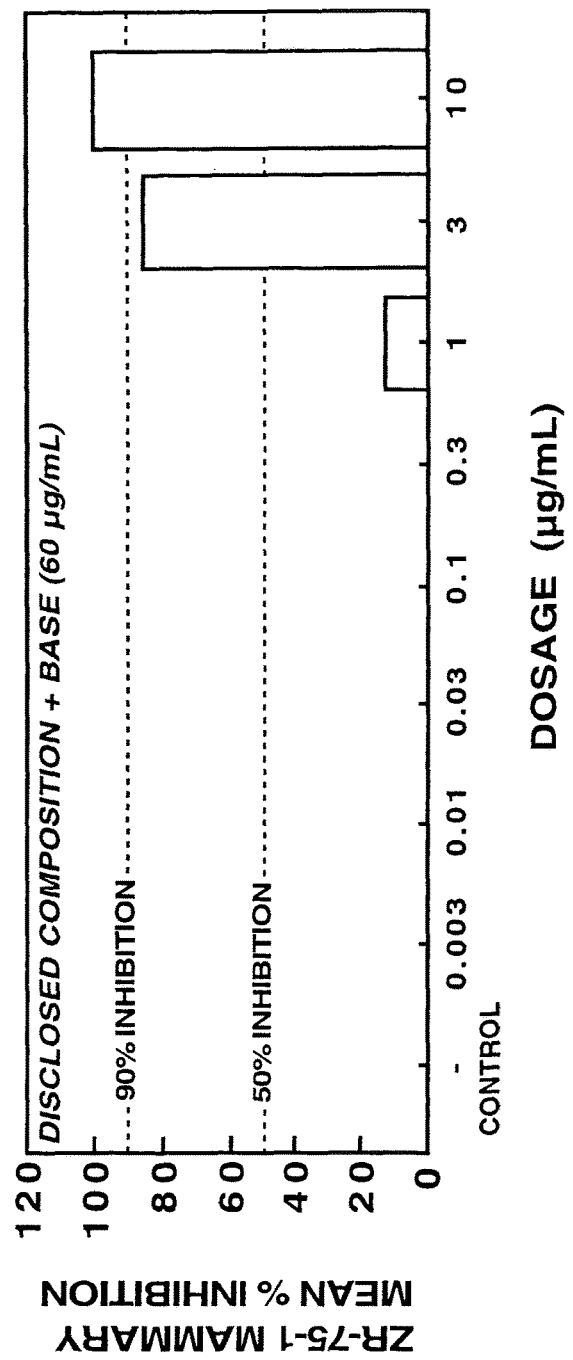
FIG. 5D is a graph of the concentration of the Composition plus Base Compound plotted against ZR-75-1 mammary cells mean % inhibition.

FIG. 5D discloses the very high activity of the combination of the disclosed Composition and the Base Compound against the ZR-75-1 mammary cells. The $IC_{50}$ of this combination was found to be a surprising concentration and calculated to approximately 2.031 µg/mL. The resistance of ZR-75-1 mammary cells was essentially eliminated with the addition of the Base Compound to the Composition. The 10 µg/ml of the Composition plus the Base Compound resulted in an approximately 100% cell kill for this cell line, a very effective therapeutic with few side effects or negative aspects. FIG. 5E provides the absorbance values and inhibition percentages of this experiment with significant inhibition at 3 µg/ml and 10 µg/ml dosages. FIG. 5F discloses a calculated $IC_{50}$ rate of a low concentration of approximately 2.031 µg/ml, and the regression output for the experiment.

Example 7

Figure 6A:
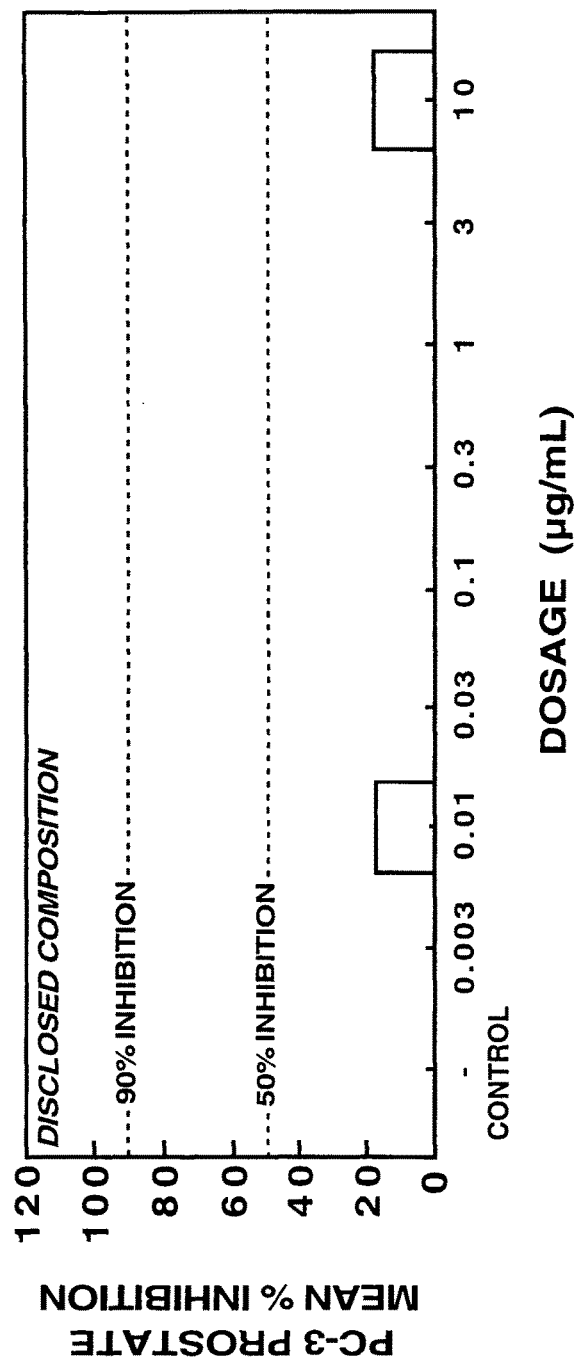
FIG. 6A is a graph of the concentration of the Composition alone plotted against PC-3 prostate cells mean percent inhibition.

FIG. 6A shows the results of toxicity tests of the Composition on PC-3 prostate cells. The PC-3 prostate cells exhibited resistance to the Composition up to concentrations of approximately 10 µg/mL, with some cellular inhibition at 0.01 µg/mL. The dosage of 10 µg/mL resulted in a 17% inhibition of the prostate cells. FIGS. 6B and 6C provide the absorbance values and statistical results of the experiment of Composition on prostate cells.

Figure 6D:
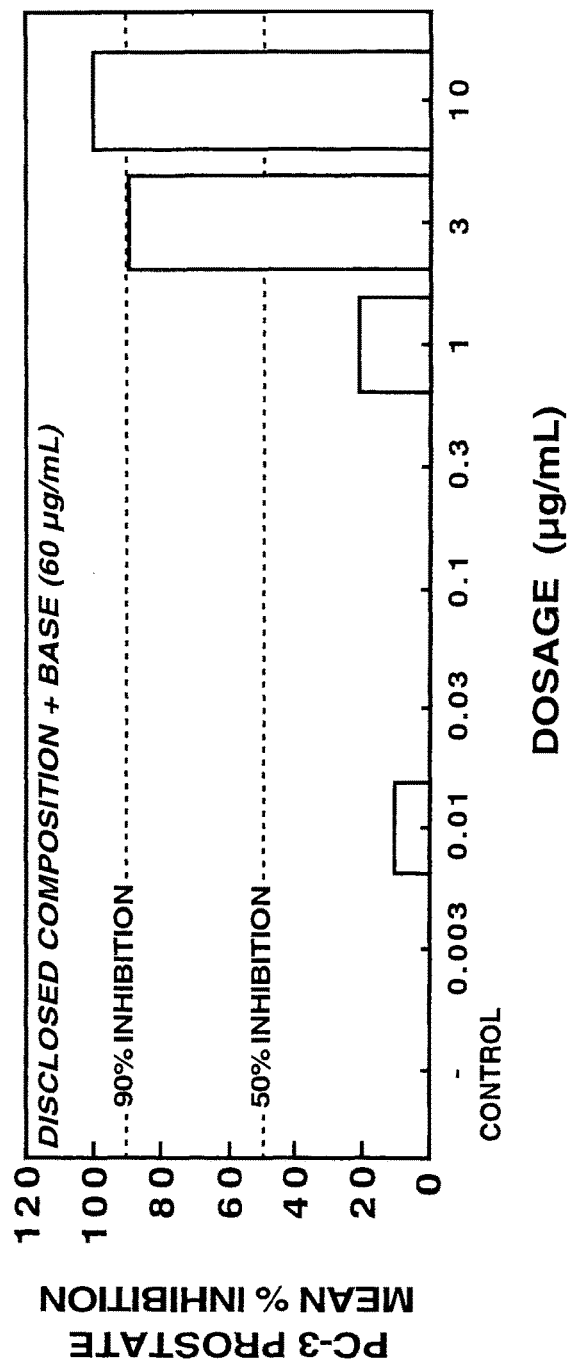
FIG. 6D is a graph of the concentration of the Composition plus Base Compound plotted against PC-3 prostate cells mean % inhibition.

FIG. 6D shows the effects of toxicity of the Composition plus the Base Compound against PC-3 prostate cells. The resistance of PC-3 prostate cells is essentially eliminated with the addition of Base Compound. The addition of the Base Compound shows an enhanced cell kill in these tests to this cell line, as compared to the Composition alone in FIG. 6A. A concentration of 10 μg/ml of Composition in combination with the Base Compound resulted in a 100% of cell kill, with an $IC_{50}$ that was extremely low at a concentration of 1.869 μg/ml. Concentrations as low as 3 μg/ml resulted in approximately 90% inhibition of the cell line. FIGS. 6E and 6F provide the absorbance value and statistical results of this experiment.

The cause of the aberrant experimental results found in both FIGS. 6A and 6D at the 0.01 μg/ml concentration level was not determined.

Example 8

Figure 7A:
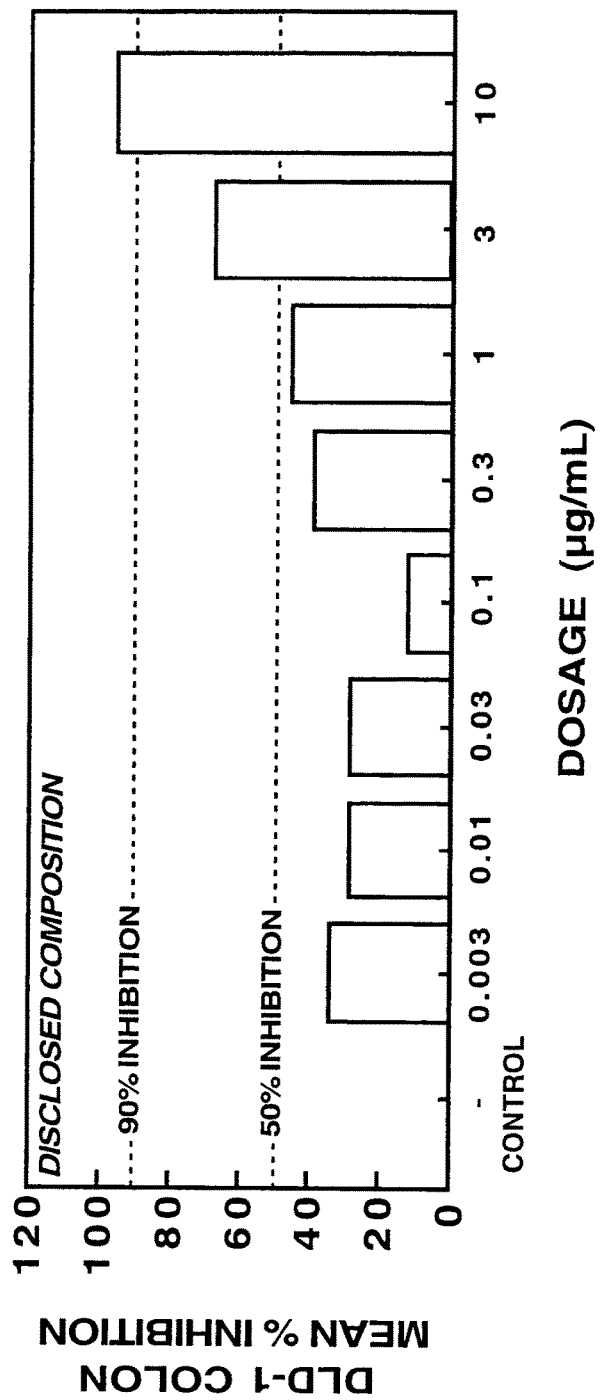
FIG. 7A is a graph of the concentration of the Composition alone plotted against DLD-1 colon cells mean percent inhibition.

FIG. 7A shows the high toxicity effect of the Composition on DLD-1 colon cells. The Composition displayed significant cell kill rates at all concentrations, including at very low concentrations. The resulting inhibition percentages, as shown in FIG. 7B, were very high with a 95% inhibition of the DLD-1 colon cells with 10 μg/mL of the Composition. FIG. 7C provides the statistical analysis of the experimental results.

Figure 7D:
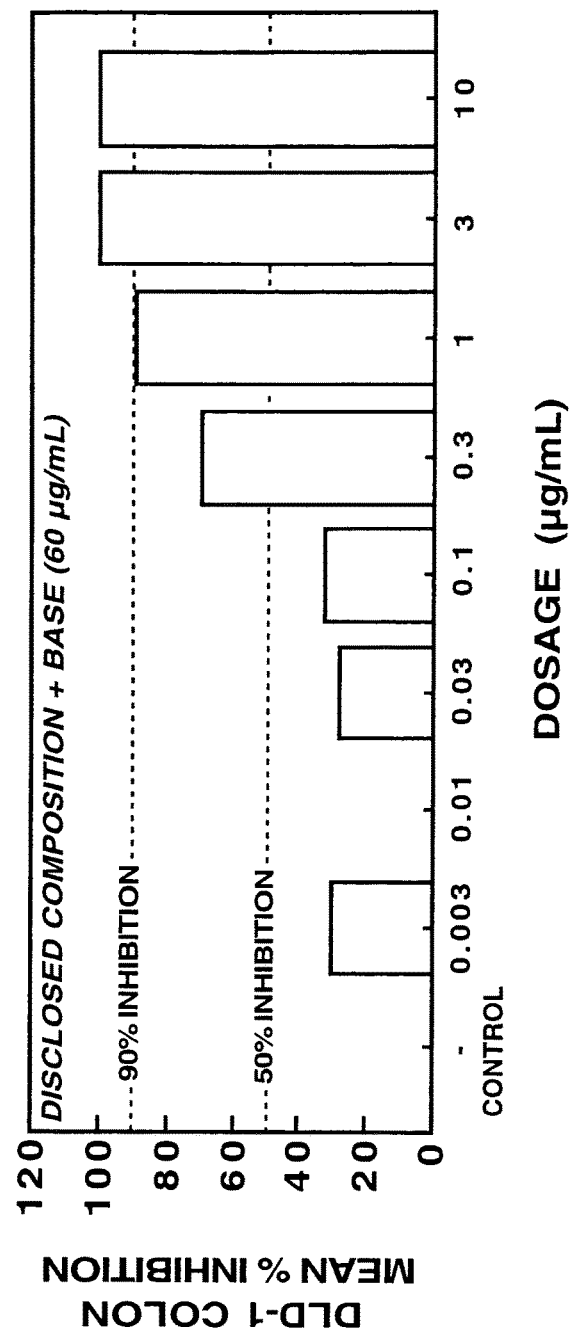
FIG. 7D is a graph of the concentration of the Composition plus Base Compound plotted against DLD-1 colon cells mean % inhibition.

FIG. 7D provides the results of toxicity experiments with the Composition in combination with the Base Compound on DLD-1 colon cells. These tests showed an enhanced cell kill with the addition of Base Compound as compared to the Composition alone. As shown in FIGS. 7D and 7E, an exceedingly low concentration of 3 μg/ml of Composition plus Base Compound was required for 100% of cell kill, as compared to a 95% cell kill by 10 μg/ml of the Composition alone, shown in FIGS. 7A and 7B. The $IC_{50}$ was lowered with the addition of Base Compound for the same cell line to 0.196 μg/ml from an $IC_{50}$ of 1.430 μg/ml for the Composition alone.

Example 9

Figure 8A:
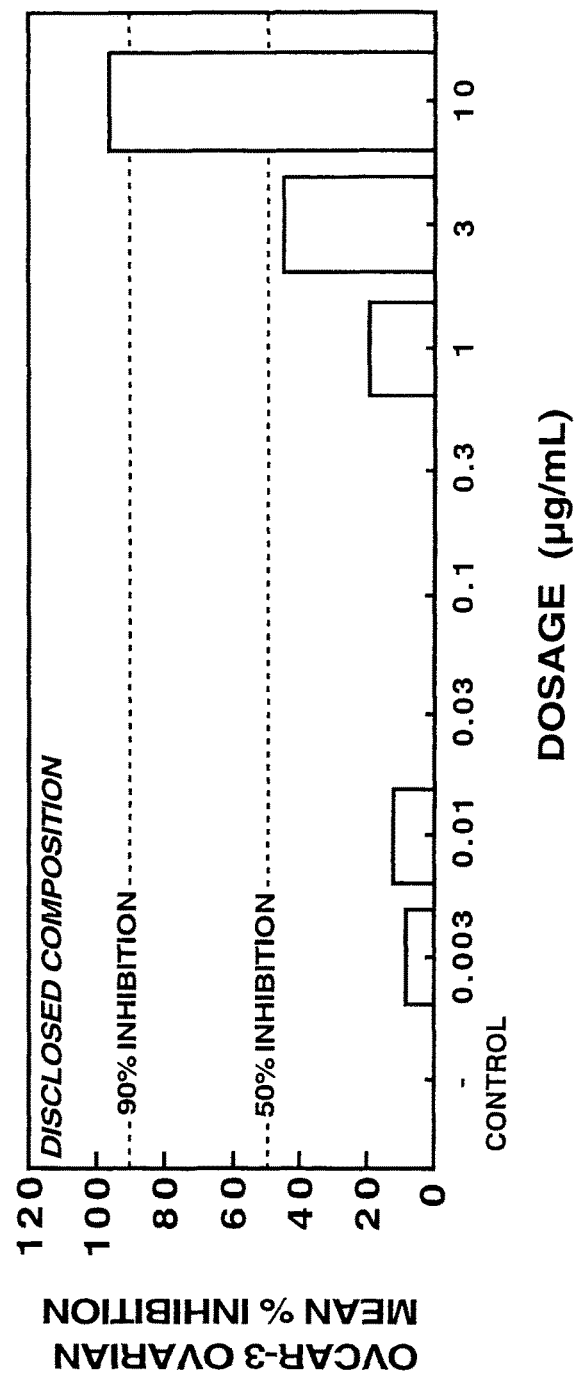
FIG. 8A is a graph of the concentration of the Composition alone plotted against OVCAR-3 ovarian cells mean percent inhibition.

FIG. 8A discloses the highly toxic effect of the Composition against OVCAR-3 ovarian cells with over 90% inhibition rate at very low concentrations of 1 μg/mL, 3 μg/mL and 10 μg/mL. The absorbance values and statistical results of these experiments are given in FIGS. 8B and 8C.

Figure 8D:
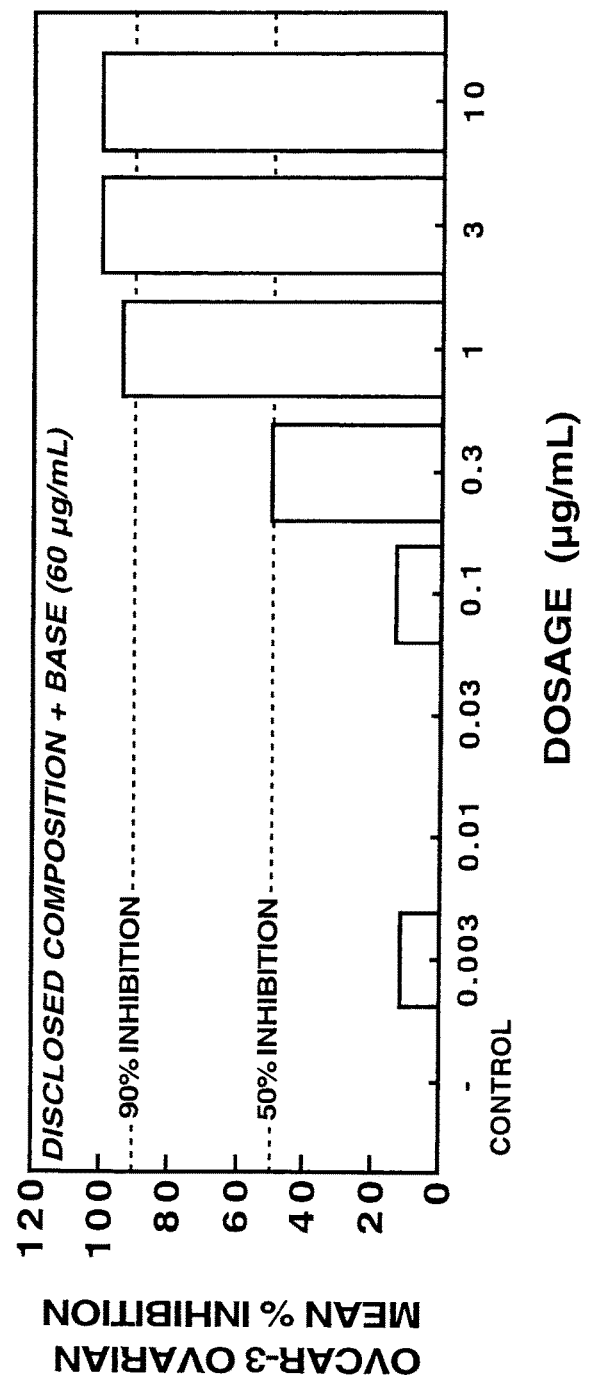
FIG. 8D is a graph of the concentration of the Composition plus Base Compound plotted against OVCAR-3 ovarian cells mean % inhibition.

The toxicity effects of the Composition in combination with the Base Compound on OVCAR-3 ovarian cells are shown in FIG. 8D. These tests showed an enhanced cell kill with the addition of the Base Compound as compared to Composition alone. The combination of the Composition with the Base Compound resulted in a 100% cell kill at the concentration of 3 μg/ml, whereas the application of the Composition alone required 10 μg/ml for a resulting 95% cell kill. The $IC_{50}$ for the combination of the Composition and the Base Compound was lowered to the very low concentration of 0.299 μg/mL.

Example 10

Figure 9A:
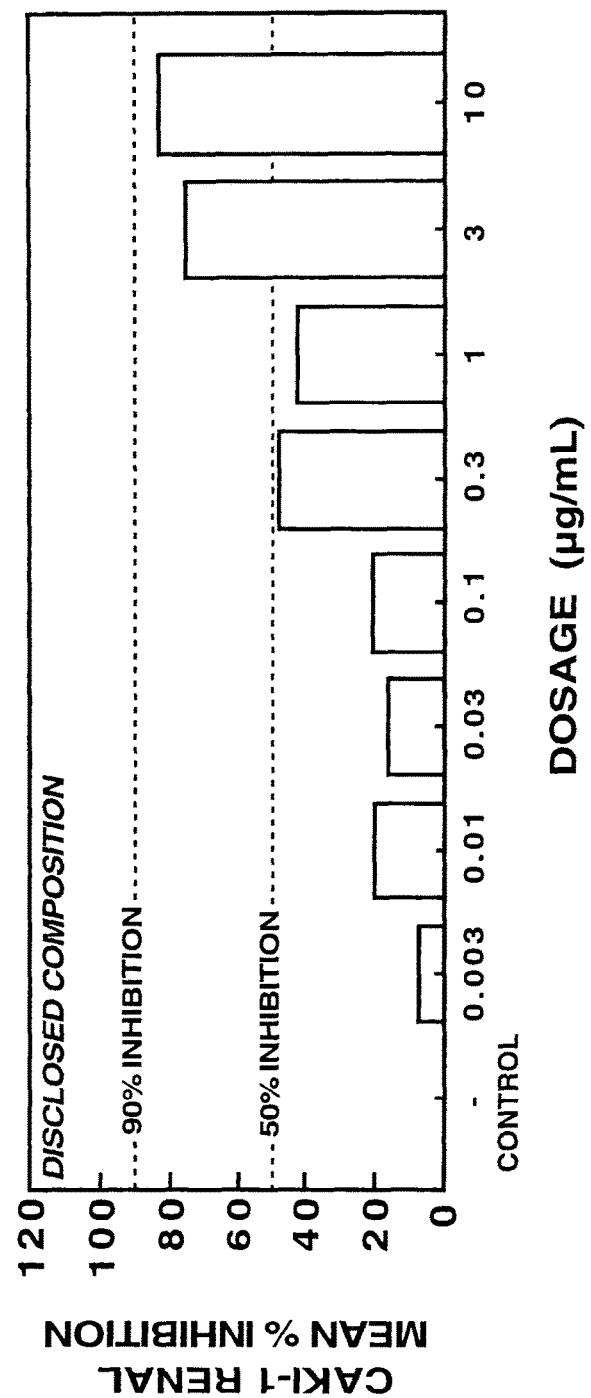
FIG. 9A is a graph of the concentration of the Composition alone plotted against CAKI-1 renal cells mean percent inhibition.

The toxicity effects of the Composition on CAKI-1 renal cells are shown in FIG. 9A. The Composition showed very high activity against this cell line, even at low dosages. The inhibition percentages showed significant activity of the Composition at concentrations as low as 0.01 μg/mL for 20.3% inhibition, and 83.6% inhibition of the cell line at the concentration of 10 μg/ml. See, FIGS. 9B and 9C.

Figure 9D:
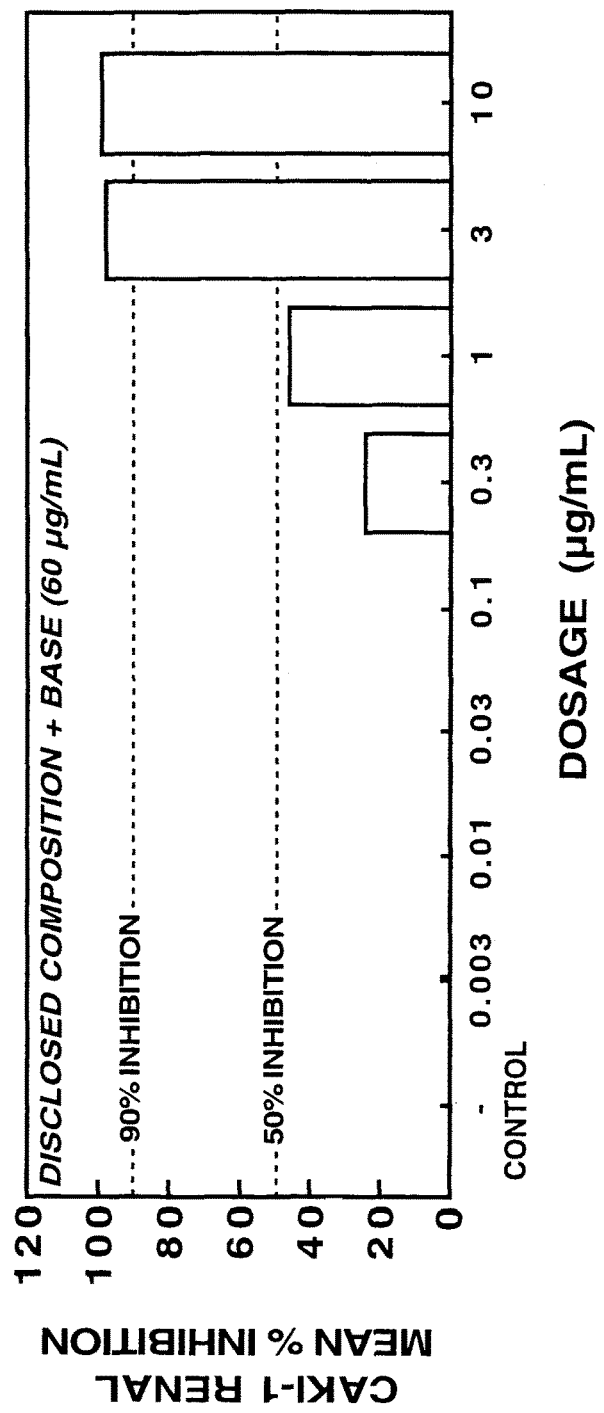
FIG. 9D is a graph of the concentration of the Composition plus Base Compound plotted against CAKI-1 renal cells mean % inhibition.

The combination of the Composition plus the Base Compound showed very high activity against CAKI-1 renal cells, as shown in FIG. 9D. These tests show an enhanced cell kill with the addition of Base Compound as compared to the use of the Composition alone as shown in FIG. 9A. A concentration of 10 μg/ml of the Composition resulted in a 99% cell kill. The $IC_{50}$ was lowered with the addition of Base Compound to 1.138 μg/mL for this cell line in contrast to the $IC_{50}$ of Composition alone, which was 1.44 μg/mL. In the experiments on the CAKI-1 renal cells, both the Composition and the Composition plus the Base Compound demonstrated very significant activity with low $IC_{50}$ rates.

Example 11

Figure 10A:
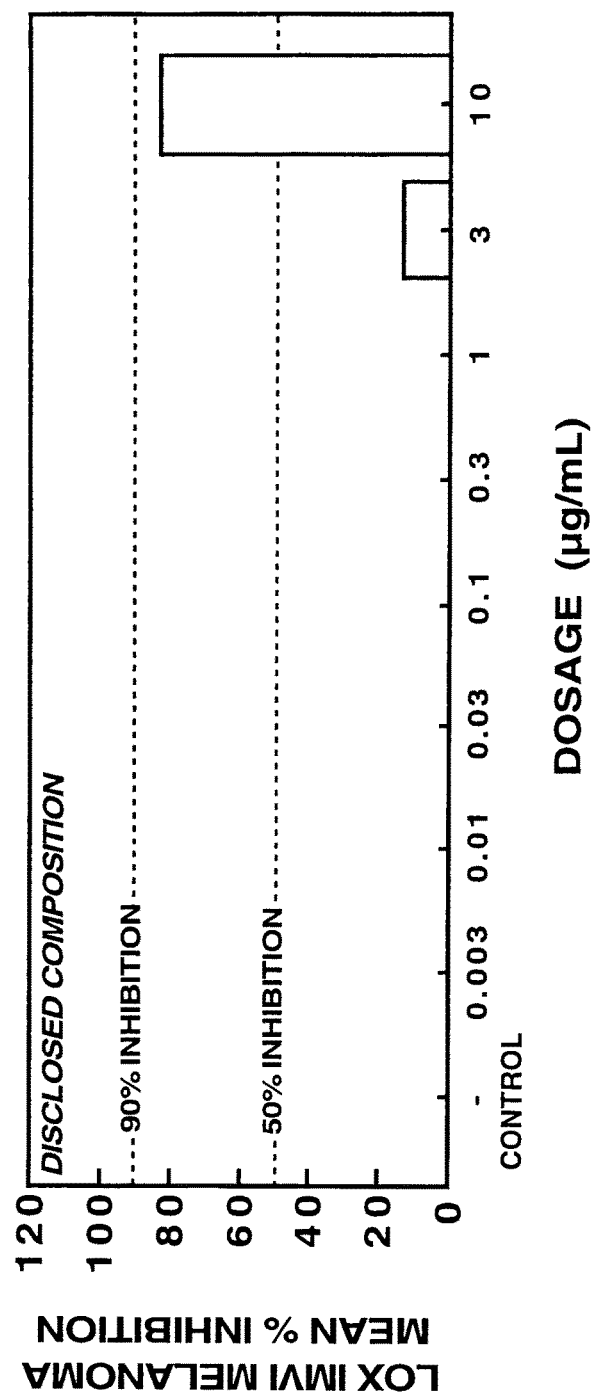
FIG. 10A is a graph of the concentration of the Composition alone plotted against LOX IMVI melanoma cells mean percent inhibition.

FIG. 10A shows the toxic effect the Composition against LOX IMVI melanoma cells. The experiment showed high activity of the Composition and resulted in an approximately 82% inhibition of the cell line at a concentration of 10 μg/mL. FIG. 10B shows the absorbance rates and the inhibition percentages of the experiments with some inhibition at 3 μg/mL. FIG. 1C provides the statistical analysis of the results, including a calculated $IC_{50}$ of 6.718 μg/mL.

Figure 10D:
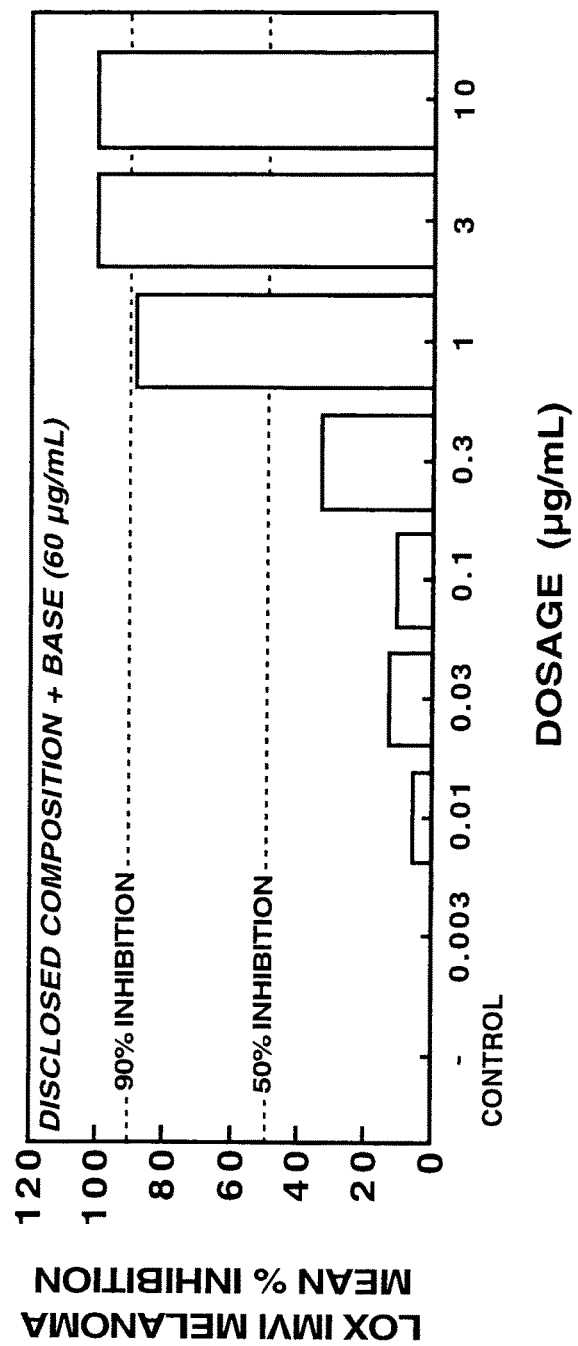
FIG. 10D is a graph of the concentration of the Composition plus Base Compound plotted against LOX IMVI melanoma cells mean % inhibition.

FIG. 10D shows the high activity of the Composition plus the Base Compound on LOX IMVI melanoma cells. The Composition in combination with the Base Compound had highly toxic effects on this cell line, including at very low dosages. These tests show an enhanced cell kill with the addition of Base Compound to this cell line as compared to the use of Composition alone, as shown in FIG. 10A. A 3 μg/ml concentration of the Composition resulted in 100% cell kill, whereas 10 μg/ml were required for 82% cell kill with the Composition alone, as shown as FIG. 10A. The $IC_{50}$ of Composition alone was 6.718 μg/mL, the $IC_{50}$ was lowered with the addition of the Base Compound for the same cell line to 0.513 μg/mL.

Example 12

Figure 11A:
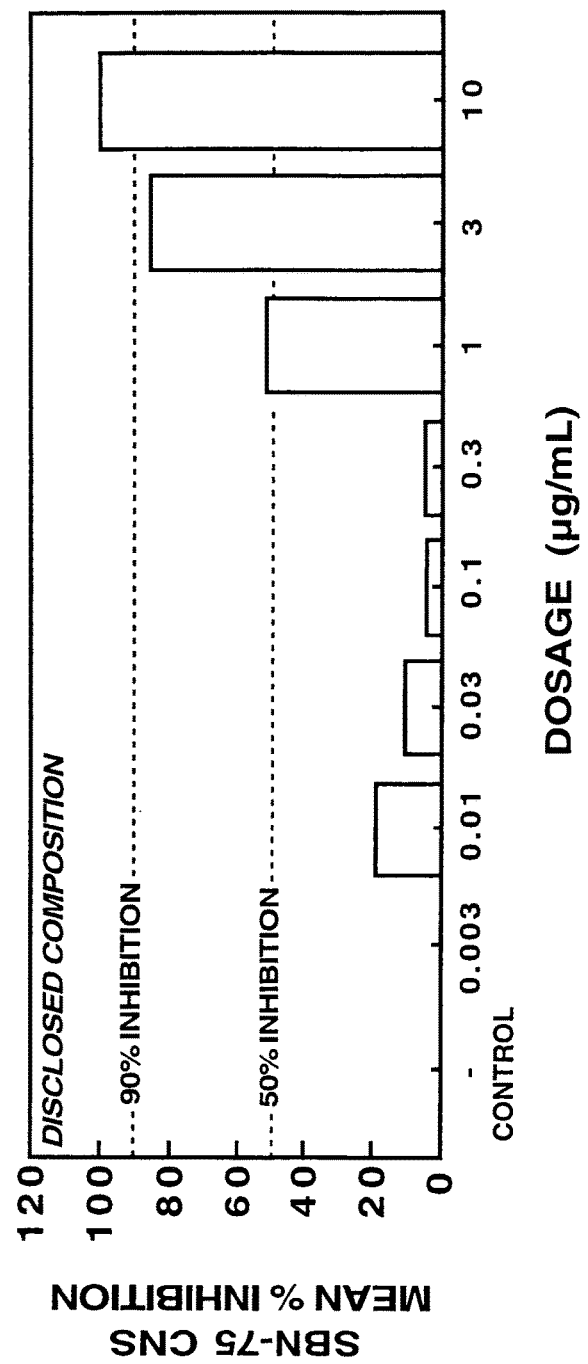
FIG. 11A is a graph of the concentration of the Composition alone plotted against SBN-75 CNS cells mean percent inhibition.

The toxicity of the Composition was tested against SBN-75 CNS cells. The results are shown in FIG. 11A, and show very high activity of the Composition. A concentration of 10 μg/mL resulted in a 100% inhibition of the SBN-75 CNS cells, and a concentration of only 3 μg/mL resulted in an approximately 85% inhibition of this cell line. FIGS. 11B and 11C provide the absorbance values and the statistical analysis of the results.

Figure 11D:
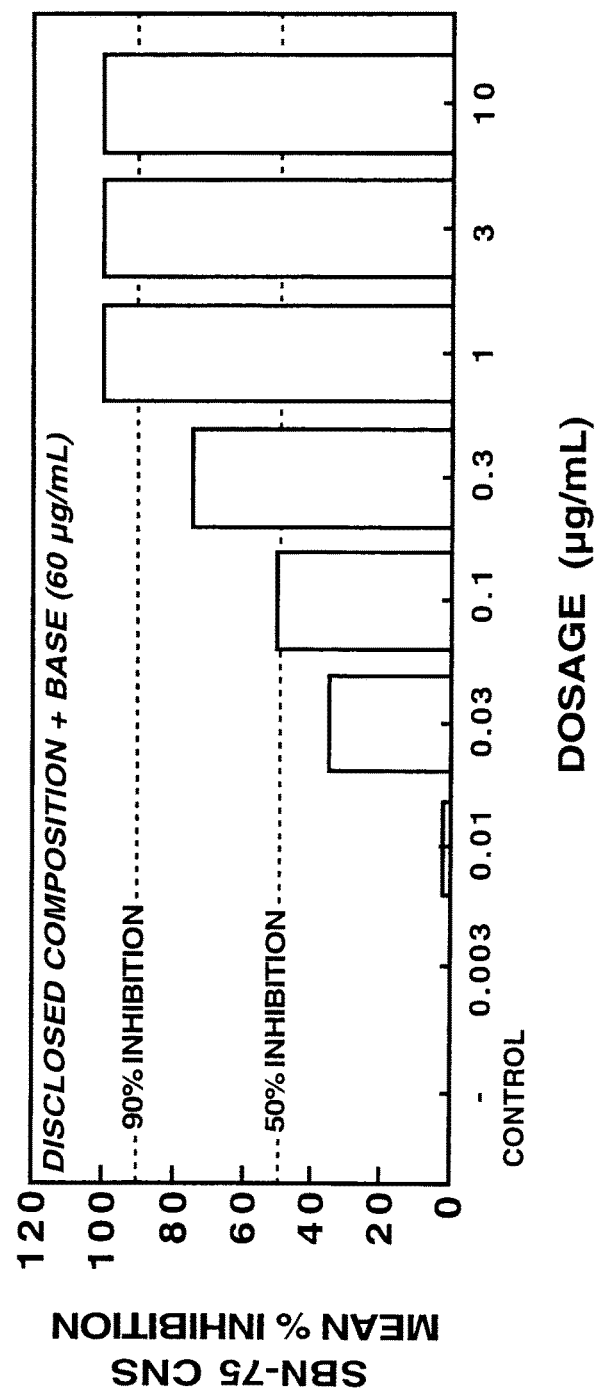
FIG. 11D is a graph of the concentration of the Composition plus Base Compound plotted against SBN-75 CNS cells mean % inhibition.

FIG. 11D discloses the high toxicity effects of the Composition plus the Base Compound against SBN-75 CNS cells. The combination of the Composition and the Base Compound resulted in a very successful 100% inhibition rate at dosages of 1 μg/mL, 3 μg/mL, and 10 μg/mL. These tests show an enhanced cell kill with the addition of the Base Compound to this cell line as compared to the use of the Composition alone. A concentration of 1 μg/ml of Composition plus Base Compound resulted in 100% of cell kill, as compared to a concentration of 10 μg/ml of the Composition alone for 100% cell kill. The $IC_{50}$ was lowered with the addition of Base Compound for the same cell line to 0.095 μg/ml.

Example 13

The CEM-SS cells were obtained from the AIDS Research and References Reagent Repository (Bethesda, Md.). These cells were passaged in T-75 flasks in tissue culture media, which included RPMI 1640 medium (no phenol red), with 10% fetal bovine serum (heat inactivated), 2 mM L-glutamine, 100 U/mL penicillin, 100 µg/ml streptomycin, and 10 µg/ml gentamycin. One day preceding the tritated thymidine assay, the cells were split 1:2 to assure that they were in an exponential growth phase at the time of the cytotoxicity tests. On the day of the assay, the cells were collected by centrifugation, washed twice with tissue culture medium, above, and resuspended at $5\times10^4$ cells per mL, and resuspended in fresh tissue culture medium. The total cell and viability counting was performed with a hemacytometer. Cell viability prior to the assay was determined by trypan blue dye exclusion and exceeded, as it must 95%. Cultures were incubated for 6 days at 37° C., 5% $CO_2$.

Figure 12A:
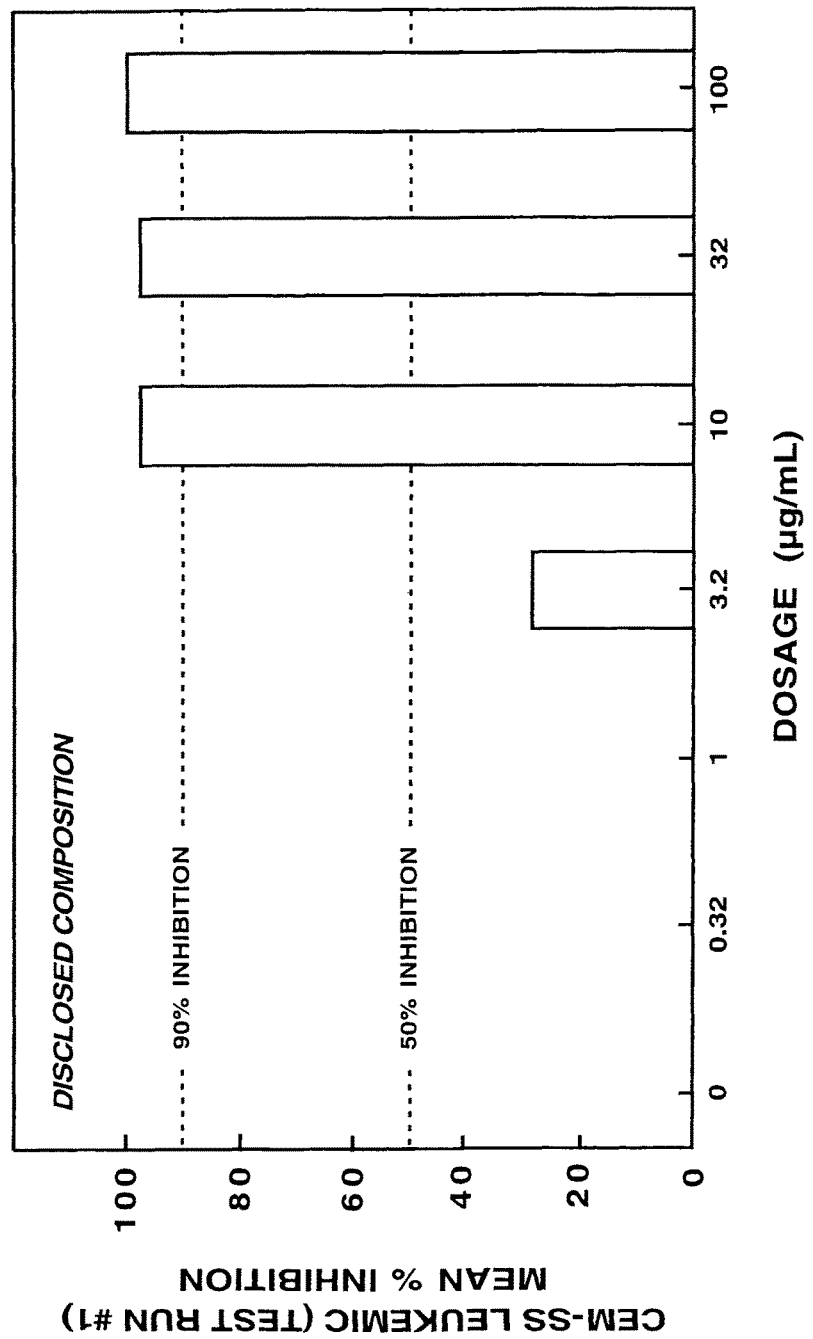
FIG. 12A is a graph of the concentration of the Composition alone plotted against CEM-SS Leukemic cells mean percent inhibition.
Figure 13A:
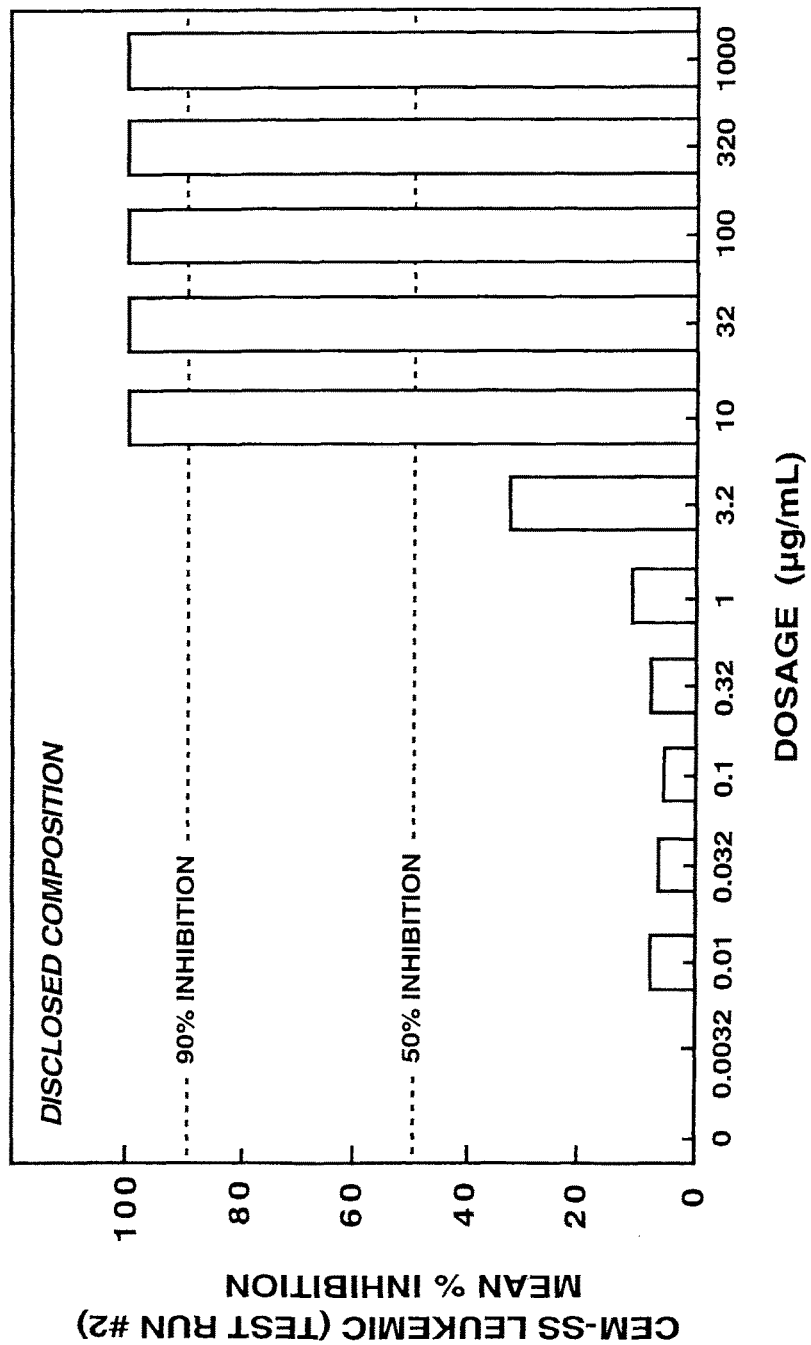
FIG. 13A is a graph of the concentration of the Composition alone plotted against CEM-SS leukemic cells mean percent inhibition.
Figure 19D:
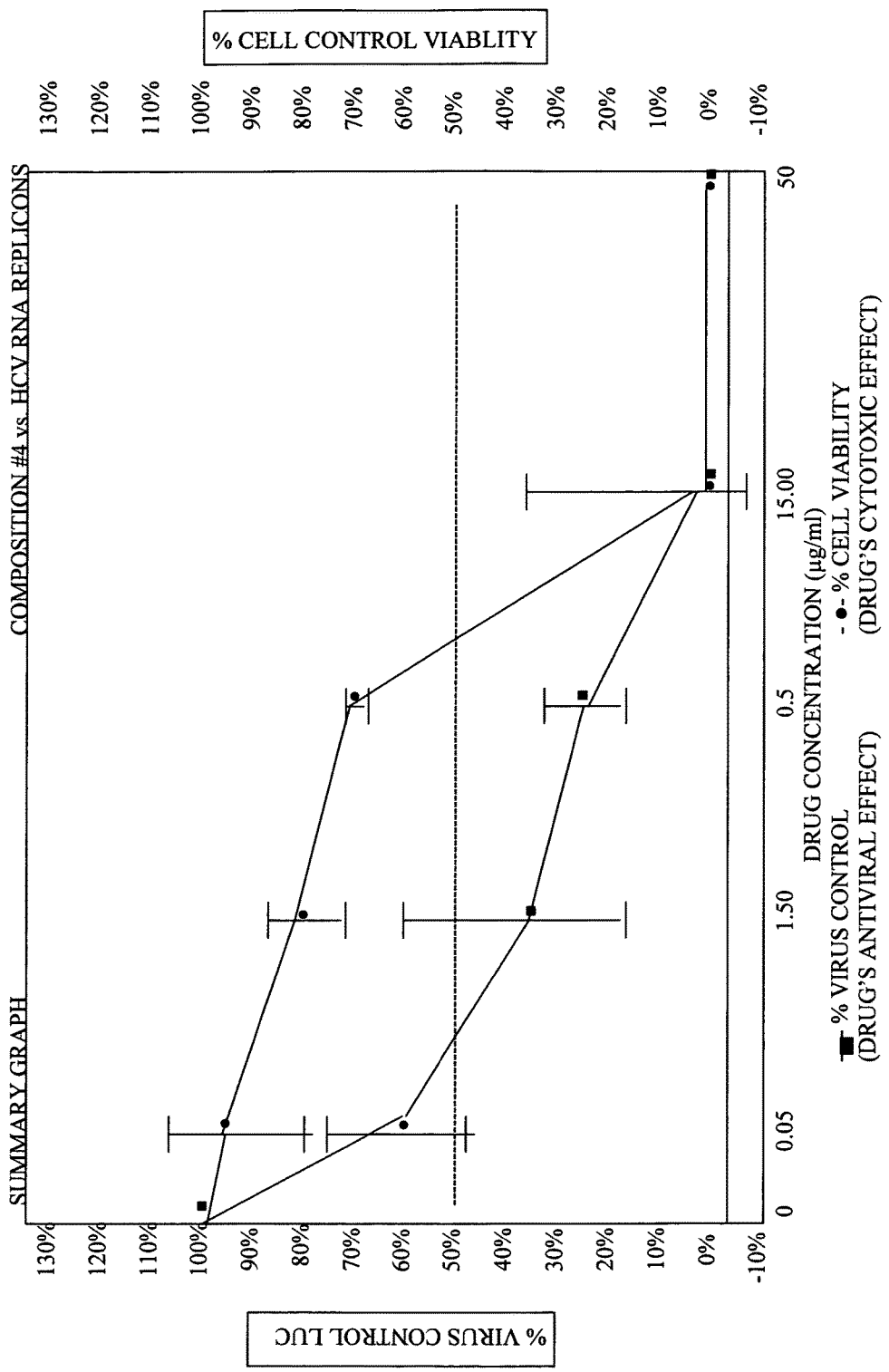
Figure 20D:
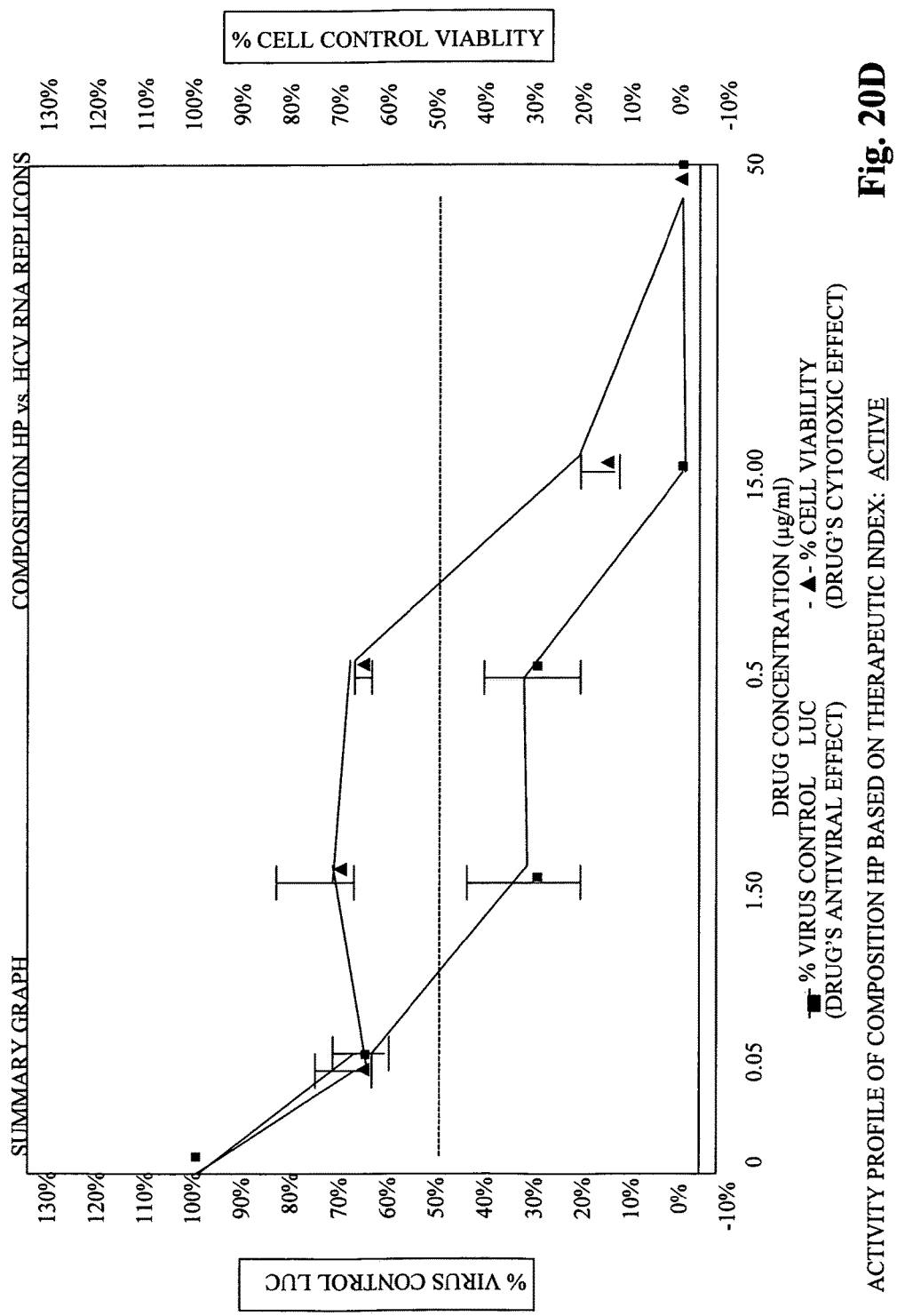
Figure 21D:
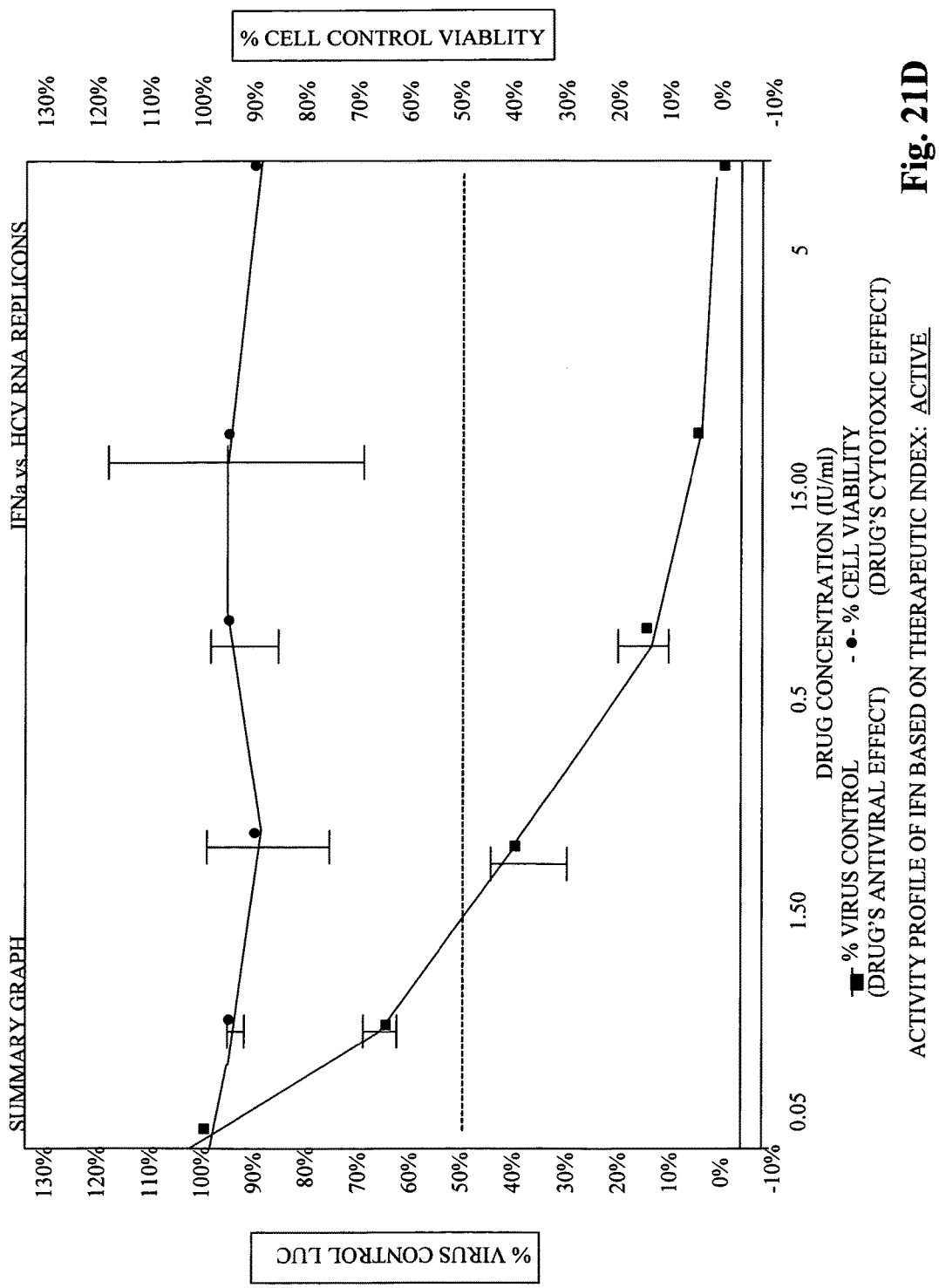
Figure 22D:
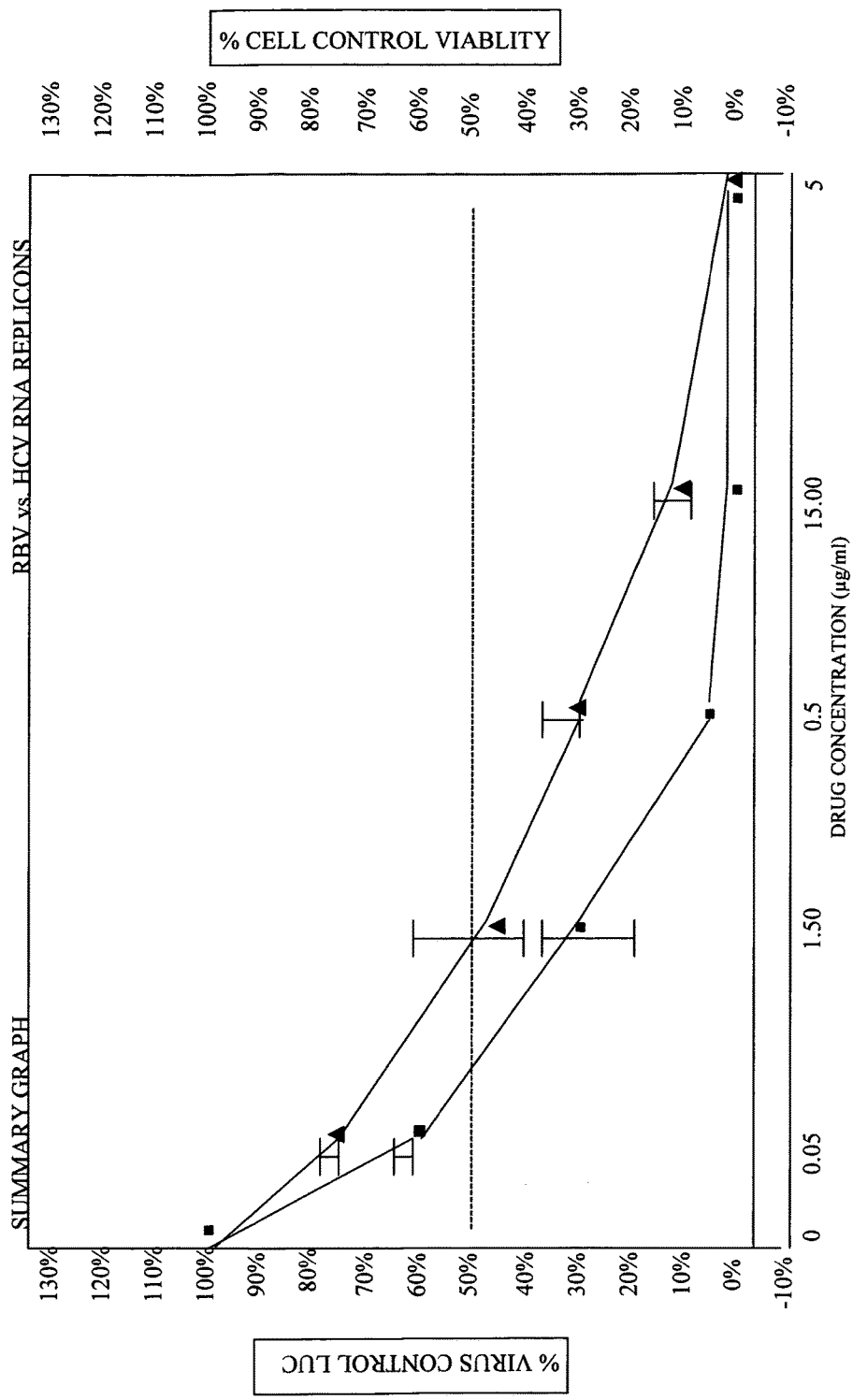
Figure 25B:
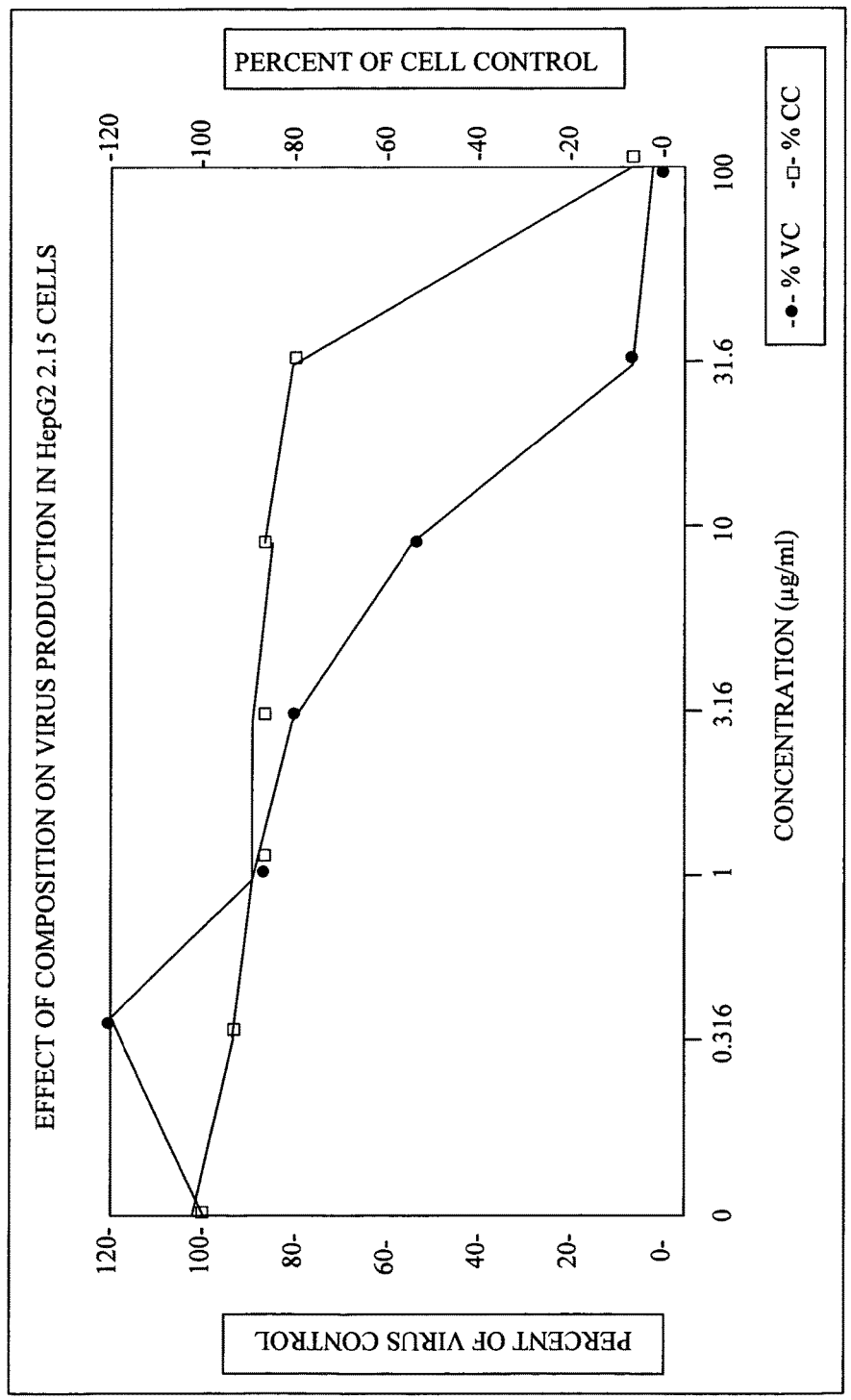
Figure 26B:
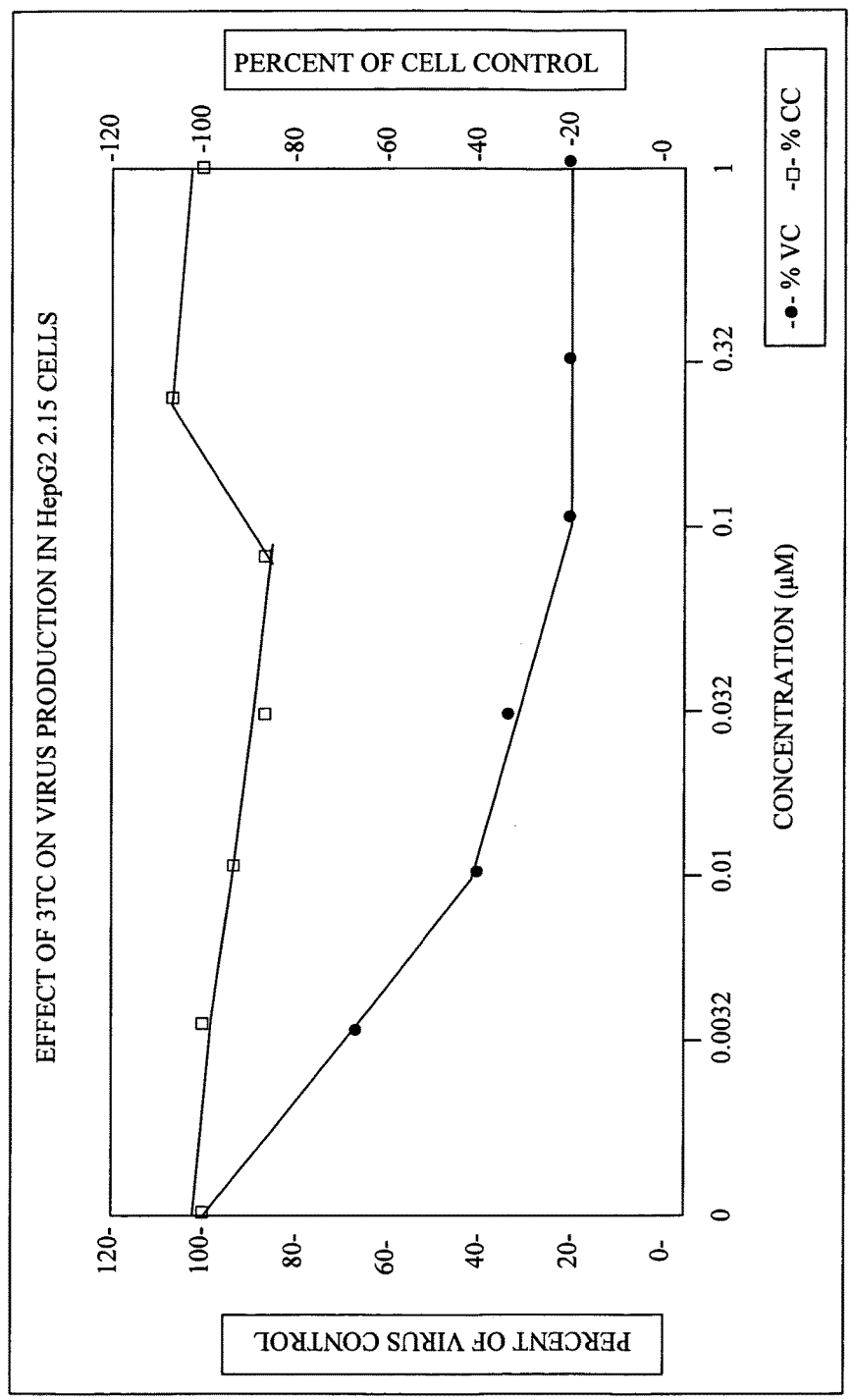
Figure 27B:
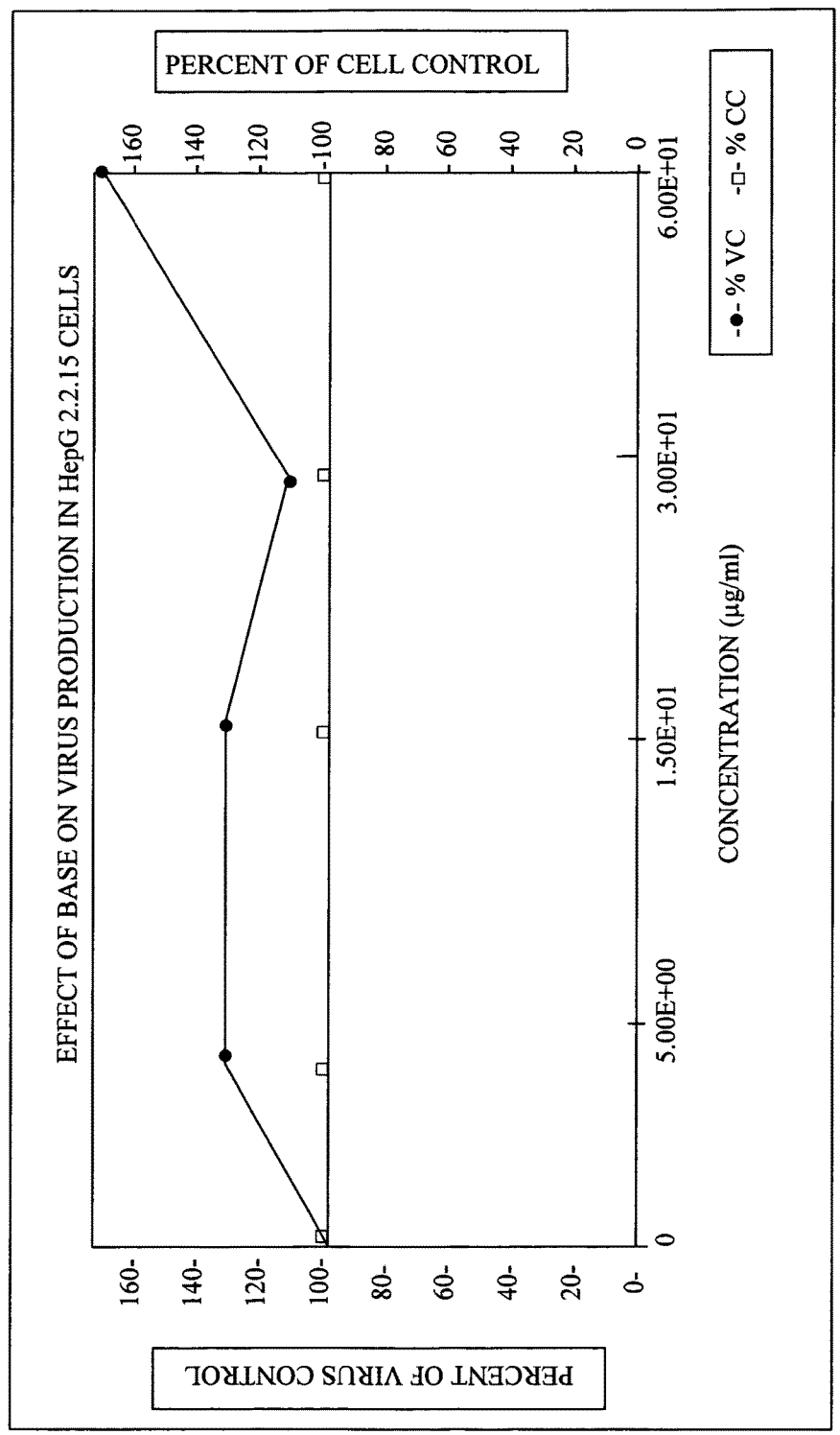
Figure 28B:
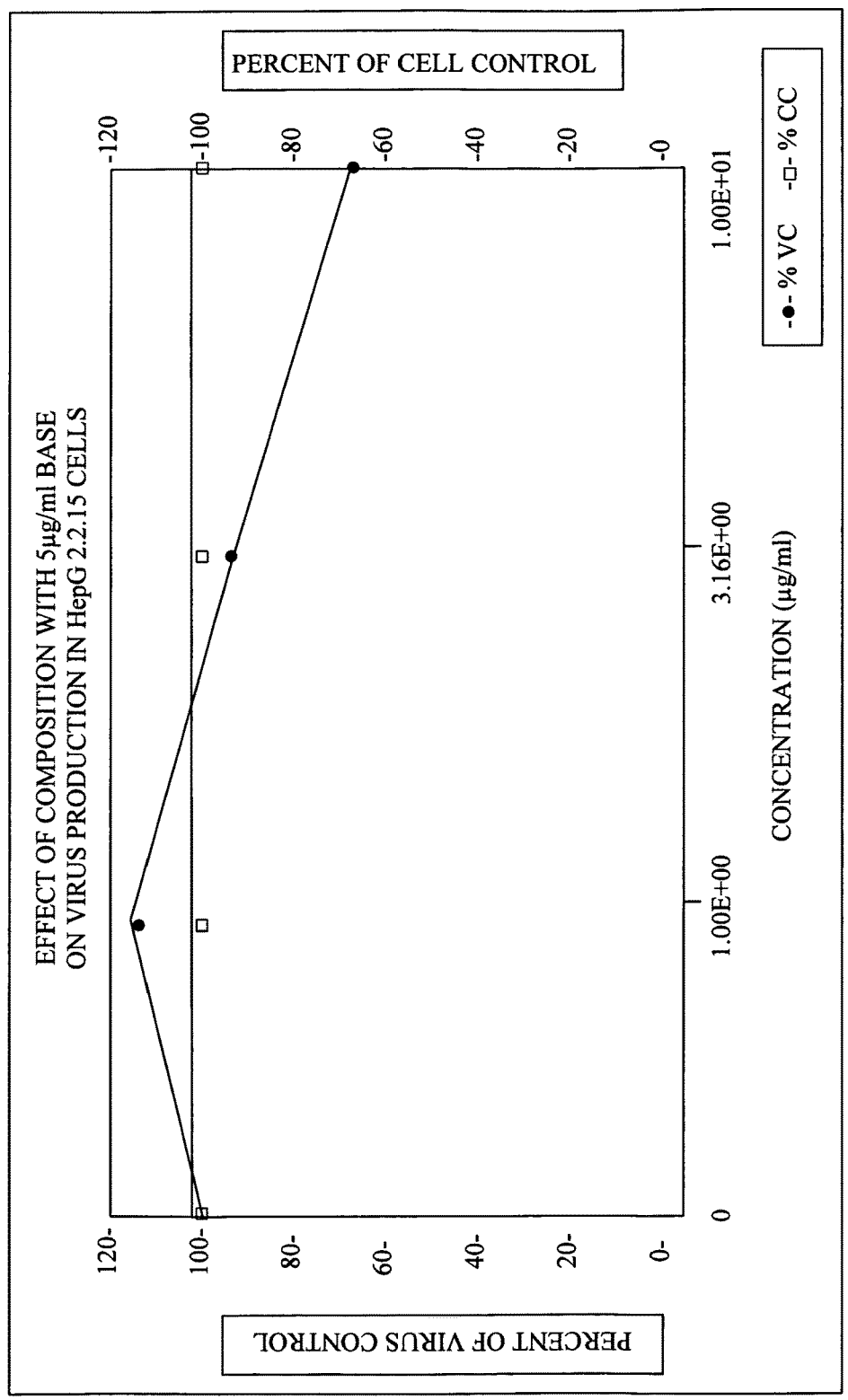
Figure 29B:
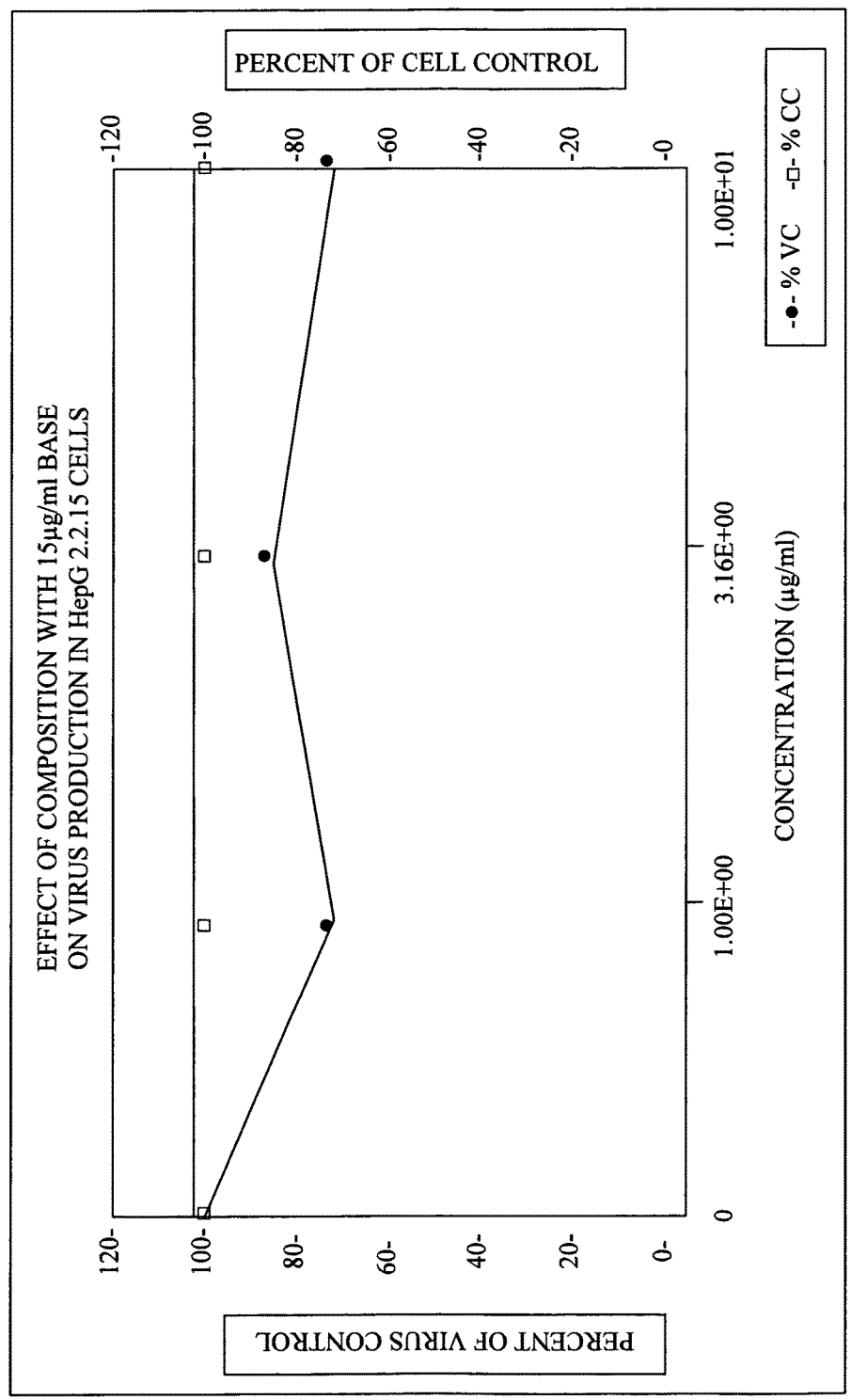
Figure 30B:
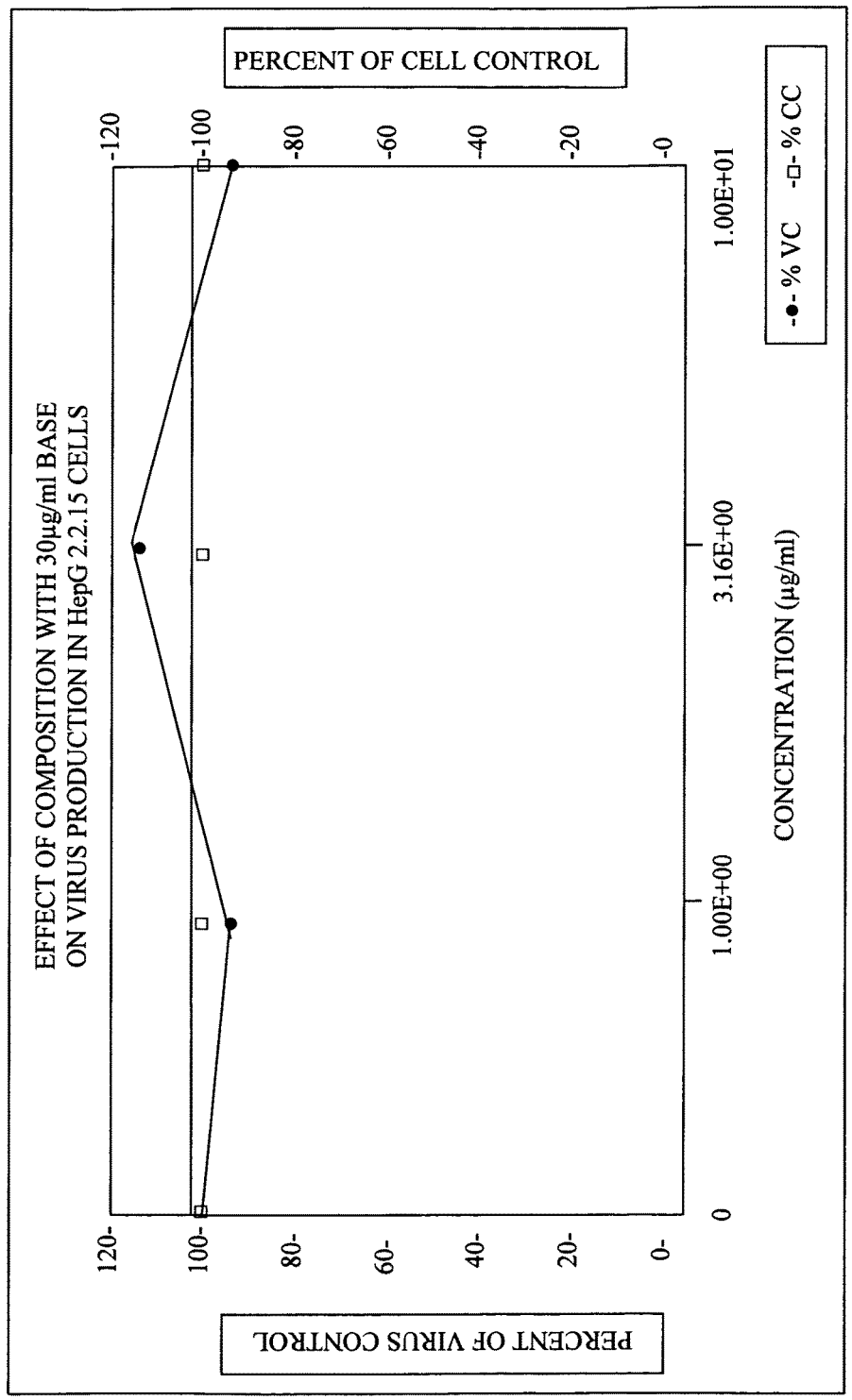
Figure 31B:
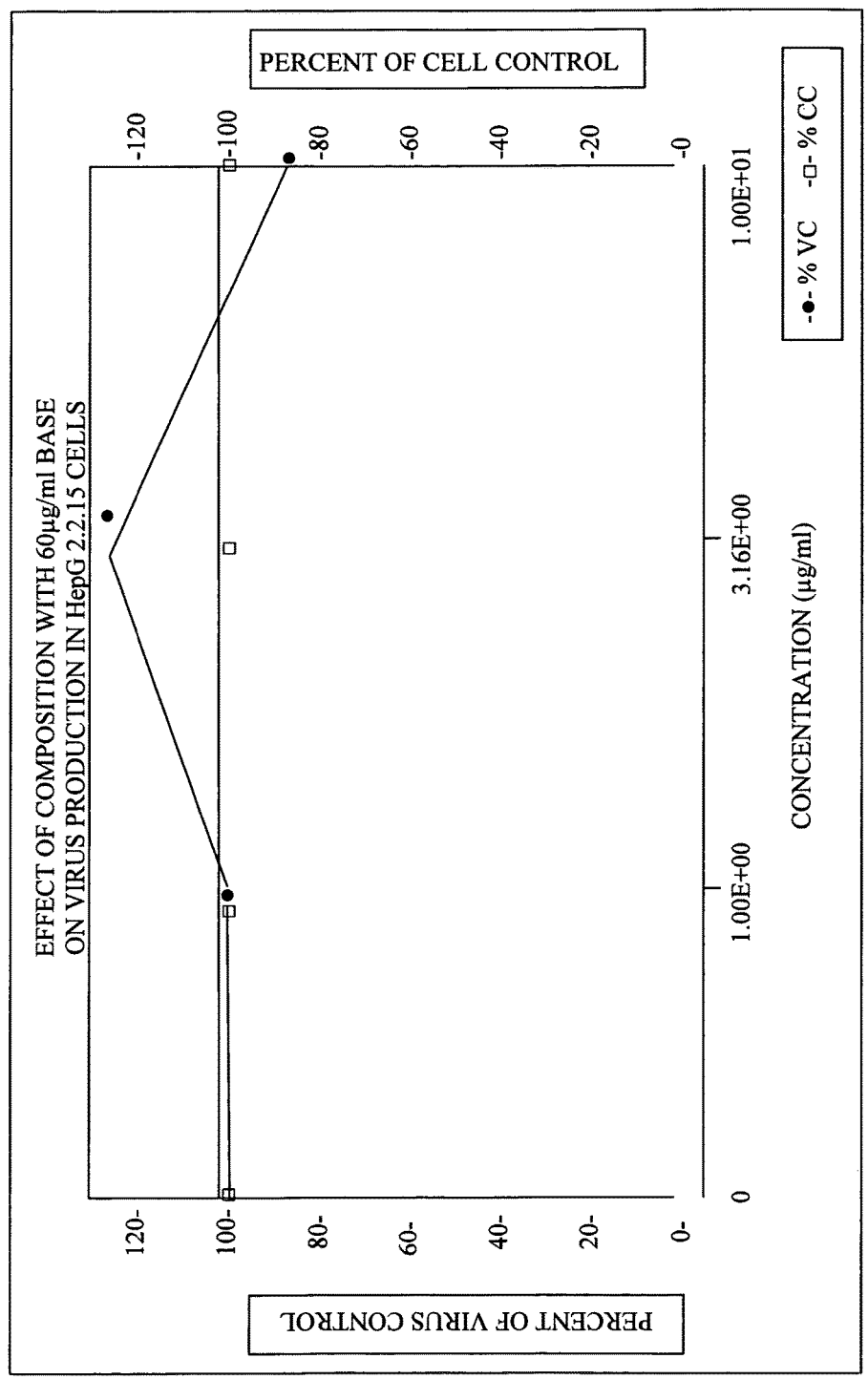
Figure 32B:
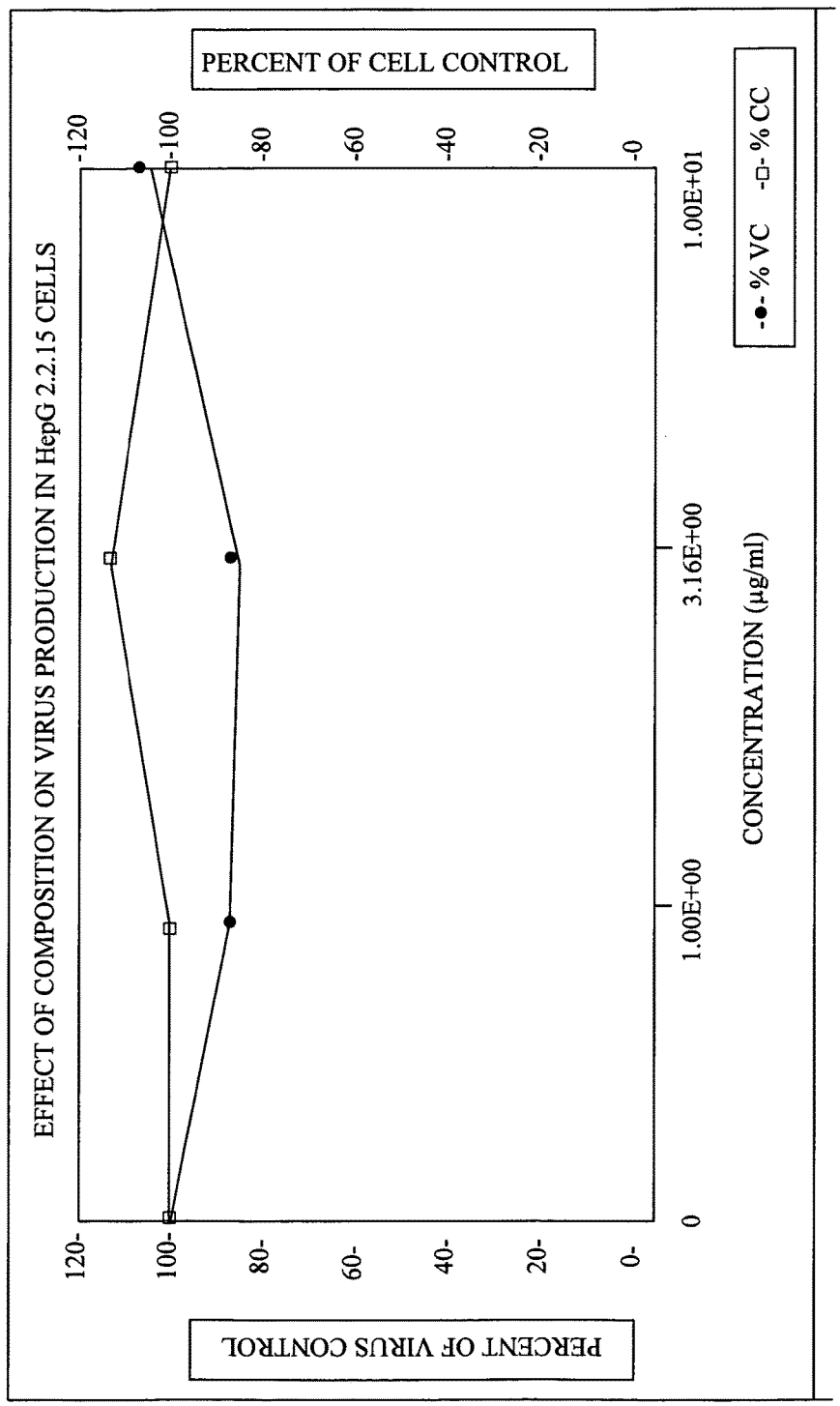
Figure 33B:
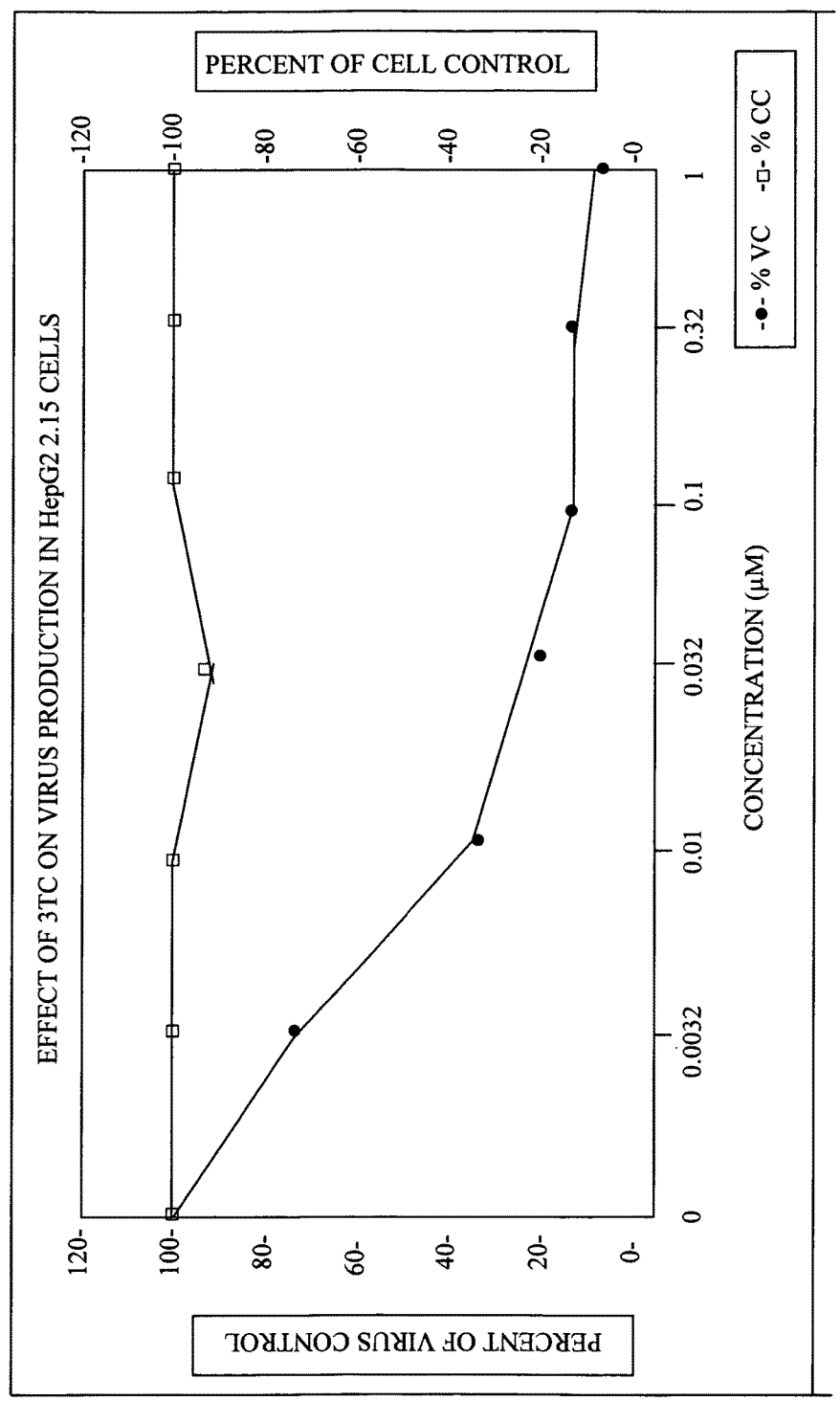
Figure 34B:
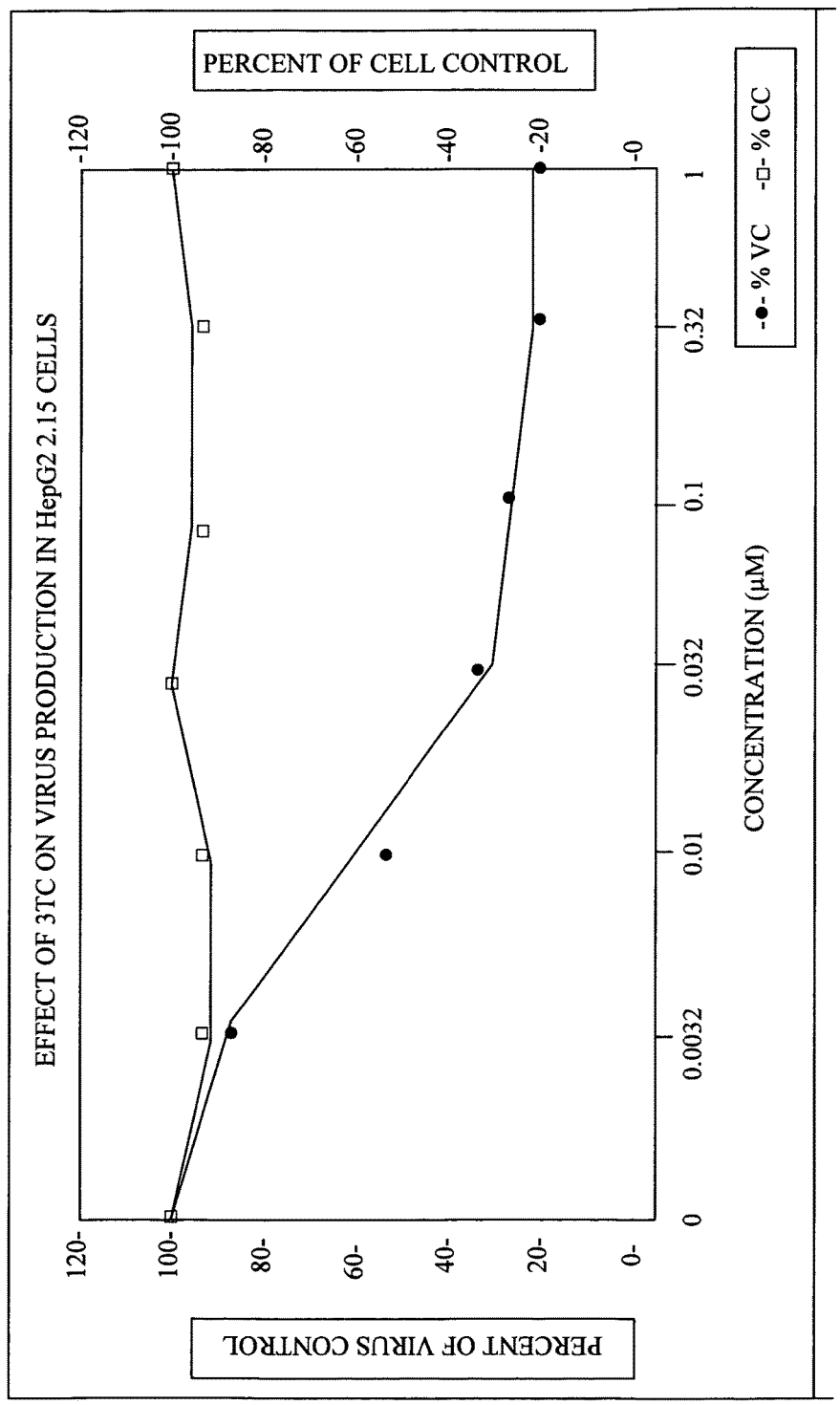
Figure 35:
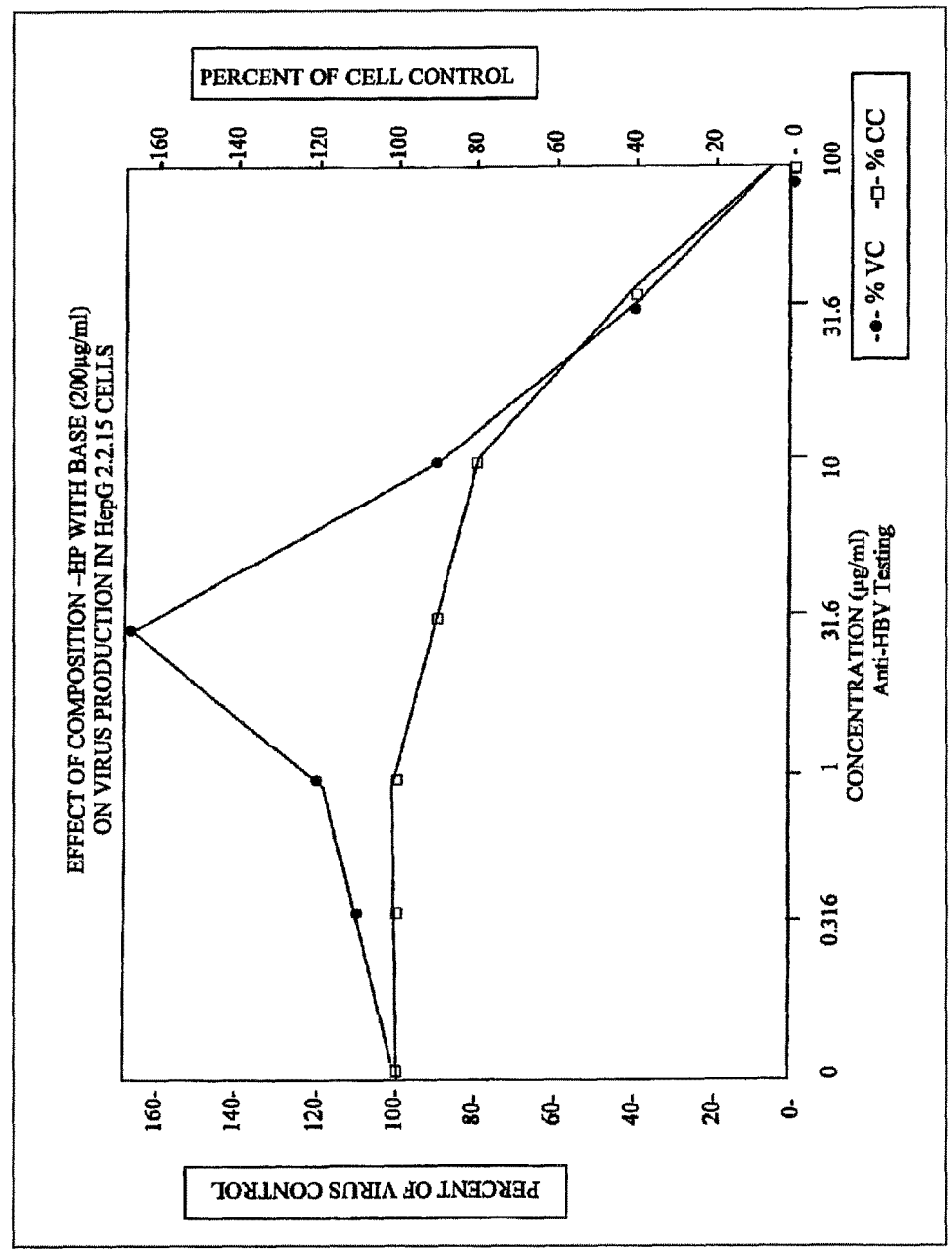
FIGS. 35A and 35B show results of in vitro antiviral screen of the Composition HP and the Base Compound on virus production in HepG2.15 cells.
Figure 36B:
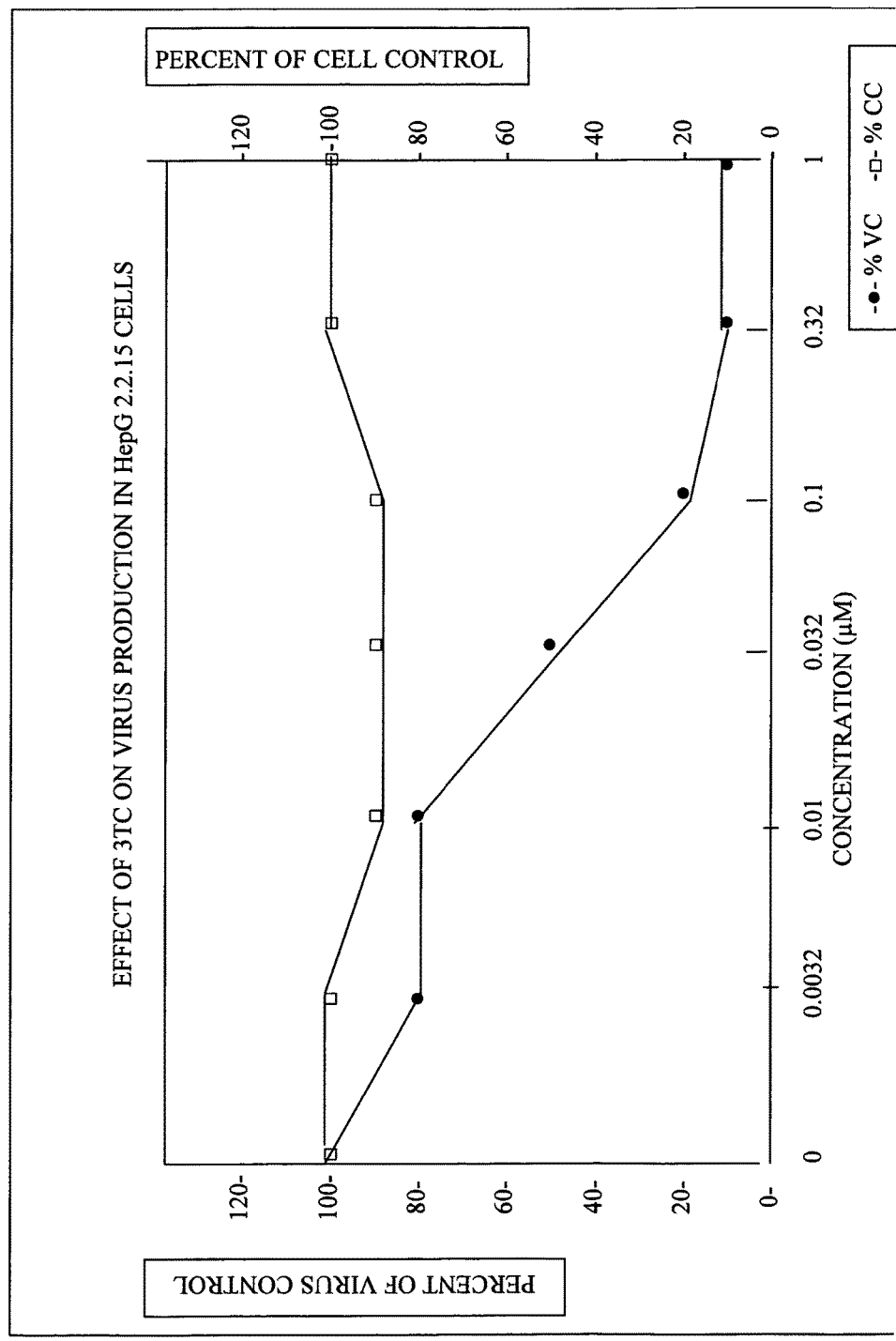
Figure 37B:
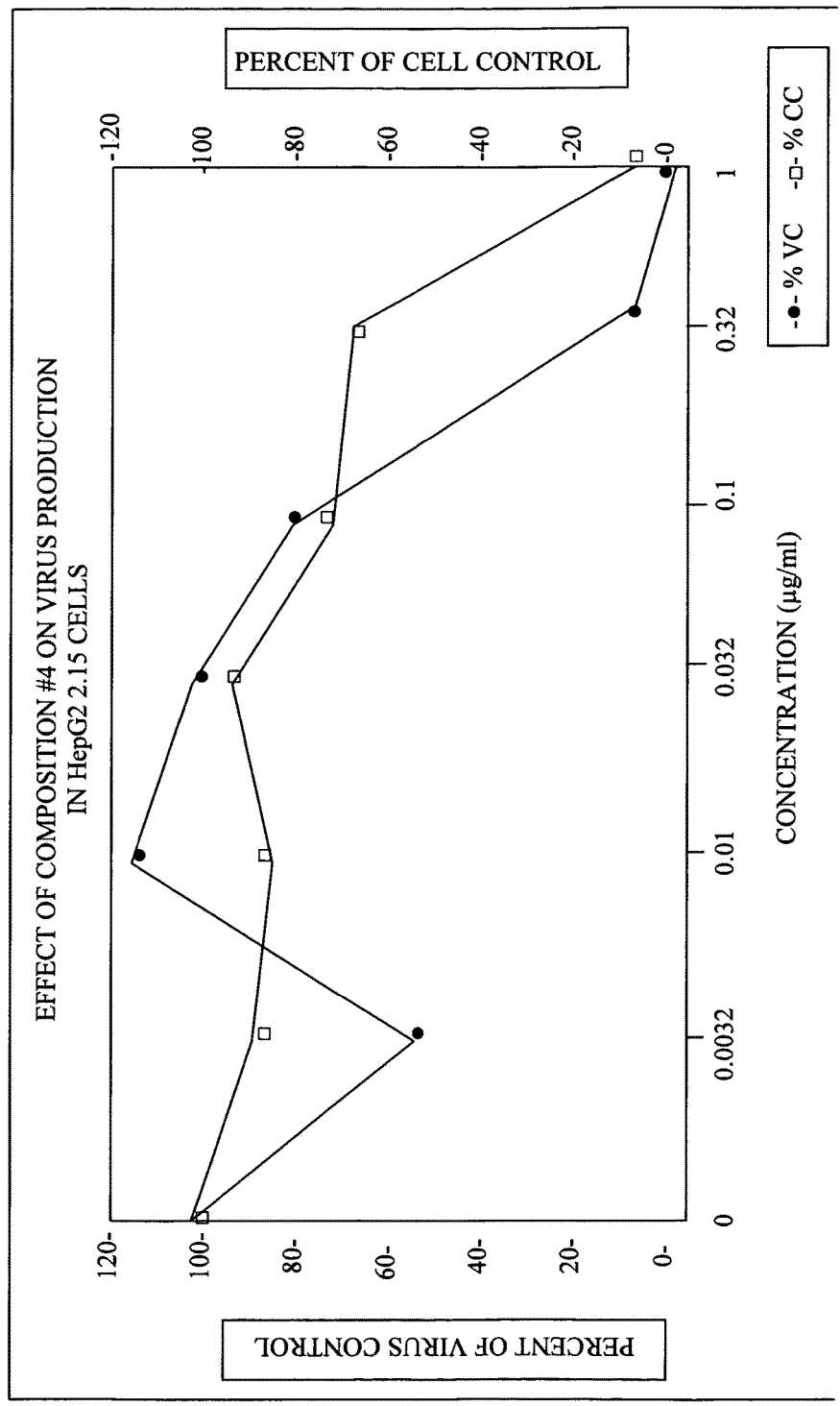
Figure 38B:
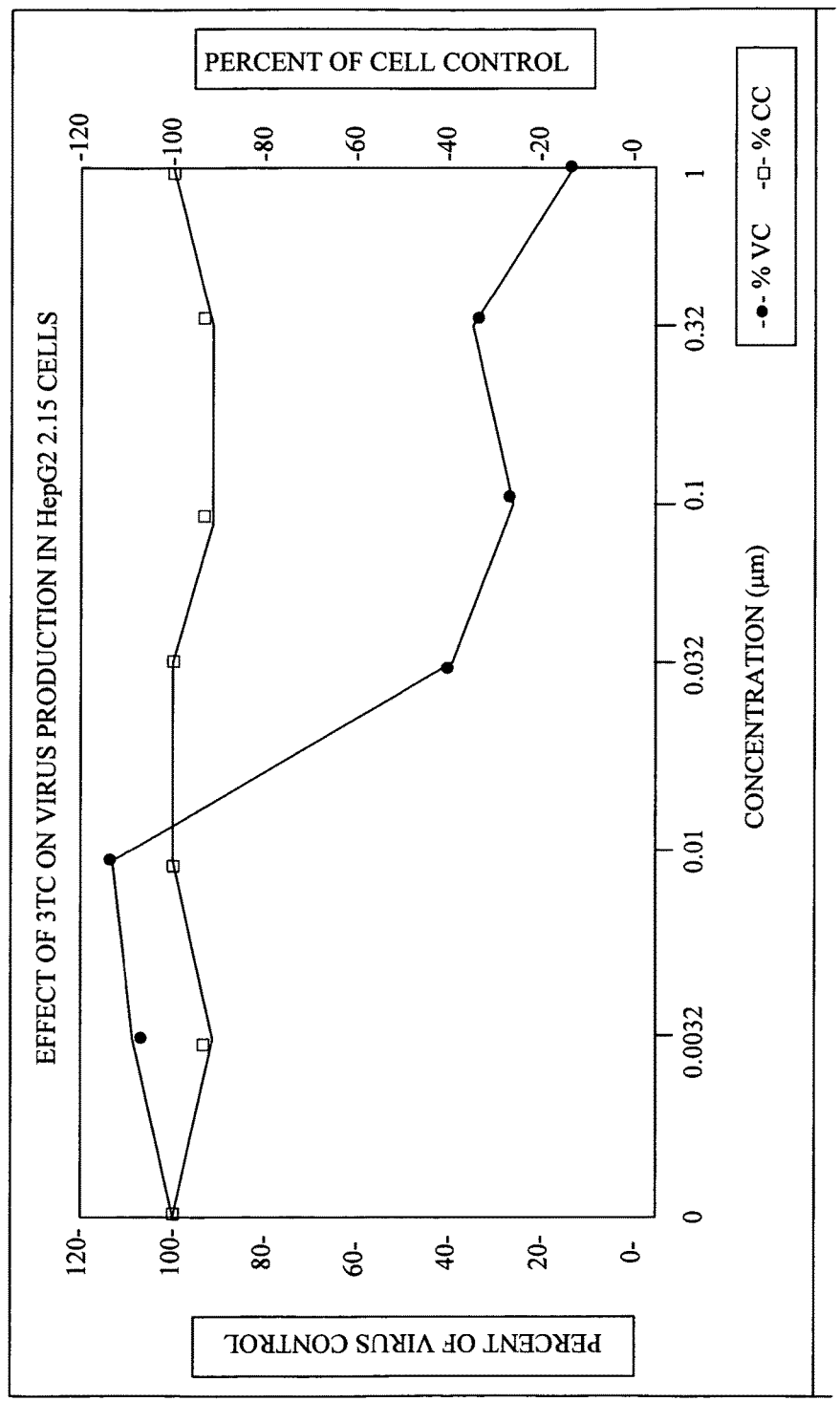
Figure 39B:
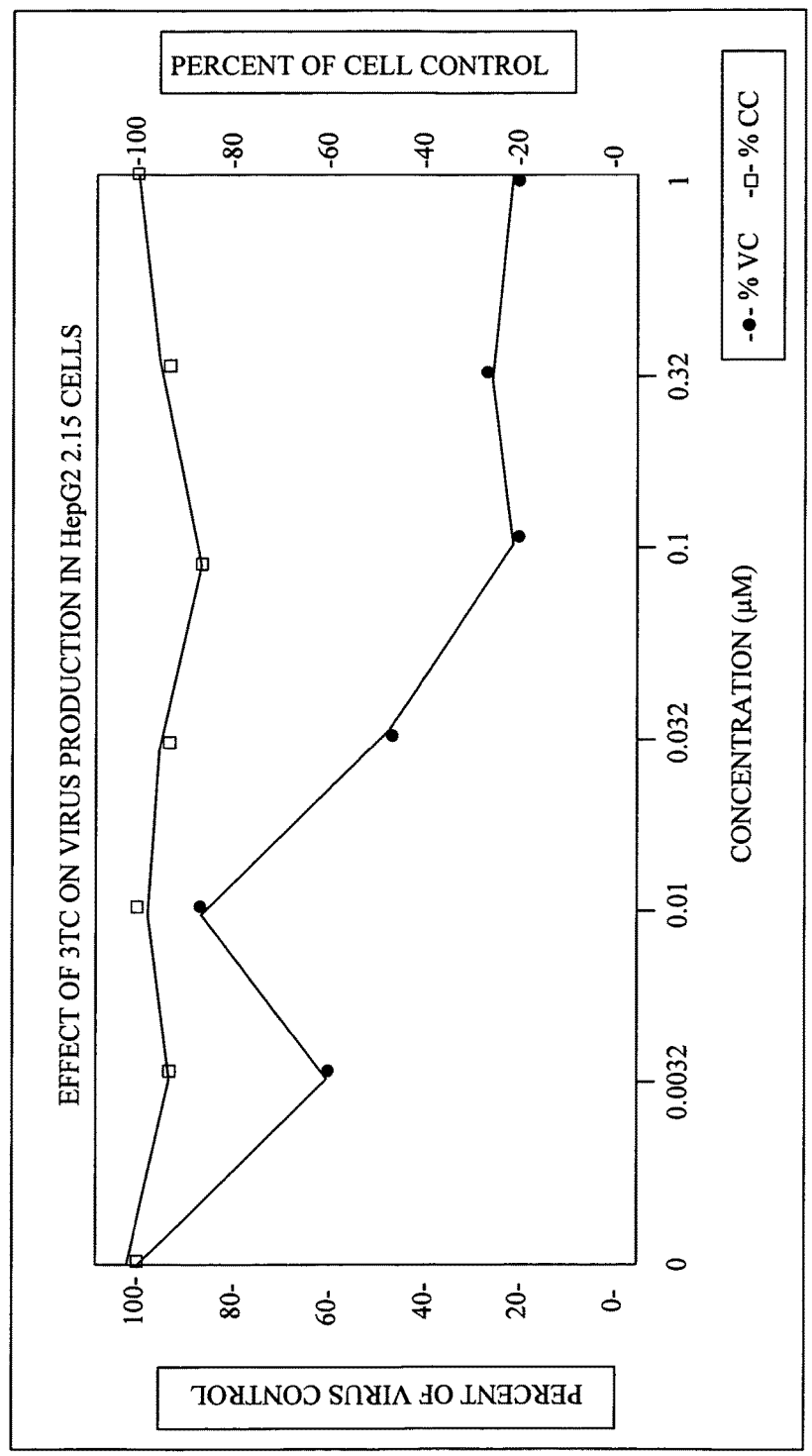
Figure 40C:
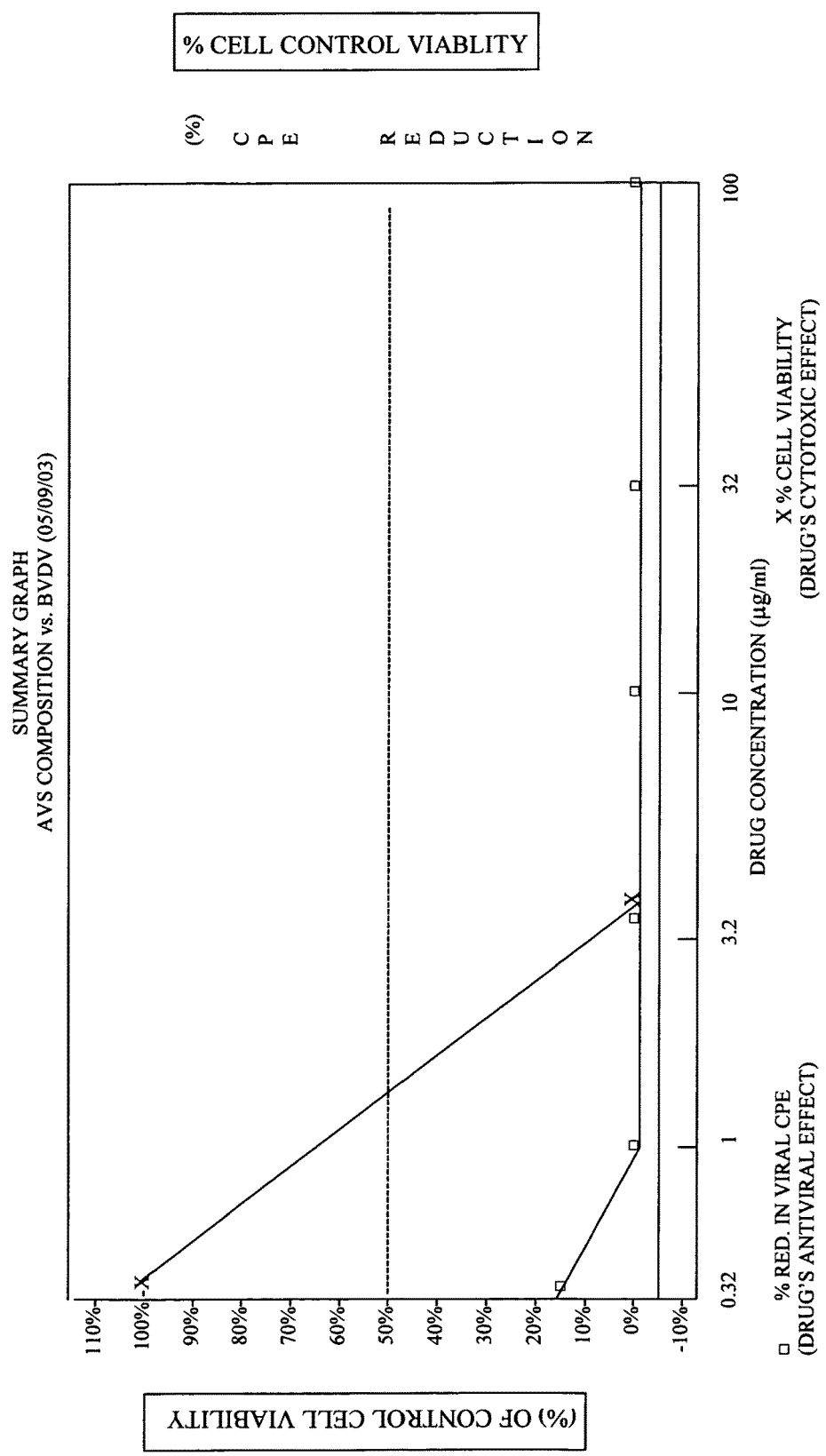
Figure 41C:
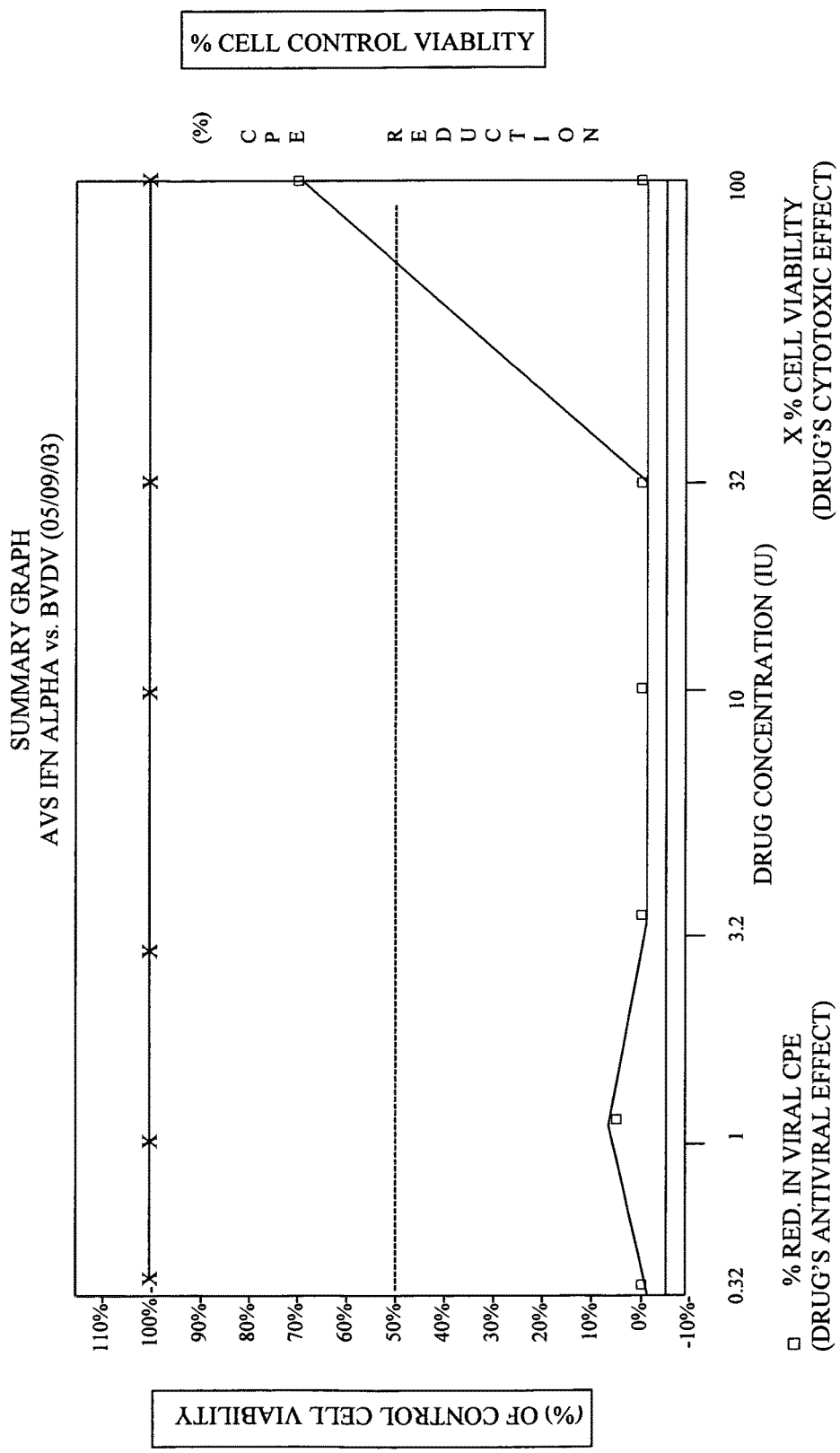
Figure 42C:
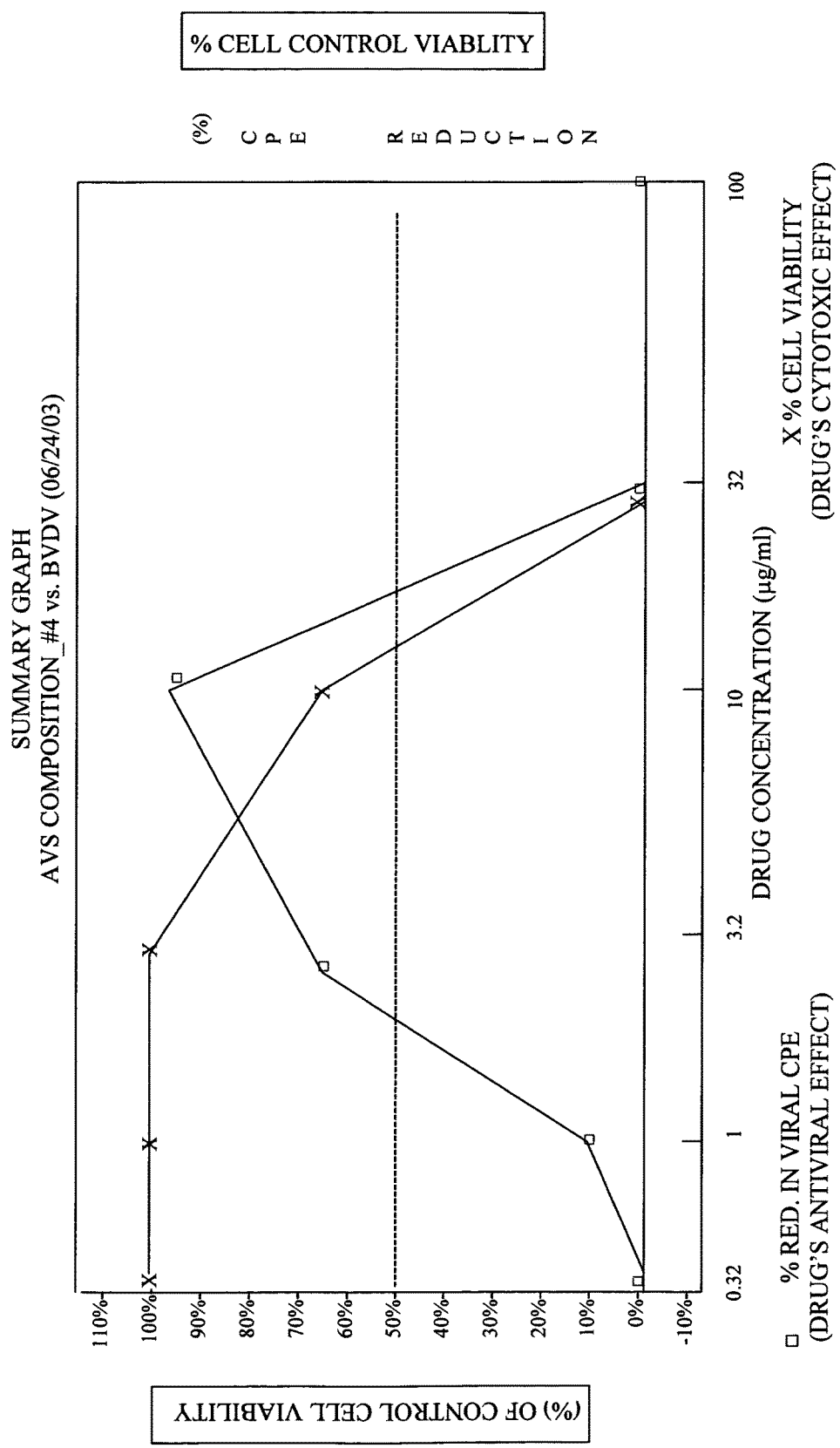
Figure 43C:
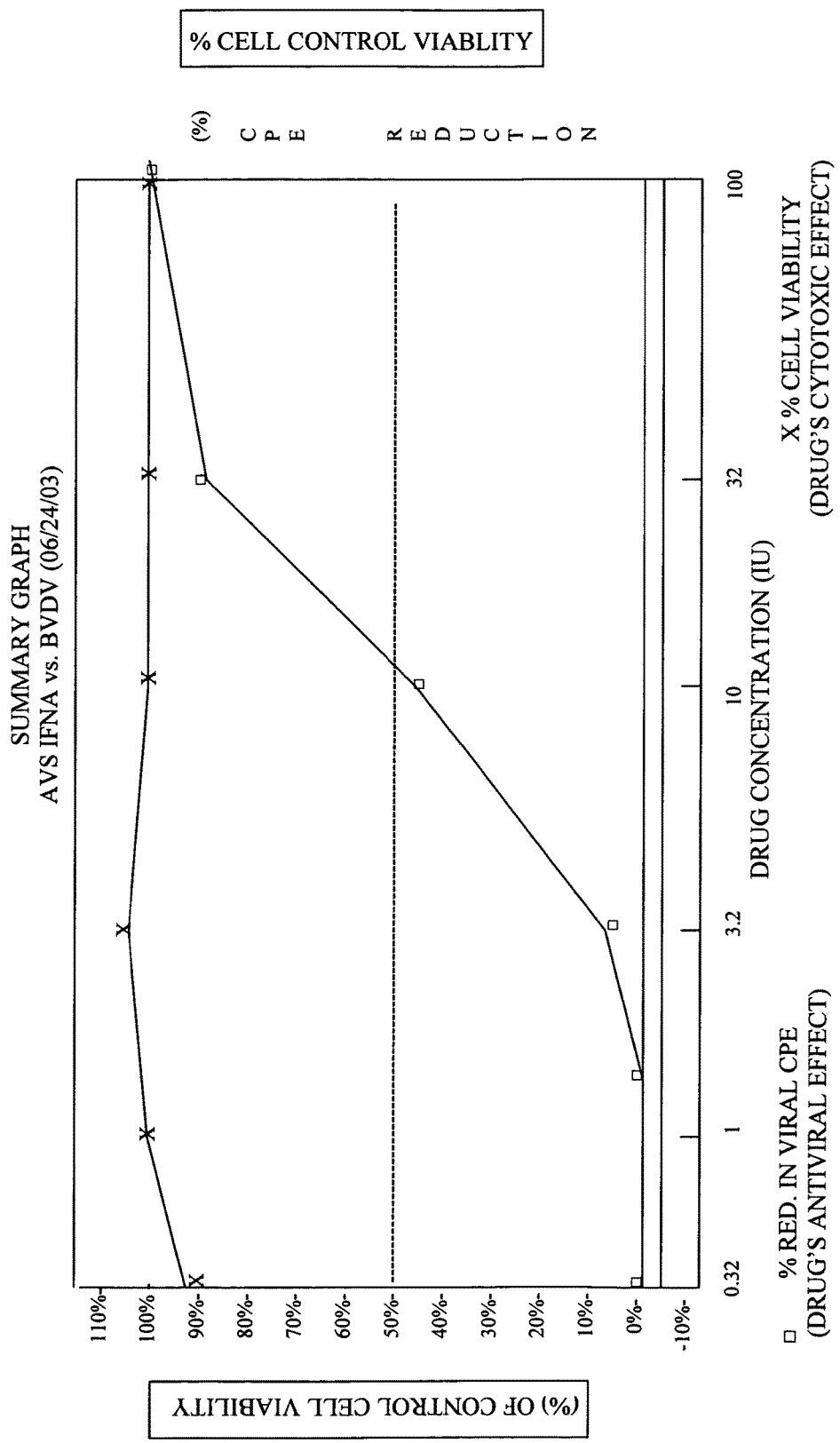

The highly toxic effects of the Composition alone against CEM-SS leukemic cells are shown in FIGS. 12A, 12B, 12C. These Figures show an $IC_{50}$ of 5.87 µg/mL and a highly efficient cell kill rate of approximately 98% at a dosage of 10 µg/mL.

Example 14

The high activity of the Composition alone against CEM-SS leukemic cells are shown in FIGS. 13A, 13B, 13C and 13D. These Figures show $IC_{50}$ of 4.975 µg/mL and a highly efficient cell kill rate of approximately 100% at a dosage of 10 µg/mL.

Experimental Design II.

This experiment was designed to evaluate the anti-viral effects and cytotoxic effects of the disclosed Composition alone, and in combination with Base Compound of iron dextran, in vitro using HCV RNA replicons. All iron dextran amounts are measured as the approximate equivalent of elemental iron derived from the iron dextran. The Base Compound of iron dextran was also run alone as a control. This protocol may also be applied to other viral, bacterial and protozoal experiments, as desired to determine effective concentrations for mammalian treatments.

Example 2

Materials and Methods

The following experiments were preformed with the Composition "HP" variation having 4.527 mg/ml of the Composition in a sterile colloidal solution, and a pH 7.8; and Composition "4" variation having 4.939 mg/ml of the Composition in a sterile colloidal solution. Both Composition-HP and Composition-4 were adjusted to pH 7.8-8.0 using sodium hydroxide before use. The Base Compound was 50 mg/ml of sterile colloidal solution.

HCV RNA Replicons

The cell line ET (luc-ubi-neo/ET) was used. ET is a new HCV RNA replicon that contains a stable luciferase ("LUC") reporter, and this particular construct has not been described in the scientific literature. It is similar to the cell line 5-2 (1), but contains additional modifications that make the cell line more robust and provide stable LUC expression for antiviral screening. This conformation of the replicon is shown diagrammatically below.

The structure of the HCV RNA replicon of cell line ET contains the 5' non-translated region ("NTR") ("IRES") of HCV (5') which drives the production of a firefly luciferase ("Luc"), Ubiquitin ("Ubiq"), and neomycin phosphotransferase ("Neo") fusion protein. Ubiquitin cleavage releases the LUC and Neo genes. The EMCV IRES element (E-I) controls the translation of the HCV structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of the HCV. (Not drawn to scale).

The LUC reporter is used as an indirect measure of HCV replication. The activity of the LUC reporter is directly proportional to HCV RNA levels, and positive control antiviral compounds behave comparably using either LUC or RNA endpoints. The use of the LUC endpoint is more economical than HCV RNA and can be used for high-throughput applications to screen libraries of compounds.

The HCV RNA replicon antiviral evaluation assay examined the effects of compounds at five half-log concentrations each. The plate layouts are shown below in FIGS. 7A, 17B, 18A and 18B. Human interferon alpha-2b was included in each run as a positive control compound. Subconfluent cultures of the ET line were plated out into 96-well plates that were dedicated for the analysis of cell numbers (cytotoxicity) or antiviral activity, and the following day both variations of the Composition and the Base Compound were added to the appropriate wells. Cells were processed 72 hr later, when the cells are still subconfluent. Compound $IC_{50}$ and $IC_{90}$ values were derived from HCV RNA replicon-derived LUC activity using steady-glo reagent (Promega). Compound $TC_{50}$ and $TC_{90}$ values were calculated using the CytoTox-1 cell proliferation assay (Promega), a colorimetric indicator of cell numbers and cytotoxicity. Compound $TI_{50}$ and $TI_{90}$ values were calculated from spreadsheets.

Results

HCV RNA Replicon Antiviral Evaluation

The Composition "HP" variety, without the addition of the Base Compound, had a weak to moderate antiviral activity against HCV RNA replicons. The results found an IC (Inhibitory Concentration)~0=0.77~µg/ml; a TC (Toxicity Concentration)~0=6.23 µg/ml, and a TI (Therapeutic Index, where $TI=TC_{50}/IC_{50}$)=8.1. See FIGS. 20A, 20B, 20C and 20D. The Composition 4 variation displayed weak to moderate antiviral activity against HCV RNA replicons without the addition of the Base Compound, having an IC~0=0.84 µg/ml; a TC~0=6.52~µg/ml; and a TI=7.7. See FIGS. 19A, 19B, 19C and 19D. The positive control of human interferon alpha-2b results is shown in FIGS. 21A, 21B, 21C and 21D. See also FIGS. 22A, 22B, 22C and 22D.

Optimized Concentrations of Composition 4 and the Base Compound Experiments

The Composition 4 was combined with the Base Compound to determine the antiviral activity and cytotoxicity in HCV RNA replicons. A matrix of drug dilutions (the Composition 4 and the Base Compound) was set up on the plates ranging from 0.195-50~µg/ml of the Composition 4 against 1.563-50 µg/ml Base Compound. The results of this experiment are that antiviral effects were clear at dosages of 6.25 µg/ml and above.

The Composition 4 showed a 50-75% inhibition range of HCV RNA replicon luciferase ("LUC"). As the dosages of the Composition was increased above 12.5~µg/ml, inhibit 75-100% of the replicon LUC activity.

When the active range of the Composition with the Base Compound was analyzed (50 to 100% efficacy plot), it was determined that there is a dose-dependent increase in activity as the Composition is increased above 6.25 µg/ml, and a trend was shown toward higher activity as the concentration of Base Compound increased from about 12.5~µg/ml up FIG. 22.

In the overall evaluation of compound toxicity (0 to 150% viability/toxicity curve), the Composition appears to be toxic above 12.5~µg/ml with 50% to 0% viability as the concentration increased further.

The cytotoxic portion of the curve (0 to 50% viability) was analyzed to determine whether a clear Composition dose-dependent increase in toxicity as the dose increases above 6.25~µg/ml, irrespective of Base Compound concentration. Above a 12.5% Composition concentration a majority of the cells were dead.

The viable portion of the viability/toxicity curve more closely (50-100% viability) was analyzed to determine an incremental increase in viability as the Composition was reduced from 12.5~µg/ml to 6.25~µg/ml followed by a more dramatic increase in viability as the concentration of drug is reduced further.

Optimized Concentrations of Composition 4 and Base Compound Experiment

A range of dosage concentrations were tested for that which Applicant was interested in. A matrix of combinations of Composition 4 and Base Compound were set up with Composition 4 from 5.5-13~µg/ml and Base Compound from 50-1050~µg/ml. The percent inhibition of HCV RNA replicon luciferase activity increased steadily from 8.5~µg/ml to 5.5~µg/ml Composition-4 and was positively influenced when combined with 550~µg/ml of Base Compound.

Cell viability dropped off rapidly as the concentration of Base Compound was increased beyond 50~µg/ml, especially at higher concentrations of Composition 4.

Conclusions

The Composition HP (TI=8.1) and Composition 4 (TI=7.7) were weakly to moderately active against HCV RNA replicons in vitro. A matrix of varying concentrations of Composition 4 and Base Compound were utilized to see if the combination of these drugs would result in an increase in their activity. The results of these experiments found that the optimum mixture of Composition-4 and Base Compound would be approximately 6-7 µg/ml Composition-4 with 50 µg/ml Base Compound.

Example 3

Materials And Methods

The following experiments were preformed with the Composition "HP" variation having 4.527 mg/ml of the Composition in a sterile colloidal solution, and a pH 7.8; and Composition "4" variation having 4.939 mg/ml of the Composition in a sterile colloidal solution. Both Composition-HP and Composition-4 were adjusted to pH 7.8-8.0 using sodium hydroxide before use. The Base Compound was 50 mg/ml of sterile colloidal solution.

The Tetrazolium Dye-Reduction Assay

Cell viability was measured by staining with the tetrazolium-containing dye mixture Cell Titer 96® (Promega, Madison, Wis.). The mixture is metabolized by the mitochondrial enzymes of metabolically active cells to a soluble formazan product, allowing the rapid quantitative analysis of cell numbers. The media was removed from the plates and replaced with 100 µL of fresh media and 10 µL of Cell Titer 96®. Plates were reincubated for 4 hours at 37° C. and read spectrophotometrically at 490 nm and 650 nm with a Molecular Devices Vmax plate reader. Percent cell viability of Composition treated wells compared to control wells having no Composition added was calculated using an in-house computer program.

HBV Antiviral Evaluation Assay

HepG2 2.2.15 cells, which produce HBV (hepatitis B virus) aywl strain, were plated in 96-well collagen-coated microtiter plates at a density of 2.5×10$^4$/well with DMEM medium supplemented with 2% fetal bovine serum. One day following plating of cells, the wells were washed and the medium was replaced with complete medium containing the test compound diluted in the medium in a half-log series (see FIG. 23 for a representative plate layout). The medium was replaced once with the fresh medium containing the freshly diluted compound three days after the initial addition of the Composition. 3TC (Lamivudine) was used as a positive control compound.

Six days following the initial administration of test compound, the cell culture supernatant was collected. Virion-associated HBV DNA present in the tissue culture supernatant was then PCR amplified using primers derived from HBV strain ayw. Subsequently, the PCR-amplified HBV DNA was detected in a TaqMan quantitative PCR assay in real-time, by monitoring the increases in fluorescence signals that result from exonucleolytic degradation of a quenched fluorescent probe molecule following hybridization of the probe to the amplified HBV DNA. A standard curve was prepared using HBV ayw plasmid DNA. Samples were analyzed in duplicate by PCR and the average values of samples falling within the range of the standard curve were used to assign an HBV DNA copy number.

The OD (optical density) value obtained from cell viability results and the virion DNA copy number obtained with the real time PCR were analyzed using an in-house computer program, which calculates the percentage of DNA copy number, and used to calculate the antiviral activity of samples $IC_{50}$. Cell viability data were used to calculate the $TC_{50}$. Therapeutic indices (TI) were calculated from TC/IC. These results were displayed graphically. See FIGS. 25A, 25B, 26A and 26B. An additional spreadsheet was employed to determine $IC_{50}$, $TC_{90}$ and $TI_{90}$ values from the data.

BVDV Antiviral Evaluation Assay

Madin-Darby bovine kidney ("MDBK") cells were passaged in T-75 flasks. On the day preceding the assay, the cells were trypsinized, pelleted, counted and resuspended at 1×10$^4$/well in tissue culture medium in 96-well flat bottom tissue culture plates in a volume of 100 µl per well. One day following plating of cells, the wells were washed and the medium was replaced with complete medium (2% serum) containing various concentrations of test compound diluted in the medium in a half-log series (see FIGS. 22A, 22B, 22C and 22D for a representative plate layout). A pretitered aliquot of bovine viral diarrhea virus (BVDV) was removed from the freezer (−80° C.) just before each experiment. The virus was diluted into tissue culture medium such that the amount of virus added to each well would give complete cell killing at 6-7 days post-infection.

The cell viability was measured on day 6-7 post drug addition by staining the cells with the tetrazolium containing dye mixture Cell Titer 96® (Promega, Madison, Wis.). The mixture is metabolized by the mitochondrial enzymes of metabolically active cells to a soluble formazan product, allowing the rapid quantitative analysis of cell numbers. The media was removed and replaced with 100 gl of fresh media and 10p. 1 of Cell Titer 96®. Plates were reincubated for 4 hours at 37° C., and read spectrophotometrically at 490 and 650 nm with a Molecular Devices Vmax plate reader. The percent cell viability of compound-treated wells compared to no compound control wells was calculated using an in-house computer program which graphs the percent reduction in viral cytopathic effects and the cell numbers at each drug concentration relative to control values. The program interpolates the inhibitory concentration of drug that reduces BVDV cytopathic effects by 50% ($IC_{50}$) and the toxic concentration that kills 50% of cells (TC 50).

Cytotoxicity of Composition in Cynmolgous Monkey Primary, Hepatocyte Cultures

A 24-well plate of Cynmolgous monkey primary hepatocytes of high viability and metabolic activity was prepared by Cedra Corporation. The cells were ~85% confluent when the experiment was initiated. The cytotoxicity of Composition was assessed at six concentrations of drug, diluted in Serum Free Media (SFM) in a half-log series, with 100 µg/ml used as the high-test concentration. Four untreated control wells contained SFM alone. The Composition and media were changed on days 2 and 5 post-addition. On day 7 post-addition the Composition and media were removed and the wells were rinsed with media. Cell Titer 96 (Promega) was added to fresh media in the wells and the absorbance measured as above. The average absorbance of the wells at each Composition concentration was plotted relative to the untreated cell controls and $TC_{50}$ values were extrapolated from those curves. See FIG. 44.

Results

HBV Antiviral Evaluation

The compound Composition HP displayed some antiviral activity against HBV in the HepG2 2.2.15 assay with an $IC_{50}$=11 µg/ml, a $TC_{50}$=64 µg/ml, and a TI=5.8. The raw data for the HBV antiviral evaluation experiment is in shown in FIGS. 25A, 25B, 26A, 26B, 27A and 27B.

The effect of combining the Base Compound together with the Composition HP are shown in FIGS. 28A, 28B, 29A, 29B, 30A, 30B, 31A, 31B, 32A, 32B, 33A, 33B, 34A, 34B, 35A, 35B, 36A and 36B. Base Compound was used at 5 µg/ml, 15 µg/ml, 30 µg/ml or 60 µg/ml, respectively, with three concentrations of Composition HP at 1 µg/ml, 3.16 µg/ml and 10 µg/ml. Base Compound alone and Composition HP alone were also tested. Little antiviral activity or cytotoxicity was apparent.

Since anti-HBV antiviral activity was expected in the above experiment, the concentration of the Base Compound was modified. The effect of 200 µg/ml of Base Compound on the Composition HP anti-HBV antiviral activity was tested. Little antiviral activity was apparent. A $TC_{50}$=26 µg/ml of Composition HP plus 200 µg/ml Base was observed. The raw data for this experiment is shown in FIGS. 35A, 35B, 36A and 36B. The anti-HBV antiviral activity of Composition-4 was also examined. The compound was marginally active in the assay, see FIGS. 27A, 27B, 28A, 28B, 29A and 29B.

BVDV Antiviral Evaluation

The Composition HP was toxic in MDBK cells, with a TC50=0.97 g/ml. The Composition 4 showed a reasonable antiviral activity against BVDV (see, FIGS. 40A, 40B, 40C, 41A, 41B and 41C) with $TC_{50}$=17.3, $IC_{50}$=2.6, TI=6.7. The Composition-HP displayed low antiviral activity against BVDV and an $IC_{50}$ was not reached. See FIGS. 40A, 40B, 40C, 41A, 41B and 41C.

Cytotoxicity in Cynmolgous Monkey Primary Hepatocytes

Figure 44B:
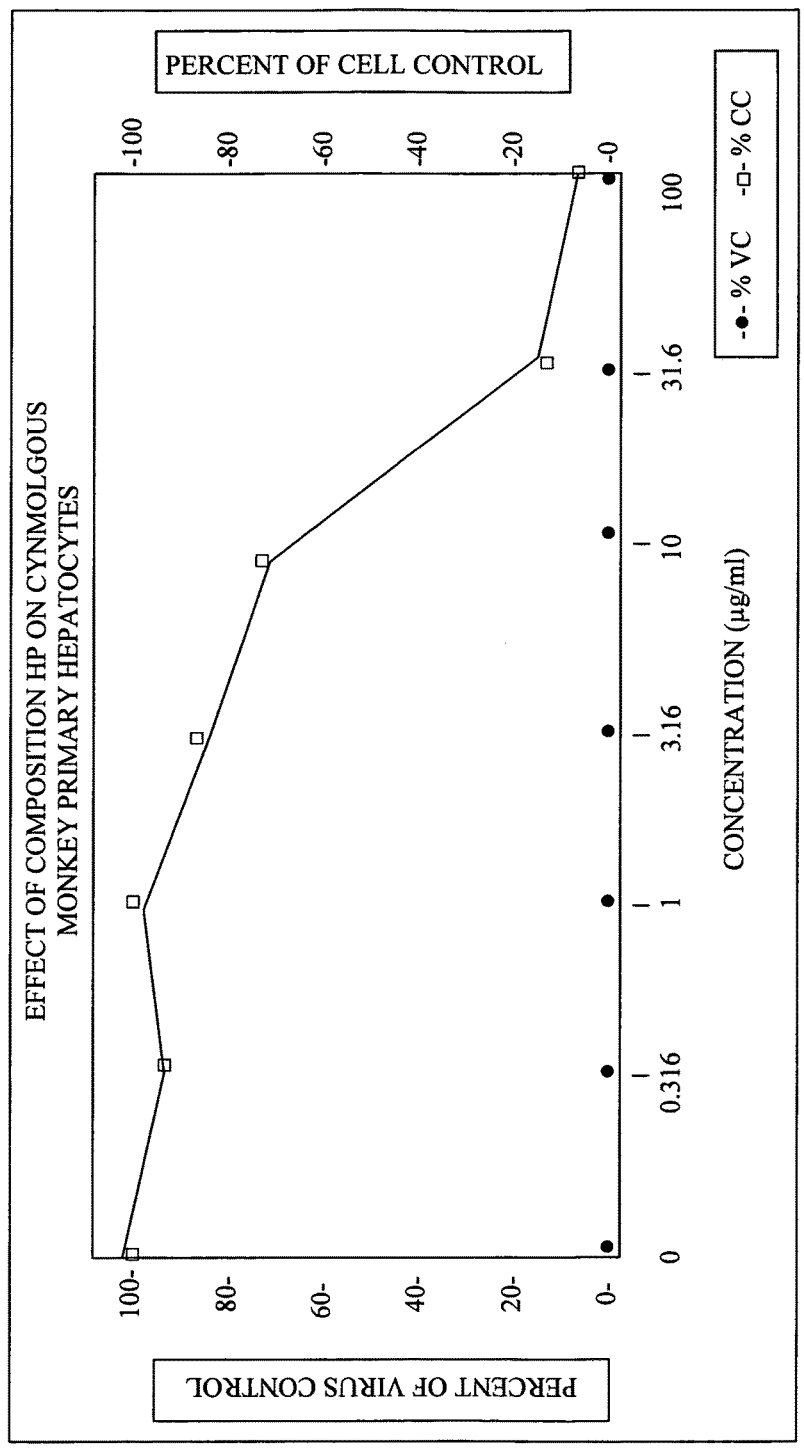
Figure 51:
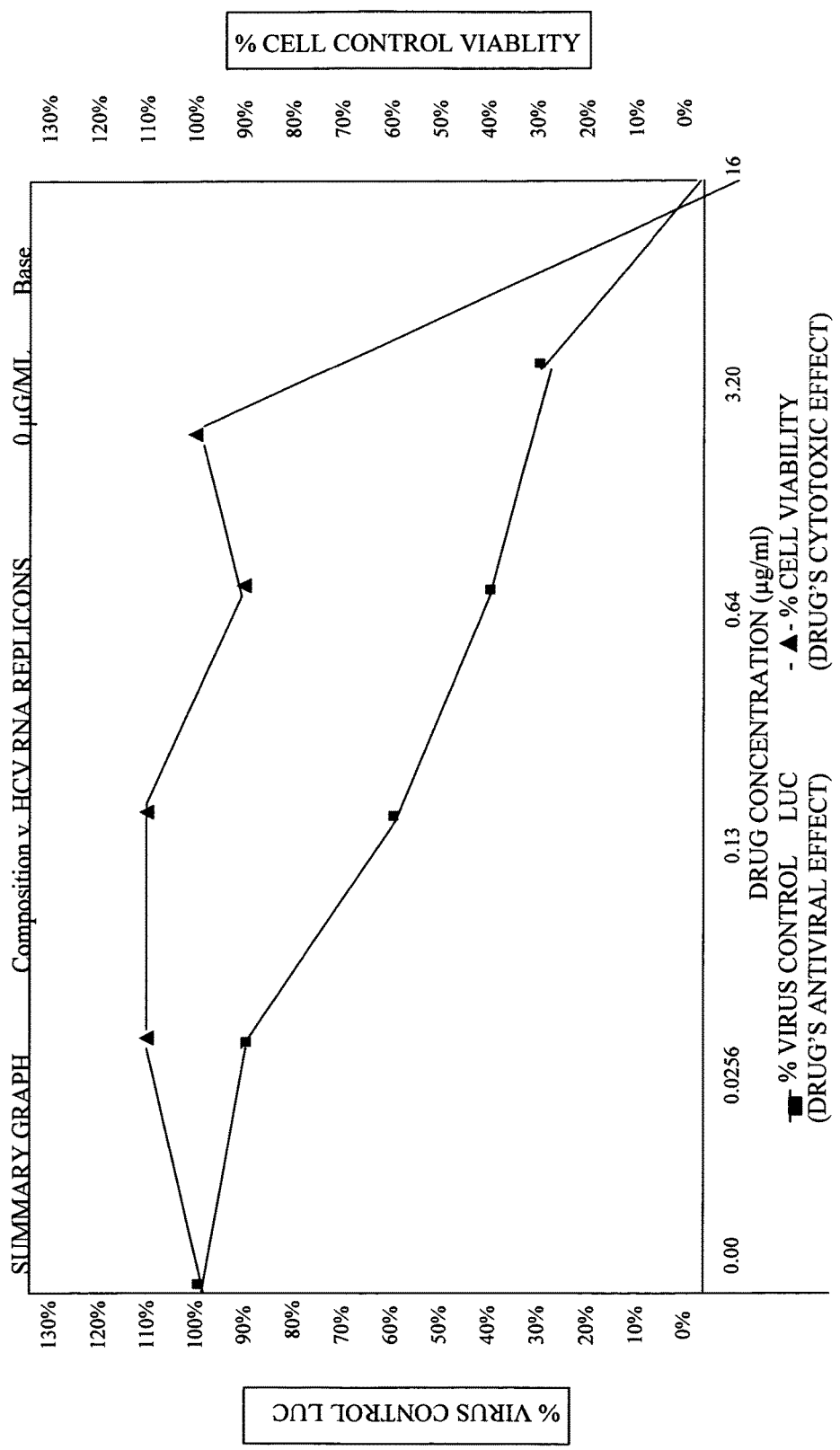
FIG. 51 shows a graph of the data displayed in FIGS. 48A, 48B, 49 and 50.
Figure 55:
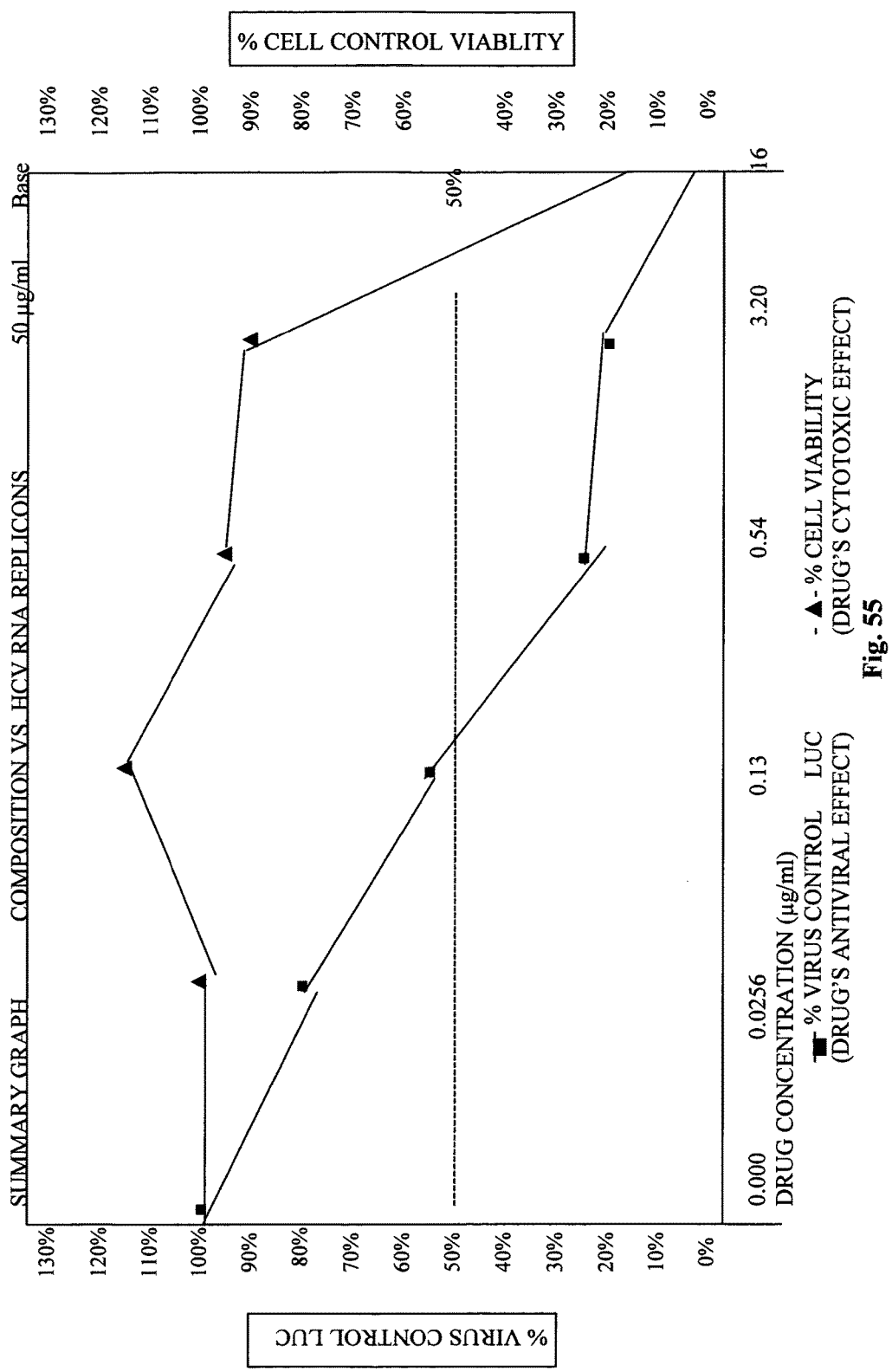
FIG. 55 shows a graph of the data displayed in FIGS. 52A, 52B, 53 and 54.
Figure 59:
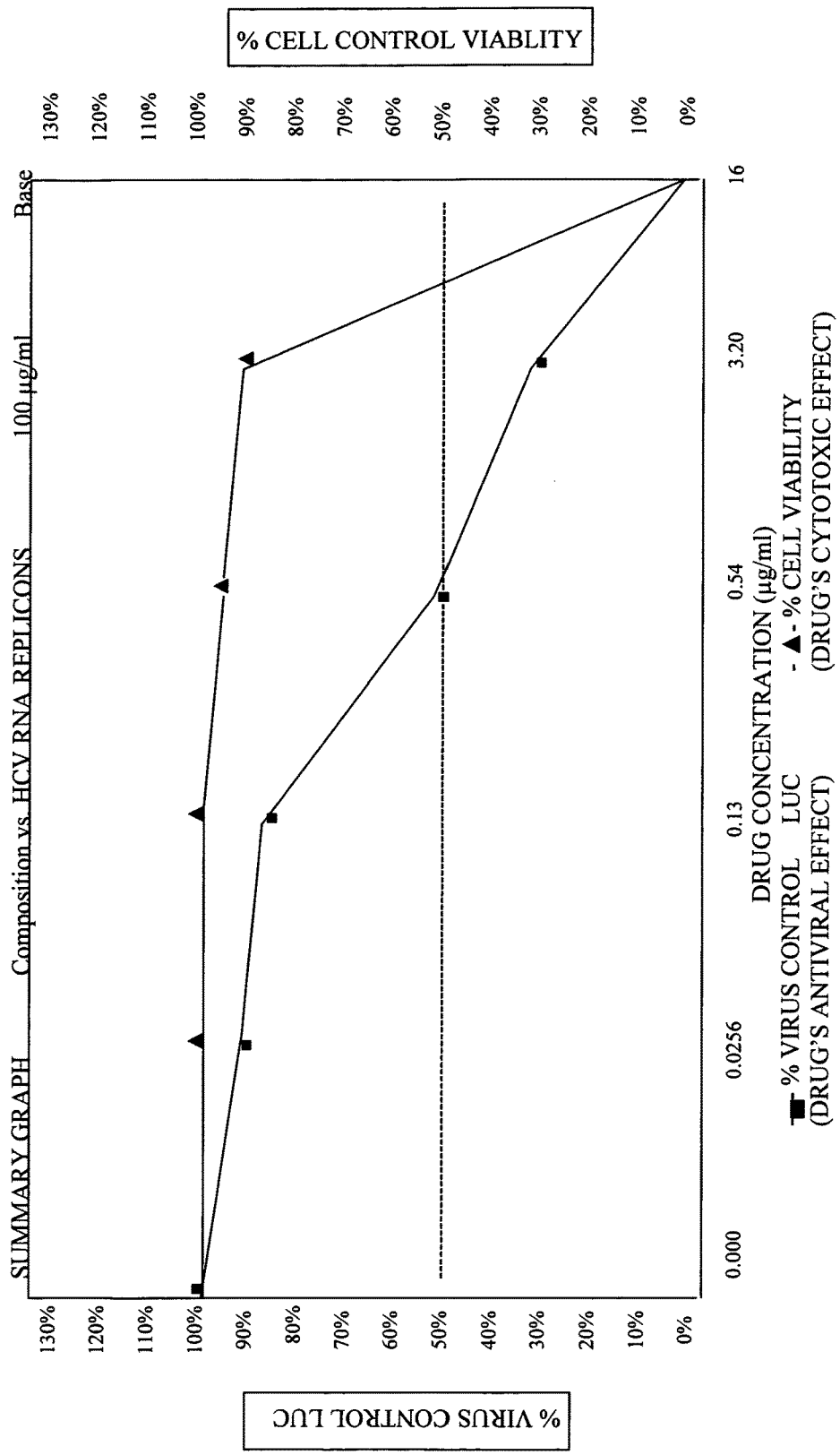
FIG. 59 shows a graph of the data displayed in FIGS. 56A, 56B, 57 and 58.
Figure 63:
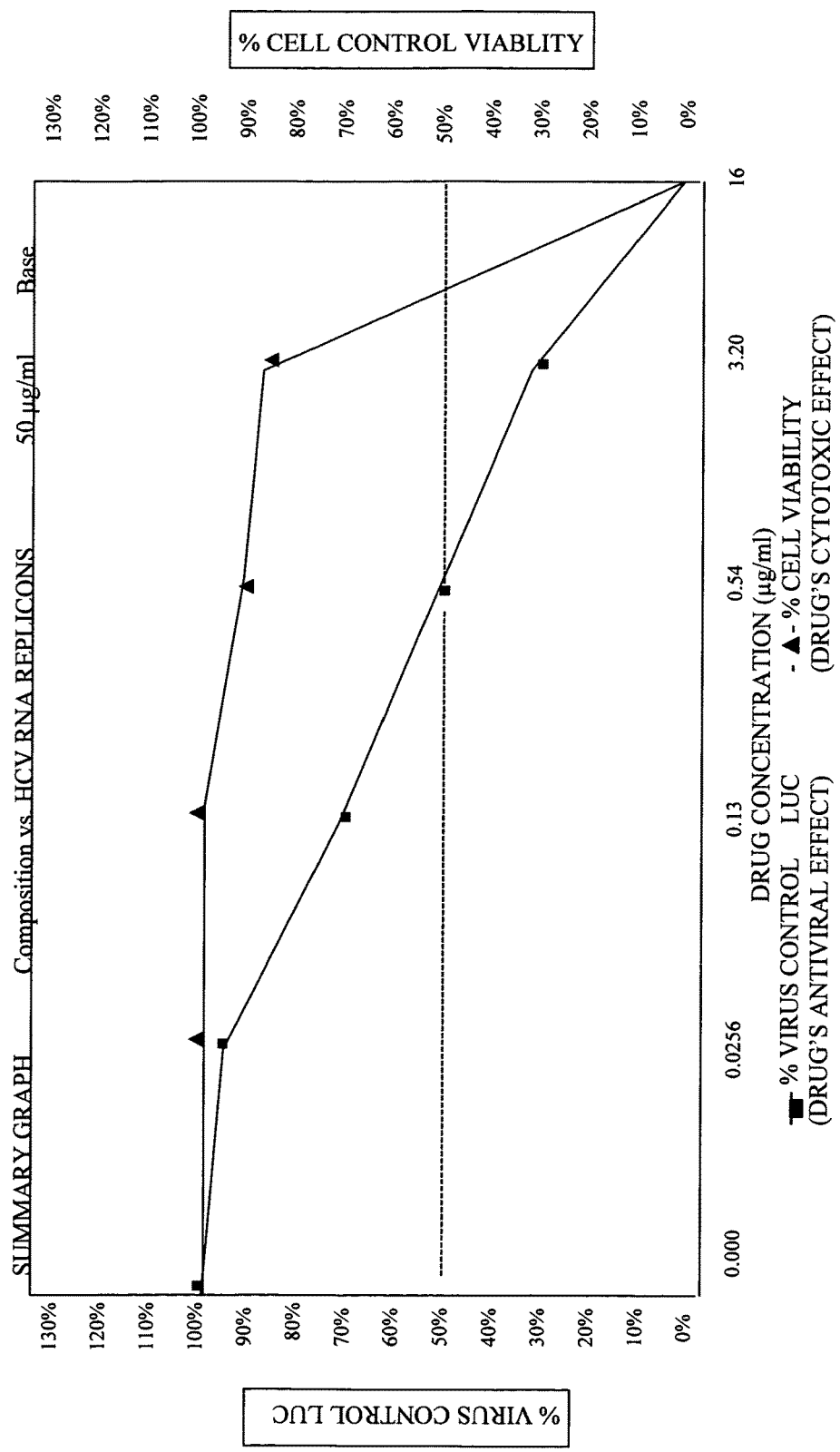
FIG. 63 shows a graph of the data displayed in FIGS. 60A, 60B, 61, and 62.
Figure 68:
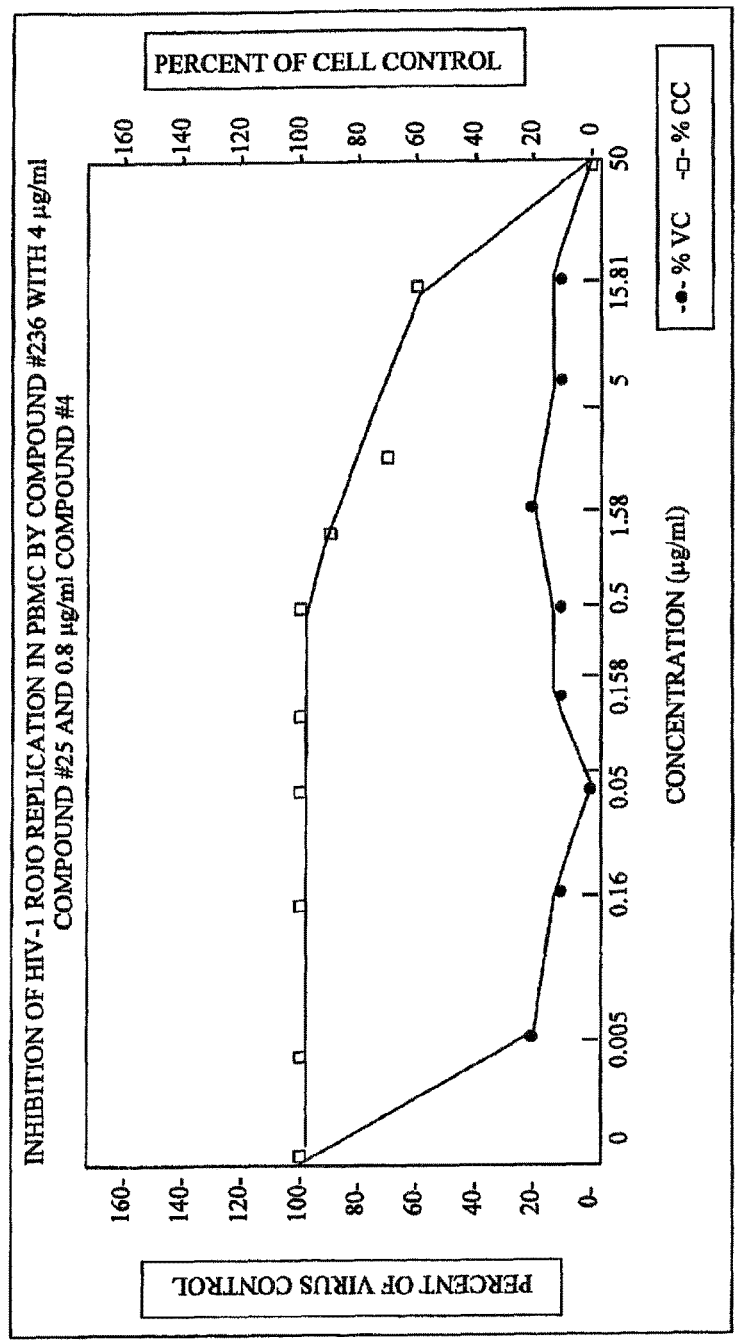
Figure 71:
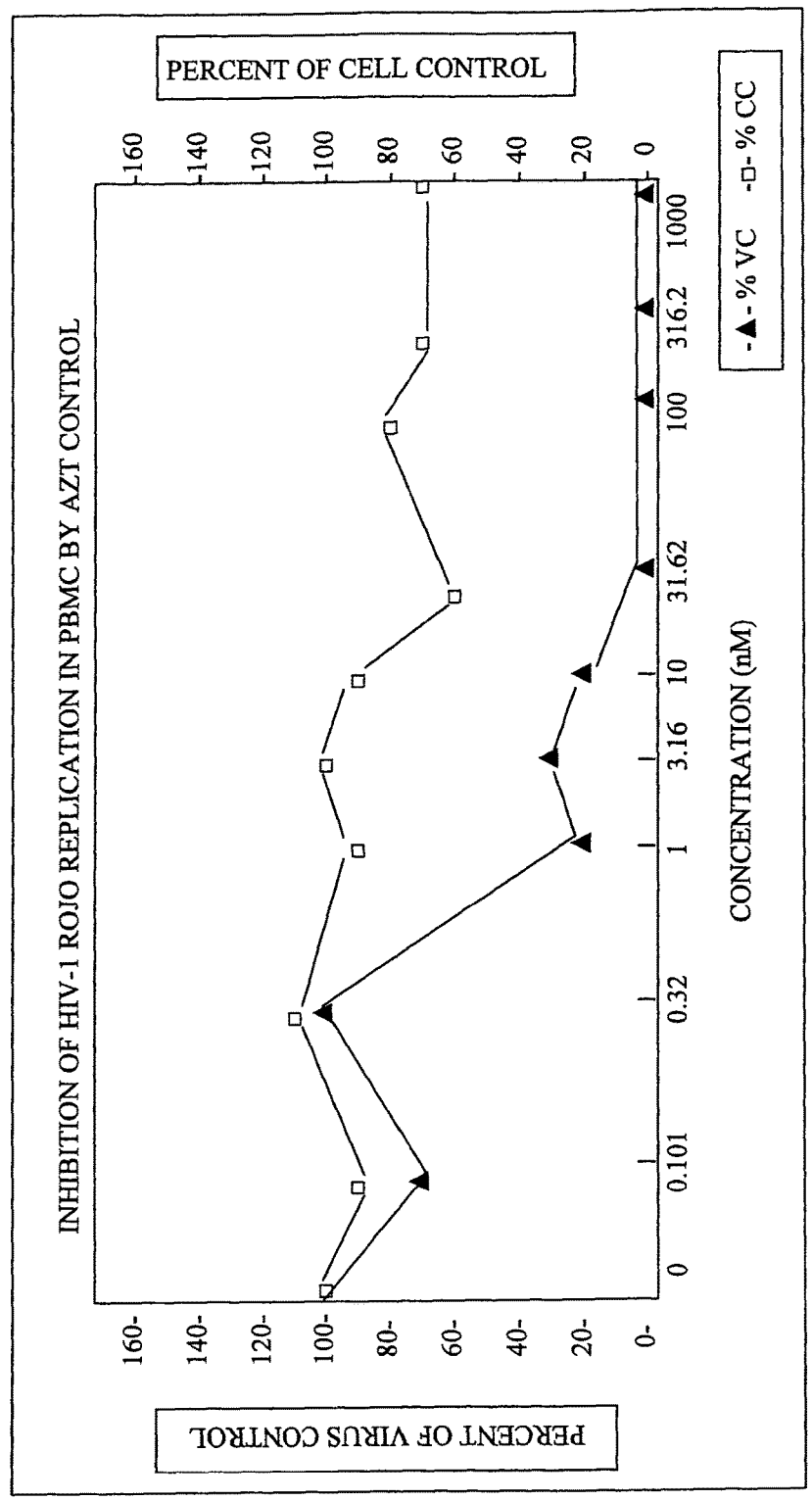
Figure 74:
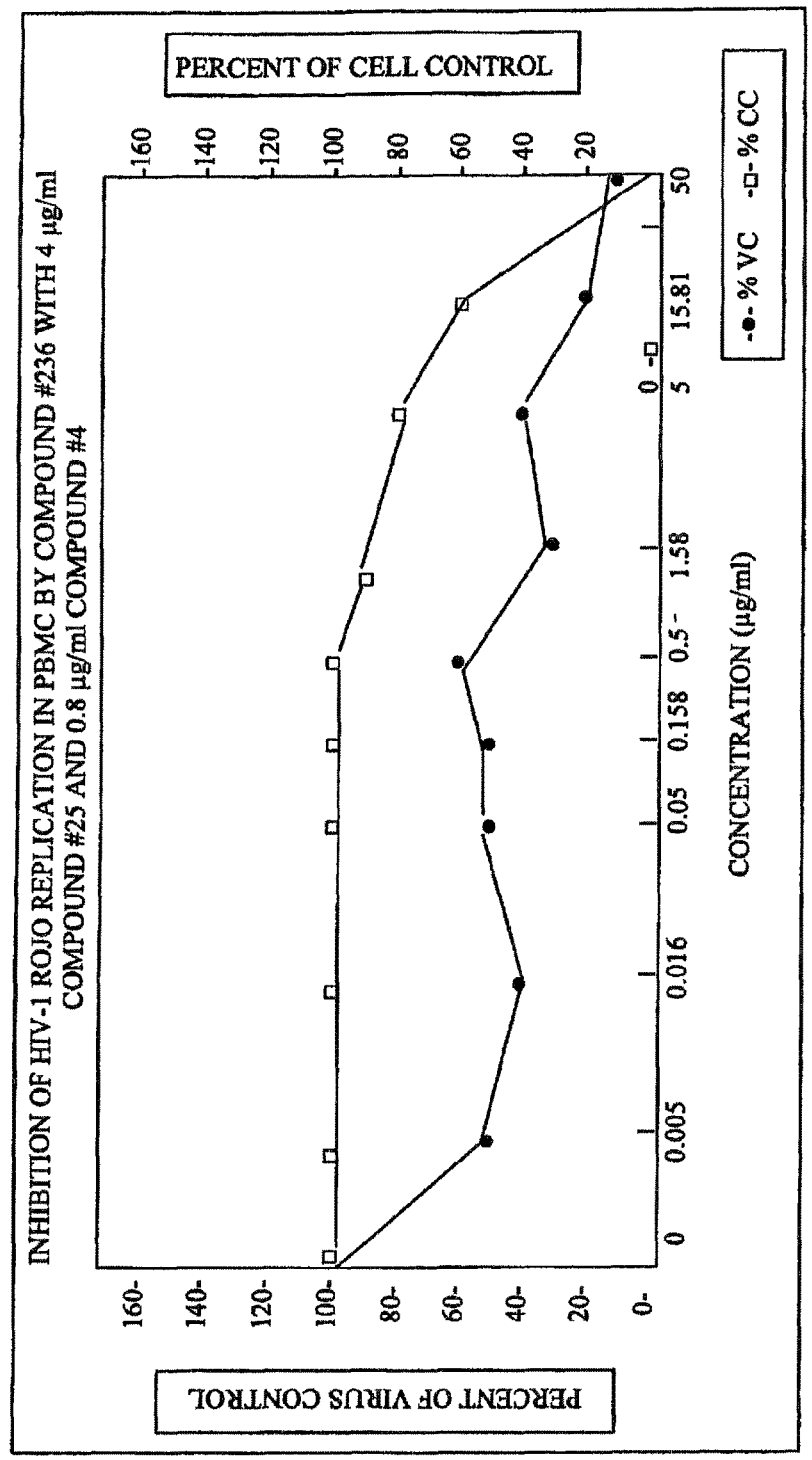

The Composition HP showed a moderate $TC_{50}$=20 µg/ml with Cynmolgous monkey primary hepatocyte cultures. The raw data for the primary hepatocyte experiment is shown in FIGS. 44A and 44B.

The FIGS. 45A through 71 disclose further experimental data to demonstrate the efficacy of the Composition with various concentrations with and without the addition of the Base.

For example, FIGS. 45A, 45B, 46 and 47 show experimental results of an in vitro activity of the Composition with *mycobacterium tuberculosis*.

Moreover, FIGS. 48A through 63 show antiviral evaluations, such as for hepatitis C virus.

Furthermore, FIGS. 64 through 106 show anti-viral activity with respect to human immuno-deficiency virus (HIV).

Discussion

The Composition-HP and Composition-4 showed weak-moderate anti HBV antiviral activity in vitro. The addition of Base to Composition-HP did little enhance its antiviral activity. The compound Composition-HP displayed little antiviral activity against BVDV in vitro, while Composition-4 displayed a modest antiviral activity against BVDV. The Composition-HP showed a $TC_{50}$=20 µg/ml using Cynmolgous monkey primary hepatocyte cultures.

Example 4

The anti-human immunodeficiency virus type-1 (HIV-1) activity of Composition was evaluated in the absence and presence of various concentrations of Base in a Standard PBMC-based cell virus assay system or CEMSS-based anti-HIV-1 cell virus assay system. Antiviral activity of Composition, Base and Composition plus Base were evaluated in HIV-1RF infected CEM-SS cells. Composition with or without Base was evaluate for antiviral activity in our standard chronic HIV-1 infection (CEMSK1 or CEMRF) assay and for activity when cells (CEMSKI) were treated long term. Activity against U1 cells lately infected with HIV-1 pretreated with compound prior to induction with TNFα was also evaluated.

Materials and Methods

Evaluation of Anti-HIV Activity of Compounds in Fresh Human Peripheral Blood Cells PBMC Isolation and Blasting Peripheral blood monocular cells (PBMCs) are obtained from normal hepatitis and HIV-1 negative donors by ficoll hypaque gradient separation. Briefly, anti-coagulated blood is diluted 1:1 with Dulbecco's phosphate buffered saline without Ca++ and Mg++ (PBS) an layered over 14 mL of Lymphocyte separation media in a 50 ml centrifuge tube. Tubes are then centrifuged for 30 minutes at 600×g. Banded PBLs are gently aspirated from the resulting interface and subsequently washed 2× with PBS by low speed centrifugation. The mononuclear cells are counted, viability determined by Trypan Blue dye exclusion and resuspended in RPMI 1640 medium supplemented with 15% FBS (heat inactivated), 2 mM L-glutamine, 100 U/mL penicillin, 100 µg/mL streptomycin, and 10 µg/mL gentamycin with 2 µg/mL phytohemagluttin (PHA) at 1×10⁶ cells/mL. The cells are cultured for 48 to 72 h at 37° C., 5 $CO_2$. Following incubation, cells are collected by centrifugation, washed and resuspended in RPMI 1640 supplemented with 15% FBS (heat inactivated), 2 mM L-glutamine, 100 U/mL penicillin, 100 µg/m streptomycin, and 10 µg/mL gentamycin with 20 U/mL recombinant IL-2 (R & D Systems, Minneapolis, Minn.). IL-2 is included in the culture medium to maintain the cell division initiated by the PHA mitogenic stimulation. The cultures are then maintained until use by 12 culture volume change with fresh IL-2 containing medium every 3 days.

PBMC Assay:

Human peripheral blood mononuclear cells from a minimum of 2 donors, that have been blasted with PHA and IL-2, are counted, viability determined by Trypan Blue dye exclusion and mixed in equal ratios. Pooled donors are used to minimize the variability observed between individual donors which results from quantitative and qualitative differences in HIV infection and overall response to the PHA and IL-2 of primary lymphocyte populations. The cells are resuspended at $1\times10^6$ cells/mL in RPMI 1640 without phenol red supplemented with 15% Fetal Bovine Serum (heat inactivated), 2 mM L-glutamine, 100 U/mL penicillin, 100 µg/ML streptomycin, 10 µg/mL gentamycin and IL-2 (20 U/mL, R & D Systems, Minneapolis, Minn.). Fifty microliters of cells are then distributed to the inner 60 wells of a 96 well round bottom microtiter culture plate in a standard format developed by the Infectious Disease Research department of Southern Research Institute. Each plate contains cell control wells (cells only), virus control wells (cells plus virus), and experimental wells (drug plus cells plus virus). Serially diluted compounds are added to the microtiter plate followed by the appropriate pre-titered strain of HIV-1. The studies presented here used the RoJo strain of HIV. RoJo is a low passage pediatric clinical isolate of HIV specifically isolated and developed in the laboratories of Southern Research Institute. All samples are assayed in triplicate with a replicate plate without virus for the determination of compound toxicity. The final volume per well was 200 µµL. The assay was incubated for 6 days in a humidified atmosphere at 37° C., 5% $CO_2$, after which supernatants are collected, for analysis of RT activity and sister plates analyzed for cell viability by MTS dye reduction. Wells are also examined and microscopically and any abnormalities noted.

Evaluation of Anti-HIV Activity of Compounds in Established Cell Lines Modified HIV Cytoprotection Assay CEM-SS cells ($5\times10^4$ cells per ml) were infected with HIV-$1_{RF}$ virus at multiplicity of infection ranging from 0.005-0.01 in T-25 flasks in the presence of compound. Concentrations of 1, 2.5, 5, 10, 20, 32 µg/ml of Composition, 0.75 µg/ml Base 1, and Composition plus Base 1 were evaluated. At 6 days post infection, virus replication was assessed in cell-free supernatants by qualification of RT. The cells were then washed and resuspended in the absence and presence of compound. Following 6 and 12 days post-wash, virus replication was assessed in cell-free supernatants by qualification of RT and extracellular p24.

Evaluation of Anti-HIV Activity of Compounds in Chronically Infected Cells Standard Chronic Assay Twenty-five thousand ($2.5\times10^3$) chronically infected CEMRF cells were plated in 100 µl per well of tissue culture medium in a 96 well microtiter plate. Old and New Composition were evaluated in the absence and presence of 0.1, 1, and 10 µg/ml Base 1. After 6 days of incubation at 37° C. in a 5% $CO_2$ incubator, virus replication was assessed in cell-free supernatants by quantification of RT and cell viability was assessed by tritiated thymidine incorporation.

Modified Chronic Assay

Chronically infected CEMSK1 cells were cultured with 1, 2.5, 5, 10, 20 and 32 µg/ml Composition, 0.75 µg/ml Base 1, and Composition plus Base1 for either 7, 14, 21, and 28 days. Following pretreatment, virus replication was assessed in cell-free supernatants by quantification of RT and extracellular p24 and cell viability was assessed by tritiated thymidine incorporation. Cells were collected at this same time points, washed to remove the compound and cultured in the absence of drug for an additional 14 days. At day 7 post-wash, virus replication was assessed by tritiated thymidine incorporation. At day 14 post-wash, virus replication was assessed in cell-free supernatants by quantification of RT and extracellular p24 and cell viability was assessed by tritiated thymidine incorporation.

Evaluation of Anti-HIV Activity of Compounds in Latently Infected Cells

U1 cells were obtained from the AIDS Research and Reference Reagent Program and maintained under standard culture conditions. Twenty-four hours prior to the assay the cells were split 1:2 in culture media (RPMI 1640 medium without phenol red) with 10% Fetal Bovine Serum (heat inactivated), 2 mM L-glutamine, 100 U/mL penicillin, and 100 µg/mL streptomycin. U1 cells were cultured in T25 flasks in the presence of 1, 2.5, 5, 10, 20, and 32 µg/ml Composition, 0.75 µg/ml Base 1, Composition plus Base 1 for 1, 3, 6, 9, and 12 days. At the time of the assay $2.5\times10^4$ cells/mL are placed in 96 well plates with media containing 10 ng/ml TNFα. Cultures were incubated for 5 days and cell-free supernatants harvested. Compound toxicity was determined by tritiated thymidine incorporation. Virus replication was assessed in cell-free supernatants by quantification of RT, intracellular p24 and extracellular p24.

Evaluation of Effect of Compound on Capture of Tritiated Thymidine

Chronic CEMSK1 cells ($10^5$) were plated where appropriate in a 96 well microtiter plate either prior to overnight incubation at 37° C. or before harvesting for quantification of thymidine incorporation following incubation. Composition (32 µg/ml), Base 1 (1 µg/ml) and Composition plus Base 1 were evaluated. The varying conditions evaluated are summarized in the table below.

| Condition | Purpose |
|---|---|
| Media + $^3$H overnight; harvest | Negative control |
| Cells + $^3$H overnight; harvest | Positive control |
| Cells + Drug overnight; harvest | Baseline drug control |
| Cells + Drug + $^3$H overnight; harvest | Drug Control |
| Drug + $^3$H overnight; harvest | Does drug capture $^3$H? |
| Drug + $^3$H overnight; add cells then harvest | Does drug capture $^3$H when cells present? |
| Media + $^3$H overnight; add drug then harvest | Baseline control |
| Media + $^3$H overnight; add drug and cells then harvest | Baseline control |

$^3$H Thymidine Incorporation

In specific experiments viability of cells was measured by [$^3$H] thymidine incorporation into cellular DNA. Twenty-four hours prior to termination of the assay 0.1 µCi (5 mCi/ml) of [$^3$H] thymidien was added per well. Incorporation was then determined on a Wallac Microbeta counter following lysis of the cells with $H_2O$ and capture on glass fiber filters using a Skatron harvester.

MTS Staining for Cell Viability

For specific assays at termination of the assay plates were stained with the soluble tetrazolium-based dye MTS (Cell-Titer®) Reagent Promega, Madison, Wis.) to determine cell viability and quantify compound toxicity. MTS is metabolized by the mitochondria enzymes of metabolically active cells to a soluble formazan product, allowing the rapid quantitative analysis cell viability and compound cytotoxicity. This reagent is a single stable solution that does not require preparation before use. At termination of the assay 20 µL of MTS reagent is added per well. The wells are incubated overnight for the HIV cytoprotection assay and for 4 h for monocyte/macrophages and PBMCs at 37° C. The incubation intervals were chosen based on empirically determined times for optimal dye reduction in each cell type. Adhesive plate sealers were used in place of the lids, the sealed plate was inverted several times to mix the soluble formazan product and the plate was read spectrophotometrically at 490 nm with a Molecular Devices Vmax plate reader.

Reverse Transcriptase Assay

Reverse transcriptase activity was measured in cell-free supernatants. Tritated thymidine tripphosphate (NEN)

(TTP) was resuspended in distilled H$_2$O at 5 Ci/mL. Poly rA and oligo dT were prepared as a stock solution which was kept at −20° C. The RT reaction buffer was prepared fresh on a daily basis and consists of 125 μL 1.0 M EGTA, 125 μL dll$_2$0, 110 μl. 10% SDS, 50 μL 1.0 M Tris (pH 7.4), 50 μL 1.0 M DTT, and 40 μL 1.0 M MgCl$_2$. These three solutions were mixed together in a ratio of 2 parts TTP, 1 part poly rA:oligo dT, and 1 part reaction buffer. Ten microliters of this reaction mixture was placed in a round bottom microtiter plate and 15 μL of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor O was added to each sample and incorporated radioactivity was quantitated utilizing a Wallac 1450 Microbetaplus liquid scintillation counter.

P24 Antigen ELISA:

ELISA kits were purchased from Coulter Electronics. The assay is performed according to the manufacturer's instructions. Control curves are generated in each assay to accurately quantitative the amount of p24 antigen in each sample. Data are obtained by spectrophotometric analysis at 450 nm using a Molecular Devices Vmax plate reader. Final concentrations are calculated from the optical density values using the Molecular Devices Soft Max software package.

Data Analysis:

Using an in-house computer program, IC$_{50}$ (50%, inhibition of virus replication), TC$_{50}$ (50% reduction in cell viability) and a therapeutic index (TI, IC$_{50}$/TC50) are provided. Raw data for both antiviral activity and toxicity with a graphic representation of the data were provided in a printout summarizing the individual compound activity. Applicant provided AZT as a relevant positive control compounds for the individual assays.

Results

Preliminary Experiments
Cytotoxicity in CEM-SS Cultures:

Composition was evaluated alone and in combination with Base or hydrogenated Base for toxicity to CEM-SS cells. Two methods were employed to measure cytotoxicity: measuring changes in optical densities following addition of MTS dye and [3H]thymidine incorporation. The cytotoxicity of the compounds is presented below in Table 1. The raw data obtained in these assays are presented in Appendix 1.

TABLE 1

Cytotoxicity of Composition in the Absence or Presence of Base

| Compound | MTSC$_{50}$ (μg/ml) | [3H] Thymidine Incorporation TC$_{50}$ (μg/ml) |
|---|---|---|
| Composition | 1.5 | 22.2 |
| Composition + Base (1 mg/ml) | 0.01 | 7.0 |
| Composition + Hydrogenated Base (1 mg/ml) | 0.003 | 2.7 |

Efficacy in PBMC Cultures:

Composition, Base 1, Base 2, Base 3 and Composition plus each individual Base (1000, 300, 200, 100, 60, 30, 20, 10, 5, 1 μg/ml) were evaluated for activity in PBMCs infected with wild type virus. AZT was used as the positive antiviral control compound in each assay and exhibited the expected anti-HIV activity (1 to 10 nM). Antiviral efficacy was evaluated by quantification of the ability of the compounds to reduce the expression of virus-associated reverse transcriptase activity in cell-free supernatants. The Composition inhibited HIV replication with EC$_{50s}$ ranging from 0.07 to 1.4 μg/ml against the ROJO clinical HIV-1 isolate. When evaluated as a monotherapy, Bases 1 through 3 demonstrated a range of antiviral activity providing therapeutic indices of 14870, 1, and 8260, respectively.

In the foregoing description, certain terms are used to illustrate the preferred embodiments. However, no unnecessary limitations are to be construed by the terms used, since the terms are exemplary only, and are not meant to limit the scope of the present invention.

It is further known that other modifications may be made to the present invention, without departing from the scope of the invention, as noted in the appended Claims.

What is claimed is:

1. A method for treating at least one disease selected from the group consisting of cancers and cell proliferating diseases in a patient comprising: forming a colloidal solution composition of at least a core of at least a biologically acceptable copper compound, wherein said copper compound is a nanoparticle of a fixed copper compound selected from the group consisting of cupric hydroxide, copper oxide, copper oxychloride, cupric carbonate basic, copper sulfate basic, cuprous oxide, cupric citrate, cupric phosphate, cuprobam, indigo copper, brochantite, langite, malachite, cometite, libethenite, pseudolibethenite, pseudomalachite, antlerite, covellite, marshite, cuprite, chalcocite, Rogojski's salt, brochantite, hydrocyanite, nantokite and dolerophane, said core being encapsulated, encoated, adsorbed, or bound in at least of a sheath, a shell, a polymeric shell, a cover, a casing, an encoating, a jacket or combination thereof, and a pharmaceutically acceptable carrier; said sheath, shell, polymeric shell, cover, casing, encoating, jacket or combination thereof being made of a material targeting at least one disease selected from the group consisting of cancerous and cell proliferating diseases and preventing immediate chemical interaction of the core with the surrounding environment; and administering the colloidal solution composition to the patient in need thereof.

2. The method of claim 1, further comprising the loading of tissues and transferrin by a redistribution agent, said redistribution agent allows the composition a longer residence time in the patient's plasma.

3. The method of claim 2, further comprising administering iron dextran as the redistribution agent.

4. The method of claim 2, further comprising administering iron glucose as the redistribution agent.

5. The method of claim 1, further comprising parenterally administering the composition to the patient.

6. The method of claim 1, further comprising orally administering the composition to the patient.

7. The method of claim 1, further comprising transderznally administering the composition to the patient.

8. The method of claim 1, further comprising inhalationally administering the composition to the patient.

9. The method of claim 1, further comprising administering the composition with an implantable polymer depot.

10. The method of claim 1, wherein the composition is administered for the total parenteral nutrition of the patient.

11. The method of claim 1, wherein the composition is administered with insulin potentiation therapy of the patient.

12. The method of claim 1, further comprising the addition of magnetic particles to the composition for imaging of cells.

13. The method of claim 1 further comprising:
monitoring the presence of at least one disease selected from the group consisting of cancers and cell proliferating diseases in the patient; and
re-administering the composition at intervals based on results of the monitoring.

14. The method of claim 1, wherein said diseases are selected from the group consisting of renal cancer, colon cancer, melanoma cancers, mammary cancer, lung cancer, ovarian cancer, prostate cancer, CNS cancer, and leukemic cancers.

15. The method of claim 1, wherein said copper compound is a copper compound that can cause catalysis of free-radical reactions in biological systems.

16. The method of claim 1, wherein said nanoparticle has a particle size of approximately 20 nm to approximately 200 nm.

* * * * *